United States Patent
Samec et al.

(10) Patent No.: US 10,719,992 B2
(45) Date of Patent: *Jul. 21, 2020

(54) AUGMENTED REALITY DISPLAY SYSTEM FOR EVALUATION AND MODIFICATION OF NEUROLOGICAL CONDITIONS, INCLUDING VISUAL PROCESSING AND PERCEPTION CONDITIONS

(71) Applicant: Magic Leap, Inc., Plantation, FL (US)

(72) Inventors: Nicole Elizabeth Samec, Fort Lauderdale, FL (US); Christopher M. Harrises, Nashua, NH (US); Mark Baerenrodt, Fort Lauderdale, FL (US); Stephen Vincent Mangiat, San Francisco, CA (US); Nastasja U. Robaina, Coconut Grove, FL (US); Adam Carl Wright, Fort Lauderdale, FL (US)

(73) Assignee: Magic Leap, Inc., Plantation, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/428,275

(22) Filed: May 31, 2019

(65) Prior Publication Data

US 2019/0287309 A1    Sep. 19, 2019

Related U.S. Application Data

(63) Continuation of application No. 15/627,208, filed on Jun. 19, 2017, now Pat. No. 10,332,315.

(Continued)

(51) Int. Cl.
*G06T 19/00* (2011.01)
*G02B 27/01* (2006.01)

(52) U.S. Cl.
CPC .......... *G06T 19/006* (2013.01); *G02B 27/017* (2013.01); *G02B 27/0172* (2013.01);
(Continued)

(58) Field of Classification Search
CPC .. G06K 9/00664–00704; G06F 3/0481; G06F 3/04817; G06F 9/4443;
(Continued)

(56) References Cited

U.S. PATENT DOCUMENTS

| 6,850,221 B1 | 2/2005 | Tickle |
| D514,570 S | 2/2006 | Ohta |

(Continued)

FOREIGN PATENT DOCUMENTS

| JP | 2003-85289 | 3/2003 |
| JP | 2011-33400 | 2/2011 |

(Continued)

OTHER PUBLICATIONS

International Search Report and Written Opinion for PCT Application No. PCT/US17/38174, dated Sep. 12, 2017.

(Continued)

*Primary Examiner* — Todd Buttram
(74) *Attorney, Agent, or Firm* — Knobbe, Martens, Olson & Bear, LLP

(57) ABSTRACT

In some embodiments, a display system comprising a head-mountable, augmented reality display is configured to perform a neurological analysis and to provide a perception aid based on an environmental trigger associated with the neurological condition. Performing the neurological analysis may include determining a reaction to a stimulus by receiving data from the one or more inwardly-directed sensors; and identifying a neurological condition associated with the reaction. In some embodiments, the perception aid may include a reminder, an alert, or virtual content that changes (Continued)

a property, e.g. a color, of a real object. The augmented reality display may be configured to display virtual content by outputting light with variable wavefront divergence, and to provide an accommodation-vergence mismatch of less than 0.5 diopters, including less than 0.25 diopters.

20 Claims, 17 Drawing Sheets

Related U.S. Application Data

(60) Provisional application No. 62/440,291, filed on Dec. 29, 2016, provisional application No. 62/366,555, filed on Jul. 25, 2016, provisional application No. 62/352,539, filed on Jun. 20, 2016.

(52) U.S. Cl.
CPC ............... *G02B 2027/0105* (2013.01); *G02B 2027/0138* (2013.01); *G02B 2027/0174* (2013.01); *G02B 2027/0187* (2013.01)

(58) Field of Classification Search
CPC ............ G06F 3/04847; G06F 11/3664; G06F 3/0304; G06F 3/011–015; G06T 19/00; G06T 17/00; G06T 19/006; G06T 2215/16; H04N 5/272; H04N 2201/3245; A63F 13/10
See application file for complete search history.

(56) References Cited

U.S. PATENT DOCUMENTS

| | | | |
|---|---|---|---|
| 8,094,927 B2* | 1/2012 | Jin | H04N 13/122 382/154 |
| 8,950,867 B2 | 2/2015 | Macnamara | |
| 9,081,426 B2 | 7/2015 | Armstrong | |
| 9,215,293 B2 | 12/2015 | Miller | |
| D752,529 S | 3/2016 | Loretan et al. | |
| 9,310,559 B2 | 4/2016 | Macnamara | |
| 9,348,143 B2 | 5/2016 | Gao et al. | |
| D758,367 S | 6/2016 | Natsume | |
| D759,657 S | 7/2016 | Kujawski et al. | |
| 9,417,452 B2 | 8/2016 | Schowengerdt et al. | |
| 9,470,906 B2 | 10/2016 | Kaji et al. | |
| 9,547,174 B2 | 1/2017 | Gao et al. | |
| 9,671,566 B2 | 6/2017 | Abovitz et al. | |
| D794,288 S | 8/2017 | Beers et al. | |
| 9,740,006 B2 | 8/2017 | Gao | |
| 9,791,700 B2 | 10/2017 | Schowengerdt et al. | |
| D805,734 S | 12/2017 | Fisher et al. | |
| 9,851,563 B2 | 12/2017 | Gao et al. | |
| 9,857,591 B2 | 1/2018 | Welch et al. | |
| 9,874,749 B2 | 1/2018 | Bradski | |
| 10,332,315 B2 | 6/2019 | Samec et al. | |
| 2006/0232665 A1* | 10/2006 | Schowengerdt | G02B 27/0093 348/51 |
| 2009/0182691 A1* | 7/2009 | Khaderi | A61B 3/024 706/12 |
| 2012/0127062 A1 | 5/2012 | Bar-Zeev et al. | |
| 2013/0082922 A1 | 4/2013 | Miller | |
| 2013/0125027 A1 | 5/2013 | Abovitz | |
| 2013/0185144 A1* | 7/2013 | Pradeep | A61B 5/04842 705/14.43 |
| 2014/0071539 A1 | 3/2014 | Gao | |
| 2014/0177023 A1 | 6/2014 | Gao et al. | |
| 2014/0192326 A1 | 7/2014 | Kiderman et al. | |
| 2014/0218468 A1 | 8/2014 | Gao et al. | |
| 2014/0244309 A1* | 8/2014 | Francois | G06Q 10/10 705/3 |
| 2014/0306866 A1 | 10/2014 | Miller et al. | |
| 2015/0016777 A1 | 1/2015 | Abovitz et al. | |
| 2015/0103306 A1 | 4/2015 | Kaji et al. | |
| 2015/0178939 A1 | 6/2015 | Bradski et al. | |
| 2015/0205126 A1 | 7/2015 | Schowengerdt | |
| 2015/0222883 A1 | 8/2015 | Welch | |
| 2015/0222884 A1 | 8/2015 | Cheng | |
| 2015/0268415 A1 | 9/2015 | Schowengerdt et al. | |
| 2015/0290460 A1* | 10/2015 | De Ridder | A61N 1/36082 607/45 |
| 2015/0302652 A1 | 10/2015 | Miller et al. | |
| 2015/0326570 A1 | 11/2015 | Publicover et al. | |
| 2015/0346490 A1 | 12/2015 | TeKolste et al. | |
| 2015/0346495 A1 | 12/2015 | Welch et al. | |
| 2016/0011419 A1 | 1/2016 | Gao | |
| 2016/0026253 A1* | 1/2016 | Bradski | G02B 27/225 345/8 |
| 2016/0131902 A1* | 5/2016 | Ambrus | G02B 27/0093 345/156 |
| 2016/0175589 A1* | 6/2016 | Wingeier | A61N 1/36025 607/45 |
| 2016/0270656 A1 | 9/2016 | Samec et al. | |
| 2017/0365101 A1 | 12/2017 | Samec et al. | |

FOREIGN PATENT DOCUMENTS

| | | |
|---|---|---|
| WO | WO 2013/049248 | 4/2013 |
| WO | WO 2015/044851 | 4/2015 |
| WO | WO 2017/222997 | 12/2017 |

OTHER PUBLICATIONS

Wikipedia: "Binaural beats", Wikipedia, printed Jun. 16, 2017, in 10 pages. URL: https://en.wikipedia.org/wiki/Binaural_beats.
Wikipedia: "Body transfer illusion", Wikipedia, as archived Aug. 10, 2017, in 4 pages. URL: https://web.archive.org/web/20170810213201/https://en.wikipedia.org/wiki/Body_transfer_illusion.
Wikipedia: "Electrocardiography", Wikipedia, printed Jun. 16, 2017, in 18 pages. URL: https://en.wikipedia.org/wiki/Electrocardiography.
Wikipedia: "Electromyography (EMG)", Mayo Clinic, Jan. 20, 2017, in 3 pages. URL: http://www.mayoclinic.org/tests-procedures/emg/basics/definition/prc-20014183?p=1.
"Electroretinography", Wikipedia, printed Jun. 16, 2017, in 3 pages. URL: https://en.wikipedia.org/wiki/Electroretinography.
Wikipedia: "Event-related potential", Wikipedia, printed Jun. 16, 2017, in 7 pages. URL: https://en.wikipedia.org/wiki/Event-related_potential.
"How Much Therapy is Enough" The Brain Recovery Project, accessed Jun. 29, 2016, in 2 pages. URL: http://www.brainrecoveryproject.org/rehabilitation/how-much-therapy-is-enough/.
Wikipedia: "McGurk Effect", Wikipedia, printed Jun. 16, 2017, in 11 pages. URL: https://en.wikipedia.org/wiki/McGurk_effect.
Wikipedia: "Mini-Mental State E amination", Wikipedia, printed Jun. 16, 2017, in 6 pages. URL: https://en.wikipedia.org/wiki/Mini%E2%80%93Mental_State_E amination.
Wikipedia: "Multisensory integration", Wikipedia, printed Jun. 16, 2017, in 24 pages. URL: https://en.wikipedia.org/wiki/Multisensory_integration.
Alleydog.com: "Nonconscious definition" accessed Jun. 29, 2016, in 3 pages. URL:http://www.alleydog.com/glossary/definition.php?term-Nonconscious.
Wikipedia: "Photoacoustic imaging", Wikipedia, printed Jun. 16, 2017, in 6 pages. URL: https://en.wikipedia.org/wiki/Photoacoustic_imaging.
"Research helps stroke victims retrain brain", Victoria University, Dec. 10, 2015, as archived Aug. 10, 2017, in 3 pages. URL: https://web.archive.org/web/20170810220140/https://www.vu.edu.au/news-events/media-releases/research-helps-stroke-victims-retrain-brain.
Bar, K. J. et al., "Correlations between the autonomic modulation of heart rate, blood pressure and the pupillary light refle in healthy subjects", Journal of Neurological Sciences, vol. 279, Apr. 15, 2009, in 5 pages.

(56) References Cited

OTHER PUBLICATIONS

Bidelman, G. M., "Musicians have enhanced audiovisual multisensory binding: e perience-dependent effects in the double-flash illusion", E perimental Brain Research, vol. 234, Oct. 2016, in 11 pages.
Blumenfeld, H., "The Neurologic Exam as a Lesson in Neuroanatomy", Neuroanatomy through Clinical Cases Chapter 3: (Second Edition), Sinauer Associates, Inc., Aug. 2010, in 10 pages.
Blumenfeld, H., "Neglect and Constructions", Neuroe am, accessed Jun. 29, 2016, in 2 pages. URL: http://www.neuroe am.com/neuroe am/content.php?p=10.
Borghino, D., "Hi-tech glasses aim to assist the blind with directions and obstacle detection", New Atlas, May 22, 2014, in 4 pages. URL: http://newatlas.com/stereoscopic-ultrasound-gps-ai-glasses-blind-assistance/32166/.
Chanubol, R. et al, "A randomized controlled trial of Cognitive Sensory Motor Training Therapy on the recovery of arm function in acute stroke patients", Clinical Rehabilitation, May 2012, in 10 pages.
Dragoi, V., "Chapter 15: Visual Processing: Cortical Pathways", Neuroscience Online, UTHealth, accessed Jun. 29, 2016, in 14 pages. URL: http://neuroscience.uth.tmc.edu/s2/chapter15.html.
Felleman, D. et al., "Distributed Hierarchical Processing in the Primate Cerebral Corte ", Cerebral Corte , Jan./Feb. 1991, in 47 pages. URL: http://cercor.o fordjournals.org/content/1/1/1.1.full.pdf+html.
Gregoire, C., "Yes, You Can Teach Yourself Synesthesia (And Here's Why You Should)", The Huffington Post, Sep. 1, 2015, in 3 pages. URL: http://www.huffingtonpost.com/entry/a-neuroscientists-guide-to-developingsynesthesia_us_55e4b004e4b0aec9f35429c9.
Hensch, T. et al., "Re-opening Windows: Manipulating Critical Periods for Brain Development", The Dana Foundation, Aug. 29, 2012, in 9 pages. URL: http://dana.org/Cerebrum/2012/Re-opening_Windows_Manipulating_Critical_Periods_for_Brain_Development/.
Iosa, M. et al., "Seven Capital Devices for the Future of Stroke Rehabilitation", Stroke Research and Treatment, vol. 2012, Nov. 2012, in 9 pages. URL: http://www.ncbi.nlm.nih.gov/pmc/articles/PMC3530851/.
Jarrett et al., "What is the Best Multi-Stage Architecture for Object Recognition?", In Computer Vision IEEE 12th International Conference Sep. 29-Oct. 2, 2009, pp. 2146-2153.
Jones, O., "Scientists Learn How to Teach Synesthesia (Let the Weirdness Begin)", Big Think, 2016, in 1 page. URL: http://bigthink.com/ideafeed/scientists-learn-how-to-teach-synesthesia-let-the-weirdness-begin.
Kovacs, I. et al., "When the brain changes its mind: Interocular grouping during binocular rivalry", Proc. Natl. Acad. Sci., Dec. 1996, vol. 93, in 4 pages. URL: http://www.pnas.org/content/93/26/15508.full.pdf.
Luzzatti, C., "Acquired Reading and Writing Disorders", Chapter 20, Handbook of the Neuroscience of Language, editors Stemmer, B. et al., Mar. 2008, in 12 pages.
Martin, B., "In-Depth: Cognitive Behavioral Therapy", Psych Central, published on May 17, 2016, retrieved on Oct. 13, 2016, in 8 pages. URL: http://psychcentral.com/lib/in-depth-cognitive-behavioral-therapy/.

McFadden, M., "New therapy helps retrain stroke patients", WNDU, Feb. 4, 2015, in 3 pages. URL: http://www.wndu.com/news/specialreports/headlines/New-therapy-helps-retrain-stroke-pat.
Paton, J. et al., "The primate amygdala represents the positive and negative value of stimuli during learning", Nature, Feb. 16, 2006, vol. 439, in 6 pages. URL: http://www.nature.com/nature/journal/v439/n7078/full/nature04490.html.
Podda, M. et al, "Anodal transcranial direct current stimulation boosts synaptic plasticity and memory in mice via epigenetic regulation of Bdnf e pression", Scientific Reports, Feb. 24, 2016, in 19 pages. URL: http://www.nature.com/articles/srep22180.
Prasad, S. et al., "Eye Movement Abnormalities in Multiple Sclerosis", Neurologic Clinics, vol. 28, Aug. 2010, in 15 pages.
Robertson, C. et al., "Reduced GABAergic Action in the Autistic Brain", Current Biology, 2016, in 7 pages. URL: http://www.cell.com/current-biology/abstract/S0960-9822(15)01413.
Salomon, R. et al., "The Insula Mediates Access to Awareness of Visual Stimuli Presented Synchronously to the Heartbeat", Journal of Neuroscience, May 6, 2016, vol. 36(18), in 13 pages. URL: http://www.jneurosci.org/content/36/18/5115.short.
Sugiyama, T. et al., "Use of laser speckle flowgraphy in ocular blood flow research", Acta Ophthalmologica, vol. 88, Nov. 2010, in 7 pages.
Swain, F., "Can Synaesthesia be learnt?" BBC, Jun. 11, 2014, in 4 pages. URL: http://www.bbc.com/future/story/20140611-can-synaesthesia-be-learnt.
Takase, S. et al., "Recovery from perceptual filling-in is gated by interocular matching", Vision Research, vol. 49, Jul. 2009, in 7 pages.
Tayefeh, F. et al., "Time-dependent changes in heart rate and pupil size during desflurane or sevoflurane anesthesia", Anesthesia & Analgesia, vol. 85, Dec. 1997, in 5 pages.
The New York Times, "MIT Computer Program Reveals Invisible Motion in Video | The New York Times", YouTube, published Feb. 27, 2013, as archived Sep. 8, 2017, in 10 pages (with video transcription). URL: https://web.archive.org/web/20170906180629/https://www.youtube.com/watch?feature-youtu.be&t=1m5s&v=3rWycBEHn3s&app=desktop.
Wang, W. et al., "Neural Interface Technology for Rehabilitation: E ploiting and Promoting Neuroplasticity", Physical Medicine Rehabilitation Clinics of North America, vol. 21, Feb. 2010, in 22 pages. URL: http://www.ncbi.nlm.nih.gov/pmc/articles/PMC2788507/.
Watanabe, K., "The motion-induced position shift depends on the visual awareness of motion", Vision Research, vol. 45, Apr. 2005, in 7 pages.
International Preliminary Report on Patentability for PCT Application No. PCT/US17/38174, dated Dec. 25, 2018.
Goldman-Rakic, P. et al., "Preface: Cerebral Cortex Has Come of Age", Cerebral Cortex , vol. 1, Jan. 1991, in 2 pages. URL: http://cercor.o fordjournals.org/content/1/1/1.1.full.pdf+html.
Wikipedia, "Ganzfeld effect", https://web.archive.org/web/20160305082958/https://en.wikipedia.org/wiki/Ganzfeld_effect as archived Mar. 5, 2016 in 2 pages.
European Extended Search Report, re EP Application No. 17816009.9, dated Jan. 28, 2020.

* cited by examiner

AUGMENTED REALITY DISPLAY SYSTEM FOR EVALUATION AND MODIFICATION OF NEUROLOGICAL CONDITIONS, INCLUDING VISUAL PROCESSING AND PERCEPTION CONDITIONS

PRIORITY CLAIM

This application is a continuation of U.S. application Ser. No. 15/627,208 filed on Jun. 19, 2017, which claims the benefit of priority under 35 U.S.C. 119(e) of U.S. Provisional Application No. 62/352,539 filed on Jun. 20, 2016; U.S. Provisional Application No. 62/366,555 filed on Jul. 25, 2016; and U.S. Provisional Application No. 62/440,291 filed on Dec. 29, 2016. The entire disclosure of each of these priority documents is incorporated herein by reference.

INCORPORATION BY REFERENCE

This application incorporates by reference the entirety of each of the following patent applications: U.S. application Ser. No. 14/555,585 filed on Nov. 27, 2014, published on Jul. 23, 2015 as U.S. Publication No. 2015/0205126; U.S. application Ser. No. 14/690,401 filed on Apr. 18, 2015, published on Oct. 22, 2015 as U.S. Publication No. 2015/0302652; U.S. application Ser. No. 14/212,961 filed on Mar. 14, 2014, now U.S. Pat. No. 9,417,452 issued on Aug. 16, 2016; U.S. application Ser. No. 14/331,218 filed on Jul. 14, 2014, published on Oct. 29, 2015 as U.S. Publication No. 2015/0309263; and U.S. application Ser. No. 15/072,290 filed on Mar. 16, 2016, published on Sep. 22, 2016 as U.S. Publication No. 2016/0270656.

BACKGROUND

Field

The present disclosure relates to display systems and, more particularly, to augmented reality display systems.

Description of the Related Art

Modern computing and display technologies have facilitated the development of systems for so called "virtual reality" or "augmented reality" experiences, wherein digitally reproduced images or portions thereof are presented to a user in a manner wherein they seem to be, or may be perceived as, real. A virtual reality, or "VR", scenario typically involves presentation of digital or virtual image information without transparency to other actual real-world visual input; an augmented reality, or "AR", scenario typically involves presentation of digital or virtual image information as an augmentation to visualization of the actual world around the user. A mixed reality, or "MR", scenario is a type of AR scenario and typically involves virtual objects that are integrated into, and responsive to, the natural world. For example, in an MR scenario, AR image content may be blocked by or otherwise be perceived as interacting with objects in the real world.

Referring to FIG. 1, an augmented reality scene 1 is depicted wherein a user of an AR technology sees a real-world park-like setting 1100 featuring people, trees, buildings in the background, and a concrete platform 1120. In addition to these items, the user of the AR technology also perceives that he "sees" "virtual content" such as a robot statue 1110 standing upon the real-world platform 1120, and a cartoon-like avatar character 1130 flying by which seems to be a personification of a bumble bee, even though these elements 1130, 1110 do not exist in the real world. Because the human visual perception system is complex, it is challenging to produce an AR technology that facilitates a comfortable, natural-feeling, rich presentation of virtual image elements amongst other virtual or real-world imagery elements.

Systems and methods disclosed herein address various challenges related to AR and VR technology.

SUMMARY

In some embodiments, a display system comprises a head-mountable, augmented reality display configured to output light with variable wavefront divergence to display virtual content. The display system also comprises one or more inwardly-directed sensors; one or more outwardly-directed sensors; one or more processors; and one or more computer storage media storing instructions that, when executed by the one or more processors, cause the one or more processors to perform various operations. The operations comprise performing a neurological analysis; determining environmental triggers associated with the neurological condition; monitoring an ambient environment with the one or more outwardly-directed sensors; detecting a presence of an environmental trigger in the ambient environment; and providing a perception aid based on the detected presence of the triggering variable. Performing the neurological analysis comprises determining a reaction to a stimulus by receiving data from the one or more inwardly-directed sensors, and identifying a neurological condition associated with the reaction.

In some other embodiments, the display system comprises a head-mountable, augmented reality display configured to output light with variable wavefront divergence to display virtual content. The display system also comprises one or more inwardly-directed sensors; one or more processors; and one or more computer storage media storing instructions that, when executed by the one or more processors, cause the one or more processors to perform various operations. The operations comprise performing a neurological analysis by determining a reaction to a stimulus by receiving data from the one or more inwardly-directed sensors; and identifying a neurological condition associated with the reaction.

In yet other embodiments, a method is performed by a display system comprising one or more processors, one or more inwardly-directed sensors, and a head-mounted display. The method comprises performing a neurological analysis by determining a user reaction to a stimulus by collecting data from the one or more inwardly-directed sensors; and identifying a neurological condition associated with the reaction.

In addition, various innovative aspects of the subject matter described in this disclosure can be implemented in the following embodiments:

Embodiment 1: A display system comprising:
a head-mounted display configured to project light to a user to display augmented reality image content on a plurality of depth planes, the display comprising:
  one or more waveguides configured to project the light to the user, wherein the one or more waveguides are further configured to transmit light from a surrounding environment to the user,
wherein the display system is configured to:
  provide a stimulus to the user;
  determine a reaction of the user to the stimulus; and
  determine in the user a presence of a neurological condition or neurological state associated with the reaction.

Embodiment 2: The display system of Embodiment 1, wherein the stimulus comprises the augmented reality image content.

Embodiment 3: The display system of any of the Embodiments 1-2, wherein the display system is configured to display to the user a list of neurological conditions corresponding to the reaction.

Embodiment 4: The display system of any of the Embodiments 1-3, wherein the neurological conditions are neurological abnormalities.

Embodiment 5: The display system of any of the Embodiments 1-4, wherein the display system is configured to communicate the list of neurological conditions to a clinician.

Embodiment 6: The display system of any of the Embodiments 1-5, wherein the display system is configured to communicate the list of neurological conditions to one or more other users.

Embodiment 7: The display system of any of the Embodiments 1-6, wherein the display system is configured to:
provide the stimulus by displaying a plurality of images to the user, wherein one of the images is on a different depth plane than another of the images; and
  determine the reaction by:
  measuring an accommodation, vergence state and/or other efferent system responses of the user's eyes; and
  determining the image perceived by the user by matching the measured accommodation, vergence state and/or other efferent system responses with an expected accommodation and/or vergence state for the one of the images or the other of the images.

Embodiment 8: The display system of any of the Embodiments 1-7, wherein the display is configured to display augmented reality image content continuously to the user for 3 or more hours while the user wears the display.

Embodiment 9: The display system of any of the Embodiments 1-8, wherein the display is configured to display the augmented reality image content for 5 or more hours.

Embodiment 10: The display system of any of the Embodiments 1-9, wherein the display system is configured to automatically perform the following sequence a plurality of times over a plurality of months:
  provide a stimulus to the user;
  determine a reaction of the user to the stimulus; and
  determine in the user a presence of a neurological condition associated with the reaction.

Embodiment 11: A display system comprising:
a head-mounted display configured to project light to a user to display augmented reality image content on a plurality of depth planes, the display comprising:
  one or more waveguides configured to project the light to the user, wherein the one or more waveguides are further configured to transmit light from a surrounding environment to the user,
  wherein the display system is configured to:
  determine a reaction of the user to a stimulus; and
  determine in the user a presence of a neurological condition associated with the reaction.

Embodiment 12: The display system of any of Embodiments 1-11, wherein the display system is configured to provide information associated with the neurological condition to a population of other users.

Embodiment 13: The display system of Embodiment 12, wherein the display system is configured to determine the neurological condition based upon a norm determined from the population of other users.

Embodiment 14: The display system of any of Embodiments 12-13, wherein the display system is configured to retrieve a norm for a subset of the population based upon criteria corresponding to the user.

Embodiment 15: The display system of any of Embodiments 12-14, wherein the display system is configured to dynamically alter a norm by providing information associated with the neurological condition to the population of other users.

Embodiment 16: A display system comprising:
a head-mounted display configured to project light to a user to display augmented reality image content on a plurality of depth planes, the display comprising:
  one or more waveguides configured to project the light to the user, wherein the one or more waveguides are further configured to transmit light from a surrounding environment to the user,
  wherein the display system is configured to:
  determine whether a stimulus is associated with a neurological condition; and
  display a perception aid for the neurological condition.

Embodiment 17: A display system comprising:
a head-mounted display configured to project light to a user to display augmented reality image content on a plurality of depth planes, the display comprising:
  one or more waveguides configured to project the light to the user, wherein the one or more waveguides are further configured to transmit light from a surrounding environment to the user; and
  one or more sensors configured to monitor the environment,
  wherein the display system is configured to:
  determine an expected emotional reaction of the user to an object in the environment;
  determine whether the expected emotional reaction of the user to the object is targeted for modification; and
  modify the expected emotional reaction of the user to the object by presenting augmented reality content to the user.

Embodiment 18: The display system of Embodiment 17, wherein the augmented reality content is the augmented reality image content.

Embodiment 19: The display system of any of Embodiments 17-18, wherein the object is associated with a user phobia.

Embodiment 20: The display system of any of Embodiments 17-19, wherein the display system is configured to visually overlay the augmented reality content on the object.

Embodiment 21: The display system of any of Embodiments 17-21, wherein the display system is configured to:
  determine a distance of the object from the user; and
  present the augmented reality content overlaying the object on a depth plane corresponding to the distance.

Embodiment 22: A display system comprising:
a head-mounted display configured to project light to a user to display augmented reality image content on a plurality of depth planes, the display comprising:
  one or more waveguides configured to project the light to the user, wherein the one or more waveguides are further configured to transmit light from a surrounding environment to the user;
  a sensor configured to monitor the environment,
  wherein the display system is configured to:
  determine an expected physical or behavioral reaction of the user to an object in the environment;

determine whether the expected physical or behavioral reaction of the user to the object is targeted for modification; and modify the expected physical or behavioral reaction of the user to the object by presenting augmented reality content to the user.

Embodiment 23: The display system of Embodiment 1, wherein the provided stimulus comprises one or more images presented to at least one eye of the user.

Embodiment 24: The display system of Embodiment 23, wherein the one or more images comprise:

a first image presented to a first eye of the user; and a second image presented to a second eye of the user, wherein the second image differs from the first image.

Embodiment 25: The display system of any of Embodiments 23-24, wherein the one or more images comprise a first image and a second image presented to a same eye of the user, wherein the second image differs from the first image.

Embodiment 26: The display system of any of Embodiments 23-25, wherein the second image differs from the first image in contour, color, luminance, flicker rate, or contrast.

Embodiment 27: The display system of any of Embodiments 23-26, wherein the first image comprises first portions, wherein the second image comprises second portions, and wherein the first portions and the second portions form a coherent image.

Embodiment 28: The display system of any of Embodiments 23-27, wherein the first image comprises a static image and the second image comprises a series of dynamic images.

Embodiment 29: The display system of any of Embodiments 23-28, wherein the first image comprises a stationary image and the second image comprises a moving image.

Embodiment 30: The display system of any of Embodiments 23-29, wherein one of the one or more images comprise a stationary portion and a moving portion.

Embodiment 31: The display system of any of Embodiments 23-30, wherein the one or more images comprise one or more images with different contrasts.

Embodiment 32: The display system of any of Embodiments 23-31, wherein the reaction comprises visual perception of the user in response to the presented one or more images.

Embodiment 33: The display system of Embodiment 32, wherein the reaction comprises a perceptual state of dominance or suppression.

Embodiment 34: The display system of any of Embodiments 32-33, wherein the reaction comprises:

suppression of one of the one or more images;

reassembly of portions of the one or more images; or disappearance of at least a portion of one of the one or more images.

Embodiment 35: The display system of any of Embodiments 33-34, further comprising a user interface to measure the perceptual state of dominance or suppression.

Embodiment 36: The display system of any of Embodiments 33-35, wherein the display system is configured to use data from optokinetic nystagmus (OKN), visual evoked potential (VEP), magnetoencephalography (MEG), or blood-oxygen level dependent (BOLD) contrast imaging using functional magnetic resonance imaging (fMRI) to infer the perceptual state of dominance or suppression.

Embodiment 37: The display system of any of Embodiments 33-36, wherein the display system is configured to determine in the user the presence of a neurological condition associated with visual processing.

Embodiment 38: The display system of Embodiment 1, further comprising electrodes configured to measure electrical potentials from at least one or more sensors a user's head or related to a user's head.

Embodiment 39: The display system of Embodiment 38, wherein the electrodes are configured to be disposed at a plurality of locations on a user's head, and wherein the display system is configured to simultaneously derive electrical potential measurements from the plurality of locations.

Embodiment 40: The display system of any of Embodiments 38-39, wherein the display system is configured to present a stimulus to a single eye of the user.

Embodiment 41: The display system of any of Embodiments 38-40, wherein the display system is configured to present a stimulus to a both eyes of the user simultaneously.

Embodiment 42: The display system of any of Embodiments 38-41, wherein the display system is configured to present a checkerboard stimulus alternating between colors.

Embodiment 43: The display system of any of Embodiments 38-42, wherein the display system is configured to present a stimulus that changes size within a time interval.

Embodiment 44: The display system of any of Embodiments 38-43, wherein the display system is configured to determine a smallest change that produces a response.

Embodiment 45: The display system of any of Embodiments 38-44, wherein the display system is configured to present a stimulus that changes color.

Embodiment 46: The display system of Embodiment 45, wherein the color changes to different shades of a similar color.

Embodiment 47: The display system of any of Embodiments 38-46, wherein the display system is configured to present a stimulus that changes luminance.

Embodiment 48: The display system of any of Embodiments 38-47, wherein the display system is configured to present a stimulus on a portion of the user's visual field.

Embodiment 49: The display system of any of Embodiments 38-48, wherein the display system is configured to present a stimulus on a portion of the user's visual field.

Embodiment 50: The display system of any of Embodiments 38-49, wherein the display system is configured to present stimuli on a plurality of depth planes.

Embodiment 51: The display system of any of Embodiments 38-50, wherein the display system is configured to present stimulus that alternates between different portions of the user's visual field, and wherein the display system is configured to measure at least the difference in evoked event-related potentials between the stimulus alternating between the different portions.

Embodiment 52: The display system of any of Embodiments 38-51, wherein the display system is configured to present stimulus that changes between at least two colors.

Embodiment 53: The display system of Embodiment 52, wherein the display system is configured to present stimulus to the entire visual field of the user.

Embodiment 54: The display system of any of Embodiments 38-53, wherein the display system is configured to present stimulus that changes location from one area on the visual field to another.

Embodiment 55: The display system of any of Embodiments 38-54, wherein the display system is configured to present stimulus that changes orientation.

Embodiment 56: The display system of any of Embodiments 38-55, wherein the display system is configured to present stimulus that changes in boundary sharpness.

Embodiment 57: The display system of any of Embodiments 38-56, wherein the display system is configured to present stimulus that changes in boundary contrast.

Embodiment 58: The display system of any of Embodiments 38-57, wherein the display system is configured to present stimulus that changes a characteristic at a particular frequency.

Embodiment 59: The display system of Embodiment 58, wherein the display system is configured to measure a response in the user at the frequency that the stimulus is changing.

Embodiment 60: The display system of any of Embodiments 38-59, wherein the display system is configured to present stimulus comprising random dot stereograms.

Embodiment 61: The display system of any of Embodiments 38-60, wherein the display system is configured to compare the measured reaction to a predetermined response which indicates a normal reaction.

Embodiment 62: The display system of any of Embodiments 38-61, wherein the display system is configured to compare the measured reaction to a predetermined response indicating a particular neurological abnormality.

Embodiment 63: The display system of Embodiment 1, wherein the provided stimulus comprises a bright light.

Embodiment 64: The display system of Embodiment 63, wherein the reaction of the user comprises a reduced speed or a decreased amplitude at which a pupil of an eye of the user constricts.

Embodiment 65: The display system of any of Embodiments 63-64, wherein the neurological condition is associated with at least one of: lesions of the ipsilateral optic nerve, lesions of the pretectal area, lesions of the ipsilateral parasympathetics travelling in cranial nerve III, lesions of the pupillary constrictor muscle of the iris, lesions of the contralateral optic nerve, epilepsy, anxiety, addiction, intoxication, stroke, brain aneurysm, Guillain-Barre syndrome, and traumatic brain injury.

Embodiment 66: The display system of any of Embodiments 63-65, wherein the provided stimulus comprises a patch of light that is moved back and forth alternates between the first and second eyes of the user.

Embodiment 67: The display system of Embodiment 66, wherein the reaction of the user comprises dilation of a pupil of an eye of the user when illuminated by the patch of light.

Embodiment 68: The display system of any of Embodiments 66-67, wherein the neurological condition is at least one of multiple sclerosis, neuromyelitis optica, optic neuritis or traumatic optic neuropathy.

Embodiment 69: The display system of Embodiment 1, wherein the provided stimulus comprises an object that is moved from a distant vision zone to a near vision zone.

Embodiment 70: The display system of Embodiment 69, wherein the reaction of the user comprises abnormalities in constriction of a pupil of one or both eyes of the user as the object is moved from the distant vision zone to the near vision zone.

Embodiment 71: The display system of any of Embodiments 69-70, wherein the neurological condition is associated with at least one of: lesions of the ipsilateral optic nerve, lesions of the ipsilateral parasympathetics travelling in cranial nerve III, lesions of the pupillary constrictor muscle of the iris, bilateral lesions of the pathways from the optic tracts to the visual cortex, cognitive impairment, dementia, Alzheimer's disease, Lewy body dementia, and cortical blindness.

Embodiment 72: The display system of Embodiment 1, wherein the provided stimulus comprises an object that is moved across the horizontal or vertical field of view.

Embodiment 73: The display system of Embodiment 73, wherein the reaction of the user comprises impairments in a smooth movement of one or both eyes of the user along horizontal or vertical axes in a field of view of the user.

Embodiment 74: The display system of any of Embodiments 72-73, wherein the neurological condition is associated with at least one of: cognitive impairment, Parkinson's disease, dementia, Alzheimer's disease, frontotemporal dementia, progressive supranuclear palsy, intoxication, addiction, traumatic brain injury, and cortical blindness.

Embodiment 75: The display system of Embodiment 1, wherein the provided stimuli comprises an object that is moved towards one or both eyes of the user.

Embodiment 76: The display system of Embodiment 75, wherein the reaction of the user comprises deviation of one or both eyes of the user along directions that are not medial.

Embodiment 77: The display system of any of Embodiments 75-76, wherein the neurological condition corresponds to at least one of dystonia, Parkinson's disease, cortical basal degeneration or Lewy body degeneration.

Embodiment 78: The display system of Embodiment 1, wherein the provided stimuli comprises a first object at a first location and a second object at a second location, wherein the first and the second location are spaced apart.

Embodiment 79: The display system of Embodiment 78, wherein the reaction of the user comprises measurement of a speed, amplitude or frequency of saccadic movement of one or both eyes of the user.

Embodiment 80: The display system of any of Embodiments 76-79, wherein the neurological condition is associated with at least one of: cognitive impairment, dementia, Alzheimer's disease, Huntington's disease, Parkinson's disease, cortical basal degeneration, Lewy body dementia and progressive supra nuclear palsy.

Embodiment 81: The display system of Embodiment 1, wherein the provided stimuli comprises a motionless target and an a different object located to a side of the motionless target.

Embodiment 82: The display system of Embodiment 81, wherein the reaction of the user comprises a failure to inhibit reflexive saccade.

Embodiment 83: The display system of any of Embodiments 81-82, wherein the neurological condition is associated with at least one of: dementia, Alzheimer's disease, Huntington's disease, Parkinson's disease, cortical basal degeneration, Lewy body dementia, frontotemporal dementia and schizophrenia.

Embodiment 84: The display system of Embodiment 1, wherein the provided stimuli comprises bright and dark stripes that are moved across a visual field of the user.

Embodiment 85: The display system of Embodiment 84, wherein the reaction of the user comprises a movement of both eyes of the user that does not exhibit a movement across the visual field followed by a movement to midline at a greater speed than the movement across the visual field.

Embodiment 86: The display system of any of Embodiments 84-85, wherein the neurological condition is associated with at least one of: hemispatial neglect, multiple sclerosis, neuromyelitis optica, ataxia, intoxication, and stroke.

Embodiment 87: The display system of Embodiment 1, wherein the provided stimuli comprises a flickering patch of light and a non-flickering patch of light.

Embodiment 88: The display system of Embodiment 87, wherein the reaction of the user comprises a change in hue perception of the flickering patch of light.

Embodiment 89: The display system of any of Embodiments 87-88, wherein the neurological condition corresponds to active optic neuritis.

Embodiment 90: The display system of Embodiment 1, wherein the provided stimuli comprises an object that is moved rapidly towards one or both eyes of the user from different directions.

Embodiment 91: The display system of Embodiment 90, wherein the reaction of the user comprises a failure to blink.

Embodiment 92: The display system of any of Embodiments 90-91, wherein the neurological state corresponds to coma.

Embodiment 93: The display system of Embodiment 1, wherein the provided stimuli comprises an object that is simultaneously displayed on either side of the user.

Embodiment 94: The display system of Embodiment 93, wherein the reaction of the user comprises failure to perceive the object on one side when simultaneously displayed on either side of the user.

Embodiment 95: The display system of any of Embodiments 93-94, wherein the neurological condition is associated with stroke.

Embodiment 96: The display system of Embodiment 16, wherein the neurological state comprises increased neural plasticity.

Embodiment 97: The display system of Embodiment 16, wherein the display system is configured to provide stimuli to the user to increase neural plasticity.

Embodiment 98: The display system of Embodiment 97, wherein the stimuli are provided as part of a video game.

Embodiment 99: The display system of Embodiment 16, wherein the perception aid comprises guided image therapy.

Embodiment 100: The display system of Embodiment 16, wherein the perception aid comprises guided image and music therapy.

Embodiment 101: The display system of Embodiment 16, wherein the perception aid comprises visual stimuli associated by the user with positive feedback.

Embodiment 102: The display system of Embodiment 16, wherein the perception aid comprises visual stimuli associated by the user with negative feedback.

Embodiment 103: The display system of Embodiment 16, wherein the perception aid comprises audiovisual stimuli configured to condition a user through classical conditioning techniques.

Embodiment 104: The display system of Embodiment 16, wherein the perception aid comprises a audiovisual stimuli configured to condition a user through operant conditioning techniques.

Embodiment 105: The display system of Embodiment 16, wherein the display system is further configured to associate visual stimuli with positive or negative values.

Embodiment 106: The display system of Embodiment 16, wherein the neurological condition comprises pain.

Embodiment 107: The display system of Embodiment 106, wherein the perception aid comprises audiovisual stimuli configured to distract the user to alleviate sensation of the pain.

Embodiment 108: The display system of any of Embodiments 106-107, wherein the perception aid comprises audiovisual stimuli configured to relax the user to alleviate sensation of the pain.

Embodiment 109: The display system of any of Embodiments 106-108, wherein the perception aid comprises guided imagery to alleviate sensation of the pain.

Embodiment 110: The display system of any of Embodiments 106-109, wherein the display system further comprises a user interface element to receive user input regarding pain levels.

Embodiment 111: The display system of any of Embodiments 106-110, wherein the perception aids comprise audiovisual stimuli configured to alter a mood of a user.

Embodiment 112: The display system of Embodiment 111, wherein the perception aids comprise guided imagery.

Embodiment 113: The display system of Embodiment 16, wherein the perception aids comprise audiovisual stimuli configured to provide perceptual learning techniques to improve a user's skills and abilities.

Embodiment 114: The display system of Embodiment 16, wherein the skills and abilities comprise skills of perception.

Embodiment 115: The display system of Embodiment 16, wherein the display system is configured to provide eye movement desensitization and reprocessing (EMDR) therapy.

Embodiment 116: The display system of Embodiment 115, wherein the perception aids comprise bilateral sensory input configured to induce side-to-side eye movement in the user.

Embodiment 117: The display system of Embodiment 16, wherein the display system is further configured to provide computer games that are tailored to enhance perceptual and cognitive abilities.

Embodiment 118: The display system of Embodiment 16, wherein the display system is configured to provide auditory discrimination applications to address speech and language difficulties.

Embodiment 119: The display system of Embodiment 16, wherein the display system is configured to provide a primary stimulus configured to engage a primary cognitive or sensory pathway and a secondary stimulus configured to engage a second cognitive or sensory pathway.

Embodiment 120: The display system of Embodiment 119, wherein the perception aids comprise letters or numbers associated with colors.

Embodiment 121: The display system of any of Embodiments 119-120, wherein the perception aids comprise music associated with colors.

Embodiment 122: The display system of any of Embodiments 119-121, wherein the perception aids comprise numbers and/or letters positioned in 3D space around the user.

Embodiment 123: The display system of Embodiment 16, wherein the perception aids comprise a virtual reflected image of the user, wherein a first portion of the image comprises an accurate depiction of the user and a second portion of the image, complementary to the first portion of the image, comprises a virtual reflection of the first portion to form a full image of the user.

Embodiment 124: The display system of Embodiment 123, wherein the display system is configured to cause the entire image to move with left-right symmetry.

Embodiment 125: The display system of Embodiment 16, wherein the perception aids comprise audiovisual stimuli that are based on objects presented to the user and that are configured to stimulate the senses of the user.

Embodiment 126: The display system of Embodiment 16, wherein the perception aids comprise audiovisual stimuli comprising objects at a first distance and objects at a second distance, wherein the objects at the second distance are shown to be blurred or obscured.

Embodiment 127: The display system of Embodiment 16, wherein the display system is configured to provide speech recognition and to display recognized speech as text, wherein the perception aids comprise text corresponding to speech detected by the display system.

Embodiment 128: The display system of Embodiment 1, further comprising a speaker configured to transmit audio content to an ear of the user, wherein the stimulus comprises the audio content.

Embodiment 129: The display system of Embodiment 128, wherein the stimulus comprises one or more instructions audible to the user.

Embodiment 130: The display system of Embodiment 2, wherein the stimulus comprises one or more visual instructions projected to the user.

Embodiment 131: The display system of Embodiment 1, further comprising a microphone configured to detect vocalization of the user.

Embodiment 132: The display system of Embodiment 1, wherein the display system is further configured to evaluate the alertness of the user based at least in part on the reaction of the user to the stimulus.

Embodiment 133: The display system of Embodiment 1 or Embodiment 16, wherein the neurological condition comprises a neurological condition associated with the alertness of the user.

Embodiment 134: The display system of Embodiment 16, wherein the perception aid comprises visual content selected to increase the alertness of the user.

Embodiment 135: The display system of Embodiment 16, wherein the perception aid comprises modifying visual content to increase the alertness of the user.

Embodiment 136: The display system of Embodiment 1, wherein the display system is further configured to evaluate the attention of the user based at least in part on the reaction of the user to the stimulus.

Embodiment 137: The display system of Embodiment 1, wherein the stimulus comprises an instruction to recite a sequence of words.

Embodiment 138: The display system of Embodiment 137, wherein the display system is further configured to evaluate the ability of the user to recite the sequence.

Embodiment 139: The display system of Embodiment 1, wherein the stimulus comprises an array of symbols and an instruction to identify one or more of the symbols based on one or more criteria presented to the user.

Embodiment 140: The display system of Embodiment 139, wherein the display system is further configured to determine the accuracy of the user's identification of the one or more symbols.

Embodiment 141: The display system of Embodiment 1, wherein the display system is further configured to evaluate the state of orientation of the user based at least in part on the reaction of the user to the stimulus.

Embodiment 142: The display system of Embodiment 1, wherein the stimulus comprises an instruction to state information comprising the user's full name.

Embodiment 143: The display system of Embodiment 1, wherein the stimulus comprises an instruction to state information comprising the user's location.

Embodiment 144: The display system of Embodiment 1, wherein the stimulus comprises an instruction to state information comprising the current date.

Embodiment 145: The display system of any of Embodiments 142-144, wherein the display system is further configured to evaluate the user's state of orientation based at least in part on the ability of the user to accurately state the instructed information.

Embodiment 146: The display system of Embodiment 145, further comprising one or more physiological sensors, wherein the display system is configured to determine if the user is experiencing panic based at least in part on physiological data.

Embodiment 147: The display system of Embodiment 146, wherein the display system is configured to evaluate the user's state of orientation based at least in part on physiological data.

Embodiment 148: The display system of Embodiment 1 or Embodiment 16, wherein the neurological condition comprises a neurological condition associated with the state of orientation of the user.

Embodiment 149: The display system of Embodiment 16, wherein the perception aid comprises an audible or visual indication of the user's location.

Embodiment 150: The display system of Embodiment 16, wherein the perception aid comprises an audible or visual indication of the time.

Embodiment 151: The display system of Embodiment 16, wherein the perception aid comprises calming audio or visual content responsive to a determination that the user is experiencing panic.

Embodiment 152: The display system of Embodiment 1, wherein the display system is further configured to evaluate a memory capability of the user based at least in part on the reaction of the user to the stimulus.

Embodiment 153: The display system of Embodiment 1, wherein the display system is further configured to evaluate a learning capability of the user based at least in part on the reaction of the user to the stimulus.

Embodiment 154: The display system of Embodiment 1, wherein the stimulus comprises information to be remembered by the user.

Embodiment 155: The display system of Embodiment 1, wherein the stimulus comprises instructing the user to recall information.

Embodiment 156: The display system of Embodiment 155, wherein the information comprises historical data.

Embodiment 157: The display system of Embodiment 1, wherein the stimulus comprises presenting information to the user and instructing the user to recall the information after a time delay.

Embodiment 158: The display system of Embodiment 157, wherein the time delay is at least one minute.

Embodiment 159: The display system of Embodiment 157, wherein the display system is configured to distract the user during the time delay.

Embodiment 160: The display system of Embodiment 1 or Embodiment 16, wherein the neurological condition is a neurological condition associated with the memory capability of the user.

Embodiment 161: The display system of Embodiment 1 or Embodiment 16, wherein the neurological condition is a neurological condition associated with the learning capability of the user.

Embodiment 162: The display system of Embodiment 16, wherein the perception aid comprises one or more instructions to perform a task.

Embodiment 163: The display system of Embodiment 1, wherein the display system is further configured to evaluate a language function of the user based at least in part on the reaction of the user to the stimulus.

Embodiment 164: The display system of Embodiment 1, wherein the stimulus comprises an instruction to speak about a topic.

Embodiment 165: The display system of Embodiment 164, wherein the display is configured to detect vocalization of the user following the instruction and evaluate the user's spontaneous speech function based on the vocalization.

Embodiment 166: The display system of any of Embodiments 1, wherein the stimulus comprises a picture of an object and an instruction to state the name of the object.

Embodiment 167: The display system of Embodiment 164, wherein the display system is further configured to determine if the user accurately stated the name of the object.

Embodiment 168: The display system of Embodiment 1 or Embodiment 16, wherein the neurological condition is a neurological condition associated with the language function of the user.

Embodiment 169: The display system of Embodiment 16, wherein the perception aid comprises displaying a word to the user in response to a determination that the user is unable to recall the word.

Embodiment 170: The display system of Embodiment 16, wherein the perception aid comprises a notification to the user of a detected error in the user's speech.

Embodiment 171: The display system of Embodiment 1, wherein the stimulus comprises a finger agnosia test.

Embodiment 172: The display system of Embodiment 1, wherein the reaction of the user comprises a user's eye gaze.

Embodiment 173: The display system of Embodiment 1, wherein the reaction of the user comprises an amount of elapsed time from the stimulus to the reaction of the user.

Embodiment 174: The display system of Embodiment 1, wherein the neurological condition comprises Gerstmann Syndrome.

Embodiment 175: The display system of Embodiment 1, wherein the stimulus comprises an agraphia test.

Embodiment 176: The display system of Embodiment 175, wherein the agraphia test comprises prompting the user to write a word in space.

Embodiment 177: The display system of Embodiment 175, wherein the agraphia test comprises prompting the user to write a word on a document.

Embodiment 178: The display system of Embodiment 1, wherein the stimulus comprises a right-left disorientation test.

Embodiment 179: The display system of Embodiment 178, wherein the right-left disorientation test comprises prompting the user to touch a body part with a finger on the opposite side of the body as the finger.

Embodiment 180: The display system of Embodiment 178, wherein the right-left disorientation test comprises prompting the user to identify a direction.

Embodiment 181: The display system of Embodiment 1, wherein the stimulus comprises a calculations test.

Embodiment 182: The display system of Embodiment 181, wherein the calculations test comprises prompting the user to solve an arithmetic problem.

Embodiment 183: The display system of Embodiment 1, wherein the reaction of the user comprises a miscalculation.

Embodiment 184: The display system of Embodiment 1 or Embodiment 16, wherein the neurological condition comprises dyspraxia.

Embodiment 185: The display system of Embodiment 1 or Embodiment 16, wherein the neurological condition comprises Huntington's Disease.

Embodiment 186: The display system of Embodiment 1 or Embodiment 16, wherein the neurological condition comprises posterior cortical atrophy.

Embodiment 187: The display system of Embodiment 1 or Embodiment 16, wherein the neurological condition comprises aphasia.

Embodiment 188: The display system of Embodiment 1 or Embodiment 16, wherein the neurological condition comprises agnosia.

Embodiment 189: The display system of Embodiment 1 or Embodiment 16, wherein the neurological condition comprises agraphia.

Embodiment 190: The display system of Embodiment 1 or Embodiment 16, wherein the neurological condition comprises dyslexia.

Embodiment 191: The display system of Embodiment 1 or Embodiment 16, wherein the neurological condition comprises dysgraphia.

Embodiment 192: The display system of Embodiment 1, wherein the stimulus comprises an apraxia test.

Embodiment 193: The display system of Embodiment 192, wherein the apraxia test comprises prompting the user to imitate a hand gesture.

Embodiment 194: The display system of Embodiment 1, wherein the display device is configured to compare an overlay of an augmented normal response with the reaction of the user.

Embodiment 195: The display system of Embodiment 16, wherein the display system is further configured to monitor the user's arm, hand, leg, or foot movement.

Embodiment 196: The display system of Embodiment 16, wherein the stimuli directed to the user is repeated periodically to develop a habit, routine, or physical activity of the user.

Embodiment 197: The display system of Embodiment 16, wherein the perception aid comprises a hint to the user of the correct response.

Embodiment 198: The display system of Embodiment 16, wherein the perception aid comprises a visual aid that is provided to the user.

Embodiment 199: The display system of Embodiment 198, wherein the perception aid comprises a writing strategy that is provided to the user.

Embodiment 200: The display system of Embodiment 16, wherein the perception aid comprises a location provided by the display system of the location of the body part prompted by the display system.

Embodiment 201: The display system of Embodiment 16, wherein the perception aid comprises a display of the missing step of an arithmetic solution.

Embodiment 202: The display system of Embodiment 16, wherein the perception aid comprises an identification of the correct answer to a calculations test.

Embodiment 203: The display system of Embodiment 16, wherein the perception aid comprises images showing how a task is performed.

Embodiment 204: The display system of Embodiment 203, wherein the perception aid comprises images breaking a task down into its constituent components.

Embodiment 205: The display system of Embodiment 16, wherein the perception aid comprises providing an example of correct behavior.

Embodiment 206: The display system of Embodiment 16, wherein the perception aid comprises visual or auditory content for motivating the user to complete a task.

Embodiment 207: The display system of Embodiment 16, wherein the perception aid comprises a language translation.

Embodiment 208: The display system of Embodiment 1, wherein the provided stimulus comprises a visuospatial task.

Embodiment 209: The display system of Embodiment 208, wherein the reaction of the user comprises an indication of neglect or an abnormal construction ability.

Embodiment 210: The display system of Embodiment 209, wherein the neurological condition is associated with right parietal dysfunction.

Embodiment 211: The display system of Embodiment 1, wherein the provided stimulus comprises a cognitive task.

Embodiment 212: The display system of Embodiment 211, wherein the reaction of the user comprises an indication of an abnormal executive function.

Embodiment 213: The display system of Embodiment 212, wherein the neurological condition is associated with frontal lobe dysfunction.

Embodiment 214: The display system of Embodiment 1, wherein the provided stimulus comprises a logic or abstraction task.

Embodiment 215: The display system of Embodiment 214, wherein the reaction of the user comprises an indication of difficulty in thinking, reasoning, multi-step instructions, or categorizing.

Embodiment 216: The display system of Embodiment 215, wherein the neurological condition is associated with an area involving higher-order association cortex.

Embodiment 217: The display system of Embodiment 6, wherein the sensed stimuli comprise a visuospatial task.

Embodiment 218: The display system of Embodiment 217, wherein the display system is configured to determine an indication of neglect or an abnormal construction ability based at least in part on user response to the visuospatial task.

Embodiment 219: The display system of Embodiment 218 wherein the neurological condition is associated with right parietal dysfunction.

Embodiment 220: The display system of Embodiment 6, wherein the sensed stimuli comprise a cognitive task.

Embodiment 221: The display system of Embodiment 220, wherein the display system is configured to determine an indication of an abnormal executive function based at least in part on user response to the cognitive task Embodiment 222: The display system of Embodiment 221, wherein the neurological condition is associated with frontal lobe dysfunction.

Embodiment 223: The display system of Embodiment 6, wherein the sensed stimuli comprise a logic or abstraction task.

Embodiment 224: The display system of Embodiment 1, wherein the provided stimulus comprises a light pattern having wavelength in one or more spectral ranges.

Embodiment 225: The display system of Embodiment 224, wherein the reaction of the user comprises a change in size of the pupil, wherein the change in the size of the pupil can vary based on the wavelengths in the light pattern.

Embodiment 226: The display system of any of Embodiments 224-225, wherein the neurological condition is associated with abnormalities in circadian rhythm.

Embodiment 227: The display system of Embodiment 69, wherein the reaction of the user comprises a change in near point of convergence.

Embodiment 228: The display system of Embodiment 227, wherein the neurological condition is associated with a concussion or subconcussive impact.

Embodiment 229: A display system comprising:
a head-mounted display configured to project light to a user to display augmented reality image content on a plurality of depth planes, the display comprising:
one or more waveguides configured to project the light to the user,
wherein the one or more waveguides are further configured to transmit light from a surrounding environment to the user,
wherein the display system is configured to provide one or more stimuli that increases neural plasticity.

Embodiment 230: The display system of Embodiment 229, wherein the one or more stimuli is provided as part of a video game.

Embodiment 231: The display system of any of Embodiments 229 or 230, wherein the one or more stimuli includes electrical signals applied to the cranium of the user via electrodes connected to the display system.

Embodiment 232: The display system of Embodiment 231, wherein the electrical signals replicate brain activity of another individual.

Embodiment 233: The display system of any of Embodiments 229-232, further configured to:
determine a response of the user to the provided stimulus; and
tailor the stimulus based on the determined response.

Embodiment 234: The display system of any of Embodiments 229-233, further configured to:
determine a response of the user to the provided stimulus; and
trigger a perception aid that modifies the determined response.

Embodiment 235: A display system comprising:
a head-mounted display configured to project light to a user to display augmented reality image content on a plurality of depth planes, the display comprising:
one or more waveguides configured to project the light to the user, wherein the one or more waveguides are further configured to transmit light from a surrounding environment to the user; and
a probe that delivers electromagnetic or acoustic energy to the user.

Embodiment 236: The display system of Embodiment 235, wherein the auxiliary component includes an electrode, an ultrasonic transducer or an optical source.

Embodiment 237: The display system of any of Embodiments 235-236, wherein the probe is configured to deliver electromagnetic or acoustic energy to the user's eye or cranium.

Embodiment 238: The display system of Embodiment 237, wherein the auxiliary component is configured to deliver electromagnetic energy configured to penetrate the cranium and to stimulate portions of the user's brain.

Embodiment 239: The display system of any of Embodiments 237-238, wherein the electromagnetic energy includes wavelengths in at least one of ultraviolet, non-visible, visible or infrared spectral ranges.

Embodiment 240: The display system of any of Embodiments 237-239, wherein the electromagnetic energy includes a pulsed optical signal having a frequency between about 1-50 Hz.

Embodiment 241: The display system of Embodiment 247, wherein the acoustic energy includes an ultrasound signal to a cranium of the user.

Embodiment 242: The display system of Embodiment 241, wherein the display system is configured to obtain images of blood flow through the middle cerebral artery.

Embodiment 243: The display system of any of Embodiments 235-242, wherein the probe is configured to generate a collimated laser beam that illuminates structures in the user's eye and generate a speckle pattern, and wherein the display system is configured to detect the speckle pattern and correlate a parameter associated with the speckle pattern with blood flow rates in ocular tissue.

Embodiment 244: The display system of Embodiment 243, wherein the parameter associated with the speckle pattern is normalized blur.

Embodiment 245: A display system comprising:
a head-mounted display configured to project light to a user to display augmented reality image content on a plurality of depth planes, the display comprising:
one or more waveguides configured to project the light to the user,
wherein the one or more waveguides are further configured to transmit light from a surrounding environment to the user,
wherein the display system is configured to track ocular movements and determine a neurological condition associated with one or more abnormalities in the tracked ocular movements; and
wherein the display system is configured to provide one or more stimuli to inhibit the one or more abnormalities in the tracked ocular movements or to retrain one or more portions of the brain responsible for the associated neurological condition.

Embodiment 246: The display system of Embodiment 245, wherein the tracked ocular movements include pupillary movements due to nystagmus and the one or more stimuli include images that are moved by an amount smaller than an amplitude of the nystagmatic eye movement.

Embodiment 247: A display system comprising:
a head-mounted display configured to project light to a user to display augmented reality image content on a plurality of depth planes, the display comprising:
one or more waveguides configured to project the light to the user,
wherein the one or more waveguides are further configured to transmit light from a surrounding environment to the user,
wherein the transmitted light is used to examine the fundus of the user; and
wherein the display system is configured to determine a neurological condition based on the examination of the fundus.

Embodiment 248: The display system of Embodiment 247, wherein the neurological condition includes at least one of intracranial pressure, intracranial hypertension, compressive optic neuropathy, arteritic ischemic optic neuropathy, non-arteritic ischemic optic neuropathy, optic neuritis or radiation optic neuropathy.

Embodiment 249: The display system of Embodiment 69, wherein the reaction of the user comprises inability to fixate on an object for a predefined interval of time.

Embodiment 250: The display system of Embodiment 249, wherein the neurological condition is associated with autism, attention deficit hyperactivity disorder, or Parkinson's disease.

Embodiment 251: The display system of Embodiment 116, wherein the perception aids comprise visual sensory deprivation.

Embodiment 252: The display system of Embodiment 116, wherein the perception aids comprise displaying a uniform color field to the user.

Embodiment 253: The display system of Embodiment 116, wherein the perception aids comprise noise cancelling.

Embodiment 254: The display system of Embodiment 116, wherein the perception aids comprise audio and visual sensory deprivation.

Embodiment 255: The display system of Embodiment 1, wherein the display system is configured to map blood flow in the user's brain using functional near-infrared spectroscopy.

Embodiment 256: The display system of Embodiment 11, wherein the display system is configured to map blood flow in the user's brain using functional near-infrared spectroscopy.

Embodiment 257: A display system comprising:
a head-mountable, augmented reality display configured to output light with variable wavefront divergence to display virtual content;
one or more inwardly-directed sensors;
one or more outwardly-directed sensors;
one or more processors; and
one or more computer storage media storing instructions that, when executed by the one or more processors, cause the one or more processors to perform operations comprising:
performing a neurological analysis by:
determining a reaction to a stimulus by receiving data from the one or more inwardly-directed sensors; and
identifying a neurological condition associated with the reaction;
determining environmental triggers associated with the neurological condition;
monitoring an ambient environment with the one or more outwardly-directed sensors;
detecting a presence of an environmental trigger in the ambient environment; and
providing a perception aid based on the detected presence of the triggering variable.

Embodiment 258: The display system of Embodiment 257, wherein providing the perception aid comprises displaying virtual content.

Embodiment 259: The display system of Embodiment 258, wherein the neurological condition comprises memory loss, wherein the perception aid comprises one or more of a reminder and an alert.

Embodiment 260: The display system of Embodiment 258, wherein providing the perception aid comprises altering a perceived color of a real object.

Embodiment 261: The display system of Embodiment 257, wherein the perception aids comprise sounds associated with the environmental trigger.

Embodiment 262: The display system of Embodiment 257, wherein performing the neurological analysis is conducted automatically a plurality of times over a plurality of months, further comprising updating a user neurological profile based on performing the neurological analysis.

Embodiment 263: The display system of Embodiment 257, wherein the display comprises a waveguide comprising diffractive optical elements configured to output the light by extracting the light out of the waveguide, wherein the waveguide is one of a stack of waveguides, wherein each of the stack waveguides is configured to output light with different wavefront divergence.

Embodiment 264: A display system comprising:
a head-mountable, augmented reality display configured to output light with variable wavefront divergence to display virtual content;
one or more inwardly-directed sensors;
one or more processors; and one or more computer storage media storing instructions that, when executed by the one or more processors, cause the one or more processors to perform operations comprising:
  performing a neurological analysis by:
    determining a reaction to a stimulus by receiving data from the one or more inwardly-directed sensors; and
    identifying a neurological condition associated with the reaction.

Embodiment 265: The display system of Embodiment 264, wherein the operations further comprise causing the display system to display a perception aid.

Embodiment 266: The display system of Embodiment 265, wherein the perception aid is selected based on one or more of the identified neurological condition and the reaction.

Embodiment 267: The display system of Embodiment 265, wherein the perception aid is selected based on a user profile.

Embodiment 268: The display system of Embodiment 264, wherein performing the neurological analysis comprises providing the stimulus, wherein the stimulus comprises virtual content output by the display.

Embodiment 269: The display system of Embodiment 264, wherein the stimulus comprises a virtual object moved from a distant depth plane to a near depth plane.

Embodiment 270: The display system of Embodiment 264, wherein the neurological condition is at least one of: a visual processing deficiency and a memory deficiency.

Embodiment 271: The display system of Embodiment 264, wherein the stimulus is a stimulus present in an ambient environment.

Embodiment 272: The display system of Embodiment 264, wherein identifying the neurological condition comprises generating a list of potential neurological conditions.

Embodiment 273: The display system of Embodiment 264, wherein the operations further comprise:
  automatically repeating the neurological analysis a plurality of times over a plurality of months,
  wherein repeating the neurological analysis comprises updating the identified neurological condition.

Embodiment 274: The display system of Embodiment 264, wherein the operations further comprise transmitting the identified neurological condition to a plurality of other display systems.

Embodiment 275: The display system of Embodiment 274, wherein the operations comprise identifying the neurological condition based upon a norm determined from a population of users of the other display systems.

Embodiment 276: The display system of Embodiment 264, wherein the display is configured to output virtual content with an accommodation-vergence mismatch of less than 0.25 diopters.

Embodiment 277: The display system of Embodiment 264, wherein the one or more inwardly-directed sensors comprises an electrode configured to measure electrical potentials.

Embodiment 278: A method performed by a display system comprising one or more processors, one or more inwardly-directed sensors, and a head-mounted display, the method comprising:
  performing a neurological analysis by:
    determining a user reaction to a stimulus by collecting data from the one or more inwardly-directed sensors; and
    identifying a neurological condition associated with the reaction.

Embodiment 279: The method of Embodiment 278, further comprising displaying a perception aid.

Embodiment 280: The method of Embodiment 278, wherein the perception aid is based on the identified neurological condition, the reaction, or a user profile.

Embodiment 281: The method of Embodiment 278, further comprising automatically repeating the neurological analysis a plurality of times over a plurality of months and updating the identified neurological condition.

Figure 1:
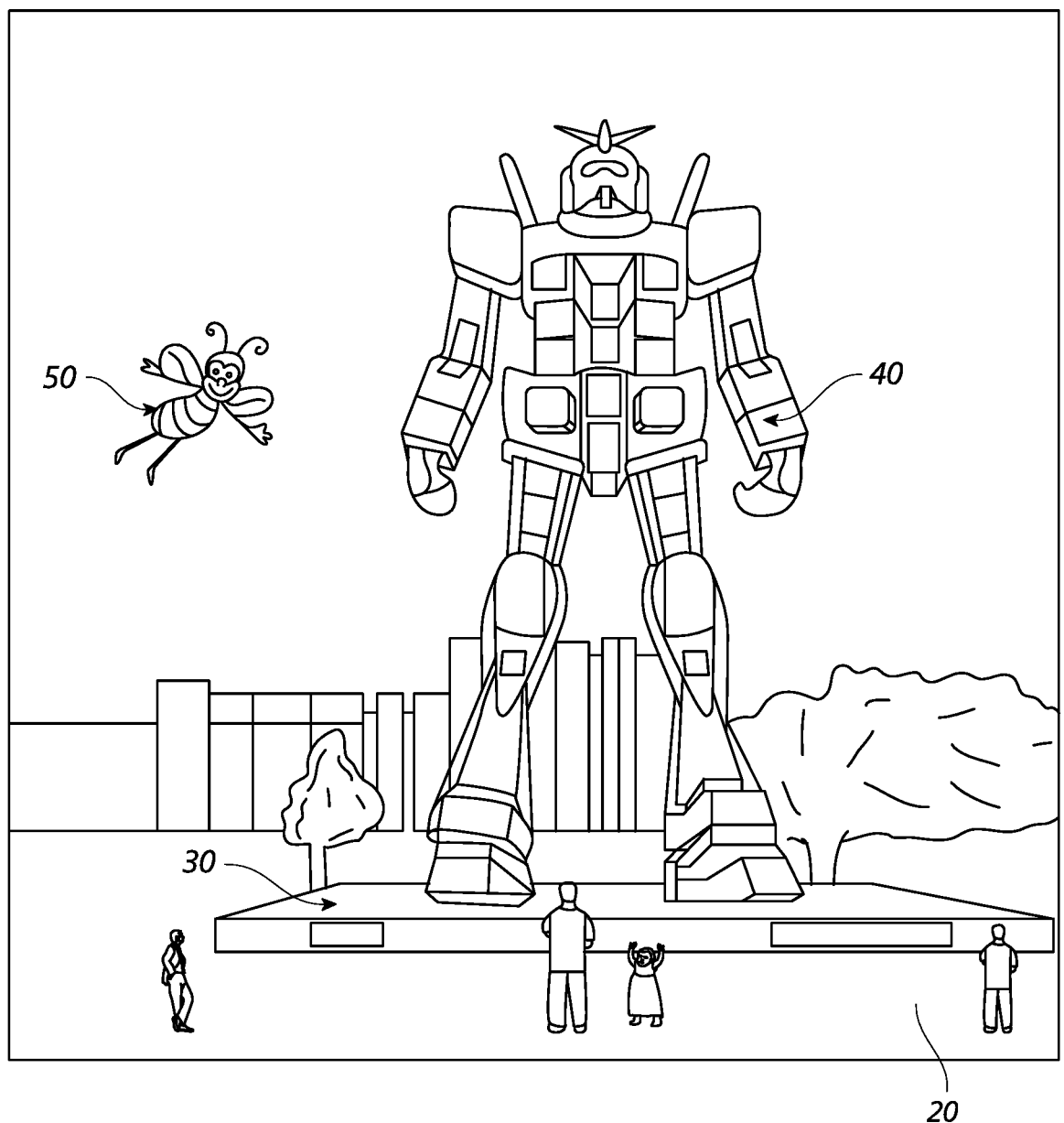
FIG. 1 illustrates a user's view of augmented reality (AR) through an AR device.

The drawings are provided to illustrate example embodiments and are not intended to limit the scope of the disclosure.

DETAILED DESCRIPTION

Many individuals have neurological conditions, including visual processing conditions, that undesirably interfere with their lives. Such neurological conditions may be abnormalities or deficiencies in the individual's visual processing pathway and/or nervous system, including abnormalities in the individual's brain. For example, some individuals may be unable to see objects in certain locations. As another example, some individuals may have memory deficiencies, which may increase in prevalence with the age of the individuals. As yet another example, some individuals may have neuromuscular conditions that impede normal oculomotor function.

Advantageously, in some embodiments, augmented reality (AR) display systems disclosed herein may be configured to determine the presence of neurological conditions, including visual processing abnormalities. Moreover, the AR display systems may be configured to address and/or alter neurological conditions, including the brain's processing of information.

It will be appreciated that the AR systems may display virtual content to a user, or viewer, while still allowing the user to see the world around them. Preferably, this content is displayed on a head-mounted display, e.g., as part of eyewear, that projects image information to the user's eyes. In addition, the display may also transmit light from the surrounding environment to the user's eyes, to allow a view of that surrounding environment. As used herein, it will be appreciated that a "head-mounted" or "head-mountable" display is a display that may be mounted on the head of a viewer.

As discussed further below, many VR, AR, and MR display devices suffer from accommodation-vergence mismatches when displaying image information. Such mismatches may cause user discomfort and may make long-term wear of the device infeasible. Advantageously, display devices according to embodiments herein allow for long-term wear of the device by, among other things, providing a correct match between accommodation and vergence in the user. For example, images displayed to the viewer may have an accommodation-vergence mismatch of about 0.5 diopter or less, about 0.33 diopter or less, or about 0.25 diopter or less, including about 0.1 diopter or less in some embodiments. As a result, users of the device may be able to wear and use the device substantially continuously for durations of 3 hours or more, 4 hours or more, 5 hours or more, 6 hours or more, or all day, without removing the device for more than 25%, more than 20%, more than 15%, more than 10%, or more than 5% of the duration. In some embodiments, the display device may display augmented reality images substantially continuously for the above-noted durations.

The wearability of display systems disclosed herein and the long-term nature of that wearability, coupled with the close proximity of the display system, including sensory components, to the user, advantageously facilitate various neurological evaluations and treatments. As discussed herein, the sensory components may include inwardly-directed sensors configured to sense parameters related to the user and outwardly-directed sensors configured to detect parameters related to the ambient environment around the user. In some embodiments, the display system may be configured to actively monitor the user's environment using the outwardly-directed sensors and to provide corrective aids, e.g., perception aids, to help the user address shortcomings in their ability to perceive and/or interact with the world. For example, the display system may monitor the ambient environment for the presence of environmental triggers that are associated with a neurological condition. When an environmental trigger is detected, the display system provides a perception aid based on that detected environmental trigger. For users with memory deficiencies, the display system may be configured to monitor external variables such as time, and provide reminders to take particular actions (e.g., intake medication, follow-up with a health care provider, etc.). In addition to helping the user accomplish individual tasks, the display system, due to its long-term wearability (e.g., daily wearability, for the majority of the day), may allow a consistent routine to be established, thereby further facilitating the user's ability to function independently of others.

In some embodiments, the display system may be configured to present a conclusion regarding the presence of various neurological conditions (e.g., abnormalities) in the user. For example, the display system may be configured to provide stimuli, e.g., pre-selected content, to the user and to measure the user's reaction to that content using, e.g., inwardly-directed sensors. The stimuli may take the form of visual and/or audio content. In addition or alternatively, the stimuli may be provided by the ambient environment. For example, scenes (including landscapes, people, and other visual features) or sounds not generated by the display system but experienced by the user, may be detected by the display system and categorized. If the system determines that the environmental visual or audio stimulus is an appropriate type for a particular neurological test, the display system may also measure the user's reaction to the stimulus to effectively conduct that neurological test. Thus, as used herein, a stimulus provided by the display system may be generated and directed by the display system to the user, or may be present in the ambient environment and registered and identified by the display system. The known variables of the content provided and the user reaction may be analyzed to determine the presence of a neurological condition, such as abnormalities in visual processing. It will be appreciated that the display system may display visual content for each eye, and may vary various visual parameters, including the location of the visual content, the depth plane on which the content is displayed, the duration of exposure to the visual content, etc. By varying the visual content and these visual parameters, different analyses may be performed, as described herein.

Such analyses may be performed simply for diagnostic, therapeutic, and/or monitoring purposes, e.g., to assist the user and/or a clinician in monitoring the user's health. Preferably, the conclusions derived from the analysis are stored in the display system and/or in a remote database accessible to the display system, and the conclusions may subsequently be utilized to determine whether a particular perception aid (e.g., a corrective aid) should be applied. In various embodiments, the conclusions derived from the analysis may also be used to monitor the effectiveness of the applied perception aid. For example, the user may be retested for a condition to determine the efficacy of a perception aid applied to address that condition.

In some embodiments, the perception aid may be a mental exercise or activity for modifying the processing of information by the user's brain. For example, the display system may be configured to function as a learning aid, and various "mind exercises" may be provided by the display system. In some embodiments, these mind exercises may be provided manually, upon selection by the user, or the user may automatically be given an option to perform the mind exercises, based on biofeedback, prescription, and/or the results of a neurological analysis. In some embodiments, the implementation and provision of an option to conduct the mind exercises may be triggered by external stimuli sensed by the display system and/or by a user input directing the display system to conduct the mind exercises. For example, activities such as games for improving memory may be displayed to the user in response to the detection of memory impairment and then adjusted manually or automatically through biofeedback.

Advantageously, the long-term wearability of the display system (e.g., due to the ability to provide a correct accommodation-vergence match) provides a platform that allows long-term neurological analyses to be performed, and also allows the real-time, selective provision of corrective or learning aids as needed (e.g., due to the identification of a condition requiring such a corrective aid and/or by sensing the presence of a stimulus in the environment necessitating the aid). Moreover, these benefits may be achieved without requiring a user to visit a medical facility to conduct the various analyses. Rather, the analyses may be performed regularly, or at an arbitrary time, e.g., when triggered by particular stimulus, when selected by the user, based on prescription, etc. This flexibility and ubiquity allows the user to conduct regular diagnostics and to update corrective aids as necessary. It will be appreciated that the determinations and conclusions made by the system are made based on available inputs and current programming, and these conclusions are not necessarily correct. As discussed herein, accuracy may be improved over time in some embodiments, by repeatedly performing analyses.

Without being limited to theory, some researchers believe that the efficacy of retraining and/or altering neural tissues of (rewiring) the brain may be enhanced by long and/or repeated exposure to stimuli and learning regimens. Thus, due at least in part to the wearability of the display system, a user may wear the display system for longer periods of time and more frequently, thereby increasing the number of repetitions and the duration over which the retraining exercises may be applied. Moreover, the various retraining exercises may be conducted at arbitrary times throughout a day and in a variety of different environments (e.g., whenever the user has "free time"), thereby further increasing the number of repetitions that may be conducted. As a result, the effects and efficacy of the retraining exercises may be increased.

In addition, the display system may allow the user to track their health over time and to determine their progress when undergoing treatment plans, e.g., mind exercises. It will be appreciated that such active monitoring and feedback to the user can increase the likelihood that the user will continue on a particular treatment plan, particularly where the feedback provides positive reinforcement and an indication of progress. Because the display device may be worn daily, for extended durations each day, the frequency of tracking of various conditions and/or the ability to provide feedback to the user is increased, which may increase the efficacy of the treatment plan.

It will also be appreciated that the display system may provide benefits for increasing the accuracy of the diagnosis of various neurological conditions. For example, the display systems may be configured to allow the gathering of sets of data that may not otherwise be easily obtained. Because the display system may be worn for long durations, preferably, as the user is going about part or all of their daily lives, the number and/or repetition of the various analyses may be higher than that obtained if the user are required to visit a clinician's office (although the system may also be advantageously applied in the context of the clinician's office). Moreover, the various analyses may also be linked to data that may not be detected in a clinician's office. For example, the environment in which the analysis is performed (e.g., including the presence of pollutants, etc.), the time of day, the time of year, etc. may be linked with the measured reaction of the user. As a result, among other things, the duration of the data collection, the variety of the data, the variety of locations of the data collection, and the ability to collect multiple types of data simultaneously (thereby allowing different data to be cross-referenced, e.g., using time stamps and/or location stamps applied to all of the data), may increase the accuracy of any analysis performed on a user and may reveal relationships between health conditions or treatments and various measured variables that are otherwise not be readily apparent. In addition, the wearability of the display device over extended durations can allow for subtle automatic adjustments based on biofeedback, signal noise filtering of reccurring and/or predictive artifacts, or direct user interactions to identify adverse or favorable display system performance conditions. It will be appreciated that the display system may include various sensors, such as electrodes, and sensors for detecting gaze and head pose. In some embodiments, signal noise filtering of recurring and/or predictive artifacts may be aided by data from gaze tracking and/or head pose cameras, electrodes (e.g., EEG), or other data sources. Signals may be de-noised after being collected and before further processing. In some embodiments, the system may discard data and/or filter the data to enhance or improve the signal based on detected movement of the user.

It will be appreciated that the display system may collect information regarding the person over time and have access to this information. This provides a more complete profile of the user, including environmental stimuli that the user may be exposed to. This profile provides additional inputs and criteria that may be taken into account to evaluate conclusions for an analysis and the likelihood of particular conclusions. In addition, by allowing testing to be conducted at will by a user and/or and at regularly scheduled times, the display system may increase the number of tests being conducted, thereby increasing the dataset, which may be expected to increase the accuracy of the test. For example, the display system may be configured to discount or ignore outlying data points. Conversely, the display system can be programmed to conduct testing at arbitrary and different times to seek out the best conditions for user participation, signal acquisition performance, and system noise or artifact minimization. In some embodiments, because the user preferably wears the display system daily, the display system may be configured to automatically conduct various tests periodically over the span of weeks, months, or years as the user wears the device over that time span.

Advantageously, the display system allows multiple ones of the analyses disclosed herein to be performed simultaneously, or in succession. The ability to perform multiple tests directed to a given visual processing pathway, or condition, may also increase the accuracy of any conclusions drawn from those tests. The various analyses disclosed herein may be evaluated for variability between people (inter-individual variability) and within a given person (intra-individual variability), e.g., over time.

In some embodiments, information may be shared between different users of display systems configured to conduct the analyses disclosed herein. For example, the information may be transmitted directly between display systems (e.g., via wired and/or wireless connections) and/or via a central server that receives information from the display systems and distributes information from other display systems to a given display system. In some embodiments, the display systems may share information regarding the type of stimuli applied, the user reaction to the stimuli, and the conclusions drawn from the analyses. In some embodiments, the display systems may further share visual data such as a user's view (e.g., analogous to "screen sharing"), for example, so that a physician may view the user's perspective while the user is undergoing an analysis. In some embodiments, the display system may also be configured to share other information related to other parameters (preferably parameters that do not specifically identify the user) that may impact a user's health or physiological state, including location, age, gender, ethnicity, etc. It will be appreciated that many of the analyses herein rely on comparisons to a norm in order to draw conclusions about the presence of neurological conditions (e.g., by determining that there is an abnormality). It will also be appreciated that norms within certain subsets of the general population may differ, and the amount of this difference may vary, among other things, depending on the subset and/or the neurological condition being analyzed and inclusion or exclusion of inputs from sensing peripheral activities or extenuating environmental factors. Advantageously, as noted above, the set of data used in analyses for a particular user may be made more accurate due to the ability to conduct a large number of tests using the display system. In addition, the ability to share information between users may further increase the accuracy of any conclusions drawn, by analyzing this more accurate set of data from individual users, and by having a larger set of data from amongst the population of users. As a result, norms between the general population of users and particular subsets of users may be compiled. Sharing information between multiple display system users can allow for increased test design sophistication, such as inclusion of control groups and double blind placebo type testing. The display system, which may be connected to a remote processing unit, may be configured to draw comparisons between variances between the norms in particular subsets of users and to the general population. Such a comparison may be utilized to determine whether the norm to which a particular user's results are compared may be the norm for the general population or the norm for a particular subset of users. As a result, more meaningful comparisons may be made and, from these comparisons, more accurate or nuanced conclusions maybe drawn by the display system.

In addition to providing an improved basis for comparison, it will be appreciated that the sharing of other information regarding users may improve the accuracy of the conclusions drawn from the analyses by allowing additional variables to be considered. For example, some combinations of stimuli and reactions may be associated with multiple conclusions (e.g., may indicate multiple processing deficiencies). The display system may be configured to access a database, which may be part of the display system and/or may be in a remote database accessible by the display system, to obtain information regarding conclusions derived from tests of other users. This information may include data regarding conclusions associated with other variables, e.g., one or more of user location, age, ethnicity, activities, interactions, etc. Such information maybe cross-referenced with the user's measured reactions to aid in determining the most likely correct conclusion, or in ordering the possible conclusions.

In some embodiments, the ability of the display system to display images on multiple depth planes may advantageously be applied to determine which of multiple images that a viewer is perceiving or reacting to, advantageously without requiring direct user input or complex external instrumentation to measure brain activity. For example, the images to be evaluated may be displayed on different depth planes, and the accommodation and/or vergence of the user's eyes may be measured (e.g., using eye-tracking cameras on the display device). It will be appreciated that images on different depth planes that are perceived by the viewer will cause the eye to assume different accommodation and/or vergence states. Consequently, the image that is perceived by the user may be inferred by determining: 1) the accommodation and/or vergence states of the user's eyes; and 2) matching that accommodation and/or vergence state with the images or depth planes of the images being displayed. The image corresponding to the measured accommodation and/or vergence states of the user is then interpreted to be the image that is perceived by the user. In some embodiments, the images may be displayed on widely disparate depth planes (e.g., infinity and the closest depth plane outputted by the display system) to increase the expected difference in accommodation and/or vergence states between the images. In some embodiments, the duration of the user's fixation on an image (e.g., the amount of time that the user's eyes assume a particular accommodation and/or vergence state) may also be measured to infer whether the user is actively perceiving a particular image, or whether the change in accommodation and/or vergence states is a result of an involuntary reflex, such as microsaccades. In various embodiments, the display system may also be used to measure microsaccade amplitudes while engaging the user to fixate on displayed images. It will be appreciated that such a scheme for detecting user perception may be utilized for various perception tests, including without limitation, tests related to rivalry, dominance and/or suppression, backward masking, and forward masking.

Reference will now be made to the drawings, in which like reference numerals refer to like parts throughout.

Figure 2:
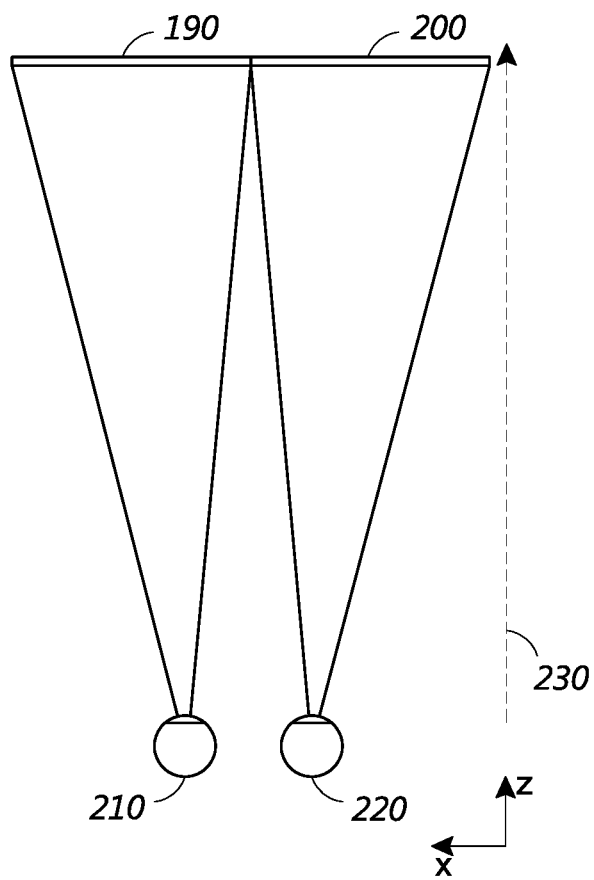
FIG. 2 illustrates a conventional display system for simulating three-dimensional imagery for a user.

FIG. 2 illustrates a conventional display system for simulating three-dimensional imagery for a user. It will be appreciated that a user's eyes are spaced apart and that, when looking at a real object in space, each eye will have a slightly different view of the object and may form an image of the object at different locations on the retina of each eye. This may be referred to as binocular disparity and may be utilized by the human visual system to provide a perception of depth. Conventional display systems simulate binocular disparity by presenting two distinct images 190, 200 with slightly different views of the same virtual object—one for each eye 210, 220—corresponding to the views of the virtual object that would be seen by each eye were the virtual object a real object at a desired depth. These images provide binocular cues that the user's visual system may interpret to derive a perception of depth.

With continued reference to FIG. 2, the images 190, 200 are spaced from the eyes 210, 220 by a distance 230 on a z-axis. The z-axis is parallel to the optical axis of the viewer with their eyes fixated on an object at optical infinity directly ahead of the viewer. The images 190, 200 are flat and at a fixed distance from the eyes 210, 220. Based on the slightly different views of a virtual object in the images presented to the eyes 210, 220, respectively, the eyes may naturally rotate such that an image of the object falls on corresponding points on the retinas of each of the eyes, to maintain single binocular vision. This rotation may cause the lines of sight of each of the eyes 210, 220 to converge onto a point in space at which the virtual object is perceived to be present. As a result, providing three-dimensional imagery conventionally involves providing binocular cues that may manipulate the vergence of the user's eyes 210, 220, and that the human visual system interprets to provide a perception of depth.

Figure 3A:
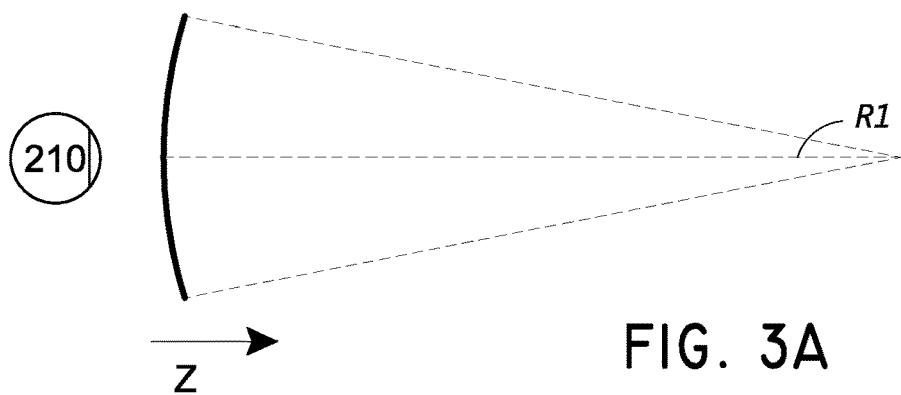
FIGS. 3A-3C illustrate relationships between radius of curvature and focal radius.
Figure 3B:
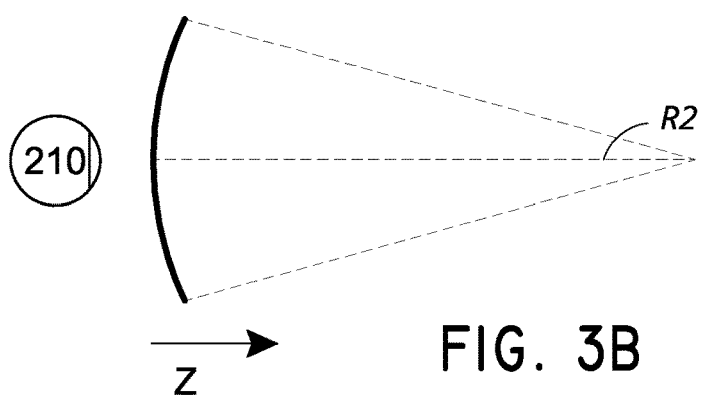
Figure 3C:
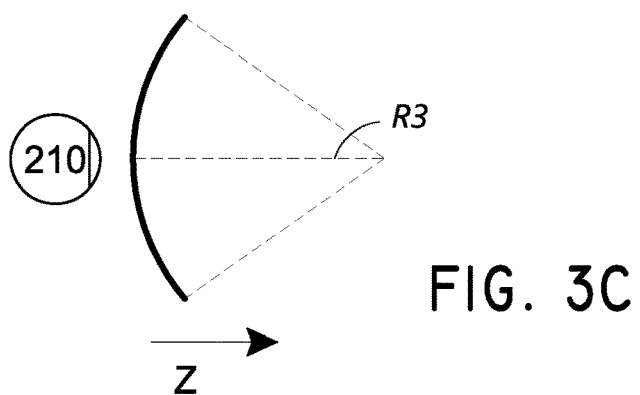

Generating a realistic and comfortable perception of depth is challenging, however. It will be appreciated that light from objects at different distances from the eyes have wavefronts with different amounts of divergence. FIGS. 3A-3C illustrate relationships between distance and the divergence of light rays. The distance between the object and the eye 210 is represented by, in order of decreasing distance, R1, R2, and R3. As shown in FIGS. 3A-3C, the light rays become more divergent as distance to the object decreases. Conversely, as distance increases, the light rays become more collimated. Stated another way, it may be said that the light field produced by a point (the object or a part of the object) has a spherical wavefront curvature, which is a function of how far away the point is from the eye of the user. The curvature increases with decreasing distance between the object and the eye 210. While only a single eye 210 is illustrated for clarity of illustration in FIGS. 3A-3C and other figures herein, the discussions regarding eye 210 may be applied to both eyes 210 and 220 of a viewer.

With continued reference to FIGS. 3A-3C, light from an object that the viewer's eyes are fixated on may have different degrees of wavefront divergence. Due to the different amounts of wavefront divergence, the light may be focused differently by the lens of the eye, which in turn may require the lens to assume different shapes to form a focused image on the retina of the eye. Where a focused image is not formed on the retina, the resulting retinal blur acts as a cue to accommodation that causes a change in the shape of the lens of the eye until a focused image is formed on the retina. For example, the cue to accommodation may trigger the ciliary muscles surrounding the lens of the eye to relax or contract, thereby modulating the force applied to the suspensory ligaments holding the lens, thus causing the shape of the lens of the eye to change until retinal blur of an object of fixation is eliminated or minimized, thereby forming a focused image of the object of fixation on the retina (e.g., fovea) of the eye. The process by which the lens of the eye changes shape may be referred to as accommodation, and the shape of the lens of the eye required to form a focused image of the object of fixation on the retina (e.g., fovea) of the eye may be referred to as an accommodative state.

Figure 4A:
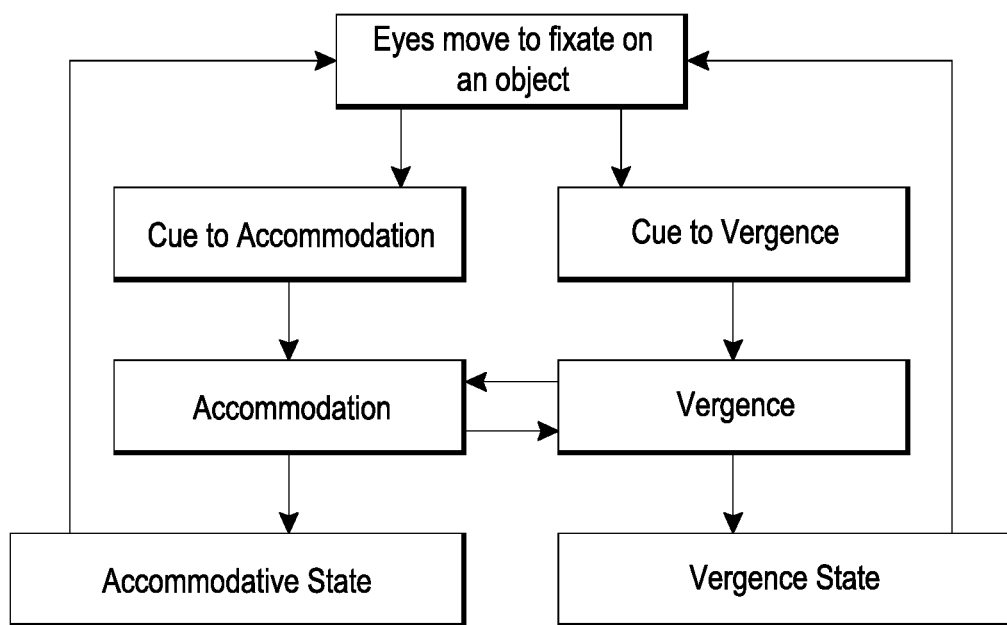
FIG. 4A illustrates a representation of the accommodation-vergence response of the human visual system.

With reference now to FIG. 4A, a representation of the accommodation-vergence response of the human visual system is illustrated. The movement of the eyes to fixate on an object causes the eyes to receive light from the object, with the light forming an image on each of the retinas of the eyes. The presence of retinal blur in the image formed on the retina may provide a cue to accommodation, and the relative locations of the image on the retinas may provide a cue to vergence. The cue to accommodation causes accommodation to occur, resulting in the lenses of the eyes each assuming a particular accommodative state that forms a focused image of the object on the retina (e.g., fovea) of the eye. On the other hand, the cue to vergence causes vergence movements (rotation of the eyes) to occur such that the images formed on each retina of each eye are at corresponding retinal points that maintain single binocular vision. In these positions, the eyes may be said to have assumed a particular vergence state. With continued reference to FIG. 4A, accommodation may be understood to be the process by which the eye achieves a particular accommodative state, and vergence may be understood to be the process by which the eye achieves a particular vergence state. As indicated in FIG. 4A, the accommodative and vergence states of the eyes may change if the user fixates on another object. For example, the accommodated state may change if the user fixates on a new object at a different depth on the z-axis.

Without being limited by theory, it is believed that viewers of an object may perceive the object as being "three-dimensional" due to a combination of vergence and accommodation. As noted above, vergence movements (e.g., rotation of the eyes so that the pupils move toward or away from each other to converge the lines of sight of the eyes to fixate upon an object) of the two eyes relative to each other are closely associated with accommodation of the lenses of the eyes. Under normal conditions, changing the shapes of the lenses of the eyes to change focus from one object to another object at a different distance will automatically cause a matching change in vergence to the same distance, under a relationship known as the "accommodation-vergence reflex." Likewise, a change in vergence will trigger a matching change in lens shape under normal conditions.

Figure 4B:
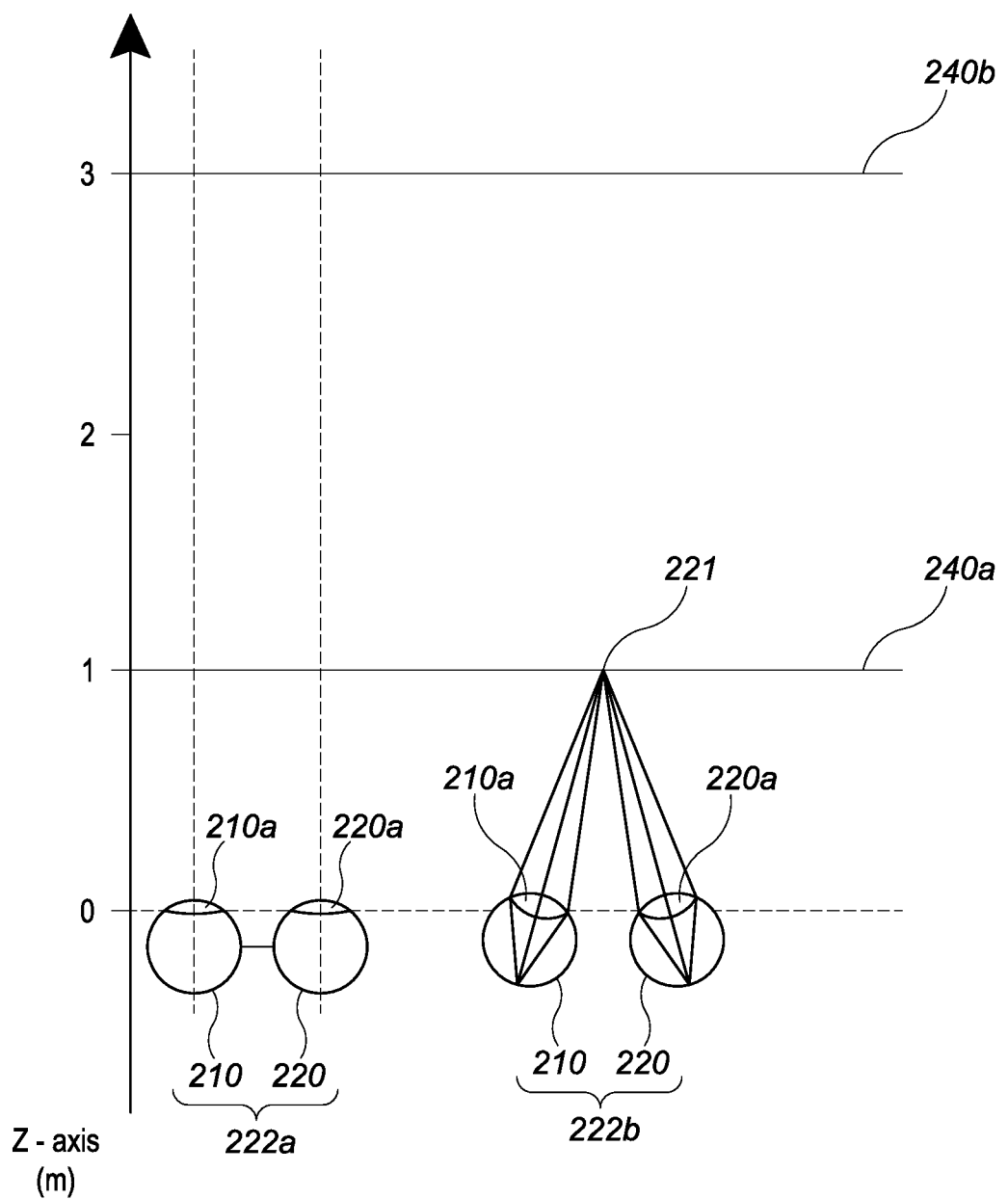
FIG. 4B illustrates examples of different accommodative states and vergence states of a pair of eyes of the user.

With reference now to FIG. 4B, examples of different accommodative and vergence states of the eyes are illustrated. The pair of eyes 222a are fixated on an object at optical infinity, while the pair eyes 222b are fixated on an object 221 at less than optical infinity. Notably, the vergence states of each pair of eyes is different, with the pair of eyes 222a directed straight ahead, while the pair of eyes 222 converge on the object 221. The accommodative states of the eyes forming each pair of eyes 222a and 222b are also different, as represented by the different shapes of the lenses 210a, 220a.

Undesirably, many users of conventional "3-D" display systems find such conventional systems to be uncomfortable or may not perceive a sense of depth at all due to a mismatch between accommodative and vergence states in these displays. As noted above, many stereoscopic or "3-D" display systems display a scene by providing slightly different images to each eye. Such systems are uncomfortable for many viewers, since they, among other things, simply provide different presentations of a scene and cause changes in the vergence states of the eyes, but without a corresponding change in the accommodative states of those eyes. Rather, the images are shown by a display at a fixed distance from the eyes, such that the eyes view all the image information at a single accommodative state. Such an arrangement works against the "accommodation-vergence reflex" by causing changes in the vergence state without a matching change in the accommodative state. This mismatch is believed to cause viewer discomfort. Display systems that provide a better match between accommodation and vergence may form more realistic and comfortable simulations of three-dimensional imagery.

Without being limited by theory, it is believed that the human eye typically may interpret a finite number of depth planes to provide depth perception. Consequently, a highly believable simulation of perceived depth may be achieved by providing, to the eye, different presentations of an image corresponding to each of these limited numbers of depth planes. In some embodiments, the different presentations may provide both cues to vergence and matching cues to accommodation, thereby providing physiologically correct accommodation-vergence matching.

With continued reference to FIG. 4B, two depth planes 240, corresponding to different distances in space from the eyes 210, 220, are illustrated. For a given depth plane 240, vergence cues may be provided by the displaying of images of appropriately different perspectives for each eye 210, 220. In addition, for a given depth plane 240, light forming the images provided to each eye 210, 220 may have a wavefront divergence corresponding to a light field produced by a point at the distance of that depth plane 240.

In the illustrated embodiment, the distance, along the z-axis, of the depth plane 240 containing the point 221 is 1 m. As used herein, distances or depths along the z-axis may be measured with a zero-point located at the exit pupils of the user's eyes. Thus, a depth plane 240 located at a depth of 1 m corresponds to a distance of 1 m away from the exit pupils of the user's eyes, on the optical axis of those eyes with the eyes directed towards optical infinity. As an approximation, the depth or distance along the z-axis may be measured from the display in front of the user's eyes (e.g., from the surface of a waveguide), plus a value for the distance between the device and the exit pupils of the user's eyes. That value may be called the eye relief and corresponds to the distance between the exit pupil of the user's eye and the display worn by the user in front of the eye. In practice, the value for the eye relief may be a normalized value used generally for all viewers. For example, the eye relief may be assumed to be 20 mm and a depth plane that is at a depth of 1 m may be at a distance of 980 mm in front of the display.

Figure 4C:
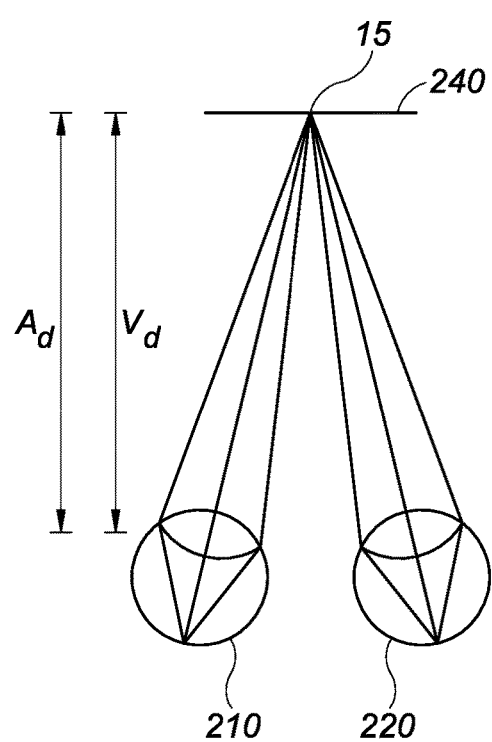
FIG. 4C illustrates an example of a representation of a top-down view of a user viewing content via a display system.
Figure 4D:
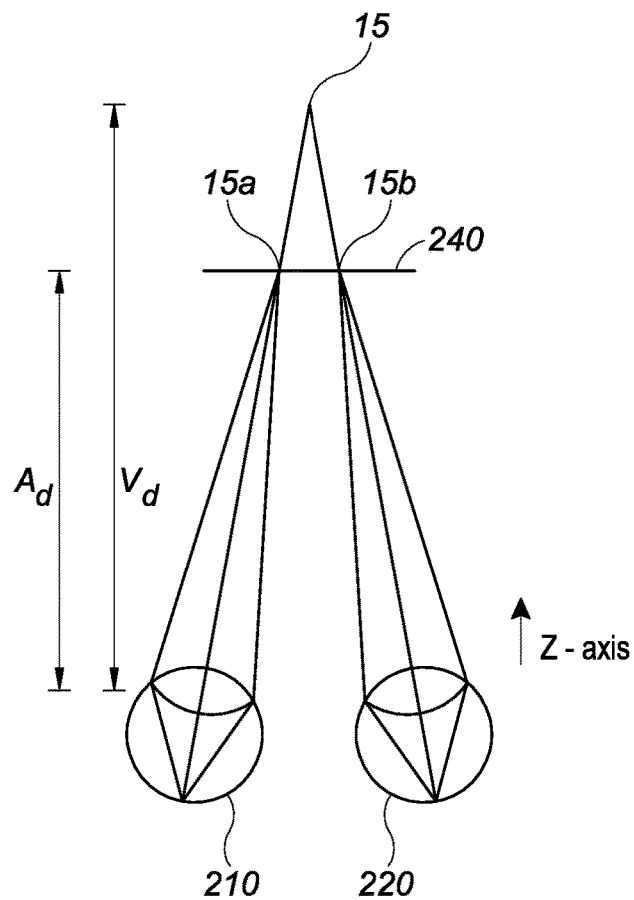
FIG. 4D illustrates another example of a representation of a top-down view of a user viewing content via a display system.

With reference now to FIGS. 4C and 4D, examples of matched accommodation-vergence distances and mismatched accommodation-vergence distances are illustrated, respectively. As illustrated in FIG. 4C, the display system may provide images of a virtual object to each eye 210, 220. The images may cause the eyes 210, 220 to assume a vergence state in which the eyes converge on a point 15 on a depth plane 240. In addition, the images may be formed by a light having a wavefront curvature corresponding to real objects at that depth plane 240. As a result, the eyes 210, 220 assume an accommodative state in which the images are in focus on the retinas of those eyes. Thus, the user may perceive the virtual object as being at the point 15 on the depth plane 240.

It will be appreciated that each of the accommodative and vergence states of the eyes 210, 220 are associated with a particular distance on the z-axis. For example, an object at a particular distance from the eyes 210, 220 causes those eyes to assume particular accommodative states based upon the distances of the object. The distance associated with a particular accommodative state may be referred to as the accommodation distance, Ad. Similarly, there are particular vergence distances, Vd, associated with the eyes in particular vergence states, or positions relative to one another. Where the accommodation distance and the vergence distance match, the relationship between accommodation and vergence may be said to be physiologically correct. This is considered to be the most comfortable scenario for a viewer.

In stereoscopic displays, however, the accommodation distance and the vergence distance may not always match. For example, as illustrated in FIG. 4D, images displayed to the eyes 210, 220 may be displayed with wavefront divergence corresponding to depth plane 240, and the eyes 210, 220 may assume a particular accommodative state in which the points 15a, 15b on that depth plane are in focus. However, the images displayed to the eyes 210, 220 may provide cues for vergence that cause the eyes 210, 220 to converge on a point 15 that is not located on the depth plane 240. As a result, the accommodation distance corresponds to the distance from the exit pupils of the eyes 210, 220 to the depth plane 240, while the vergence distance corresponds to the larger distance from the exit pupils of the eyes 210, 220 to the point 15, in some embodiments. The accommodation distance is different from the vergence distance. Consequently, there is an accommodation-vergence mismatch. Such a mismatch is considered undesirable and may cause discomfort in the user. It will be appreciated that the mismatch corresponds to distance (e.g., Vd–Ad) and may be characterized using diopters.

In some embodiments, it will be appreciated that a reference point other than exit pupils of the eyes 210, 220 may be utilized for determining distance for determining accommodation-vergence mismatch, so long as the same reference point is utilized for the accommodation distance and the vergence distance. For example, the distances could be measured from the cornea to the depth plane, from the retina to the depth plane, from the eyepiece (e.g., a waveguide of the display device) to the depth plane, and so on.

Without being limited by theory, it is believed that users may still perceive accommodation-vergence mismatches of up to about 0.25 diopter, up to about 0.33 diopter, and up to about 0.5 diopter as being physiologically correct, without the mismatch itself causing significant discomfort. In some embodiments, display systems disclosed herein (e.g., the display system 250, FIG. 6) present images to the viewer having accommodation-vergence mismatch of about 0.5 diopter or less. In some other embodiments, the accommodation-vergence mismatch of the images provided by the display system is about 0.33 diopter or less. In yet other embodiments, the accommodation-vergence mismatch of the images provided by the display system is about 0.25 diopter or less, including about 0.1 diopter or less.

Further, head and eye motion are coordinated with the "vestibulo-ocular reflex", which stabilizes image information relative to the retina during head rotations, thus keeping the object image information approximately centered on the retina. In response to a head rotation, the eyes are reflexively and proportionately rotated in the opposite direction to maintain stable fixation on an object. As a result of this compensatory relationship, many humans can read a book while shaking their head back and forth (interestingly, if the book is panned back and forth at the same speed with the head approximately stationary, the same generally is not true—the person is not likely to be able to read the moving book; the vestibulo-ocular reflex is one of head and eye motion coordination, generally not developed for hand motion). This paradigm may be significant for patient-worn health systems, because head motions of the user may be associated relatively directly with eye motions, and the system preferably is configured to work with this relationship. Thus, when designing a patient-worn or stationary display-based health system, characteristics and sometimes, limitations, of the human eye are preferably taken into account to provide meaningful virtual reality content that works with eye's natural mechanisms rather than stressing it. Furthermore, in the context of health-related applications of augmented reality display systems, this can provide a variety of advantages, as disclosed herein. As discussed above, the display of the health system may be implemented independently of augmented reality (AR) systems, but many embodiments below are described in relation to AR systems for illustrative purposes only.

Figure 5:
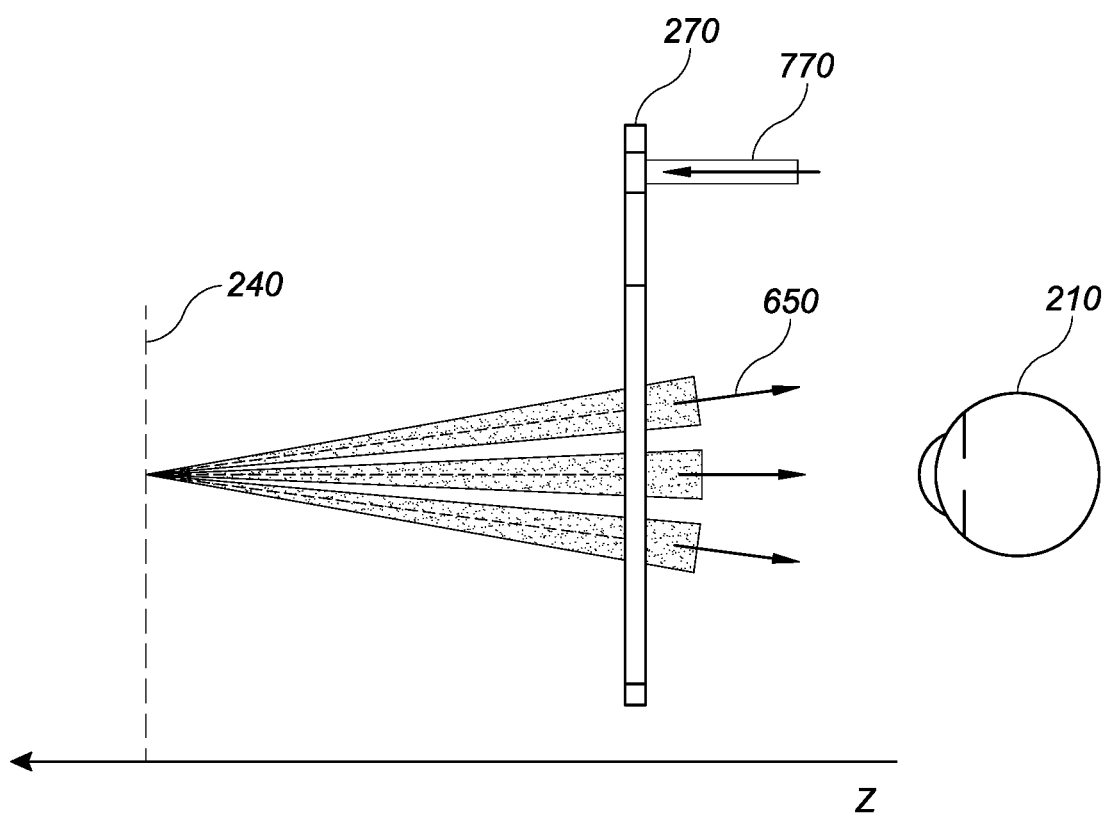
FIG. 5 illustrates aspects of an approach for simulating three-dimensional imagery by modifying wavefront divergence.

FIG. 5 illustrates aspects of an approach for simulating three-dimensional imagery by modifying wavefront divergence. The display system includes a waveguide 270 that is configured to receive light 770 that is encoded with image information, and to output that light to the user's eye 210. The waveguide 270 may output the light 650 with a defined amount of wavefront divergence corresponding to the wavefront divergence of a light field produced by a point on a desired depth plane 240. In some embodiments, the same amount of wavefront divergence is provided for all objects presented on that depth plane. In addition, it will be illustrated that the other eye of the user may be provided with image information from a similar waveguide.

In some embodiments, a single waveguide may be configured to output light with a set amount of wavefront divergence corresponding to a single or limited number of depth planes and/or the waveguide may be configured to output light of a limited range of wavelengths. Consequently, in some embodiments, a plurality or stack of waveguides may be utilized to provide different amounts of wavefront divergence for different depth planes and/or to output light of different ranges of wavelengths. As used herein, it will be appreciated at a depth plane may follow the contours of a flat or a curved surface. In some embodiments, for simplicity, the depth planes may follow the contours of flat surfaces.

Figure 6:
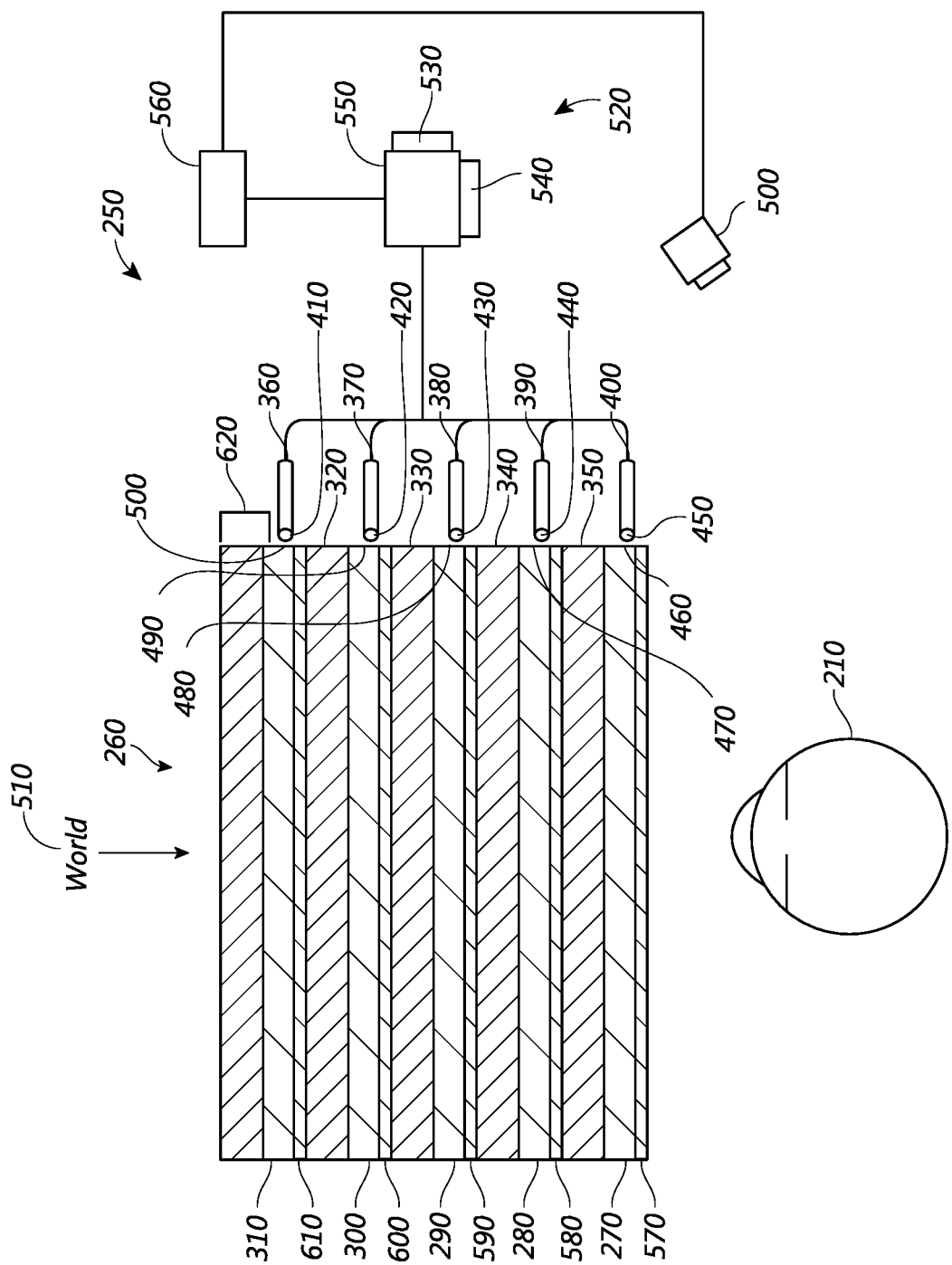
FIG. 6 illustrates an example of a waveguide stack for outputting image information to a user.

FIG. 6 illustrates an example of a waveguide stack for outputting image information to a user. A display system 250 includes a stack of waveguides, or stacked waveguide assembly, 260 that may be utilized to provide three-dimensional perception to the eye/brain using a plurality of waveguides 270, 280, 290, 300, 310. It will be appreciated that the display system 250 may be considered a light field display in some embodiments. In addition, the waveguide assembly 260 may also be referred to as an eyepiece.

In some embodiments, the display system 250 may be configured to provide substantially continuous cues to vergence and multiple discrete cues to accommodation. The cues to vergence may be provided by displaying different images to each of the eyes of the user, and the cues to accommodation may be provided by outputting the light that forms the images with selectable discrete amounts of wavefront divergence. Stated another way, the display system 250 may be configured to output light with variable levels of wavefront divergence. In some embodiments, each discrete level of wavefront divergence corresponds to a particular depth plane and may be provided by a particular one of the waveguides 270, 280, 290, 300, 310.

With continued reference to FIG. 6, the waveguide assembly 260 may also include a plurality of features 320, 330, 340, 350 between the waveguides. In some embodiments, the features 320, 330, 340, 350 may be one or more lenses. The waveguides 270, 280, 290, 300, 310 and/or the plurality of lenses 320, 330, 340, 350 may be configured to send image information to the eye with various levels of wavefront curvature or light ray divergence. Each waveguide level may be associated with a particular depth plane and may be configured to output image information corresponding to that depth plane. Image injection devices 360, 370, 380, 390, 400 may function as a source of light for the waveguides and may be utilized to inject image information into the waveguides 270, 280, 290, 300, 310, each of which may be configured, as described herein, to distribute incoming light across each respective waveguide, for output toward the eye 210. Light exits an output surface 410, 420, 430, 440, 450 of the image injection devices 360, 370, 380, 390, 400 and is injected into a corresponding input surface 460, 470, 480, 490, 500 of the waveguides 270, 280, 290, 300, 310. In some embodiments, each of the input surfaces 460, 470, 480, 490, 500 may be an edge of a corresponding waveguide, or may be part of a major surface of the corresponding waveguide (that is, one of the waveguide surfaces directly facing the world 510 or the viewer's eye 210). In some embodiments, a single beam of light (e.g. a collimated beam) may be injected into each waveguide to output an entire field of cloned collimated beams that are directed toward the eye 210 at particular angles (and amounts of divergence) corresponding to the depth plane associated with a particular waveguide. In some embodiments, a single one of the image injection devices 360, 370, 380, 390, 400 may be associated with and inject light into a plurality (e.g., three) of the waveguides 270, 280, 290, 300, 310.

In some embodiments, the image injection devices 360, 370, 380, 390, 400 are discrete displays that each produce image information for injection into a corresponding waveguide 270, 280, 290, 300, 310, respectively. In some other embodiments, the image injection devices 360, 370, 380, 390, 400 are the output ends of a single multiplexed display which may, e.g., pipe image information via one or more optical conduits (such as fiber optic cables) to each of the image injection devices 360, 370, 380, 390, 400. It will be appreciated that the image information provided by the image injection devices 360, 370, 380, 390, 400 may include light of different wavelengths, or colors (e.g., different component colors, as discussed herein).

In some embodiments, the light injected into the waveguides 270, 280, 290, 300, 310 is provided by a light projector system 520, which comprises a light module 530, which may include a light emitter, such as a light emitting diode (LED). The light from the light module 530 may be directed to and modified by a light modulator 540, e.g., a spatial light modulator, via a beam splitter 550. The light modulator 540 may be configured to change the perceived intensity of the light injected into the waveguides 270, 280, 290, 300, 310 to encode the light with image information. Examples of spatial light modulators include liquid crystal displays (LCD) including a liquid crystal on silicon (LCOS) displays. It will be appreciated that the image injection devices 360, 370, 380, 390, 400 are illustrated schematically and, in some embodiments, these image injection devices may represent different light paths and locations in a common projection system configured to output light into associated ones of the waveguides 270, 280, 290, 300, 310. In some embodiments, the waveguides of the waveguide assembly 260 may function as ideal lens while relaying light injected into the waveguides out to the user's eyes. In this conception, the object may be the spatial light modulator 540 and the image may be the image on the depth plane.

In some embodiments, the display system 250 may be a scanning fiber display comprising one or more scanning fibers configured to project light in various patterns (e.g., raster scan, spiral scan, Lissajous patterns, etc.) into one or more waveguides 270, 280, 290, 300, 310 and ultimately to the eye 210 of the viewer. In some embodiments, the illustrated image injection devices 360, 370, 380, 390, 400 may schematically represent a single scanning fiber or a bundle of scanning fibers configured to inject light into one or a plurality of the waveguides 270, 280, 290, 300, 310. In some other embodiments, the illustrated image injection devices 360, 370, 380, 390, 400 may schematically represent a plurality of scanning fibers or a plurality of bundles of scanning fibers, each of which are configured to inject light into an associated one of the waveguides 270, 280, 290, 300, 310. It will be appreciated that one or more optical fibers may be configured to transmit light from the light module 530 to the one or more waveguides 270, 280, 290, 300, 310. It will be appreciated that one or more intervening optical structures may be provided between the scanning fiber, or fibers, and the one or more waveguides 270, 280, 290, 300, 310 to, e.g., redirect light exiting the scanning fiber into the one or more waveguides 270, 280, 290, 300, 310.

A controller 560 controls the operation of one or more of the stacked waveguide assembly 260, including operation of the image injection devices 360, 370, 380, 390, 400, the light source 530, and the light modulator 540. In some embodiments, the controller 560 is part of the local data processing module 140. The controller 560 includes programming (e.g., instructions in a non-transitory medium) that regulates the timing and provision of image information to the waveguides 270, 280, 290, 300, 310 according to, e.g., any of the various schemes disclosed herein. In some embodiments, the controller may be a single integral device, or a distributed system connected by wired or wireless communication channels. The controller 560 may be part of the processing modules 140 or 150 (FIG. 9D) in some embodiments.

With continued reference to FIG. 6, the waveguides 270, 280, 290, 300, 310 may be configured to propagate light within each respective waveguide by total internal reflection (TIR). The waveguides 270, 280, 290, 300, 310 may each be planar or have another shape (e.g., curved), with major top and bottom surfaces and edges extending between those major top and bottom surfaces. In the illustrated configuration, the waveguides 270, 280, 290, 300, 310 may each include out-coupling optical elements 570, 580, 590, 600, 610 that are configured to extract light out of a waveguide by redirecting the light, propagating within each respective waveguide, out of the waveguide to output image information to the eye 210. Extracted light may also be referred to as out-coupled light and the out-coupling optical elements light may also be referred to light extracting optical elements. An extracted beam of light may be outputted by the waveguide at locations at which the light propagating in the waveguide strikes a light extracting optical element. The out-coupling optical elements 570, 580, 590, 600, 610 may, for example, be gratings, including diffractive optical features, as discussed further herein. While illustrated disposed at the bottom major surfaces of the waveguides 270, 280, 290, 300, 310, for ease of description and drawing clarity, in some embodiments, the out-coupling optical elements 570, 580, 590, 600, 610 may be disposed at the top and/or bottom major surfaces, and/or may be disposed directly in the volume of the waveguides 270, 280, 290, 300, 310, as discussed further herein. In some embodiments, the out-coupling optical elements 570, 580, 590, 600, 610 may be formed in a layer of material that is attached to a transparent substrate to form the waveguides 270, 280, 290, 300, 310. In some other embodiments, the waveguides 270, 280, 290, 300, 310 may be a monolithic piece of material and the out-coupling optical elements 570, 580, 590, 600, 610 may be formed on a surface and/or in the interior of that piece of material.

With continued reference to FIG. 6, as discussed herein, each waveguide 270, 280, 290, 300, 310 is configured to output light to form an image corresponding to a particular depth plane. For example, the waveguide 270 nearest the eye may be configured to deliver collimated light (which was injected into such waveguide 270), to the eye 210. The collimated light may be representative of the optical infinity focal plane. The next waveguide up 280 may be configured to send out collimated light which passes through the first lens 350 (e.g., a negative lens) before it may reach the eye 210; such first lens 350 may be configured to create a slight convex wavefront curvature so that the eye/brain interprets light coming from that next waveguide up 280 as coming from a first focal plane closer inward toward the eye 210 from optical infinity. Similarly, the third up waveguide 290 passes its output light through both the first 350 and second 340 lenses before reaching the eye 210; the combined optical power of the first 350 and second 340 lenses may be configured to create another incremental amount of wavefront curvature so that the eye/brain interprets light coming from the third waveguide 290 as coming from a second focal plane that is even closer inward toward the person from optical infinity than was light from the next waveguide up 280.

The other waveguide layers 300, 310 and lenses 330, 320 are similarly configured, with the highest waveguide 310 in the stack sending its output through all of the lenses between it and the eye for an aggregate focal power representative of the closest focal plane to the person. To compensate for the stack of lenses 320, 330, 340, 350 when viewing/interpreting light coming from the world 510 on the other side of the stacked waveguide assembly 260, a compensating lens layer 620 may be disposed at the top of the stack to compensate for the aggregate power of the lens stack 320, 330, 340, 350 below. Such a configuration provides as many perceived focal planes as there are available waveguide/lens pairings. Both the out-coupling optical elements of the waveguides and the focusing aspects of the lenses may be static (i.e., not dynamic or electro-active). In some alternative embodiments, either or both may be dynamic using electro-active features.

In some embodiments, two or more of the waveguides 270, 280, 290, 300, 310 may have the same associated depth plane. For example, multiple waveguides 270, 280, 290, 300, 310 may be configured to output images set to the same depth plane, or multiple subsets of the waveguides 270, 280, 290, 300, 310 may be configured to output images set to the same plurality of depth planes, with one set for each depth plane. This may provide advantages for forming a tiled image to provide an expanded field of view at those depth planes.

With continued reference to FIG. 6, the out-coupling optical elements 570, 580, 590, 600, 610 may be configured to both redirect light out of their respective waveguides and to output this light with the appropriate amount of divergence or collimation for a particular depth plane associated with the waveguide. As a result, waveguides having different associated depth planes may have different configurations of out-coupling optical elements 570, 580, 590, 600, 610, which output light with a different amount of divergence depending on the associated depth plane. In some embodiments, the light extracting optical elements 570, 580, 590, 600, 610 may be volumetric or surface features, which may be configured to output light at specific angles. For example, the light extracting optical elements 570, 580, 590, 600, 610 may be volume holograms, surface holograms, and/or diffraction gratings. In some embodiments, the features 320, 330, 340, 350 may not be lenses; rather, they may simply be spacers (e.g., cladding layers and/or structures for forming air gaps).

In some embodiments, the out-coupling optical elements 570, 580, 590, 600, 610 are diffractive features that form a diffraction pattern, or "diffractive optical element" (also referred to herein as a "DOE"). Preferably, the DOE's have a sufficiently low diffraction efficiency so that only a portion of the light of the beam is deflected away toward the eye 210 with each intersection of the DOE, while the rest continues to move through a waveguide via TIR. The light carrying the image information is thus divided into a number of related exit beams that exit the waveguide at a multiplicity of locations and the result is a fairly uniform pattern of exit emission toward the eye 210 for this particular collimated beam bouncing around within a waveguide.

In some embodiments, one or more DOEs may be switchable between "on" states in which they actively diffract, and "off" states in which they do not significantly diffract. For instance, a switchable DOE may comprise a layer of polymer dispersed liquid crystal, in which microdroplets comprise a diffraction pattern in a host medium, and the refractive index of the microdroplets may be switched to substantially match the refractive index of the host material (in which case the pattern does not appreciably diffract incident light) or the microdroplet may be switched to an index that does not match that of the host medium (in which case the pattern actively diffracts incident light).

In some embodiments, a camera assembly 630 (e.g., a digital camera, including visible light and infrared light cameras) may be provided to capture images of the eye 210 and/or tissue around the eye 210 (e.g., to conduct eyelid monitoring, pupil monitoring, eye movement monitoring, movement pattern monitoring, blinking pattern monitoring, eye color monitoring, etc.) to, e.g., detect user inputs and/or to monitor the physiological state of the user. As used herein, a camera may be any image capture device. In some embodiments, the camera assembly 630 may include an image capture device and a light source to project light (e.g., infrared light) to the eye, which may then be reflected by the eye and detected by the image capture device. In some embodiments, the camera assembly 630 may be attached to the frame 80 (FIG. 9D) and may be in electrical communication with the processing modules 140 and/or 150, which may process image information from the camera assembly 630. In some embodiments, one camera assembly 630 may be utilized for each eye, to separately monitor each eye.

Figure 7:
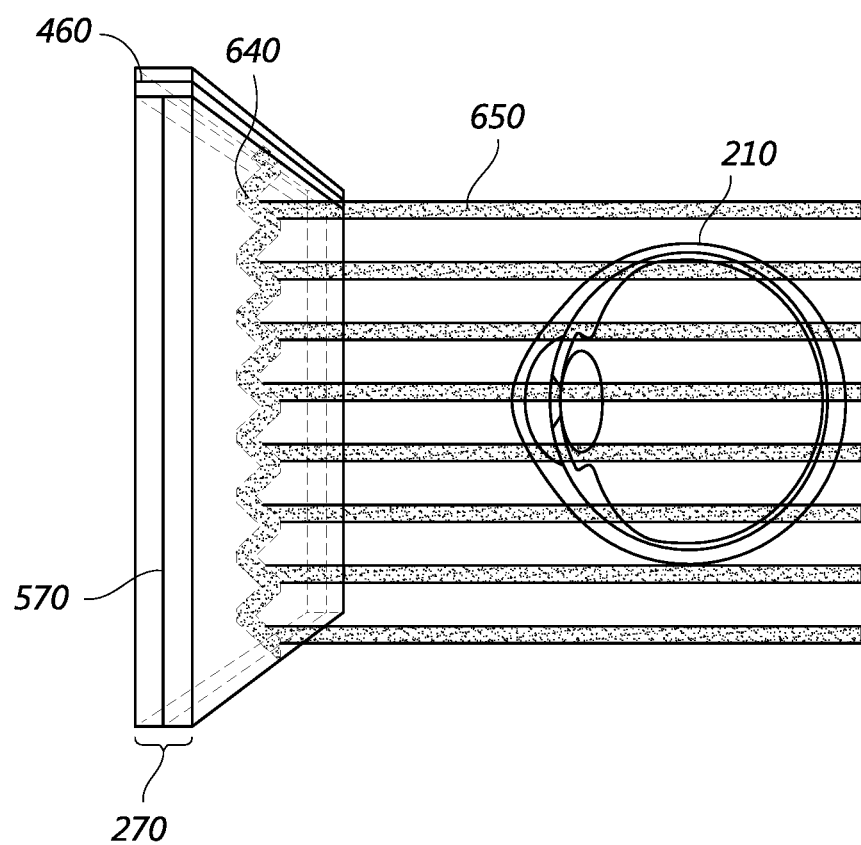
FIG. 7 illustrates an example of exit beams outputted by a waveguide.

With reference now to FIG. 7, an example of exit beams outputted by a waveguide is shown. One waveguide is illustrated, but it will be appreciated that other waveguides in the waveguide assembly 260 (FIG. 6) may function similarly, where the waveguide assembly 260 includes multiple waveguides. Light 640 is injected into the waveguide 270 at the input surface 460 of the waveguide 270 and propagates within the waveguide 270 by TIR. At points where the light 640 impinges on the DOE 570, a portion of the light exits the waveguide as exit beams 650. The exit beams 650 are illustrated as substantially parallel but, as discussed herein, they may also be redirected to propagate to the eye 210 at an angle (e.g., forming divergent exit beams), depending on the depth plane associated with the waveguide 270. It will be appreciated that substantially parallel exit beams may be indicative of a waveguide with out-coupling optical elements that out-couple light to form images that appear to be set on a depth plane at a large distance (e.g., optical infinity) from the eye 210. Other waveguides or other sets of out-coupling optical elements may output an exit beam pattern that is more divergent, which would require the eye 210 to accommodate to a closer distance to bring it into focus on the retina and would be interpreted by the brain as light from a distance closer to the eye 210 than optical infinity.

Figure 8:
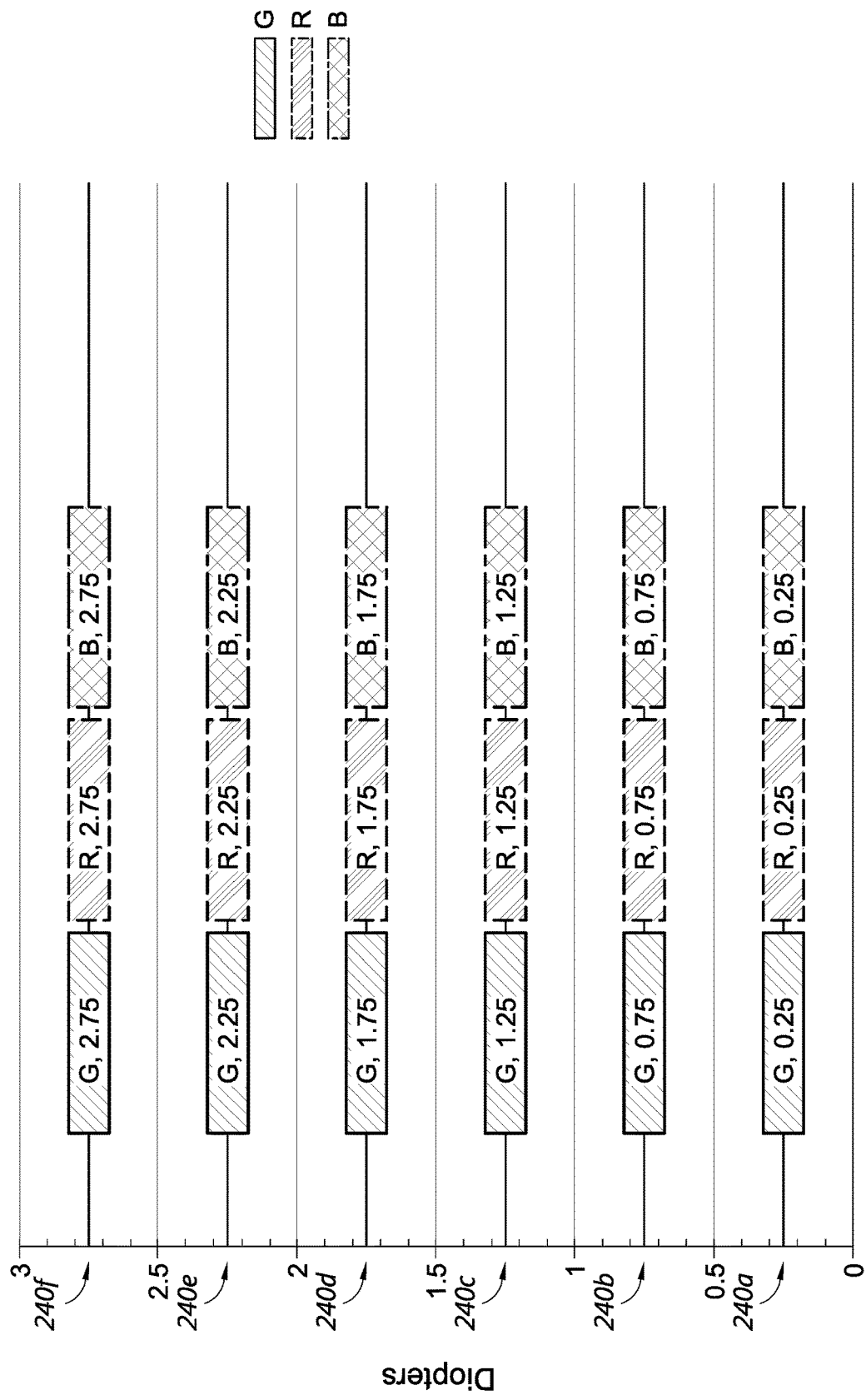
FIG. 8 illustrates an example of a stacked waveguide assembly in which each depth plane includes images formed using multiple different component colors.

In some embodiments, a full color image may be formed at each depth plane by overlaying images in each of the component colors, e.g., three or more component colors. FIG. 8 illustrates an example of a stacked waveguide assembly in which each depth plane includes images formed using multiple different component colors. The illustrated embodiment shows depth planes 240a-240f, although more or fewer depths are also contemplated. Each depth plane may have three or more component color images associated with it, including: a first image of a first color, G; a second image of a second color, R; and a third image of a third color, B. Different depth planes are indicated in the figure by different numbers for diopters (dpt) following the letters G, R, and B. Just as examples, the numbers following each of these letters indicate diopters (1/m), or inverse distance of the depth plane from a viewer, and each box in the figures represents an individual component color image. In some embodiments, to account for differences in the eye's focusing of light of different wavelengths, the exact placement of the depth planes for different component colors may vary. For example, different component color images for a given depth plane may be placed on depth planes corresponding to different distances from the user. Such an arrangement may increase visual acuity and user comfort and/or may decrease chromatic aberrations.

In some embodiments, light of each component color may be outputted by a single dedicated waveguide and, consequently, each depth plane may have multiple waveguides associated with it. In such embodiments, each box in the figures including the letters G, R, or B may be understood to represent an individual waveguide, and three waveguides may be provided per depth plane where three component color images are provided per depth plane. While the waveguides associated with each depth plane are shown adjacent to one another in this drawing for ease of description, it will be appreciated that, in a physical device, the waveguides may all be arranged in a stack with one waveguide per level. In some other embodiments, multiple component colors may be outputted by the same waveguide, such that, e.g., only a single waveguide may be provided per depth plane.

With continued reference to FIG. 8, in some embodiments, G is the color green, R is the color red, and B is the color blue. In some other embodiments, other colors associated with other wavelengths of light, including magenta and cyan, may be used in addition to or may replace one or more of red, green, or blue.

It will be appreciated that references to a given color of light throughout this disclosure will be understood to encompass light of one or more wavelengths within a range of wavelengths of light that are perceived by a viewer as being of that given color. For example, red light may include light of one or more wavelengths in the range of about 620-780 nm, green light may include light of one or more wavelengths in the range of about 492-577 nm, and blue light may include light of one or more wavelengths in the range of about 435-493 nm.

In some embodiments, the light source 530 (FIG. 6) may be configured to emit light of one or more wavelengths outside the visual perception range of the viewer, for example, infrared and/or ultraviolet wavelengths. In addition, the in-coupling, out-coupling, and other light redirecting structures of the waveguides of the display 250 may be configured to direct and emit this light out of the display towards the user's eye 210, e.g., for imaging and/or user stimulation applications.

Figure 9A:
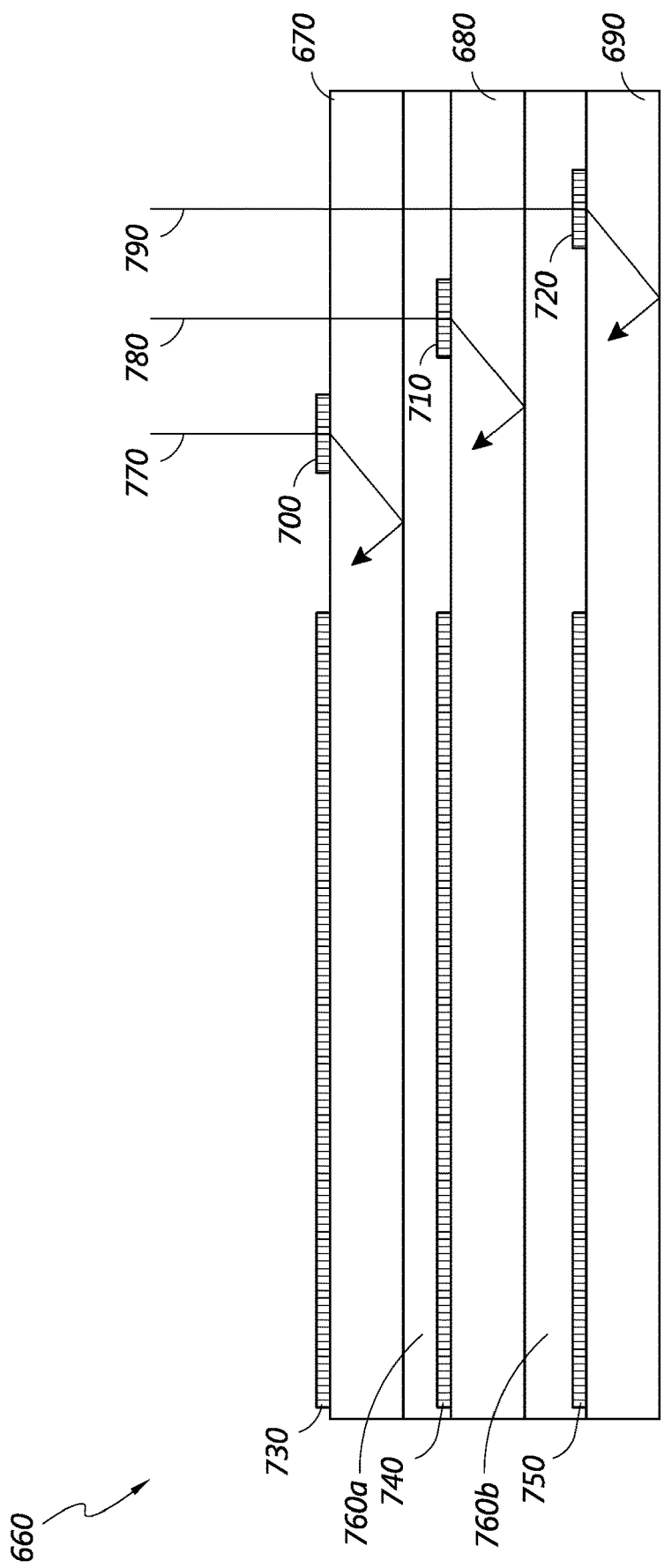
FIG. 9A illustrates a cross-sectional side view of an example of a set of stacked waveguides that each includes an incoupling optical element.

With reference now to FIG. 9A, in some embodiments, light impinging on a waveguide may need to be redirected to in-couple that light into the waveguide. An in-coupling optical element may be used to redirect and in-couple the light into its corresponding waveguide. FIG. 9A illustrates a cross-sectional side view of an example of a plurality or set 660 of stacked waveguides that each includes an in-coupling optical element. The waveguides may each be configured to output light of one or more different wavelengths, or one or more different ranges of wavelengths. It will be appreciated that the stack 660 may correspond to the stack 260 (FIG. 6) and the illustrated waveguides of the stack 660 may correspond to part of the plurality of waveguides 270, 280, 290, 300, 310, except that light from one or more of the image injection devices 360, 370, 380, 390, 400 is injected into the waveguides from a position that requires light to be redirected for in-coupling.

The illustrated set 660 of stacked waveguides includes waveguides 670, 680, and 690. Each waveguide includes an associated in-coupling optical element (which may also be referred to as a light input area on the waveguide), with, e.g., in-coupling optical element 700 disposed on a major surface (e.g., an upper major surface) of waveguide 670, in-coupling optical element 710 disposed on a major surface (e.g., an upper major surface) of waveguide 680, and in-coupling optical element 720 disposed on a major surface (e.g., an upper major surface) of waveguide 690. In some embodiments, one or more of the in-coupling optical elements 700, 710, 720 may be disposed on the bottom major surface of the respective waveguide 670, 680, 690 (particularly where the one or more in-coupling optical elements are reflective, deflecting optical elements). As illustrated, the in-coupling optical elements 700, 710, 720 may be disposed on the upper major surface of their respective waveguide 670, 680, 690 (or the top of the next lower waveguide), particularly where those in-coupling optical elements are transmissive, deflecting optical elements. In some embodiments, the in-coupling optical elements 700, 710, 720 may be disposed in the body of the respective waveguide 670, 680, 690. In some embodiments, as discussed herein, the in-coupling optical elements 700, 710, 720 are wavelength selective, such that they selectively redirect one or more wavelengths of light, while transmitting other wavelengths of light. While illustrated on one side or corner of their respective waveguide 670, 680, 690, it will be appreciated that the in-coupling optical elements 700, 710, 720 may be disposed in other areas of their respective waveguide 670, 680, 690 in some embodiments.

As illustrated, the in-coupling optical elements 700, 710, 720 may be laterally offset from one another. In some embodiments, each in-coupling optical element may be offset such that it receives light without that light passing through another in-coupling optical element. For example, each in-coupling optical element 700, 710, 720 may be configured to receive light from a different image injection device 360, 370, 380, 390, and 400 as shown in FIG. 6, and may be separated (e.g., laterally spaced apart) from other in-coupling optical elements 700, 710, 720 such that it substantially does not receive light from the other ones of the in-coupling optical elements 700, 710, 720.

Each waveguide also includes associated light distributing elements, with, e.g., light distributing elements 730 disposed on a major surface (e.g., a top major surface) of waveguide 670, light distributing elements 740 disposed on a major surface (e.g., a top major surface) of waveguide 680, and light distributing elements 750 disposed on a major surface (e.g., a top major surface) of waveguide 690. In some other embodiments, the light distributing elements 730, 740, 750, may be disposed on a bottom major surface of associated waveguides 670, 680, 690, respectively. In some other embodiments, the light distributing elements 730, 740, 750, may be disposed on both top and bottom major surface of associated waveguides 670, 680, 690, respectively; or the light distributing elements 730, 740, 750, may be disposed on different ones of the top and bottom major surfaces in different associated waveguides 670, 680, 690, respectively.

The waveguides 670, 680, 690 may be spaced apart and separated by, e.g., gas, liquid, and/or solid layers of material. For example, as illustrated, layer 760a may separate waveguides 670 and 680; and layer 760b may separate waveguides 680 and 690. In some embodiments, the layers 760a and 760b are formed of low refractive index materials (that is, materials having a lower refractive index than the material forming the immediately adjacent one of waveguides 670, 680, 690). Preferably, the refractive index of the material forming the layers 760a, 760b is 0.05 or more, or 0.10 or less than the refractive index of the material forming the waveguides 670, 680, 690. Advantageously, the lower refractive index layers 760a, 760b may function as cladding layers that facilitate total internal reflection (TIR) of light through the waveguides 670, 680, 690 (e.g., TIR between the top and bottom major surfaces of each waveguide). In some embodiments, the layers 760a, 760b are formed of air. While not illustrated, it will be appreciated that the top and bottom of the illustrated set 660 of waveguides may include immediately neighboring cladding layers.

Preferably, for ease of manufacturing and other considerations, the material forming the waveguides 670, 680, 690 are similar or the same, and the material forming the layers 760a, 760b are similar or the same. In some embodiments, the material forming the waveguides 670, 680, 690 may be different between one or more waveguides, and/or the material forming the layers 760a, 760b may be different, while still holding to the various refractive index relationships noted above.

With continued reference to FIG. 9A, light rays 770, 780, 790 are incident on the set 660 of waveguides. It will be appreciated that the light rays 770, 780, 790 may be injected into the waveguides 670, 680, 690 by one or more image injection devices 360, 370, 380, 390, 400 (FIG. 6).

In some embodiments, the light rays 770, 780, 790 have different properties, e.g., different wavelengths or different ranges of wavelengths, which may correspond to different colors. The in-coupling optical elements 700, 710, 720 each deflect the incident light such that the light propagates through a respective one of the waveguides 670, 680, 690 by TIR. In some embodiments, the incoupling optical elements 700, 710, 720 each selectively deflect one or more particular wavelengths of light, while transmitting other wavelengths to an underlying waveguide and associated incoupling optical element.

For example, in-coupling optical element 700 may be configured to deflect ray 770, which has a first wavelength or range of wavelengths, while transmitting rays 780 and 790, which have different second and third wavelengths or ranges of wavelengths, respectively. The transmitted ray 780 impinges on and is deflected by the in-coupling optical element 710, which is configured to deflect light of a second wavelength or range of wavelengths. The ray 790 is deflected by the in-coupling optical element 720, which is configured to selectively deflect light of third wavelength or range of wavelengths.

With continued reference to FIG. 9A, the deflected light rays 770, 780, 790 are deflected so that they propagate through a corresponding waveguide 670, 680, 690; that is, the in-coupling optical elements 700, 710, 720 of each waveguide deflects light into that corresponding waveguide 670, 680, 690 to in-couple light into that corresponding waveguide. The light rays 770, 780, 790 are deflected at angles that cause the light to propagate through the respective waveguide 670, 680, 690 by TIR. The light rays 770, 780, 790 propagate through the respective waveguide 670, 680, 690 by TIR until impinging on the waveguide's corresponding light distributing elements 730, 740, 750.

Figure 9B:
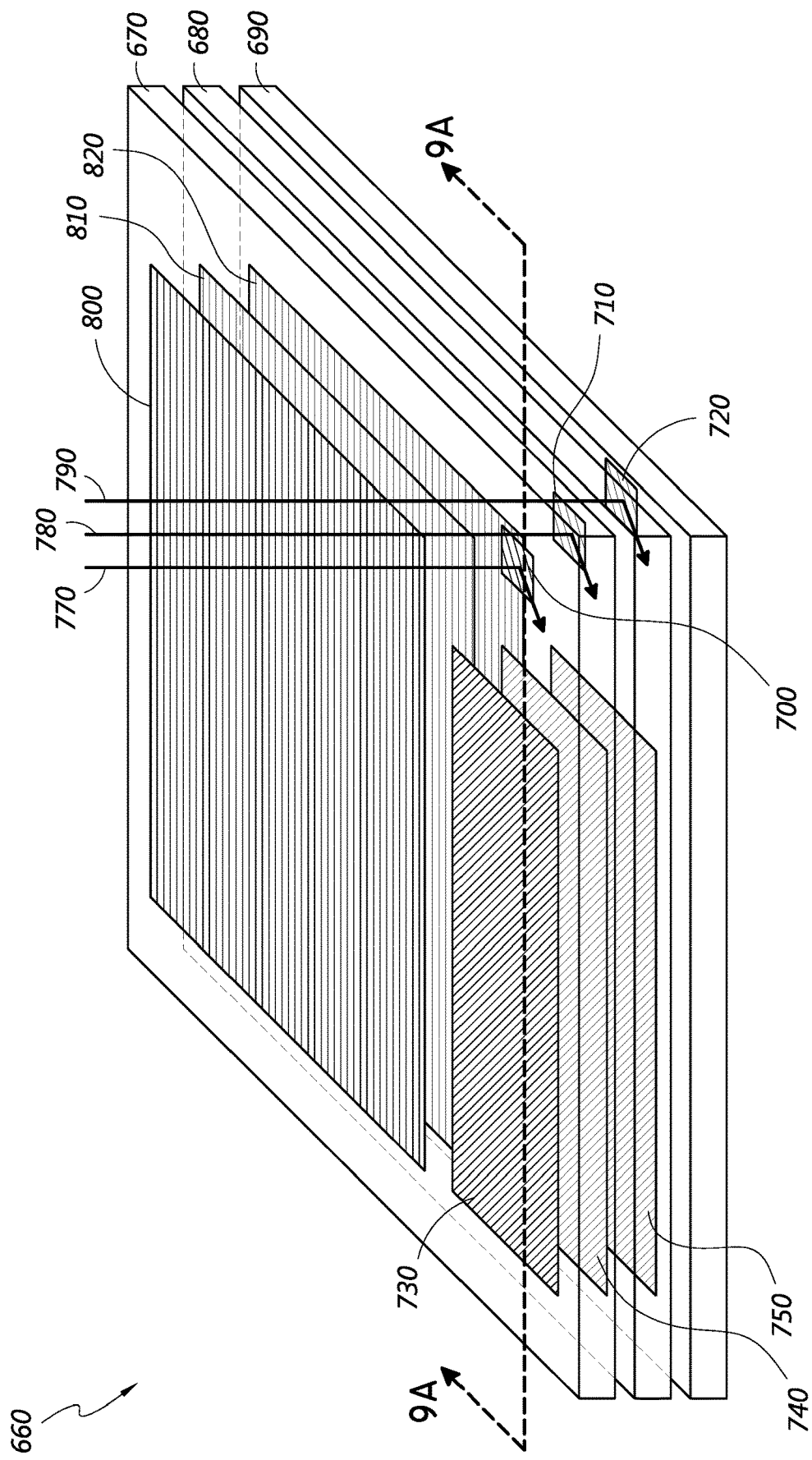
FIG. 9B illustrates a perspective view of an example of the plurality of stacked waveguides of FIG. 9A.

With reference now to FIG. 9B, a perspective view of an example of the plurality of stacked waveguides of FIG. 9A is illustrated. As noted above, the in-coupled light rays 770, 780, 790, are deflected by the in-coupling optical elements 700, 710, 720, respectively, and then propagate by TIR within the waveguides 670, 680, 690, respectively. The light rays 770, 780, 790 then impinge on the light distributing elements 730, 740, 750, respectively. The light distributing elements 730, 740, 750 deflect the light rays 770, 780, 790 so that they propagate towards the out-coupling optical elements 800, 810, 820, respectively.

In some embodiments, the light distributing elements 730, 740, 750 are orthogonal pupil expanders (OPE's). In some embodiments, the OPE's deflect or distribute light to the out-coupling optical elements 800, 810, 820 and, in some embodiments, may also increase the beam or spot size of this light as it propagates to the out-coupling optical elements. In some embodiments, the light distributing elements 730, 740, 750 may be omitted and the in-coupling optical elements 700, 710, 720 may be configured to deflect light directly to the out-coupling optical elements 800, 810, 820. For example, with reference to FIG. 9A, the light distributing elements 730, 740, 750 may be replaced with out-coupling optical elements 800, 810, 820, respectively. In some embodiments, the out-coupling optical elements 800, 810, 820 are exit pupils (EP's) or exit pupil expanders (EPE's) that direct light in a viewer's eye 210 (FIG. 7). It will be appreciated that the OPE's may be configured to increase the dimensions of the eye box in at least one axis and the EPE's may be to increase the eye box in an axis crossing, e.g., orthogonal to, the axis of the OPEs. For example, each OPE may be configured to redirect a portion of the light striking the OPE to an EPE of the same waveguide, while allowing the remaining portion of the light to continue to propagate down the waveguide. Upon impinging on the OPE again, another portion of the remaining light is redirected to the EPE, and the remaining portion of that portion continues to propagate further down the waveguide, and so on. Similarly, upon striking the EPE, a portion of the impinging light is directed out of the waveguide towards the user, and a remaining portion of that light continues to propagate through the waveguide until it strikes the EP again, at which time another portion of the impinging light is directed out of the waveguide, and so on. Consequently, a single beam of incoupled light may be "replicated" each time a portion of that light is redirected by an OPE or EPE, thereby forming a field of cloned beams of light, as shown in FIG. 6. In some embodiments, the OPE and/or EPE may be configured to modify a size of the beams of light.

Accordingly, with reference to FIGS. 9A and 9B, in some embodiments, the set 660 of waveguides includes waveguides 670, 680, 690; in-coupling optical elements 700, 710, 720; light distributing elements (e.g., OPE's) 730, 740, 750; and out-coupling optical elements (e.g., EP's) 800, 810, 820 for each component color. The waveguides 670, 680, 690 may be stacked with an air gap/cladding layer between each one. The in-coupling optical elements 700, 710, 720 redirect or deflect incident light (with different in-coupling optical elements receiving light of different wavelengths) into its waveguide. The light then propagates at an angle which will result in TIR within the respective waveguide 670, 680, 690. In the example shown, light ray 770 (e.g., blue light) is deflected by the first in-coupling optical element 700, and then continues to bounce down the waveguide, interacting with the light distributing element (e.g., OPE's) 730 and then the out-coupling optical element (e.g., EPs) 800, in a manner described earlier. The light rays 780 and 790 (e.g., green and red light, respectively) will pass through the waveguide 670, with light ray 780 impinging on and being deflected by in-coupling optical element 710. The light ray 780 then bounces down the waveguide 680 via TIR, proceeding on to its light distributing element (e.g., OPEs) 740 and then the out-coupling optical element (e.g., EP's) 810. Finally, light ray 790 (e.g., red light) passes through the waveguide 690 to impinge on the light in-coupling optical elements 720 of the waveguide 690. The light in-coupling optical elements 720 deflect the light ray 790 such that the light ray propagates to light distributing element (e.g., OPEs) 750 by TIR, and then to the out-coupling optical element (e.g., EPs) 820 by TIR. The out-coupling optical element 820 then finally out-couples the light ray 790 to the viewer, who also receives the out-coupled light from the other waveguides 670, 680.

Figure 9C:
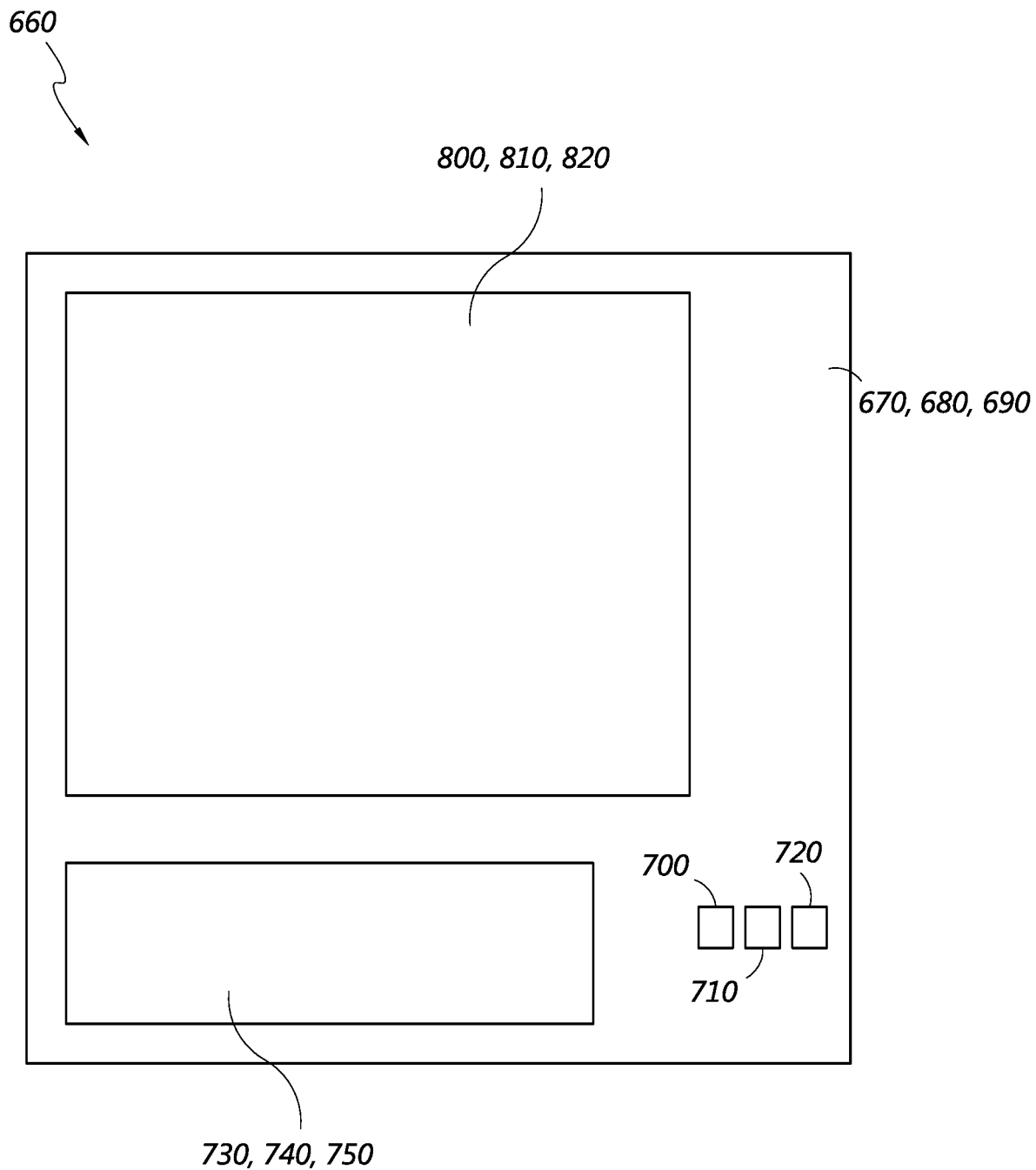
FIG. 9C illustrates a top-down plan view of an example of the plurality of stacked waveguides of FIGS. 9A and 9B.

FIG. 9C illustrates a top-down plan view of an example of the plurality of stacked waveguides of FIGS. 9A and 9B. As illustrated, the waveguides 670, 680, 690, along with each waveguide's associated light distributing element 730, 740, 750 and associated out-coupling optical element 800, 810, 820, may be vertically aligned. However, as discussed herein, the in-coupling optical elements 700, 710, 720 are not vertically aligned; rather, the in-coupling optical elements are preferably non-overlapping (e.g., laterally spaced apart as seen in the top-down view). As discussed further herein, this nonoverlapping spatial arrangement facilitates the injection of light from different resources into different waveguides on a one-to-one basis, thereby allowing a specific light source to be uniquely coupled to a specific waveguide. In some embodiments, arrangements including nonoverlapping spatially-separated in-coupling optical elements may be referred to as a shifted pupil system, and the in-coupling optical elements within these arrangements may correspond to sub pupils.

Figure 9D:
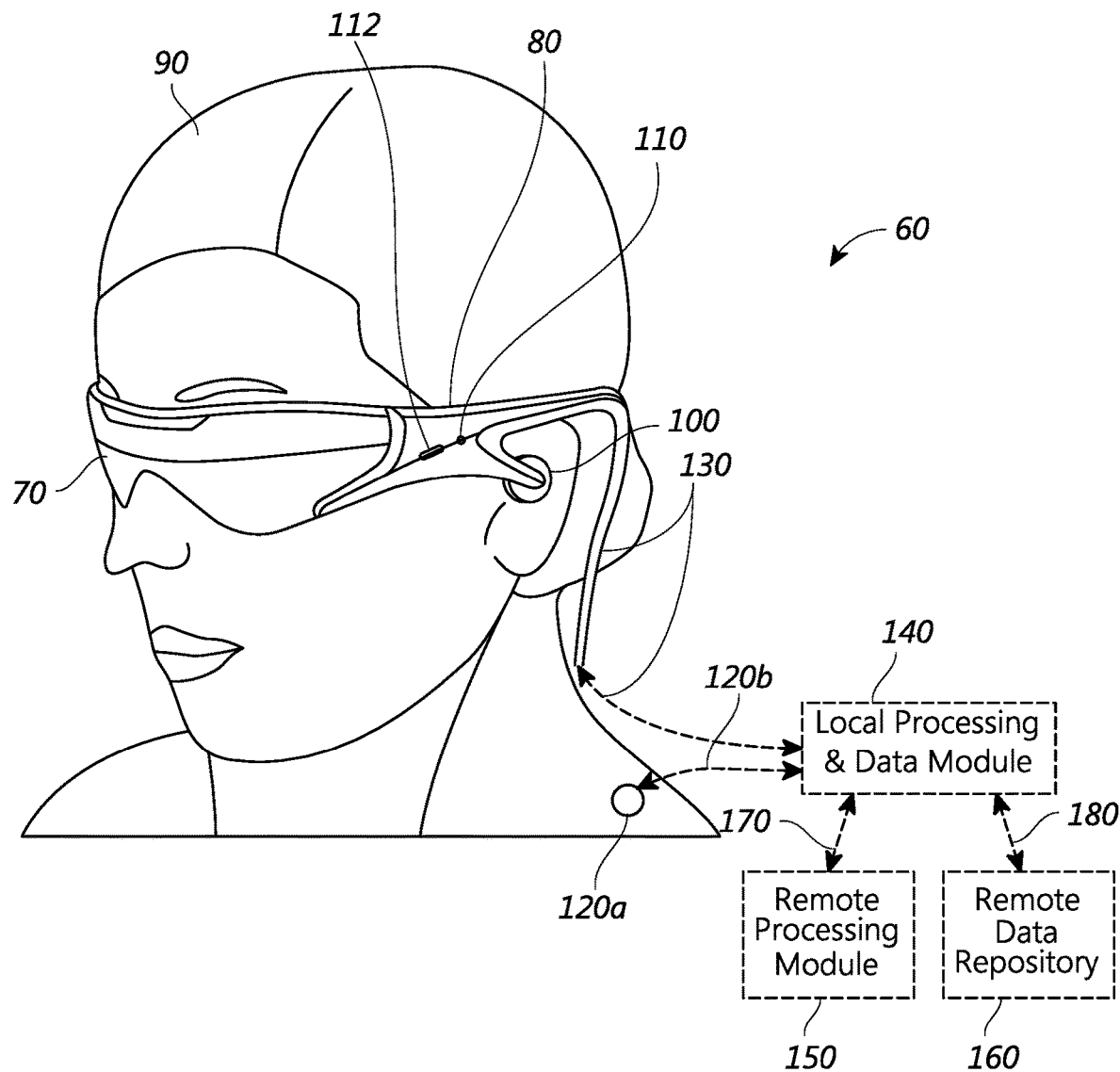
FIG. 9D illustrates an example of wearable display system.

FIG. 9D illustrates an example of wearable display system 60 into which the various waveguides and related systems disclosed herein may be integrated. In some embodiments, the display system 60 is the system 250 of FIG. 6, with FIG. 6 schematically showing some parts of that system 60 in greater detail. For example, the waveguide assembly 260 of FIG. 6 may be part of the display 70.

With continued reference to FIG. 9D, the display system 60 includes a display 70, and various mechanical and electronic modules and systems to support the functioning of that display 70. The display 70 may be coupled to a frame 80, which is wearable by a display system user or viewer 90 and which is configured to position the display 70 in front of the eyes of the user 90. The display 70 may be considered eyewear in some embodiments. In some embodiments, a speaker 100 is coupled to the frame 80 and configured to be positioned adjacent the ear canal of the user 90 (in some embodiments, another speaker, not shown, may optionally be positioned adjacent the other ear canal of the user to provide stereo/shapeable sound control). The display system 60 may also include one or more microphones 110 or other devices to detect sound. In some embodiments, the microphone is configured to allow the user to provide inputs or commands to the system 60 (e.g., the selection of voice menu commands, natural language questions, etc.), and/or may allow audio communication with other persons (e.g., with other users of similar display systems. The microphone may further be configured as a peripheral sensor to collect audio data (e.g., sounds from the user and/or environment). In some embodiments, the display system may also include a peripheral sensor 120a, which may be separate from the frame 80 and attached to the body of the user 90 (e.g., on the head, torso, an extremity, etc. of the user 90). The peripheral sensor 120a may be configured to acquire data characterizing a physiological state of the user 90 in some embodiments. For example, the sensor 120a may be an electrode. The display system may further include a stimulus delivery module 112. For example, the stimulus delivery module 112 may include a medication dispenser, ultrasound source, vibration source, and/or heat source. In various embodiments, the peripheral stimulus delivery module may be configured to provide therapies and/or alerts (e.g., by providing haptic feedback).

With continued reference to FIG. 9D, the display 70 is operatively coupled by communications link 130, such as by a wired lead or wireless connectivity, to a local data processing module 140 which may be mounted in a variety of configurations, such as fixedly attached to the frame 80, fixedly attached to a helmet or hat worn by the user, embedded in headphones, or otherwise removably attached to the user 90 (e.g., in a backpack-style configuration, in a belt-coupling style configuration). Similarly, the sensor 120a may be operatively coupled by communications link 120b, e.g., a wired lead or wireless connectivity, to the local processor and data module 140. The local processing and data module 140 may comprise a hardware processor, as well as digital memory, such as non-volatile memory (e.g., flash memory or hard disk drives), both of which may be utilized to assist in the processing, caching, and storage of data. Optionally, the local processor and data module 140 may include one or more central processing units (CPUs), graphics processing units (GPUs), dedicated processing hardware, and so on. The data may include data a) captured from sensors (which may be, e.g., operatively coupled to the frame 80 or otherwise attached to the user 90), such as image capture devices (such as cameras), microphones, inertial measurement units, accelerometers, compasses, GPS units, radio devices, gyros, and/or other sensors disclosed herein; and/or b) acquired and/or processed using remote processing module 150 and/or remote data repository 160 (including data relating to virtual content), possibly for passage to the display 70 after such processing or retrieval. The local processing and data module 140 may be operatively coupled by communication links 170, 180, such as via a wired or wireless communication links, to the remote processing module 150 and remote data repository 160 such that these remote modules 150, 160 are operatively coupled to each other and available as resources to the local processing and data module 140. In some embodiments, the local processing and data module 140 may include one or more of the image capture devices, microphones, inertial measurement units, accelerometers, compasses, GPS units, radio devices, and/or gyros. In some other embodiments, one or more of these sensors may be attached to the frame 80, or may be standalone structures that communicate with the local processing and data module 140 by wired or wireless communication pathways.

With continued reference to FIG. 9D, in some embodiments, the remote processing module 150 may comprise one or more processors configured to analyze and process data and/or image information, for instance including one or more central processing units (CPUs), graphics processing units (GPUs), dedicated processing hardware, and so on. In some embodiments, the remote data repository 160 may comprise a digital data storage facility, which may be available through the internet or other networking configuration in a "cloud" resource configuration. In some embodiments, the remote data repository 160 may include one or more remote servers, which provide information, e.g., information for generating augmented reality content, to the local processing and data module 140 and/or the remote processing module 150. In some embodiments, all data is stored and all computations are performed in the local processing and data module, allowing fully autonomous use from a remote module. Optionally, an outside system (e.g., a system of one or more processors, one or more computers) that includes CPUs, GPUs, and so on, may perform at least a portion of processing (e.g., generating image information, processing data) and provide information to, and receive information from, modules 140, 150, 160, for instance via wireless or wired connections.

Figure 10:
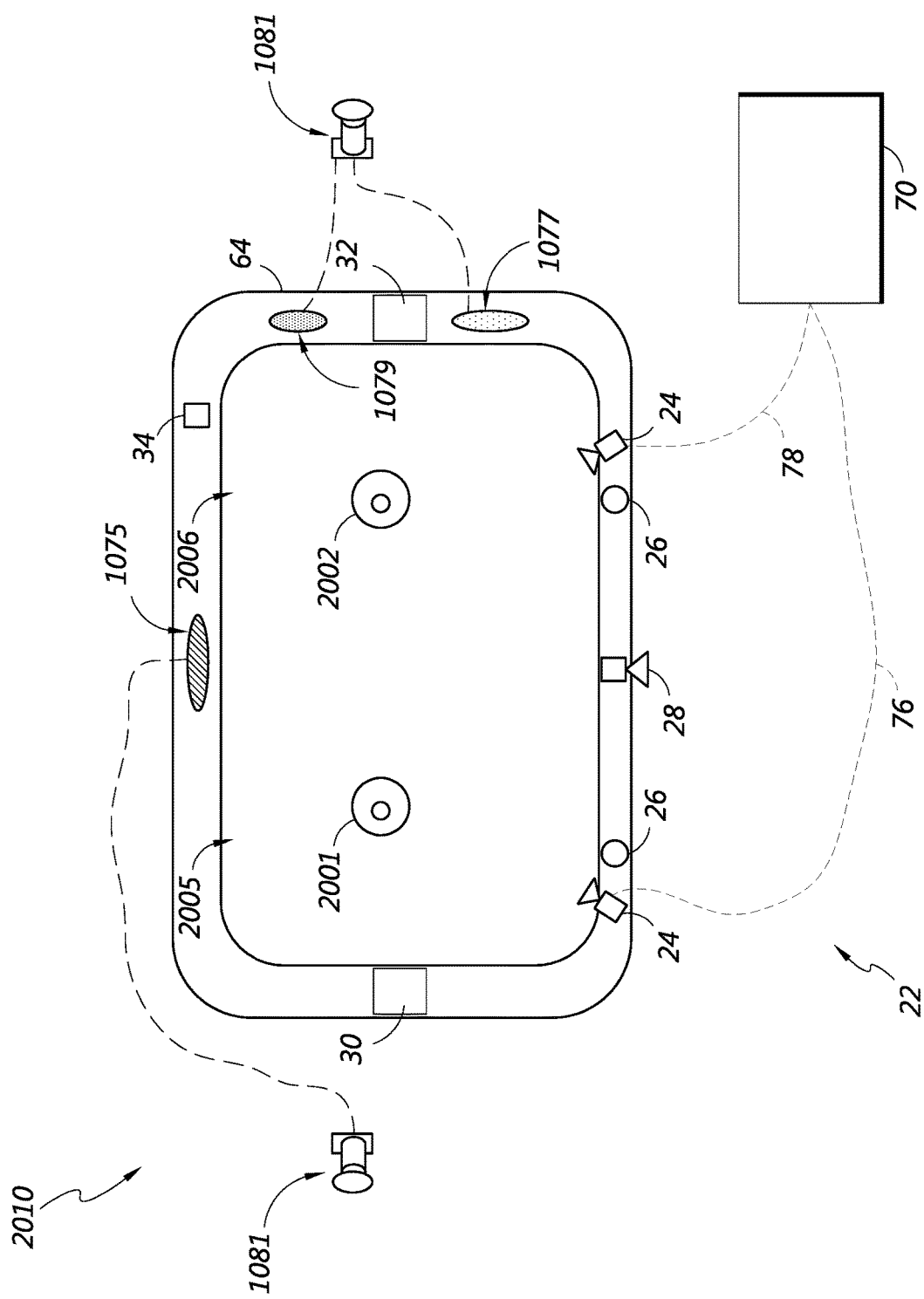
FIG. 10 shows a schematic view of an example of various components of an augmented reality system comprising environmental and user sensors.

With reference now to FIG. 10, which shows a schematic view of an example of various components of an augmented reality display system comprising user sensors 24, 28, 30, 32 and environmental sensors 34. In some embodiments, the augmented reality display system may be a mixed reality display system. As shown, the user sensors 24, 28, 30, 32 may be configured to detect data regarding the state of the user, and the environmental sensors 34 may be configured to collect data regarding parameters external to the user. In some embodiments, the display system may be configured to store data related to and/or characterizing AR content delivered to the user (e.g., the time, location, color make-up, sound volume etc., of the AR content).

The user sensors will be discussed first. As illustrated, an augmented reality display system 2010 may include various user sensors, which may also be referred to as inwardly-directed sensors. The augmented reality display system 2010 may correspond to the system 80 of FIG. 2 and may include a viewer imaging system 22. The system 22 may include cameras 24 (e.g., infrared, UV, and/or visible light cameras) paired with light sources 26 (e.g., infrared light sources) directed at and configured to monitor the user (e.g., the eyes 2001, 2002 and/or surrounding tissues of the user). In some other embodiments, the light sources 26 may be configured to emit light to provide light stimulation to the user. For example, the light sources may be configured to generate content that varies in one or more of the following properties: colors at one or more intensities, patterns, brightness, two- or three-dimensional enhancement or de-enhancement, sharpened or blurred focus, higher or lower resolution, enhanced or de-enhanced contrast, motion, lack of motion, higher or lower refresh rate, magnification, shape, intensity, distortion or other qualities, all of which may change over time. The cameras 24 and light sources 26 may be operatively coupled to the local processing module 70. Such cameras 24 may be configured to monitor one or more of the orientation, shape, and symmetry of pupils (including pupil sizes) or irises of the respective eyes, and/or tissues surrounding the eye, such as eyelids or eyebrows to conduct the various analyses disclosed herein. In some embodiments, imaging of the iris and/or retina of an eye may be used for secure identification of a user.

With continued reference to FIG. 10, cameras 24 may further be configured to image the retinas and/or irises of the respective eyes, such as for diagnostic purposes and/or for orientation tracking based on the location of retinal features and/or features of the iris, such as the fovea or features of the fundus. Iris and retina imaging or scanning may be performed for secure identification of users for, e.g., correctly associating user data with a particular user and/or to present private information to the appropriate user. In some embodiments, in addition to or as an alternative to the cameras 24, one or more cameras 28 may be configured to detect and/or monitor various other aspects of the status of a user. For example, one or more cameras 28 may be inward-facing and configured to monitor the shape, position, movement, color, and/or other properties of features other than the eyes of the user, e.g., one or more facial features (e.g., facial expression, voluntary movement, involuntary tics). In another example, one or more cameras 28 may be downward-facing and configured to monitor the position, movement, and/or other features or properties of the arms, hands, legs, feet, neck, and/or torso of a user.

In some embodiments, as disclosed herein, the display system 2010 may include a spatial light modulator that variably projects, through a fiber scanner (e.g., the image injection devices in FIGS. 6-200, 202, 204, 206, 208), light beams across the retina of the user to form an image. In some embodiments, the fiber scanner may be used in conjunction with, or in place of, the cameras 24 or 28 to, e.g., track or image the user's eyes. For example, as an alternative to or in addition to the scanning fiber being configured to output light, the health system may have a separate light-receiving device to receive light reflected from the user's eyes, and to collect data associated with that reflected light.

With continued reference to FIG. 10, the cameras 24, 28 and light sources 26 may be mounted on the frame 64, which may also hold the waveguide stacks 2005, 2006. In some embodiments, sensors and/or other electronic devices (e.g., the cameras 24, 28 and light sources 26) of the display system 2010 may be configured to communicate with the local processing and data module 70 through communication links 76, 70.

In some embodiments, in addition to providing data regarding the user, one or both of the cameras 24 and 28 may be utilized to track the eyes to provide user input. For example, the viewer imaging system 22 may be utilized to select items on virtual menus, and/or provide other input to the display system 2010, such as for providing user responses in the various tests and analyses disclosed herein.

In some embodiments, the display system 2010 may include other sensors 30 configured to monitor physiological and/or behavioral aspects of the user. For example, such sensors 30 may include one or more of the sensors noted below. Examples of such sensors 30 include sensors configured for ophthalmic testing such as confocal microscopy sensors, electronystagmography (ENG) sensors, electrooculography (EOG), electroretinography (ERG) sensors, laser Doppler flowmetry (LDF) sensors, photoacoustic imaging and pressure reading sensors, two-photon excitation microscopy sensors, and/or ultrasound sensors. Other examples of sensors 30 include sensors configured for other electrodiagnostic technologies, such as electrocardiography (ECG) sensors, electroencephalography (EEG) sensors, electromyography (EMG) sensors, electrophysiological testing (EP) sensors, event-related potential (ERP) sensors, functional near-infrared spectroscopy (fNIR) sensors, low-resolution brain electromagnetic tomography (LORETA) sensors, and/or optical coherence tomography (OCT) sensors. Yet other examples of sensors 30 include additional physiological sensors such as blood glucose meters, blood pressure meters, electrodermal activity sensors, photoplethysmography equipment, sensing equipment for computer-aided auscultation, magnetic field detectors, and/or a body temperature sensor. In some embodiments, the display system 2010 may include motion sensors 32, such as one or more accelerometers, gyros, gesture sensors, gait sensors, balance sensors, and/or IMU sensors. Sensors 30 may also include $CO_2$ monitoring sensors, respiratory rate sensors, end-title $CO_2$ sensors, and/or breathalyzers. The sensors 30 may include one or more inwardly directed (user directed) microphones configured to detect sounds, and various properties of those sound, including the intensity and type of sounds detected, the presence of multiple signals, and/or signal location.

The sensors 30 are schematically illustrated as being connected to the frame 64. It will be appreciated that this connection may take the form of a physical attachment to the frame 64 and may be anywhere on the frame 64, including the ends of the temples of the frame 64 which extend over the user's ears. For example, the sensors 30 may be mounted at the ends of the temples of the frame 64, at a point of contact between the frame 64 and the user. In some other embodiments, the sensors 30 may extend away from the frame 64 to contact the user 60 (FIG. 9D). In yet other embodiments, the sensors 30 may not be physically attached to the frame 64; rather, the sensors 30 may take the form of peripheral sensors 30a (FIG. 9D), which may be spaced apart from the frame 64.

In some embodiments, the display system 2010 may further include one or more outwardly-directed environmental sensors 34 configured to detect objects, stimuli, people, animals, locations, or other aspects of the world around the user. For example, environmental sensors 34 may include one or more cameras, altimeters, barometers, chemical sensors, humidity sensors, temperature sensors, external microphones, thermal imaging sensor, timing devices (e.g., clocks or calendars), or any combination or subcombination thereof. In some embodiments, multiple (e.g., two) microphones may be spaced-apart, to facilitate sound source location determinations. In various embodiments including environment sensing cameras, cameras may be located, for example, facing outward so as to capture images similar to at least a portion of an ordinary field of view of a user. Environmental sensors may further include emissions devices configured to receive signals such as laser, visible light, invisible wavelengths of light, sound (e.g., audible sound, ultrasound, or other frequencies). Physical contact sensors, such as strain gauges, curb feelers, or the like, may also be included as environmental sensors.

In some embodiments, the display system 2010 may further include one or more ultrasonic probes 1081 configured to direct acoustical energy to or contact parts of the user's eye (e.g., upper eyelid, eye orbit, sclera, cornea, etc.), the user's head, (e.g., forehead, temple, portions of the skull, etc.), the user's face, or the user's neck. The one or more probes 1081 may be configured to transmit ultrasound to various regions of the user's eye, head/face or neck as well as receive ultrasound reflected from various regions of the user's eye, head/face or neck. For example, the one or more probes 1081 may be connected to an ultrasonic transmitter 1077 configured to emit ultrasonic energy to the user's eye, user's head, user's face, or user's neck and an ultrasonic receiver 1079 configured to receive ultrasonic energy reflected and/or scattered back from various structures in the user's eye, head, face, or neck. In some embodiments, the one or more probes 1081 may be connected to an ultrasonic transceiver 1075 that combines both the ultrasonic transmitter and receiver. In some embodiments, the display system may be configured to deliver ultrasonic energy to various parts of the user's eye, head, face, or neck without contacting one or more parts of the user's eye, head/face or neck. For example, the display system 2010 may comprise an electromagnetic acoustic transducer (EMAT) that is configured to deliver ultrasonic energy without contacting various parts of the user's anatomy.

In some embodiments, the display system 2010 may further be configured to receive other environmental inputs, such as GPS location data, weather data, date and time, or other available environmental data which may be received from the internet, satellite communication, or other suitable wired or wireless data communication method. The processing module 70 may be configured to access further information characterizing a location of the user, such as pollen count, demographics, air pollution, environmental toxins, information from smart thermostats, lifestyle statistics, or proximity to other users, buildings, or a healthcare provider. In some embodiments, information characterizing the location may be accessed using cloud-based or other remote databases. The processing module 70 may be configured to obtain such data and/or to further analyze data from any one or combinations of the environmental sensors.

The display system 2010 may be configured to collect and store data obtained through any of the sensors and/or inputs described above for extended periods of time. Data received at the device may be processed and/or stored at the local processing module 70 and/or remotely (e.g., as shown in FIG. 9D, at the remote processing module 72 or remote data repository 74). In some embodiments, additional data, such as date and time, GPS location, or other global data may be received directly at the local processing module 70. Data regarding content being delivered to the user by the system, such as images, other visual content, or auditory content, may be received at the local processing module 70 as well.

Neural Connections and Neuroplasticity

I. Neural Processing of Information Including Visual and Multisensory Processing In various embodiments, the systems and methods described herein may be used to investigate and/or modify the brain's processing of visual and/or other sensory information (e.g., multisensory information). The multisensory information can include audio and/or visual information. As discussed herein, the display system may monitor the user's objective and/or subjective reactions or responses to stimuli. The stimuli reactions may be used to determine deficiencies or abnormalities, e.g., identify a neurological condition associated with reactions. Examples of objective responses include eye movements, neural signals, and autonomic responses. Examples of eye movements include, but are not limited to, saccades, pursuits, fixation, vergence, and/or aversion. Examples of subjective responses to stimuli include the user's psychological or emotional reaction to stimuli. Thus, the display system may be configured to use visual stimuli responses to determine the existence of various neurological conditions in the user by measuring neural and psychophysical non-conscious (e.g., preconscious and unconscious) and conscious processing of the visual stimuli.

In some embodiments, the display system may be configured to provide a known stimulus (or stimuli) with known characteristics to the user's eye(s) as a visual input. After the user's eye receives the stimulus, nerve impulses may be generated and carried to the brain and the brain may process the information to form a visual perception. Then, a involuntary or voluntary reaction may occur in the user. The display system may detect these involuntary or voluntary responses as well as other detected biometric information. From the known stimuli and the measured responses, the display system may compare the responses to expected or otherwise known responses to provide a conclusion regarding the presence of a condition, such as a neurological condition, in the user. In some embodiments, the display system may use the response and stimuli information to determine the presence of a deficiency or injury in the brain More generally, the display system may be configured to study the overall processing of visual information by the visual system, including by the afferent and efferent visual systems. By the system or environment providing a stimulus, filtering noise and artifacts from user actions or environment, measuring the user's reaction to the stimulus, and comparing this reaction with an expected reaction or other known reactions, different visual processing pathways and phenomena may be evaluated. Visual processing pathways and phenomena may be evaluated passively, without providing a particular stimulus, as is described in greater detail below.

Because the brain processes visual information at least partially retinotopically and sometimes uses specific anatomy for specific functions, the display system may be configured to identify and assess various features of the user's brain by using stimuli that allow for isolation and localization of the processing or other functionality of such feature. The display system may determine if there is an abnormality if the visual perception, as inferred by the measured user reaction, is not as expected. For example, the display system may determine where an injury is located in the visual pathway (e.g., in the optic tract or optic chiasm) based on the location of a blind spot detected by the system (e.g., in the nasal visual field or temporal visual field). This conclusion may be drawn because damage to the optic chiasm typically causes loss of vision laterally or in the outer temporal field in both eyes (a condition called bitemporal hemianopsia) while damage to the optic tract typically causes loss of half of the visual field in each eye, on the opposite side of the user from the location of the damage to the optic tract. Another example involves identifying damage to the fusiform face area, which is the facial recognition portion of the brain, if the user cannot recognize faces or distinguish between similar or familiar stimuli. Yet another example is a lesion on the primary visual cortex that may cause a user to have blindsight where the user responds to visual stimulus without consciously seeing the stimulus. In some embodiments, the display system may determine if it is a type 1 blindsight where the user may guess aspects of the visual stimulus with a high percentage of accuracy, or a type 2 blindsight where the user may detect that there had been a visual input change within the area of their blindspot.

In various embodiments, the display system may be configured to determine whether the user may be experiencing a hallucination by determining whether they are making a response to a non-existent external stimulus. For example, if the user is experiencing a hallucination, he/she may interact with a non-existent external stimulus by, e.g., talking, looking, or feeling something which is not present (e.g., not detected by sensors of the display system). Hallucinations may be a result of corruption in sensory pathways and/or one or more parts of the brain. For example, where there is a lesion in the fusiform face area and the signal from the eye is also corrupted in some way, the brain may try to resolve the inconsistencies in inputs received through these different pathways by creating a solution that provides a meaning. The content of the hallucination may be governed by the functional regions of the brain affected. Accordingly, the display system maybe configured to detect whether the user is experiencing a hallucination, due to detecting the user making responses to non-existent external stimuli. The presence of a hallucination may be interpreted by the display system to indicate that lesions in the brain may be present.

From the identification of the abnormality, the display system may save the measurements and calculated parameters to a database. The display system may generate an alert to send to the user, or other system or person, to provide notification of the identified abnormality. The display system may also generate a corrective aid to correct the visual abnormality for the user. The display system may save such corrective aid information to a database. The display system may save the measurements and/or calculated parameters to a user profile for future use.

Figure 11:
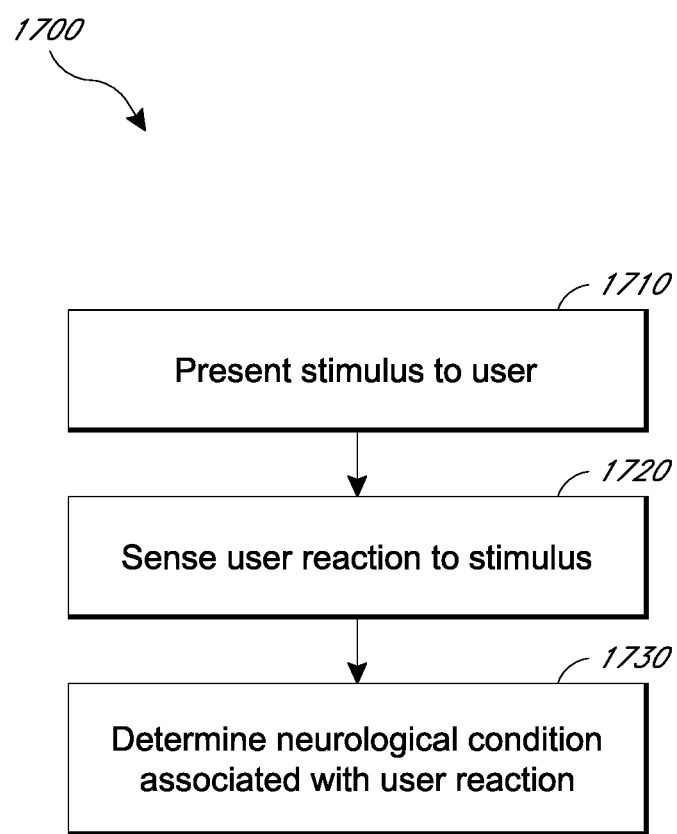
FIG. 11 illustrates an example of a method for determining the presence of a neurological condition using a display system.

With reference now to FIG. 11, an example of a method for determining the presence of a neurological condition 2010 using a display system is illustrated. The display system may be the display systems 80, 1000, or 2010 of FIGS. 9D, 6, and 10, respectively. In some embodiments, the method 1700 may be actively initiated by the user and/or a clinician, e.g., by selecting a particular method 1700 on a menu or otherwise consciously signaling to the display system to commence the method 1700. In some other embodiments, the display system may automatically initiate the method 1700. For example, because the display system may be worn for long durations, e.g., throughout the day, and may monitor the user's behavior in the background, the display system may sense behaviors that may indicate that an impairment or other condition is present. Advantageously, the system may automatically initiate a test to diagnose the possible condition with or without the user's knowledge. Initiating the test without the user's knowledge may be advantageous in eliminating bias caused by the conscious awareness that a test is being performed. For example, if the display system detects that the user is unable to follow directions from a mapping program, it may initiate a right-left disorientation test to determine whether the user is unable to understand prompts to turn left or right.

With continued reference to FIG. 11, at block 1710, the display system may be configured to provide a stimulus that may include visual or audio content displayed to one or both eyes of the user or audio content directed to one or more ears of the user. In addition, the stimulus may be a stimulus in the ambient environment, and providing the stimulus may involve providing a signal regarding an identification of the stimulus detected by the display system.

At block 1720, the display system may sense the user reaction to the stimulus. In some embodiments, the display system may include a physical user interface (e.g., one or more buttons such as a touch sensor on a surface of the display system), a virtual user interface (e.g., one or more icons on a virtual touch screen), an audio recognition system (e.g., a voice recorder), or a movement recognition system (e.g., a motion detector) to allow a user to indicate his or her reaction to the presented image or images. As another example, the display system may include one or more sensors configured to detect the user's reaction. For example, the display system may include cameras (e.g., cameras 24, 28 of the display system 2010, FIG. 10) and/or electrodes (e.g., peripheral sensor electrodes 30a, FIG. 9D) to measure the user's reaction. In some embodiments, sensors external to the display system may be configured to measure the user's reaction and to communicate the measured data to the display system. In addition, the display system may also be configured to monitor environmental variables to, e.g., correlate those environmental variables with the user reaction and/or the eventual conclusion drawn by the display system.

At block 1730, the display system may be configured to determine whether the measured user reaction is indicative of various neurological conditions (e.g., abnormalities), including visual processing conditions. It will be appreciated that the various determinations connected by a display system may be performed by the local processing and data module 70, or the remote processing module 72 (FIG. 9D). In some other embodiments, the display system may be configured to communicate the user reaction data obtained at block 1720 to a health care professional and/or a diagnostic system remote from the display system. The health care professional and/or diagnostic system may make the determination of the neurological condition or may aid in making the determination. For example, the health care professional and/or a diagnostic system may review a preliminary determination made by the display system and/or revise the determination (e.g., by reducing the list of possible neurological conditions).

It will be appreciated that the various blocks 1710, 1720, 1730 may be performed in sequence in some embodiments. In some other embodiments, any one or more of these blocks (e.g., one or both of blocks 1710 and 1720) may be repeated before proceeding to a subsequent block. In yet other embodiments, one of the blocks 1710, 1720, 1730 may be omitted. For example, block 1710 may be omitted and particular features of the user may simply be observed at block 1720 before the display system makes a conclusion regarding a neurological condition.

Neuropsychological Tests, Including Visual Perception Tests

In some embodiments, the display system (e.g., display systems 80, 1000, and 2010 of FIGS. 6, 9D, and 10, respectively) may be configured to perform the method 1700 in relation with various neuropsychological tests, such as visual perception tests. In such neuropsychological tests, the user may be presented a visual stimulus (e.g., one or more images) and then asked to perform a task based on their perception of the visual stimulus. For example, the user may be asked to fixate on the display and then localize the appearance of a stimulus or to indicate whether he or she perceived the stimulus. In some embodiments, to remove the potential for bias that may be caused by placing virtual stimuli on different depth planes or at different locations, the stimuli may be presented such that they are not noticeably on different depth planes or locations. In some other embodiments, the stimuli may be placed in slightly different locations (e.g., at different vergence points), but with the difference too small to be consciously notice by the user. Such lightly different locations may provide advantages by preventing the brain from fusing the two images. Many variations in visual perception tests are contemplated to isolate different structures or mechanisms related to how the brain perceives the stimulus. Example display systems configured to perform the method 1700 to conduct a visual perception test will now be described.

Binocular Rivalry

In some embodiments, the display system may be configured to perform visual perception tests such as binocular rivalry-based tests. Referring to block 1710 in FIG. 11, in these tests, the display system may be configured to provide stimuli that may include a different image displayed to each eye, which may create conflict in processing visual input in the brain. Instead of a fusion of the two images, such a conflict may cause visual perception to alternate between the images as the images compete for perceptual dominance. When a dominant percept begins to be suppressed, a mixed percept may be perceived, which may then switch to the other, now dominant, percept. As one example, a first image may be presented to one eye, and a second image, different from the first image, may be presented to the other eye. When the first image is the dominant percept, only the first image may be perceived. When the second image is the dominant percept, only the second image may be perceived. During transitions alternating between the first and second images, a mixed image of the first and second images may be perceived.

The images for each eye may be presented in various embodiments simultaneously, in alternation, selectively to one eye, or combinations thereof. The images may trigger rivalry and may influence the alternations of perception over time. In some instances, the binocular rivalry-based test may include one or more different types of rivalry. For example, in some embodiments, the presented images may provide for contour rivalry by differing in contour or spatial configurations. In contour rivalry, a same image may be perceived differently such as an image having lines that form a first design (e.g., a vase) when viewed a first way, and a second design (e.g., two faces) when viewed in a second, different way (e.g., by flipping or turning the image). When such an image is presented to one eye, and the inverse of the image is presented to the other eye, the images may compete for perceptual dominance. As another example, in some embodiments, the presented images may provide for chromatic rivalry by differing in color configurations. As yet another example, in some embodiments, the presented images may provide for binocular luster by differing in luminances.

It will be appreciated that the perception of the stimuli (e.g., the images) by the user may be influenced by various aspects of visual perception including but not limited to interocular suppression, interocular grouping, and/or the Troxler's effect. The occurrence of these aspects of visual perception may be engaged by presenting particular stimuli in a particular fashion. For example, some embodiments may provide for interocular suppression by presenting a certain image to only one eye. The typical brain may perceive the image until it is suppressed by a blank field, in which the display system blocks light reaching the user's eye or displays a blank image, or until the image is suppressed by an image presented to the other eye. As another example, some embodiments may provide for interocular grouping by presenting portions of an image to one eye, and other portions of the image to the other eye. The typical brain may reassemble the portions from each eye to perceive a coherent image. As another example, some embodiments may also provide for interocular grouping by switching back and forth between two different images among the eyes. The typical brain sometimes may perceive only one of the two images for a duration of time even though both images continue to be exchanged back and forth. As yet another example, the display system may be configured to provide stimuli that invokes the Troxler effect. When focusing on a particular portion of an image, the typical brain may cause spontaneous fading of another portion of the image (e.g., a portion of the image located away from the portion focused upon) due to retinal adaptation.

Referring to block 1720 in FIG. 11, in various embodiments configured to perform a binocular rivalry-based test, the display system may sense the user reaction to the stimulus (e.g., by measuring or inferring the perceptual states of dominance and/or suppression). In some embodiments, the display system may include a physical user interface (e.g., one or more buttons such as a touch sensor on a surface of the display system), a virtual user interface (e.g., one or more icons on a virtual touch screen), an audio recognition system (e.g., a voice recorder), or a movement recognition system (e.g., a motion detector) to allow a user to indicate his or her perception in response to the presented image or images, while allowing the display system to sense the user reaction. For example, the user may indicate whether he or she perceives the first image, the second image, and/or the mixed image. As another example, the user may indicate what portions and/or colors of an image he or she perceives, whether he or she perceives a reassembled coherent image, etc.

As another example, some embodiments may use sensors that are part of the display system and/or sensors that are separate from the display system to measure the user's reaction to the applied stimuli. In some embodiments, the display system may be configured to determine the user's reaction (e.g., determining which image is being perceived) by measuring actions (e.g., using an inwardly facing camera 24 (FIG. 10)) governed by the efferent visual system, e.g., fixation, saccades, pursuits, etc. In some embodiments, the display system may be configured to determine the user's reaction by displaying the images on two or more different depth planes and/or in two or more different locations. Because the suppressed image is not perceived, both eyes may change to provide the accommodation and/or vergence that is correct for the dominant image. Thus, the display system may determine which image is perceived by the user by measuring (e.g., imaging) the user's eyes to determine which image corresponds to the accommodation and/or vergence of the user's eyes. In some other embodiments, the user's reaction may be determined by measuring the length of time spent viewing each image. The length of time spent on an image may expose which image is more dominant (and viewed for longer durations) and/or could be tied to determining one's preference in stimuli based on user experiences, knowledge, etc. In some other embodiments, optokinetic nystagmus (OKN), visual evoked potential (VEP), magnetoencephalography (MEG), and/or blood-oxygen level dependent (BOLD) contrast imaging using functional magnetic resonance imaging (fMRI) may be used to infer the perceptual states of dominance and/or suppression (e.g., by determining which eye appears to be actively viewing an image). Using VEP, MEG, and BOLD, the amplitude of dominance and/or suppression may be determined. Using OKN, the velocity may be determined.

Referring to block 1730 in FIG. 11, in various embodiments configured to perform a binocular rivalry-based test, the display system may be configured to determine whether the measured or inferred perceptual dominance and/or suppression is indicative of various visual perception and/or neurological conditions involving physiological dominance and/or neural connections. It will be appreciated, that the various determinations connected by a display system may be performed by the local processing and data module 70, or the remote processing module 72 (FIG. 9D). In some other embodiments, a health care professional and/or a diagnostic system in communication with the display system may make the determination of the neurological condition or made aid in making the determination. For example, the health care professional and/or a diagnostic system may review a preliminary determination made the by the display system and/or revise the determination (e.g., by reducing the list of possible neurological conditions).

As an example, the strength of dominance and/or suppression may be associated with the balance of inhibitory (e.g., GABAergic neuron bursts) and/or excitatory (e.g., glutaminergic neuron bursts) cortical dynamics. Longer times to make the perception switch, e.g., suppress one image, compared to a typical brain may indicate reduced levels of GABAergic action. Some embodiments may be used in evaluations for autism, where fewer perceptual switches and a reduced proportion of perceptual suppression are generally demonstrated.

As another example, the contribution of the non-dominant eye in contour rivalry may be suppressed by visuomotor mechanisms (e.g., the pupillary light reflex). Thus, in some embodiments, the measured or inferred perceptual suppression may be used to determine whether the user has a visual processing condition relating to visuomotor mechanisms.

As yet another example, the reassembly process of portions of an image during interocular grouping may occur beyond the input layers of the visual cortex of the brain, suggesting that suppressed portions of an image may be represented in the primary visual cortex even for a short duration. Thus, in various embodiments, the strength of a user's ability or inability to reassemble parts of an image may be used to determine whether the user has an abnormality relating to the primary visual cortex of the brain.

In some embodiments, personality and/or social influences on perception may also be analyzed to determine whether a user has a neurological condition relating to personality and/or social influences. When there is rivalry, the brain is generally attracted to the stronger or more dominant stimulus. For example, if the stimulus presented to one eye comprises an image with high contrast, and the stimulus presented to the other eye comprises an image with lower contrast, the eye is generally drawn more to the higher contrast image since the brain distinguishes objects and features based on the difference in light and color. Based on one's experiences, as described herein, there may also be different learned associations with objects, features, etc. If there is a negative association with the object, the brain may suppress it in avoidance. If there is a positive association, the brain may make the image more dominant. For example, when presented with portions of two different images in both eyes, the user may reassemble (e.g., using interocular grouping) and perceive only one of the two images. In some embodiments, this may be attributed to positive social or behavioral experience/association with the object in the reassembled image. As another example, gaze aversion as determined from tracking the eyes of the viewer, may be attributed to personality and/or social influences. In some cases, gaze aversion may be indicative of shyness, guilt, or autism in the user. Gaze aversion may also be indicative of the user's culture (e.g., where direct gaze is deemed confrontational).

Monocular Rivalry/Pattern Alternation

In some embodiments, the display system may be configured to perform visual perception tests such as monocular rivalry-based tests in which different images are presented to the same eye. Referring back to block 1710 in FIG. 11, in these tests, the display system may be configured to provide stimuli that may include a first image and a second, different image displayed superimposed to one eye. After viewing the superimposed images for some time, the first image may be perceived as clearer than the second image, then the second image may be perceived as clearer than the first image. At times, only the first or the second image may be perceived. Without being limited by theory, monocular rivalry may be explained to occur by similar mechanisms as for binocular rivalry (e.g., competition for perceptual states of dominance or suppression), or by afterimages and/or eye movements. In some embodiments, the display system may also similarly, separately present one or more images to the other eye.

Referring to block 1720 in FIG. 11, in various embodiments configured to perform a monocular rivalry-based test, the display system may sense the user's reaction to the stimulus (e.g., by measuring the user's perceptual states of dominance and/or suppression) similarly as described herein for binocular rivalry-based tests. In some embodiments, the display system may include a physical user interface, a virtual user interface, an audio recognition system, or a movement recognition system to allow a user to indicate his or her perception in response to the presented images (e.g., whether he or she perceives superimposed images, superimposed images with a clearer first image, superimposed images with a clearer second image, only the first image, and/or only the second image), while allowing the display system to sense the user reaction.

As described herein for binocular rivalry-based tests, some embodiments configured to perform monocular rivalry-based tests may determine the user's reaction by measuring components of the efferent visual system (e.g. fixation, saccades, pursuits, etc.), by placing the images on two different depth planes, or at two different locations on a given depth plane, and/or by determining the length of time spent on each image. The matching of the vergence/accommodation of the user's eyes with a particular image and/or the length of time spent on an image may expose which image is more dominant and/or could be tied to determining one's preference in stimuli based on user experiences, knowledge, etc. For example, if the user's favorite color is blue, the user may view a first blue image for a longer length of time than a second superimposed red image. Some embodiments may be used to study neuropsychology and visual perception on people who are color blind to determine how well they are able to distinguish between the two images and if their eyes changed in accommodation and/or vergence (e.g., if the a red image was on a different depth plane or at a different location than a second superimposed green image). In some embodiments, OKN, VEP, MEG, and/or BOLD may also be used to determine the user's reaction to the images to infer dominance and/or suppression.

Referring to block 1730 in FIG. 11, in various embodiments configured to perform a monocular rivalry-based test, the display system may be configured to determine whether the measured perceptual dominance and/or suppression is indicative of various neurological conditions involving physiological dominance and/or neural connections. Similar to the examples described with respect to binocular rivalry-based tests, some embodiments may be configured to determine whether a user has a neurological condition relating to abnormalities in the user's balance of inhibitory and/or excitatory cortical dynamics, visuomotor mechanisms, the primary visual cortex of the brain, personality and/or social influences.

Flash Suppression

In some embodiments, the display system may be configured to perform visual perception tests such as flash suppression-based tests. By presenting images differing in respective rates of flicker, the user's visual perception may cause a visible image to be invisible. Referring to block 1710 in FIG. 11, in such tests, the display system may be configured to provide stimuli that may include a first image presented to one eye that may be suppressed by a second image flashed to the other eye. The stimuli may be delivered at different frequencies (e.g., different images may be exposed to the viewer with different exposure times or durations), with different images, intensities, etc. As one example, the first image may be displayed to a first eye. A blank field may be presented to the second eye. The second image may then be flashed to the second eye (e.g., on the blank field at a corresponding location as the first image in the first eye). Although the first image is still displayed to the first eye, the different stimulus of the second image may result in perception of only the second image. Thus, the second image presented to the second eye may suppress the first image presented to the first eye. Some embodiments may vary the timing of the transition from the first image to the second image.

Referring to block 1720 in FIG. 11, in various embodiments configured to perform a flash suppression-based test, the perceptual state of suppression may be measured or inferred by the display system similarly as described herein for binocular rivalry-based tests. In some embodiments, the display system may include a physical user interface, a virtual user interface, an audio recognition system, or a movement recognition system to allow a user to indicate his or her perception in response to the presented images (e.g., whether he or she perceives the first image and/or the second image), while allowing the display system to sense the user reaction. As described herein for binocular rivalry-based tests, some embodiments configured to perform flash suppression-based tests may determine the user's reaction by measuring components of the efferent visual system (e.g., fixation, saccades, pursuits, accommodation, vergence, etc.), by placing the images on two different depth planes, at two different locations, and/or by determining the length of time spent on each image. The matching of the vergence/accommodation of the user's eyes with a particular image and/or the length of time spent on an image may expose which image is more dominant and/or could be tied to determining one's preference in stimuli based on user experiences, knowledge, etc. As another example, some embodiments may use OKN, VEP, MEG, and/or BOLD to infer the perceptual state of suppression (e.g., by determining which eye appears to be actively viewing an image).

Referring to block 1730 in FIG. 11, in various embodiments configured to perform a flash suppression-based test, the measured or inferred perceptual suppression may be used by the display system as inputs to study the mechanisms of conscious and/or non-conscious visual processing. For example, in flash suppression, when the second image appears, the first image disappears even though it is still present. Without being limited by theory, the brain is understood to be receiving both inputs but because the second image is a new stimulus, the brain subconsciously sees both images and filters out the old image allowing only the new image to be "seen" through conscious awareness. Similar to visual processing by people who are cortically blind or have blindsight, visual information can be used to guide behavior in the absence of visual awareness because of the dissociation of perceiving objects (features, recognition, etc.) and acting/reacting to them. By using a flash suppression-based test, some embodiments may determine the extent of this selective visual attention filter and one's cortical blindness, study the primary visual cortex (V1) independent vision, and/or deliver content purely to the subconscious. Some embodiments may be used for psychological manipulation (e.g., subliminal messages) and/or persuasion in that the first image may still have a cognitive effect on the processing of the second image (e.g., contextual interpretation). For example, some embodiments may be used to desensitize negative triggers (e.g., second consciously seen image) by adding positive associations (first subconsciously seen image). This can be helpful for cognitive behavioral therapy, exposure therapy, distraction therapy, etc.

In one example, some embodiments may be used to study subconscious behaviors. For example, some embodiments may have the user act on a subconsciously seen image and/or to elicit a reaction motor response (e.g., touch a first blue image of a ball). This dorsal stream mediates grasping and reaching movements for visual processing, which is generally different than the ventral stream, which processes intrinsic features of an object.

In another example, some embodiments may be used to study how the user subconsciously reacts (e.g., fight-or-flight) to a stimulus and then to provide therapy. The therapy may include exposure therapy (e.g., treatment for Post-Traumatic Stress Disorder (PTSD), anxiety, phobias, etc.) and/or desensitizing therapy. For example, for someone with arachnophobia, some embodiments may present a first image (e.g., subconsciously seen) of a spider flying at them and a second image of a butterfly (e.g., consciously seen). Some embodiments may determine the extent of the trigger (e.g., person panicking as determined by measuring heat rate, pupil dilation, accelerated breathing patterns, etc.), and then provide for exposure therapy (e.g., providing images of spiders to help overcome the fear).

Continuous Flash Suppression

In some embodiments, the display system may be configured to perform visual perception tests such as continuous flash suppression-based tests. Similar to the flash suppression-based tests described herein, the user's visual perception during a continuous flash suppression-based test may cause a visible image to be invisible to the user when the display system presents images differing in the respective rates of flicker. Referring to block 1710 in FIG. 11, in such tests, the display system may be configured to provide stimuli that may include a static image presented to one eye that may be suppressed by a series of dynamic images flashed to the other eye. For example, the static image may be displayed to a first eye. The dynamic images may then be flashed to the second eye. Although the static image is still displayed to the first eye, the changing nature of the dynamic images may result in perception of only the dynamic images. Thus, the dynamic images presented to the second eye may suppress the static image presented to the first eye. In some embodiments, the static image may suppress the dynamic images. Compared to other tests such as binocular rivalry and/or flash suppression-based tests, continuous flash suppression-based tests may allow deeper and/or longer suppression (e.g., five, six, seven, eight, nine, ten, eleven, twelve times longer, or any ranges formed by such values). In some embodiments, suppression may last for one or two minutes. In some instances, suppression may last for three minutes or over three minutes (e.g., for 3.5, 4, 4.5, 5 minutes, or any ranges formed by such values).

Referring to block 1720 in FIG. 11, in various embodiments configured to perform a continuous flash suppression-based test, the perceptual state of suppression may be measured or inferred by the display system similarly as described herein for binocular rivalry-based tests. In some embodiments, the display system may include a physical user interface, a virtual user interface, an audio recognition system, or a movement recognition system to allow a user to indicate his or her perception in response to the presented images (e.g., whether he or she perceives the static and/or the dynamic images), while allowing the display system to sense the user reaction. As described herein for binocular rivalry-based tests, some embodiments configured to perform continuous flash suppression-based tests may determine the user's reaction by measuring components of the efferent visual system (e.g., fixation, saccades, pursuits, accommodation, vergence, etc.), by placing the images on two different depth planes, at two different locations, and/or by determining the length of time spent on each image. The matching of the vergence/accommodation of the user's eyes with a particular image and/or the length of time spent on an image may expose which image is more dominant and/or could be tied to determining one's preference in stimuli based on user experiences, knowledge, etc. As another example, some embodiments may use OKN, VEP, MEG, and/or BOLD to infer the perceptual state of suppression (e.g., by determining which eye appears to be actively viewing an image).

Referring to block 1730 in FIG. 11, in various embodiments configured to perform a continuous flash suppression-based test, the measured or inferred perceptual suppression may be used by the display system as inputs to study the mechanisms of pre-conscious and/or non-conscious visual processing. For example, visual stimuli presented concurrently with the heartbeat may suppress visual awareness and be more difficult to distinguish, suggesting that cardiac interoceptive signals may affect visual awareness. In some embodiments, the display system may be configured to analyze the influence of interoceptive signals on visual awareness and whether a user has a visual processing and/or neurological condition relating to cardiac interoceptive signals.

In addition, various embodiments may be used similarly as described herein for embodiments configured to perform flash suppression-based tests, and in some cases, may have a more pronounced effect. For example, some embodiments may create multiple reassociations to an image (e.g., stronger subliminal messaging). The static images may have a cognitive effect on the processing of the flashing images such as contextual interpretation. Thus, some embodiments may be used for psychological manipulation (e.g., subliminal messages) and/or persuasion and/or for eliciting reaction motor responses to the first static image. This can be helpful for cognitive behavioral therapy, exposure therapy, distraction therapy, etc. For example, some embodiments configured to provide distraction therapy (e.g., burn debridgement) may present words or encouragement and strength as the static underlying image (e.g., subconsciously seen) and an entertaining image as the dynamic image (e.g., consciously seen). As another example, some embodiments configured to provide cognitive behavioral therapy may subconsciously (e.g., subliminally) reassociate patterns of thought and feelings to alter unwanted behavior. Some embodiments may also be used to treat mood disorders, insomnia, depression, eating disorders, etc.

Motion-Induced Blindness (MIB)

In some embodiments, the display system may be configured to perform visual perception tests such as motion-induced blindness-based tests. Due to motion in an image, a user's visual perception may cause part of a visible image to disappear. Referring to block 1710 in FIG. 11, in such tests, the display system may be configured to provide stimuli that may include images having a stationary portion and a moving portion. For example, an image comprising a stationary portion among a moving background may be provided to the user's eyes. When the user focuses on a portion of the image (e.g., a stationary dot or a blinking dot in front of the moving background), the stationary portion of the image (e.g., stationary dots surrounding the portion focused upon) may appear to disappear. Thus, the moving background may induce blindness in the user to a portion of the image.

Referring to block 1720 in FIG. 11, in various embodiments configured to perform a motion-induced blindness-based test, the perceptual state of suppression may be measured similarly as described herein for binocular rivalry-based tests. In some embodiments, the display system may include a physical user interface, a virtual user interface, an audio recognition system, or a movement recognition system to allow a user to indicate his or her perception in response to the presented images (e.g., whether he or she may or may not perceive the stationary portion of the image), while allowing the display system to sense the user reaction. As described herein for binocular rivalry-based tests, some embodiments configured to perform motion-induced blindness-based tests may determine the user's reaction by measuring components of the efferent visual system (e.g., fixation, saccades, pursuits, accommodation, vergence, etc.), by placing the images on two or more different depth planes or in two or more different locations, and/or by determining the length of time spent on each image. The matching of the vergence/accommodation of the user's eyes with a particular image and/or the length of time spent on an image may expose which image is more dominant and/or could be tied to determining one's preference in stimuli based on user experiences, knowledge, etc. In some embodiments, OKN, VEP, MEG, and/or BOLD may also be used to infer the perceptual state of suppression (e.g., by determining which eye appears to be actively viewing an image).

Referring to block 1730 in FIG. 11, the measured perceptual suppression may be used by the display system as inputs to study the mechanisms of conscious and/or non-conscious visual processing. Some embodiments may be used to study the extent of retinal adaptation. While interocular motion vision may be limited in some instances, static observation may cause diminution of retinal photoreceptor responses. During saccades, there may be no conscious perception, while during pursuits, one may be able to fully track an object. Accordingly, various embodiments may take this into consideration and be used in studying saccades and pursuits. For example, in some embodiments performing saccades testing, new stimuli may be constantly dynamically projected to the user, causing reflexive saccades. If the user is unable to suppress the reflexive saccades, various embodiments may determine the user has a sign of dementia or Parkinson's disease. As another example, in some embodiments performing pursuits testing, if there is impaired smooth pursuits, some embodiments may determine the user has a sign of a traumatic brain injury or dementia. If there is lack of visual tracking, some embodiments may determine the user has cortical blindness.

Motion-Induced Interocular Suppression

In some embodiments, the display system may be configured to perform visual perception tests such as motion-induced interocular suppression-based tests. Referring to block 1710 in FIG. 11, in such tests, the display system may be configured to provide stimuli that may include a stationary image presented to one eye and a moving image presented to the other eye. For example, the stationary image may be displayed to a first eye. The moving image may be displayed to a second eye (e.g., with moving content at a similar location within that second eye's field of view as the location of content within the first image to the first eye). Although the stationary image is still displayed to the first eye, the moving image displayed to the second eye may suppress the stationary image (e.g., render invisible the image presented at the fovea). In some instances, the suppression may occur for a relatively long period of time. For example, if the dynamic image is constantly changing and interesting to the user, the level of engagement and interactions (e.g., suppression time of the static image) will generally increase and vice versa. In some embodiments, a user may be able to detect flicker at repetition rates lower than about 60 Hz, 55 Hz, 50 Hz, 45 Hz, 40 Hz, 35 Hz, or 30 Hz. The suppression time may be affected by various other factors such as image size and changes.

Referring to block 1720 in FIG. 11, the perceptual state of suppression may be measured or inferred by the display system similarly as described herein for binocular rivalry-based tests. In some embodiments, the display system may include a physical user interface, a virtual user interface, an audio recognition system, or a movement recognition system to allow a user to indicate his or her perception in response to the presented images (e.g., whether he or she perceives the stationary image and/or the moving image), while allowing the display system to sense the user reaction. As described herein for binocular rivalry-based tests, some embodiments configured to perform motion-induced interocular suppression-based tests may determine the user's reaction by measuring components of the efferent visual system (e.g., fixation, saccades, pursuits, accommodation, vergence, etc.), by placing the images on two different depth planes, at two different locations, and/or by determining the length of time spent on each image. The matching of the vergence/accommodation of the user's eyes with a particular image and/or the length of time spent on an image may expose which image is more dominant and/or could be tied to determining one's preference in stimuli based on user experiences, knowledge, etc. As another example, some embodiments may use OKN, VEP, MEG, and/or BOLD to infer the perceptual state of suppression (e.g., by determining which eye appears to be actively viewing an image).

Referring to block 1730 in FIG. 11, in various embodiments configured to perform a motion-induced interocular suppression-based test, the measured or inferred perceptual suppression may be used by the display system as inputs to study the mechanisms of conscious and/or non-conscious visual processing. As one example, some embodiments may be used to study the level of visual input from each eye and the suppression of visual input in a weak eye, such as in amblyopia. For example, some embodiments may compare the level of processing and perception of the dynamic image in each eye. As another example, some embodiments may be used as a therapeutic. For example, by giving the weak eye a dynamic image to focus on, motion-induced interocular suppression may suppress the static image in the strong eye and thereby strengthen the visual input coming from the weak eye.

Backward Masking

In some embodiments, the display system may be configured to perform visual perception tests such as backward masking-based tests in which visual perception may cause an image presented later in time to mask an image presented earlier in time. Referring to block 1710 in FIG. 11, in such tests, the display system may be configured to provide stimuli that may include a first image presented briefly to the eyes of the user and then a second image also presented to the user's eyes. For example, the first image may be displayed to the eyes (e.g., displayed for less than or equal to 50 ms, such as from 1 ms to 50 ms, from 1 ms to 40 ms, or from 1 ms to 30 ms). The second image may then be displayed to the eyes (e.g., displayed for greater duration than the firsts image, such as longer than 50 ms). The relatively immediate presentation of the second image may cause failure of conscious perception of the first image. Thus, the second image may mask the first image.

Referring to block 1720 in FIG. 11, in various embodiments configured to perform a backward masking-based test, the perceptual state of suppression may be measured similarly as described herein for binocular rivalry-based tests. In some embodiments, the display system may include a physical user interface, a virtual user interface, an audio recognition system, or a movement recognition system to allow a user to indicate his or her perception in response to the presented images (e.g., whether he or she may perceive the first image, the second image, and/or both images), while allowing the display system to sense the user reaction. As described herein for binocular rivalry-based tests, some embodiments configured to perform backward masking-based tests may determine the user's reaction by measuring components of the efferent visual system (e.g., fixation, saccades, pursuits, accommodation, vergence, etc.). Some embodiments may also determine if the first or second image is perceived by placing the images on two or more different depth planes or in two or more different locations such that the accommodation and/or vergence may be measured. The matching of the vergence/accommodation of the user's eyes with a particular image and/or the length of time spent on an image may expose which image is perceived. In some embodiments, based on the time required for the eye to jump to the flashed image, the display system may determine if the user response was a voluntary eye movement or a reflexive saccade to new stimuli. Since during saccades there is substantially no conscious perception, certain embodiments may determine the extent of retinal adaptation by testing the user on their comprehension of the first image. Some embodiments may also be used to train visual processing speed and attention, visual-spatial processing, and/or memory and executive functions. In some embodiments, OKN, VEP, MEG, and/or BOLD may also be used to determine which image is perceived by the viewer (e.g., by determining which eye appears to be actively viewing an image).

Referring to block 1730 in FIG. 11, in various embodiments configured to perform a backward masking-based test, the measured perceptual suppression may be used by the display system as inputs to study the mechanisms of conscious and/or non-conscious visual processing. Some embodiments may be used for psychological manipulation (e.g., subliminal messages) and/or persuasion in that the first image may still have a cognitive effect on the processing of the second image (e.g., contextual interpretation). This can be helpful for cognitive behavioral therapy, exposure therapy, distraction therapy, desensitizing therapy, etc. Some embodiments may also be used to identify abnormal responses to stimuli and diagnose disorders (e.g., triggers from Post-Traumatic Stress Disorder (PTSD), Obsessive Compulsive Disorder (OCD), anxiety, phobias, etc.) by comparing responses to particular images between different users.

Without being limited by theory, it is believed that visually masked images may influence responses by the user (e.g., due to response priming, subliminal messages, psychorama, etc.). It will be appreciated that such influence may beneficially be applied to modulate the user's responses to various stimuli and to aid the user in achieving a desired response. In some embodiments, the masked images may be used to calm the user in high-stress environments. For example, in environments in which the display system determines that the user sees an object that is known to elicit a strong negative emotional reaction, the display system may be configured to display a masked image that has previously been established to calm the user. The masked image may include graphics, photographic content, words, etc. As described herein with respect to continuous flash-suppression-based tests, some embodiments may reassociate the object having a strong negative emotional reaction with calming emotions by displaying calming stimuli, which may be, e.g., visual and/or auditory.

In some embodiments, the efficacy of the masked image in influencing user responses may be efficiently determined using the display system. For example, because the user may wear the display system everyday, a large number of opportunities exist on a daily basis for testing the efficacy of different masked images. Consequently, in some embodiments, blocks 1720 and 1730 may be performed at different times over the course of a day or multiple days (e.g., on a daily basis) with varying masked images, and the user's responses to the masked images, which may be correlated with other environmental variables or biometric data, may be catalogued by the display system. As a result, a database of masked images and expected user responses may be built. The display system may then access this database to provide the appropriate masked image, depending on the user response that is sought.

Forward Masking

In some embodiments, the display system may be configured to perform visual perception tests such as a forward masking-based test in which visual perception may cause a first image presented earlier in time to mask a second image presented later in time. Referring to block 1710 in FIG. 11, in such a test, the display system may be configured to provide stimuli that may include the first image and the second image. For example, the first image may be displayed to the eyes (e.g., for a duration longer than the duration that the later second image is displayed, such as longer than 50 ms). The second image may then be displayed to the eyes (e.g., displayed for a duration less than or equal to 50 ms, such as from ]1 ms to 50 ms, or from 1 ms to 30 ms). Thus, the first image may mask the second image.

Referring to block 1720 in FIG. 11, in various embodiments configured to perform a forward masking-based test, the perceptual state of suppression may be measured similarly as described herein for binocular rivalry-based tests. In some embodiments, the display system may include a physical user interface, a virtual user interface, an audio recognition system, or a movement recognition system to allow a user to indicate his or her perception in response to the presented images (e.g., whether he or she may perceive the first image, the second image, and/or both images), while allowing the display system to sense the user reaction. As described herein for binocular rivalry-based tests, some embodiments configured to perform forward masking-based tests may determine the user's reaction by measuring components of the efferent visual system (e.g., fixation, saccades, pursuits, accommodation, vergence, etc.). Some embodiments may also determine if the first or second image is perceived by placing the images on two different depth planes or two different locations such that the accommodation and/or vergence may be measured. The matching of the vergence/accommodation of the user's eyes with a particular image and/or the length of time spent on an image may expose which image is perceived. In some embodiments, based on the time required for the eye to jump to the flashed image, the display system may determine if the user response was a voluntary eye movement or a reflexive saccade to new stimuli. Since during saccades there is substantially no conscious perception, certain embodiments may determine the extent of retinal adaptation by testing the user on their comprehension of the first image. Some embodiments may also be used to train visual processing speed and attention, visual-spatial processing, and/or memory and executive functions. In some embodiments, OKN, VEP, MEG, and/or BOLD may also be used to determine which image is perceived by the viewer (e.g., by determining which eye appears to be actively viewing an image).

Referring to block 1730 in FIG. 11, in various embodiments configured to perform a forward masking-based test, the measured perceptual suppression may be used by the display system as inputs to study the mechanisms of conscious and/or non-conscious visual processing. Some embodiments may be used for psychological manipulation (e.g., subliminal messages) and/or persuasion in that the first image may still have a cognitive effect on the processing of the second image (e.g., contextual interpretation). This can be helpful for cognitive behavioral therapy, exposure therapy, distraction therapy, desensitizing therapy, etc. Some embodiments may also be used to identify abnormal responses to stimuli and diagnose disorders (e.g., triggers from Post-Traumatic Stress Disorder (PTSD), Obsessive Compulsive Disorder (OCD), anxiety, phobias, etc. by comparing responses to different stimuli between different users.

As disclosed above regarding backward masking, without being limited by theory, visually masked images, such as provided by forward masking, may influence responses by the user (e.g., due to response priming, subliminal messages, psychorama, etc.). This ability to influence user responses may be utilized as described above regarding forward masking.

Binocular Luster (Contrast Sensitivity)

In some embodiments, the display system may be configured to perform visual perception tests such as contrast sensitivity-based tests to determine a user's level of contrast sensitivity. Contrast may be determined by the color and luminance of an object relative to the background or other objects in the same field of view. Notably, the typical eye is generally more sensitive to contrast than to absolute luminance. Referring to block 1710 in FIG. 11, in contrast sensitivity-based tests, the display system may be configured to provide images with different levels of contrast (e.g., images with objects have different colors and/or brightness within the same image) to one or both eyes.

Referring to block 1720 in FIG. 11, in various embodiments configured to perform a contrast sensitivity-based test, the display system may sense the user reaction to the stimulus (e.g., measure the user's contrast sensitivity) similarly as described herein for binocular rivalry-based tests. In some embodiments, the display system may include a physical user interface, a virtual user interface, an audio recognition system, or a movement recognition system to allow a user to indicate his or her perception in response to the presented images (e.g., whether he or she may perceive an image and/or which image has higher/lower contrast compared to other images), while allowing the display system to sense the user reaction. One way of determining the user's reaction (e.g., determining which image is being perceived) includes measuring components of the efferent visual system, e.g., fixation, saccades, pursuits, etc. Another method for determining the user's reaction includes placing images with different color and/or luminance on two different depth planes, or at two different locations as disclosed herein, such that the accommodation and/or vergence of the user's eyes may be measured to determine which image is perceived by the user, thereby allowing the system to determine if the difference in contrast is perceived.

Referring to block 1730 in FIG. 11, in various embodiments configured to perform a contrast sensitivity-based test, the display system may be configured to characterize, monitor, and/or determine a condition relating to visual processing. For example, some disorders of the retina may cause decreased contrast sensitivity. The disorders may include Age-Related Macular Degeneration (ARMD), amblyopia, and lens abnormalities (e.g., cataracts). Thus, some embodiments may be configured to characterize, monitor, and/or determine whether the user has a condition relating to ARMD, amblyopia, or lens abnormalities. As another example, neural dysfunctions such as Alzheimer's disease and stroke, may cause decreased contrast sensitivity. Thus, some embodiments may be configured to characterize, monitor, and/or determine whether the user has a condition relating to Alzheimer's disease and/or stroke. It will be appreciated that the characterization and monitoring may be utilized to determine the degree of dysfunction caused by the various diseases and health conditions noted above to, e.g., determine the severity and/or progression of the diseases or health conditions and in turn recommend or adjust the treatment protocol based on the biofeedback.

Mental Status Testing

In some embodiments, the display system (e.g., display systems 80, 1000, and 2010 of FIGS. 9D, 6, and 10, respectively) may be configured to acquire and process data from various sensors to identify, track, and/or monitor physical and behavioral responses of a user to obtain information regarding a user's mental status. Mental status testing may be used to assess and differentiate between a patient's cognitive and behavioral functioning. Example display systems configured to perform these diagnostic, therapeutic, and perceptual learning tasks will now be described.

Mini-Mental State Examination

In some embodiments, a wearable display system such as the systems depicted in FIGS. 6, 9D, and 10 can implement the mini-mental state examination or Folstein test to assess a user's cognitive functioning. The mini-mental state examination may be implemented to detect cognitive impairment associated with conditions such as Alzheimer's disease, dementia, or other conditions, and may further be conducted repeatedly over an extended time period to assess cognitive changes of a user and/or a response of a user to a treatment and/or therapy. For example, with reference to FIG. 9D, performing the mini-mental state examination may include detecting responses to imagery and/or audio presented to the user 60 at display 62 and/or speakers 66, for example, at microphones 67. With reference to FIG. 10, the system 2010 may monitor the user through inward facing cameras 24, such as to detect eye position, movement, or gaze. The system 2010 may receive audible responses, such as spoken answers to questions of the mini-mental state examination, at sensors 30, which may include microphones.

The MMSE test may include a plurality of simple questions and problems of different types, such as asking the user to provide current time and place, repeating back lists of words, performing simple arithmetic, performing basic motor skills, copying a diagram, and using and comprehending language. The user's responses may be individually scored (e.g., by a clinician observing the test, or by the display system tracking and matching the user's answer and actions to expected answers and actions) and the aggregate score may be determined. Over time, identical or similar questions and problems may be posed (e.g. automatically posed) to a user to track changes in the mental status of the user by tracking changes in their score, both for individual tasks and for the aggregate score.

Alertness

A patient's level of alertness, awareness, or consciousness may be affected by various injuries, conditions, and disorders. Thus, alertness testing may be implemented to detect injuries, conditions, or disorders affecting mental state. In the context of visual processing and perception examination, a patient's level of alertness may also indicate how reliably an examination may be performed. Alertness testing may also be incorporated in any of various types of cognitive and/or behavioral testing as described herein, such as at or near the beginning of an examination, to indicate how reliably the remainder of the exam may be performed.

In some embodiments, alertness testing may be implemented in a wearable display system such as the systems depicted in FIGS. 9D, 6, and 10. For example, with reference to FIG. 9D, detecting and/or tracking a user's level of alertness in an augmented or virtual reality display system 80 may include detecting responses to guided imagery and/or audio presented to the user 60 at a display 62 and/or speakers 66. With reference to FIG. 10, the system 2010 may monitor the user through inward facing cameras 24 for eye tracking, such as to detect eye position, movement, or gaze. For example, the inward facing cameras 24 may detect that a user's eyes are not rotating or accommodating in response to a changing image presented by light sources 26, indicating that the user has a low level of alertness. Inward facing cameras 24 may further be configured to image the eyelids of a user to determine the position and/or motion of the eyelids. For example, drooping or closing eyelids may indicate that a user has a low level of alertness (e.g., that the user is drowsy), while eyelids that remain wide open may indicate that a user has a high level of alertness. The system 2010 may further monitor the user's head pose, such as by motion sensors 32, cameras 28, or other sensors 30. For example, the system may detect that a user's head is drooping forward, indicating the user is falling asleep. In some embodiments, imagery from inward facing cameras 24 may be used to monitor additional signs, such as heart rate based on color of skin and/or motion magnification, to monitor alertness.

Referring now to FIG. 11, the systems and sensors described above may be used according to method 1700 for detection and/or diagnosis of mental states and/or neurological conditions related to a user's level of alertness. Any of the steps of the method 1700 may be carried out at least partially by circuitry of the displays depicted in FIGS. 9D, 6, and 10, such as a processing module 70, remote processing module 72, or other circuitry. The method 1700 may begin at block 1710, where a stimulus is presented to the user. The stimulus may be any type of content delivered to the user through a wearable system such as the head-mounted systems depicted in FIGS. 9D and 10. For example, the stimulus may be a light pattern, image, series of images, video, guided imagery program, or other visual stimulus delivered by a display 62 as described above, or may be a sound or guided audio program delivered by one or more speakers 66. In other embodiments, the stimulus may be an aspect of the environment around the user, rather than content presented by the display 62 or speakers 66. For example, the stimulus may be a nearby car on the road if the user is driving a car, e.g., if the user is speeding or drifting between lanes. Thus, the presentation of a stimulus at block 1710 may be accomplished by the system detecting an object, sound, movement, or other stimulus, in the user's environment, and registering and identifying that stimulus. After a stimulus is presented to the user, the method 1700 may continue to block 1720.

At block 1720, the method may detect a user reaction to the stimulus indicative of the user's state of alertness. The user reaction may include a movement or position of the user's eyes, eye gaze, eyelids, head pose, or other reaction as described herein. The user's level of alertness may then be analyzed, determined, estimated, or otherwise quantified based on the detected reaction. For example, alertness qualities such as consciousness, drowsiness, fatigue, unconsciousness, or other quality may be determined based on the user's reaction to a stimulus. In some embodiments, a user's alertness may be used to determine the level or severity of a user's deficit due to a neurological condition. For example, a user with Alzheimer's disease may be more forgetful when tired or otherwise not alert, than when the user is alert. After the user's reaction to the stimulus has been observed and the user's level of alertness has been analyzed, the method 1700 may continue to block 1730.

At block 1730, the method 1700 may determine one or more neurological conditions associated with the detected user reaction and/or level of alertness. The determination in block 1730 may be carried out locally and/or remotely, and in some aspects may include referring to, querying, or otherwise interacting with a database or other repository of diagnostic medical information. For example, a low level of consciousness or alertness may indicate conditions such as damage to the reticular formation of the brainstem, unilateral or bilateral lesions of the thalami or cerebral hemispheres, and toxic or metabolic conditions. In an additional example, detected drowsiness may be caused by various conditions including nervous system disorders such as acute disseminated encephalomyelitis, motor disorders such as Parkinson's disease, memory disorders such as Lewy body dementia, and/or injuries such as traumatic brain injury. In yet another example of a detected neurological condition, a detected loss of awareness, alertness, or consciousness may indicate nervous system disorders such as epilepsy, neuromyelitis optica, or Schilder's disease, memory disorders such as Creutzfeldt-Jakob disease or Lewy body dementia, and/or injuries such as stroke, brain aneurysm, or traumatic brain injury. The display system may be configured to conclude that the user suffers from any of the conditions above, based upon the fit between the observed user reaction and the expected symptoms of the various conditions above.

Figure 12:
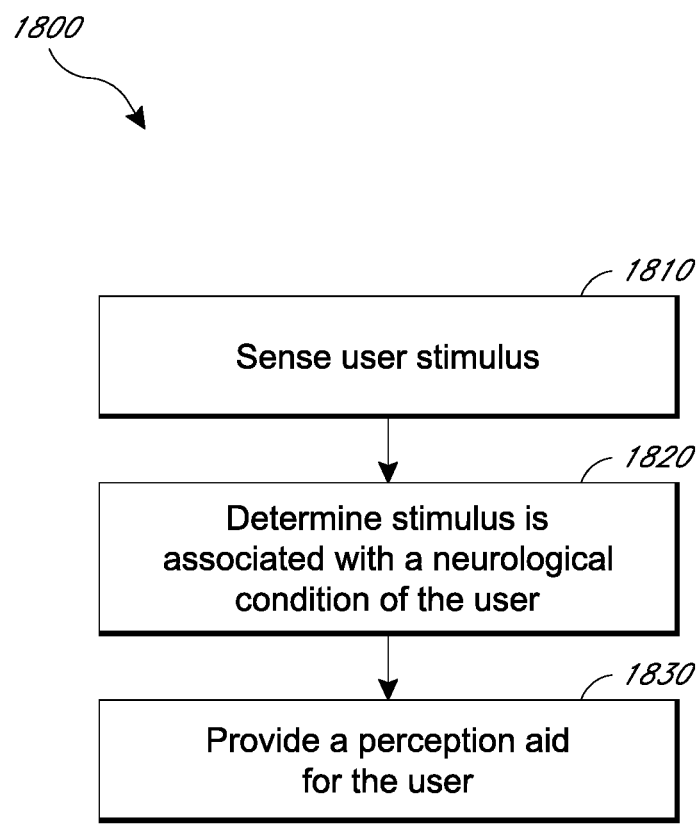
FIG. 12 is a flowchart illustrating an example of a method for displaying a perception aid to the user in response to a neurological condition of the user.

Referring now to FIG. 12, the systems and sensors described above may be used according to method 1800 for therapeutic applications. A therapeutic method 1800 may begin at block 1810, where user stimuli may be sensed or detected, such as described above with reference to FIG. 11. The method 1800 may continue to block 1820, where it is determined that the stimuli are associated with a neurological condition of the user, such as the neurological conditions described above with reference to FIG. 11. After a neurological condition of the user is detected, the method may continue to block 1830.

At block 1830, the method may display a perception aid for the user. A perception aid may be displayed for the user by any of the display systems and/or elements described herein with reference to FIGS. 9D, 6, and 10, such as a display, light source, waveguide stack, or other display element. If it is detected that a user has a neurological condition impairing alertness, attention, or consciousness, a perception aid for the user may include interesting content to increase the user's alertness. For example, the interesting content may include a bright and/or rapidly changing image, an image or video of a subject of known interest to the user, or other visual content likely to gain the attention of the user. If visual content is already being shown to the user when impaired alertness is detected, the visual content may be modified to increase the user's alertness, such as by increasing the brightness or otherwise altering the visual content.

Attention

A user's level of attention may be affected by various injuries, conditions, and disorders. In the context of visual processing and perception examination, a patient's level of attention may also indicate how reliably an examination may be performed. Thus, attention testing may be implemented to detect injuries, conditions, or disorders affecting mental state. Attention testing may also be incorporated in any of various types of cognitive and/or behavioral testing as described herein, such as at or near the beginning of an examination, to indicate how well the remainder of the exam may be performed. Attention testing may additionally be performed as an assessment of a student's engagement in an educational setting. For example, attention testing may be implemented to determine whether a student learns best using visual, auditory, or kinesthetic methods, and the results may be used to teach the student more effectively.

In some embodiments, attention testing may be implemented in a wearable display system such as the systems depicted in FIGS. 9D, 6, and 10. With reference to FIG. 9D, detecting and/or tracking a user's attention in an augmented or virtual reality display system 80 may include detecting responses to guided imagery and/or audio presented to the user 60 at a display 62 and/or speakers 66. With reference to FIG. 10, the system 2010 may monitor the user through inward facing cameras 24 for eye tracking, such as to detect eye position, movement, or gaze. For example, the inward facing cameras 24 may detect that a user's eyes are not rotating or accommodating in response to a changing image presented by light sources 26, indicating that the user is distracted, unfocused, or otherwise exhibiting diminished attention toward the imagery. The system may further monitor the user through additional sensors 30, such as a microphone, to detect spoken responses or other sounds (e.g., a yawn, sigh, involuntary sound, or the like) in response to imagery or audio presented to the wearer and/or detected in the wearer's vicinity.

Referring now to FIG. 11, the systems and sensors described above may be used according to method 1700 for detection and/or diagnosis of mental states and/or neurological conditions related to a user's level of attention. Any of the steps of the method 1700 may be carried out at least partially by circuitry of the displays depicted in FIGS. 9D and 10, such as a processing module 70, remote processing module 72, or other circuitry. The method 1700 may begin at block 1710, where a stimulus is presented to the user. The stimulus may be any type of content delivered to the user through a wearable system such as the head-mounted systems depicted in FIGS. 9D and 10, or may be an aspect of the environment around the user as detected by the wearable system, such as an object, sound, movement, or other environmental stimulus. For example, the stimulus may be a light pattern, image, series of images, video, guided imagery program, or other visual stimulus delivered by a display system as described above, or may be a sound or guided audio program delivered by one or more speakers. After a stimulus is presented to the user, the method 1700 may continue to block 1720.

At block 1720, the method may detect a user reaction to the stimulus indicative of the user's state of attention. In one example, a user in a classroom may not be looking at a teacher or presentation material (e.g., a whiteboard) during a class. Such a reaction of the user may be detected based on the direction of the user's eye gaze, as determined by inward facing cameras of the display system. The user reaction may include a movement or position of the user's eyes or eye gaze as described herein. The user's level of attention may then be analyzed, determined, estimated, or otherwise quantified based on the detected reaction. For example, attention qualities such as focus, distraction, or other quality may be determined based on the user's reaction to a stimulus. After the user's reaction to the stimulus has been observed and the user's attention level has been analyzed, the method 1700 may continue to block 1730.

At block 1730, the method 1700 may determine one or more neurological conditions associated with the detected user reaction and/or level of attention. The determination in block 1730 may be carried out locally or remotely, and in some aspects may include referring to, querying, or otherwise interacting with a database or other repository of diagnostic medical information. As examples, depending upon the reaction measured at block 1720, the display system may determine that a detected inability to maintain attention or to avoid distraction may indicate motor disorders such as Huntington's disease. In additional examples, the display system may determine that diminished attention characteristics are caused by various conditions including memory disorders such as dementia, Alzheimer's disease, Lewy body dementia, or vascular dementia, developmental disorders such as attention deficit hyperactivity disorder, Down's syndrome, fetal alcohol spectrum disorder, or schizophrenia, and/or injuries such as hydrocephalus.

Several example types of attention testing that may be carried out using method 1700 will now be described with reference to FIG. 9D and with continuing reference to FIG. 11. In one example, a user's attention may be tested by presenting the user a simple task as the stimulus at block 1710. For example, a speaker 66 may provide an audible instruction to the user to say forward, and then backward, a sequence such as the letters spelling a word, a provided sequence of numbers, an alphabet, the months of the year, or another suitable sequence. The user may then speak a response, which may be detected by a microphone 67. If the user is able to completely recite the sequence forward and backward, it may be determined that the user has a relatively high level of attention and/or is not distracted. If the user is unable to complete the task, it may be determined that the user is distracted or otherwise inattentive.

In another example, the stimulus at block 1710 may include showing the user an array of similar symbols, such as the letters d and p, or identical symbols of different colors. The user may be asked to mark, indicate, or otherwise select a particular subset of the symbols, for example, all instances of the letter d. At block 1720, the method 1700 may detect the user's response and evaluate its accuracy. For example, a processing module 70 may analyze or "grade" the response based on the number of correctly marked symbols, the number of unmarked symbols that the user should have marked, and/or the number of marked symbols that the user should not have marked based on the task provided to the user. The user's level of attention may then be determined based on the analysis of the response.

In another example, the method 1700 may be used to administer a test of variables of attention (TOVA) or a test of everyday attention (TEA). A TOVA or TEA may involve repeating blocks 1710 and 1720 with a variety of different stimuli provided at block 1710 as repeated, so as to more thoroughly analyze the user's attention. For example, as block 1710 is repeated, the user may be given stimulus tasks such as searching for symbols within a map, counting tasks such as elevator counting with visual aids and/or distractions, and/or a lottery task in which the user is prompted to listen for a predetermined "winning number" in a series of audible numbers. In some embodiments, a TEA may be administered by passively monitoring the user's performance of ordinary tasks, without providing any additional stimulus. For example, a user observed to be frequently distracted and/or constantly looking around may have an attention span deficiency. It may be observed that the user has a higher level of attention for certain tasks, and is more distracted when asked to perform other tasks. At block 1730, the method 1700 may compare the user's performance of a variety of tasks to more accurately detect a neurological condition of the user.

Referring now to FIG. 12, the systems and sensors described above may be used according to method 1800 for therapeutic applications. A therapeutic method 1800 may begin at block 1810, where user stimuli may be sensed or detected, such as described above with reference to FIG. 11. The method 1800 may continue to block 1820, where it is determined that the stimuli are associated with a neurological condition of the user, such as the neurological conditions described above with reference to FIG. 11. After a neurological condition of the user is detected, the method may continue to block 1830.

At block 1830, the method may display a perception aid for the user. A perception aid may be displayed for the user by any of the display systems and/or elements described herein with reference to FIGS. 9D and 10, such as a display, light source, waveguide stack, or other display element. In some embodiments, audible perception aids may be provided by a speaker, either alone or in addition to a visual perception aid. If it is detected that a user has a neurological condition impairing attention, a perception aid for the user may include interesting content to increase the user's attention. For example, the interesting content may include an active video game to orient, maintain, control, and/or regulate the attention of the user. In some embodiments, the perception aid may include positive or negative reinforcement. For example, the method may present positive reinforcement when a user remains focused on a task for a specified time period, and may provide negative reinforcement if the user is frequently distracted.

Orientation

In some embodiments, orientation testing may be performed to determine a user's mental orientation state. For example, orientation testing may allow a diagnostic system to determine that the user is confused or otherwise disoriented. Orientation testing may be implemented in a wearable display system such as the systems depicted in FIGS. 9D, 6, and 10. With reference to FIG. 9D, detecting and/or tracking a user's state of orientation in an augmented or virtual reality display system 80 may include detecting responses to guided imagery and/or audio presented to the user 60 at a display 62 and/or speakers 66. With reference to FIG. 10, the system 2010 may monitor the user through inward facing cameras 24 for eye tracking, such as to detect eye position, movement, gaze, pupil size, or other characteristics. Inward facing cameras 24 may further be configured to image the eyelids of a user to determine the position and/or motion of the eyelids. The system 2010 may further monitor a user's heart rate, sweating, or other physiological signs by peripheral sensors 30a, such as a heart rate sensor, electrodermal activity sensor, or other sensor. For example, a heart rate sensor may detect an elevated heart rate and inward facing cameras 24 may detect mydriasis (dilation of the pupil), indicating that the user is experiencing panic. In another example, if a user is observed to have difficulty speaking (e.g., slurred words), the system 2010 may be able to determine if the difficulty is due to the user being tired (e.g., indicated by head dipping detected at an accelerometer) or due to a condition such as a stroke (e.g., indicated by facial muscles not functioning properly, detected by an electrodermal activity sensor).

Referring now to FIG. 11, the systems and sensors described above may be used according to method 1700 for detection and/or diagnosis of mental states and/or neurological conditions related to a user's state of orientation. Any of the steps of the method 1700 may be carried out at least partially by circuitry of the displays depicted in FIGS. 9D and 10, such as a processing module 70, remote processing module 72, or other circuitry. The method 1700 may begin at block 1710, where a stimulus is presented to the user. The stimulus may be any type of content delivered to the user through a wearable system such as the head-mounted systems depicted in FIGS. 9D, 6, and 10, or may be a stimulus in the environment around the user as detected by the wearable system, such as an object, sound, movement, or other environmental stimulus. For example, the stimulus may be a light pattern, image, series of images, video, guided imagery program, or other visual stimulus delivered by a display system as described above, or may be a sound or guided audio program delivered by one or more speakers. Some stimuli may include interactive instructions directing the user to provide a response detectable by sensors of the system as described above. For example, in a system including a microphone, the stimulus may include an audible instruction to a user to state the user's full name, the user's location, and the date. After a stimulus is presented to the user, the method 1700 may continue to block 1720.

At block 1720, the method may detect a user reaction to the stimulus indicative of the user's state of orientation. The user reaction may include a movement or position of the user's eyes, eye gaze, or other reaction as described herein. In some embodiments, the user reaction may include a spoken response detectable by one or more microphones 67. The user's state of orientation may then be analyzed, determined, estimated, or otherwise quantified based on the detected reaction. For example, if the user has been instructed to state the user's full name, the user's location, and the date, the system may record the user's response at a microphone 67. The recorded response from the user may then be analyzed, such as by processing module 70 to determine if the user provided a complete and accurate answer. If the answer is incomplete or inaccurate, it may be determined that the user is at least partially disoriented. Results of analysis of a user's response may be combined with physiological data, such as pupil size, eye movement, sweating, heart rate, or other signs, to determine if a user is experiencing confusion, panic, or other sign or symptom. After the user's reaction to the stimulus has been observed and the user's state of orientation has been analyzed, the method 1700 may continue to block 1730.

At block 1730, the method 1700 may determine one or more neurological conditions associated with the detected user reaction and/or state of orientation. The determination in block 1730 may be carried out locally or remotely, and in some aspects may include referring to, querying, or otherwise interacting with a database or other repository of diagnostic medical information. For example, the display system may determine that a state of disorientation and/or confusion may indicate various neurological conditions including nervous system disorders such as acute disseminated encephalomyelitis, epilepsy, or neuromyelitis optica, memory disorders such as Alzheimer's disease, Creutzfeldt-Jakob disease, Lewy body dementia, posterior cortical atrophy, or vascular dementia, and/or injuries such as migraines, stroke, or traumatic brain injury.

Referring now to FIG. 12, the systems and sensors described above may be used according to method 1800 for therapeutic applications. A therapeutic method 1800 may begin at block 1810, where user stimuli may be sensed or detected, such as described above with reference to FIG. 11. The method 1800 may continue to block 1820, where it is determined that the stimuli are associated with a neurological condition of the user, such as the neurological conditions described above with reference to FIG. 11. After a neurological condition of the user is detected, the method may continue to block 1830.

At block 1830, the method may display a perception aid for the user to address the neurological condition determined at block 1820. A perception aid may be displayed for the user by any of the display systems and/or elements described herein with reference to FIGS. 9D, 6, and 10, such as a display, light source, waveguide stack, or other display element. In some embodiments, audible perception aids may be provided by a speaker, either alone or in addition to a visual perception aid. If it is detected that a user has a neurological condition impairing orientation, a perception aid for the user may include content likely to reduce disorientation, such as time and/or location alerts, reminders, or other indicators of person, place, or time. If the user is experiencing panic or confusion, the perception aid may further include images and/or sounds selected to calm the user.

Memory and Learning

A user's memory and/or learning abilities may be affected by various neurological injuries, conditions, and disorders. Thus, memory and learning testing may be implemented to detect injuries, conditions, or disorders affecting mental state. Memory training may further be implemented, for example, through kinesthetic learning. In some aspects, memory training can be implemented for treatment of conditions such as dysgraphia or dyslexia. In some embodiments, memory and learning tests may be implemented in a wearable display system such as the systems depicted in FIGS. 9D, 6, and 10. With reference to FIG. 9D, detecting and/or tracking a user's memory and learning capability in an augmented or virtual reality display system 80 may include detecting responses to guided imagery and/or audio presented to the user 60 at a display 62 and/or speakers 66. With reference to FIG. 10, the system 2010 may monitor the user through inward facing cameras 24 for eye tracking, such as to detect eye position, movement, gaze, or pupil size. Inward facing cameras 24 may further be configured to monitor other facial indicators such as eyelid position, facial muscle crunching, squinting, or other facial position or movement. The system 2010 may further monitor audible responses from the user, such as speech, at one or more microphones 67.

Referring now to FIG. 11, the systems and sensors described above may be used according to method 1700 for detection and/or diagnosis of mental states and/or neurological conditions related to a user's memory and learning abilities. Any of the steps of the method 1700 may be carried out at least partially by circuitry of the displays depicted in FIGS. 9D, 6, and 10, such as a processing module 70, remote processing module 72, or other circuitry. The method 1700 may begin at block 1710, where a stimulus is presented to the user. The stimulus may be any type of content delivered to the user through a wearable system such as the head-mounted systems depicted in FIGS. 9D, 6, and 10, or may be a stimulus in the environment around the user as detected by such a wearable system. For example, the stimulus may be a light pattern, image, series of images, video, guided imagery program, or other visual stimulus delivered by a display system as described above, or may be a sound or guided audio program delivered by one or more speakers. After a stimulus is presented to the user, the method 1700 may continue to block 1720.

At block 1720, the method may detect a user reaction to the stimulus indicative of the user's memory and/or learning ability. The user reaction may include a movement or position of the user's eyes, eye gaze, eyelids, facial muscles, or other reaction as described herein. The user reaction may also include a spoken or otherwise audible reaction detected at one or more microphones. The user's memory, learning, and/or perceptive capability may then be analyzed, determined, estimated, or otherwise quantified based on the detected reaction, as described in greater detail below. In addition, memory difficulties may be detected based on the crunching or squinting of facial muscles during attempts to remember forgotten or unknown information, as well as dilated pupils or elevated heart rate due to panic resulting from memory deficiency. Behavioral memory and/or forgetfulness may be detected based on anomalous behaviors, for example, if a user performs a behavior too frequently (e.g., brushing the user's teeth multiple times, calling multiple times to schedule an appointment, etc.). After the user's reaction to the stimulus has been observed and the user's memory, learning, and/or perceptive capability have been analyzed, the method 1700 may continue to block 1730.

At block 1730, the method 1700 may determine one or more neurological conditions associated with the detected user reaction and/or the user's memory, learning, and/or perceptive capability. The determination in block 1730 may be carried out locally or remotely, and in some aspects may include referring to, querying, or otherwise interacting with a database or other repository of diagnostic medical information. For example, the display system may be configured to determine that signs of impaired memory indicate nervous system disorders such as Balo concentric sclerosis or Schilder's disease, cognitive disorders such as mild cognitive impairment, injuries such as brain tumors, hydrocephalus, stroke, or traumatic brain injury, and/or memory disorders such as dementia, Alzheimer's disease, Creutzfeldt-Jakob disease, Lewy body dementia, or vascular dementia. In an additional example, signs of short-term memory loss may indicate memory disorders such as cortical basal degeneration, posterior cortical atrophy, or progressive supranuclear palsy. Signs of working memory problems may indicate developmental disorders such as schizophrenia. In yet another example, signs of dementia may indicate motor disorders such as Huntington's disease and/or memory disorders such as Creutzfeldt-Jakob disease. Signs of misrecognition of words and/or images may indicate memory disorders such as posterior cortical atrophy.

In some aspects, detected deficiencies in immediate memory (e.g., inability to remember content provided at block 1710 within a few seconds after it was presented to a user) may indicate abnormalities in memory as well as attention and/or alertness. If a user's immediate memory is not found to be deficient but the user has difficulty with recall after a longer period such as 1 minute, 2 minutes, 5 minutes, or a similar time period, damage to limbic memory structures in the medial temporal lobes and/or medial diencephalon may be implicated. Such damage may cause symptoms such as anterograde amnesia and/or retrograde amnesia. Other memory loss may indicate damage to other areas of the brain.

Several example types of memory and learning testing that may be carried out using method 1700 will now be described with reference to FIG. 9D and continuing reference to FIG. 11. In one example, method 1700 may be used to test a user's recent memory by presenting at block 1710 information such as several named items or a story to a user, and asking the user to recall the information after a delay of several minutes, such as 3 minutes or 5 minutes. The information may be presented to the user, for example, by a display 62 or a speaker 66. In some embodiments, the user may be requested to recall the information immediately, such as by speaking into a microphone 67, to ensure the user learned the information before initiating the delay period. During the delay, the user may be presented with various distractions, such as unrelated sounds or imagery. At the end of the delay, the user may be asked to repeat the original information. At block 1720, the user's response, such as a repetition of the information or attempt to repeat the information, may be detected at microphone 67. The user's short-term memory capacity may be evaluated based on the accuracy of the user's recitation of the presented information.

In another example, the method 1700 may test a user's remote memory by asking the user at block 1710 to recall information about historical events or verifiable personal events. The method 1700 may also be used to test explicit word and image recognition by providing, at block 1710, picture or sound stimuli including images, face pictures, or other recognizable stimulus, and prompting the user to identify the stimulus. At block 1720, the user may provide the requested information or may attempt to do so, such as by speaking a response into a microphone as described herein. As with the recent memory testing described above, the user's remote memory may be evaluated based on the accuracy of the user's responses.

In some embodiments, various memory tests may be administered in accordance with the Wechsler Memory Scale. For example, testing may include subtests in spatial addition, symbol span, design memory, general cognitive screening, logical memory, verbal paired associates, and/or visual reproduction. At block 1730, the results of the testing may be analyzed to determine memory index scores, including auditory memory, visual memory, visual working memory, immediate memory, and/or delayed memory.

In various embodiments, the method 1700 may be applied for cerebral assessment. In one example, the user may be presented with a video game or other interactive activity so as to detect lapses in a user's perceptual capability. At block 1710, a user may be presented with a series of images, such as a group of dots, which may move and/or change in clarity. The user may be asked to follow the dots with their eyes. At block 1720, the user's ability to follow the dots may be detected based on eye gaze tracking by the display system. At block 1730, the user's ability to follow the dots may be evaluated to determine whether the user has a neurological condition, such as early dementia or other deficiency.

Referring now to FIG. 12, the systems and sensors described above may be used according to method 1800 for therapeutic applications. A therapeutic method 1800 may begin at block 1810, where user stimuli may be sensed or detected, such as described above with reference to FIG. 11. The method 1800 may continue to block 1820, where it is determined that the stimuli are associated with a neurological condition of the user, such as the neurological conditions described above with reference to FIG. 11. After a neurological condition of the user is detected, the method may continue to block 1830.

At block 1830, the method may display a perception aid for the user. A perception aid may be displayed for the user by any of the display systems and/or elements described herein with reference to FIGS. 9D, 6, and 10, such as a display, light source, waveguide stack, or other display element. If it is detected that a user has a neurological condition impairing memory, a perception aid for the user may include alerts, reminders, games, and/or other interactive content designed to improve the user's memory. As another example, perception aids may include alerts or notifications regarding time, location, nearby people, objects, or other items that may be forgotten. A user experiencing behavioral forgetfulness may be prompted to perform necessary actions, including consistent routines, or not to perform actions too frequently. In some embodiments, perception aids may improve a user's recognition memory by presenting games, such as symbol matching exercises. Perception aids may be taught through multiple learning types (e.g., visual learning, audio learning, kinesthetic learning, etc.). In augmented reality systems, perception aids may be presented as three-dimensional augmented content. Three-dimensional content may provide enhanced spatial memory, such as by navigation within a 3D map to practice and learn a route to a frequent destination. For example, navigation within a 3D map may be used to teach a user living at home the route to the grocery store, or to teach an Alzheimer's patient living in a nursing home to get to the user's room or to a cafeteria, or to put up warnings to prevent access to doors or stairs, and the like. External triggers may be combined as well (e.g., when a user has been directed back to his or her room, an overlay, annunciator, or other visually overlaid indicator may signal that the user has reached the desired destination).

In some embodiments, as noted above, predictive algorithms and/or artificial intelligence methods may be used to provide perception aids before they are required. In one example, a microphone and processor of the display system may detect questions frequently or repetitively asked by a user and, based on the frequency of the questions, may eventually provide answers to the questions before they are asked. For example, a user with a memory deficiency may frequently ask what the time and/or date are. Based on observing when and how frequently the user asks these questions, the method may display the time and date predictively, such as constantly, every few minutes, once an hour, or at certain times of day when the user is more likely to ask, etc.

Language

A user's language functions may be affected by various neurological injuries, conditions, and disorders. In some embodiments, language function testing may be implemented in a wearable display system such as the systems depicted in FIGS. 9D, 6, and 10. With reference to FIG. 9D, evaluating a user's language function in an augmented or virtual reality display system 80 may include detecting responses to guided imagery and/or audio presented to the user 60 at a display 62 and/or speakers 66. With reference to FIG. 10, the system 2010 may monitor audible responses and/or receive any other spoken input from the user, at one or more microphones 67.

Referring now to FIG. 11, the systems and sensors described above may be used according to method 1700 for detection and/or diagnosis of mental states and/or neurological conditions related to a user's language function. Any of the steps of the method 1700 may be carried out at least partially by circuitry of the displays depicted in FIGS. 9D and 10, such as a processing module 70, remote processing module 72, or other circuitry. The method 1700 may begin at block 1710, where a stimulus is presented to the user. The stimulus may be any type of content delivered to the user through a wearable system such as the head-mounted systems depicted in FIGS. 9D, 6, and 10, or may be a stimulus in the environment around the user as detected by the wearable system, such as an object, sound, movement, or other external (environmental) stimulus. For example, the stimulus may be a light pattern, image, series of images, video, guided imagery program, or other visual stimulus delivered by a display system as described above, or may be a sound or guided audio program delivered by one or more speakers. In the context of language testing, the user may be directed by an audio instruction or a visually projected instruction to read a passage, answer a question, speak about a particular topic, or may be otherwise directed to speak. After a stimulus is presented to the user, the method 1700 may continue to block 1720.

At block 1720, the method may detect a user reaction to the stimulus indicative of the user's memory and/or learning ability. The user reaction may include a spoken or otherwise audible reaction detected and/or recorded at one or more microphones as described herein. The user's language ability or function may then be analyzed or evaluated based on the detected or recorded reaction, as described in greater detail below. For example, deficiencies in a user's language ability may be detected from signs such as aphasia, disorganized speech, difficulty reading, coprolalia, and/or very literal translation. After the user's reaction to the stimulus has been observed and the user's language function has been analyzed, the method 1700 may continue to block 1730.

At block 1730, the method 1700 may determine one or more neurological conditions associated with the detected user reaction and/or the user's language function. The determination in block 1730 may be carried out locally or remotely, and in some aspects may include referring to, querying, or otherwise interacting with a database or other repository of diagnostic medical information. For example, the display system may determine that the user's reaction to the applied stimulus is indicative of aphasia, which the display system is configured to determine may indicate nervous system disorders such as Balo concentric sclerosis or epilepsy, motor disorders such as Huntington's disease, cognitive disorders such as mild cognitive impairment or auditory/language processing disorders, injuries such as a brain tumor, migraine, or stroke, and/or memory disorders such as dementia, Alzheimer's disease, cortical basal degeneration, Creutzfeldt-Jakob disease, frontotemporal dementia, primary progressive aphasia, progressive supranuclear palsy, or vascular dementia. In another example, the display system may be configured to recognize that disorganized speech by the user may indicate memory disorders such as Lewy body dementia or frontotemporal dementia. In some embodiments, the display system may be configured to recognize that difficulty reading may indicate cognitive disorders such as auditory, language, or visual processing disorders, memory disorders such as frontotemporal dementia or posterior cortical atrophy, and/or learning disorders such as dyslexia or visual motor deficit. In addition, where coprolalia is observed in the user, the display system may be configured to recognize that coprolalia may indicate motor disorders such as Tourette syndrome, and very literal translations may be caused by non-verbal learning disabilities. In some aspects, detected deficiencies in language function may indicate lesions in various regions of the brain. For example, lesions in the dominant frontal lobe (including Broca's area), the left temporal and parietal lobes (including Wernicke's area), subcortical white matter and gray matter structures (including the thalamus and caudate nucleus), and the non-dominant hemisphere may be indicated by the various conditions described herein. In an example application, the system may be able to distinguish damage to Broca's area (e.g., if a user can understand speech but is unable to speak) from damage to Wernicke's area (e.g., if a user can speak but is unable to understand the speech of others).

Several example types of language testing that may be carried out using method 1700 will now be described with reference to FIG. 9D and continuing reference to FIG. 11. In one example, method 1700 may be used to test a user's spontaneous speech by asking the user, at block 1710, to speak about a general topic. For example, the user may be asked to speak generally about the user's childhood or any other topic likely to produce spontaneous speech. The speech prompt may be presented to the user, for example, by a display 62 or a speaker 66. At block 1720, the user's responsive speech may be detected at microphone 67. Processing module 70 may analyze the recorded speech using speech recognition software or other analytical processing. The user's spontaneous speech function may then be evaluated based on factors such as fluency, phrase length, speech rate, and abundance of spontaneous speech. The user's spontaneous speech may further be analyzed based on detection of tonal modulation, paraphasic errors, neologisms, and/or grammatical errors.

In another example, the method 1700 may test a user's language comprehension by asking the user questions and/or providing commands to the user at block 1710. For example, the questions or commands presented at block 1710 may call for a verbal response from the user. At block 1720, a microphone 67 or other sensor may detect the user's answers to the simple questions and/or responses to the simple commands provided in block 1710. In some embodiments, commands may call for non-verbal responses, which may be detected by sensors such as inward or outward facing cameras or peripheral sensors 30a. The user's compliance with the commands may similarly be detected at block 1720.

In another example, the method 1700 may evaluate a user's ability to name objects or parts of objects. At block 1710, a display 62 may show the user a picture of a common object, such as a pencil, watch, or other item, and prompt the user to say the name of the item. Less common (more "difficult") items, such as a belt buckle or stethoscope, may also be presented. In some embodiments, difficulty may be enhanced by asking a user to name parts of objects instead of or in addition to entire objects. At block 1720, the microphone 67 may detect the user's spoken response to the visual stimulus. Processing module 70 may use speech recognition software to determine if the user accurately named the object depicted.

In some embodiments, the method 1700 may be used to test a user's repetition and/or reading abilities. At block 1710, the user may be presented with a single word, several words, a short phrase, a long phrase, a sentence, or other group of words. In repetition testing, the stimulus may be presented audibly, such as by a speaker 66. In reading testing, the stimulus may be presented visually, such as by showing written words in a display 62. The user may then be prompted audibly or visually to repeat or read the stimulus. At block 1720, the user's response may be detected at a microphone 67. Processing module 70 may use speech recognition software to determine if the user accurately read or repeated the stimulus word, words, phrase, sentence, or sentences, and evaluate any discrepancy or error.

Referring now to FIG. 12, the systems and sensors described above may be used according to method 1800 for therapeutic applications. A therapeutic method 1800 may begin at block 1810, where user stimuli may be sensed or detected, such as described above with reference to FIG. 11. The method 1800 may continue to block 1820, where it is determined that the stimuli are associated with a neurological condition of the user, such as the neurological conditions described above with reference to FIG. 11. After the user is determined to have an identified neurological condition, the method may continue to block 1830.

At block 1830, the method may display a perception aid for the user. A perception aid may be displayed for the user by any of the display systems and/or elements described herein with reference to FIGS. 9D and 10, such as a display, light source, waveguide stack, or other display element. If it is detected that a user has a neurological condition impairing the user's language function, a perception aid for the user may include language and/or speech therapy. For example, the user may be notified of a speech error and prompted to correct the error. In another example, a user having difficulty remembering a word or phrase may be prompted, such as by displaying the word or phrase in a display 62. In some embodiments, visual content such as teaching materials and language games may be presented to enhance the user's ability to learn and improve the user's language skills.

Finger Agnosia Tests

In some embodiments, the display system may be configured to perform a finger agnosia test. The finger agnosia test may determine a user's ability to name and identify the digits of the hands or feet. In certain embodiments, a finger agnosia test may be administered using interactive prompts generated by the display system. The prompts may be visual, auditory, and/or tactile.

In some embodiments, finger agnosia testing may be implemented in a wearable display system such as the systems depicted in FIGS. 9D, 6, and 10. With reference to FIG. 9D, detecting and/or tracking a user's response to prompts in an augmented reality display system 80 may include detecting responses to visual content, guided imagery, and/or general audio instructions presented to the user 60 using the display 62 and/or speakers 66. With reference to FIG. 10, the system 2010 may monitor the user through inward-facing cameras 24 for eye tracking, such as to detect eye position, movement, or gaze. As disclosed herein, the cameras 24 may be used to register user inputs to the display system (e.g., by tracking the user's eyes to determine his/her selection of virtual menu items). In some embodiments, the display system may be configured to receive inputs via real input devices (e.g., physical buttons) and/or virtual input devices (e.g., virtual buttons projected by the display device). Such inputs may include, for example, eye tracking, head pose, and/or gesture.

Referring now to FIG. 11, the systems and sensors described herein may perform method 1700 to detect and/or diagnose neurological conditions related to a user's finger agnosia. Any of the steps of the method 1700 may be carried out at least partially by the display systems depicted in FIGS. 9D, 6, and 10, with processing conducted using the processing module 70, remote processing module 72, or other circuitry. At block 1710 of FIG. 11, a stimulus may be presented to the user by the display system or may be presented by the ambient environment and identified by the display system. In some embodiments, the stimulus may include a prompt for the user to complete a task. For example, a user may be prompted to identify his left index finger or draw his right hand in space. In some embodiments the user may be prompted to identify a particular finger, position the finger in a particular orientation, or distinguish between multiple fingers. For example, the user may be asked to align a particular finger with a virtual marker, point to the finger with their other hand, and/or to focus their eyes on a particular finger.

At block 1720, the display system may detect a user reaction to the stimulus. The display system may be configured to sense the user's eye gaze using the inwardly-facing cameras 24 to determine whether the user's gaze is on the correct finger. In some other embodiments, the display system may be configured to monitor the user's fingers using the environmental sensor 34 to determine whether the correct finger is correctly aligned with a virtual marker. The determination in block 1730 may be carried out locally and/or remotely, and in some aspects may include referring to, querying, or otherwise interacting with a database or other repository of diagnostic medical information.

At block 1730, the method 1700 may determine whether the user suffers from finger agnosia based upon the user's reaction to the stimulus determined at block 1720. For example, an inability to consistently identify a finger may be interpreted to be caused by finger agnosia. It will be appreciated that finger agnosia may be caused by Huntington's Disease, and the system may be configured to alert the user and/or a third-party with notification of the presence of finger agnosia and possible Huntington's Disease.

Because this test is interactive, it is possible that false positives for finger agnosia may be caused by an inability to understand instructions provided by the display system. Consequently, in some embodiments, the display system may determine whether there is a deficiency in understanding of the instructions due to, e.g. inability to understand the language that the instructions are presented in or a cognitive inability to understand the instructions. It will be appreciated that the correct language for the instructions may be determined by first presenting questions to the user to confirm that they understand the instructions before proceeding to block 1710 or 130. In some other embodiments, the display system may analyze the user's eye gaze and the time elapsed after receiving instructions from the display system to determine whether those parameters are indicative of confusion and, thus, a lack of understanding of the instructions. For example, the eyes of a user that does not understand a particular language may not track words displayed by the display system in the same way that a normal speaker of that language may track words, since the user may not understand those words and, in some cases, may not follow them linearly from the beginning to end of a sentence. In some embodiments, the display system may be configured to measure the elapsed time between the displaying of instructions and the identification of a finger by the user. An elapsed time that is longer than a reference time may indicate an inability to understand the instructions.

With reference to FIG. 12, the systems and sensors described above may be used according to method 1800 for therapeutic applications. At block 1810, in certain embodiments stimuli directed to the user may be sensed or detected, such as described above with reference to reactions in FIG. 11. For example, the display system may be configured to monitor whether the user is directing his gaze at a finger or toe using a variety of sensors, including an environmental sensor 34 or other sensor. At block 1820, in some embodiments the display system may determine that the stimuli are associated with finger agnosia.

The display system can be configured to interact with other systems, objects, totems, units, or items to provide therapy. For example, a user may wear an article of clothing (e.g., a glove) that is configured to provide the user with a sensation and/or stimulation (e.g., electrical, mechanical, thermal, biochemical). In some embodiments, the sensation and/or stimulation can be initiated in response to a user input as described herein. For example, a user may wear a glove that is configured to provide electrical stimulation using a Transcutaneous Electrical Nerve Stimulations (TENS), Electrical Muscle Stimulator (EMS), and/or a Powered Muscle Stimulator (PMS) unit. Continuing in the example, a user may activate the electrical stimulation in a finger of the user by gazing at the finger. In some embodiments, the stimulation provided can provide many benefits, such as feedback (e.g., closed loop, tactile) to the user, pain reduction, increased blood circulation, prevention of muscle atrophy, muscle conditioning, relaxation of muscle spasms, and/or increased muscle support. For example, a user who does not have full motor skill over a finger can receive electrical stimulation initiated by the display system to help compensate for a motor skill deficiency (e.g., tremor, shaking, weakness).

At block 1830 the display system may also be configured to display a perception aid for the user. For example, the display system may display a hint or a location, identification, or indication of the correct finger or toe. In some embodiments, the displayed virtual content may advantageously be directly overlaid on the correct finger or toe and may also be placed on the same depth plane as the finger or toe.

Agraphia Tests

In some embodiments, the display system (e.g., the display systems depicted in FIGS. 9D, 6, and 10) may be configured to perform an agraphia test, to evaluate a user's ability to write a word or a string of words. The display system may administer the agraphia test using interactive prompts. For example, the display system may be configured to administer the agraphia test by asking the user to write his/her name in space or to write a sentence on a piece of paper which is imaged by the display system.

Referring now to FIG. 11, the systems and sensors described herein may perform method 1700 to detect and/or diagnose neurological conditions related to a user's agraphia. At block 1710, a stimulus is presented to the user. The stimulus may also be present in the ambient environment. For example, the display system may observe the user interacting with one or more objects in the environment surrounding the user. As another example, the display system could observe when the user is writing and that may be detected and identified as being the stimulus. The stimulus may include a prompt for the user to complete a task. For example, the user may be prompted to write a word or words (e.g., her name, a sentence, a symbol) on a piece of paper, in space, or on/in some other medium. It will be appreciated that the prompt may be, e.g., a visual prompt such as text provided by the display 62, or an auditory prompt such as instructions provided through speakers 66.

At block 1720, the display system may detect a user reaction to the stimulus indicative of the presence or absence of agraphia in the user. For example, the display system may be configured to image or otherwise detect the position and movement of the user's hands, any writing implements, and/or text written on a surface. The text may be written physically, for example using ink or pencil lead, or it may be written virtually, e.g., by using the display system to track the position of the tip of the writing implement and/or a user's finger and/or gesture. In some embodiments, the text can be written using a virtual and/or physical keyboard.

At block 1730, the display system may be configured to determine whether and the degree to which the user suffers from agraphia. For example, the display system may determine that the user was unable to complete the requested tasks of writing words. The display system may also be configured to determine the degree to which the user was unable to complete their tasks. For example, the user may have been able to write a portion of the words. The display system may be configured to determine the severity of the agraphia based upon the portion of the tasks that were completed by the user. The severity of agraphia would be understood to be directly related to the number of tasks (instructions provided by the display system for writing particular content) that were not completed. In some embodiments, the display system can compare a user's current results with the user's previous results. Such comparison may be applied to determine the presence of a neurological condition or to determine the progression of a condition. For example, where a user has previously been determined to suffer from Parkinson's disease, the display system may be configured to compare the size and/or legibility of their handwriting over time, as the agraphia test is conducted periodically over a time span of, e.g., weeks, months, or years. The display system may interpret handwriting that has become increasingly smaller and/or more illegible over time as an indication of the progression of the disease.

The display system can be configured to differentiate between related types of disorders. In some embodiments, multiple tests can be used in combination to more precisely pinpoint the specific type of disorder (e.g., agraphia). For example, the display system may differentiate pure agraphia from apraxic agraphia by detecting both the user's ability to produce handwritten text (e.g., on paper, in space) and the user's ability to produce typewritten text (e.g., on a physical keyboard, using a virtual keyboard). In certain embodiments, the display system can compare the results of the handwritten text with those of the typewritten text to more precisely pinpoint the user's neurological condition.

As noted above regarding agnosia, it is possible that the false positives may be obtained due to the user's inability to understand the prompts or tasks requested by the display system. Consequently as described above regarding agnosia, the display system may be configured to confirm that the user understands the prompts provided by the display system. For example, the display system may be configured to determine that the user understands the language of the prompts and/or has the cognitive ability to understand prompts.

With reference now to FIG. 12, the systems and sensors described herein may be used according to method 1800 for therapeutic applications. At block 1810, in certain embodiments, the display system may be configured to monitor whether the user has been prompted to write his name or some other word using a variety of sensors, including the microphone 67 (FIG. 9D), the environmental sensor 34 (FIG. 10), the downward facing camera 28 (FIG. 10), or other sensor. At block 1820, in some embodiments the display system may determine that the stimuli (requests to physically write content) are associated with a neurological condition of the user, such agraphia.

As in the description for agnosia above, in some embodiments, the display system can be configured to interact with other systems, objects, totems, units, or items to provide therapy for agraphia, as described herein (e.g., clothing, processors, TENS/EMS/PMS units). In certain embodiments, the display system can be configured to initiate a sensation and/or stimulation (e.g., electrical, mechanical, thermal, biochemical) using such a system, object, totem, unit, or item, as described herein. In some embodiments, the stimulation provided can provide many benefits, as described herein.

At block 1830 the display system may be configured to display a perception aid for a user having agraphia. For example, the display system may display a writing strategy or visual aid to help the user improve her writing or successfully write a word, phrase, or sentence. In some embodiments, the display system may display augmented reality content corresponding to the words that the user has been tasked with writing. Moreover, due to the display system's ability to display content on different depth planes, the display system may display a perception aid that appears to be on the surface on which the user is writing. As a result, in some embodiments, the user may simply trace the words (displayed as augmented reality content) they would like to write.

Right-Left Disorientation Tests

In some embodiments, the display system (e.g., the display systems depicted in FIGS. 9D, 6, and 10) may be configured to perform a right-left disorientation test to test a user's disorientation in identifying parts of a body. In certain embodiments, a right-left disorientation test may be administered through interactive prompts.

Referring now to FIG. 11, the systems and sensors described herein may perform method 1700 to detect and/or diagnose neurological conditions related to a user's right-left disorientation (e.g., the inability to differentiate right from left). At block 1710, the display system may be configured to provide a right-left disorientation test to the user by providing a stimulus. The stimulus may be a prompt for the user to complete a task. For example, the user may be prompted to touch one body part with a finger on the opposite side of the body part. As a further example, the user may be prompted to touch his/her left hip with his/her right finger. In certain embodiments, the display device may project a stimulus (an image of an object) towards a particular direction. The user may be prompted, for example, to identify the direction projected. In some embodiments, the stimulus may come from the environment in addition to or instead of from the display system. For example, the stimulus may be a GPS navigation instruction directing a driving user to turn in a particular direction.

At block 1720, the display system may detect a user reaction to the stimulus, which may be indicative of the presence or absence of a right-left disorientation in the user. In some embodiments, the display system may be configured to image or otherwise detect the position and movement of the user's hands and/or other body parts, and to determine whether the prompted task was correctly completed. For example, the display system may utilize the microphone 67 (FIG. 9D), the environmental sensor 34 (FIG. 10), inward facing camera 24 (FIG. 10), and/or the downward facing camera 28 (FIG. 10) to determine the user's reaction to a prompted task, e.g., by tracking the user's eye movement or gaze.

At block 1730, the display system may be configured to determine whether and the degree to which the user suffers from right-left disorientation. For example, the display system may determine whether the user correctly performed a given task such as touching his/her left hip with his/her right finger. In some other embodiments the display system may determine whether the user correctly identified the direction of a projected augmented reality object.

With reference now to FIG. 12, the systems and sensors described herein may be used according to method 1800 for therapeutic applications. At block 1810, in certain embodiments, stimuli directed to the user may be sensed or detected. For example, the display system may be configured to monitor the user's environment using an environmental sensor 34 or microphone 67 to sense whether the user is being subjected to a stimulus that requires the user to differentiate between left and right directions. For example, the display system may recognize that the user is being given directions (e.g., by the display system itself, by a third party, or by another device). At block 1820, in some embodiments, the display system may determine that the stimuli are associated with right-left disorientation and that the user has such right-of disorientation.

At block 1830, the display system may also be configured to display a perception aid to compensate for the user's right-left disorientation. The perception aid may be, for example, a hint, a location of an object, an indicator, or a reminder of a direction. For example, in response to auditory instructions (e.g., from a map program, from a third party, etc.) to turn right or to turn left, the display system may simply display an arrow in the user's field of view pointing in the correct direction.

Calculation Tests

In certain embodiments, the display system may be configured to perform calculation tests. For example, such tests may quiz a user's ability to perform calculations (e.g., arithmetic). The calculation tests may be administered through interactive prompts provided by the display system.

Referring to block 1710 in FIG. 11, the systems and sensors described herein may perform method 1700 to detect and/or diagnose neurological conditions related to a user's ability to successfully perform calculations. At block 1710 the display system may be configured to provide a calculation test to the user. For example, the display system may display an image or oral instructions with an arithmetic problem (e.g., the addition of two numbers). The stimulus may be an audio/visual stimulus from the environment. For example, the stimulus may be an arithmetic problem present in the ambient environment (e.g., an arithmetic problem present in the whiteboard of a classroom).

At block 1720, the display system may detect a user reaction to the stimulus indicative of the user's ability to solve the problem presented. In some embodiments, sensing the reaction may involve imaging an answer written by the user on a surface, interpreting an answer given by the user orally. As with other tests herein, it will be appreciated that blocks 1710 and 1720 may be repeated a plurality of times to build a larger data set for later analysis before progressing to block 1730.

At block 1730, the method 1700 may determine one or more neurological conditions associated with the detected user reaction. As an example, the display system may be configured to diagnose a memory disorder based on a miscalculation (e.g., the user's inability to remember the multiplication table). In some embodiments, the display system may determine that a possible cause of the disorder is posterior cortical atrophy.

With reference to FIG. 12, the systems and sensors described above may be used according to method 1800 for therapeutic applications. At block 1810, in certain embodiments stimuli, the display system may be configured to monitor prompts given to the user (e.g., by a teacher or parent, or at a restaurant while calculating a bill) using a variety of sensors, such as environmental sensor 34 or microphone 67.

At block 1830 the display system may be configured to display a perception aid for the user to compensate for their inability to perform calculations. For example, the display system may display a missing step in the arithmetic solution, prompt the user through a reminder or hint of a false or missing step, or identify the correct answer or response to the problem.

Apraxia Tests

In some embodiments, the display system may be configured to test for apraxia, or the user's inability to follow a motor command. It will be appreciated that apraxia is different from a motor deficit or inability to understand language. Rather, apraxia is caused by a deficiency in higher-order planning or in conceptualization of the motor task being prompted for. The display system may be configured to prompt the user to perform complex combinations of movements and to determine whether the user successfully completed these movements and/or the extent to which the user was able to at least partially complete a command.

Referring to block 1710 in FIG. 11, the systems and sensors described herein may perform method 1700 to detect and/or diagnose neurological conditions related to a user's apraxia. At block 1710, the display system may be configured to provide a command to perform a sequence of movements of the body or body parts. For example, the user may be prompted to imitate certain hand gestures or mime the use of a tool. As another example, the user may be prompted to pretend to brush her teeth or to pretend to comb her hair. In certain embodiments, the display device may prompt the user to perform gestures that interact with physical and/or virtual objects (e.g., using a tool).

As indicated by block 1720 of FIG. 11, the display system may detect a user reaction to the stimulus indicative of the user's ability to perform the prompted skilled movements. In some embodiments, the display system may be configured to image or otherwise detect the position and movement of the user's hands, and/or any object that the user is interacting with. In addition, in some embodiments, the display system may be configured to sense the user's eye gaze, the focus of the user's eyes, or how much time has elapsed from the initiation of the stimulus (e.g., prompting the user) to the user reaction to the stimulus.

At block 1730, the display system may be configured to determine whether and the degree to which the user suffers from apraxia. In some embodiments, the display system may determine that the user was unable to complete the prompted skilled movement.

In some embodiments, the display system may conduct a reference test to confirm that the user does not have a motor deficiency or language impairment. For example, the display system may conduct block 1710 by prompting the user to conduct a simple movement, at block 1720 sense the user's movement in response to the prompt, and at 140 determine whether the prompted movement was successfully completed. If this movement was successfully completed, the system may subsequently perform blocks 1710, 1720, and 1730 with a more complex sequence of movements, as described above. If, in the subsequent test, the display system determines that the user's movements are awkward and only minimally resemble those prompted by the display system (even though the user may have intact comprehension or otherwise normal motor control as evidenced by the prior tests with simple movements), then the display system may be configured to conclude that apraxia is present in the user. In some embodiments, the display system may determine that the user was slow in completing the prompted skilled movement and/or only completed part of the movement, which may also be indicative of apraxia.

Upon determining that apraxia is present, the display system may be configured to provide a notification of the presence and/or extent of apraxia, and also of possible diseases or injuries causing apraxia. Examples of possible diseases or injuries include Gerstmann Syndrome, Huntington's, Disease, cortical basal degeneration, and stroke.

With reference to FIG. 12, the systems and sensors described herein may be used according to method 1800 for therapeutic applications. At block 1810, in certain embodiments stimuli directed to the user may be sensed or detected, such as described above with reference to reactions in FIG. 11. For example, the display system may be configured to monitor the user's daily habits, routines, physical activities, in part by using an environment sensor 34 or other sensor. At block 1820, in some embodiments the display system may determine that the stimuli are associated with apraxia.

As in the description for agnosia above, in some embodiments, the display system can be configured to interact with other systems, objects, totems, units, or items to provide therapy for apraxia, as described herein (e.g., clothing, processors, TENS/EMS/PMS units). In certain embodiments, the display system can be configured to initiate a sensation (e.g., a tactile sensation) and/or stimulation (e.g., electrical, mechanical, thermal, biochemical) using such a system, object, totem, unit, or item, as described herein. In some embodiments, the stimulation provided can provide many benefits, as described herein.

At block 1830 the display system may also be configured to display a perception aid for apraxia. For example, the display system may display how a task is performed and may optionally display images breaking the task down into its constituent components, prompting the user through a reminder or hint of a false or missing step, or providing other examples of correct behavior.

Visuospatial and other Sensory Functions

In some embodiments, the display system may be configured to perform neglect and/or construction-based tests to evaluate a user's visuospatial and other sensory functions. Without being limited by theory, tasks involving visuospatial functions may be associated with areas of the parietal lobe of the brain. Abnormalities with these functions may indicate damage to these areas (e.g., right parietal dysfunction). Neglect, other visuospatial impairments, and/or cognitive difficulties (e.g., impaired sequencing or apraxia) may cause abnormalities in construction skills.

Referring to block 1710 in FIG. 11, in such tests, the display system may be configured to provide a stimulus that instructs a user to perform one or more tasks involving visual perception, construction, and/or integration. For example, the display system may administer a test through interactive instructions and content, such as visual images and/or audio (e.g., guided imagery). The tests may include drawing tests, reading tests, manipulations tests, visualization tests, navigation tests, etc. For example, the tests may include neglect drawing tests (e.g., asking the user to complete a picture or to bisect an object), copy drawing tests (e.g., asking the user to draw one or more shapes and/or to copy one or more shapes), neglect reading tests (e.g., asking the user to read text aloud), and object manipulation tests (e.g., asking the user to manipulate objects such as blocks). Some tests may include other functions and criteria (e.g., attention, observation, organization, planning, thinking, memory, visualization, etc.). For example, the Rey-Osterrieth Complex Figure test (ROCF) (e.g., asking the user to reproduce a relatively complex drawing with the drawing viewable by the user, and to later reproduce the drawing without the drawing viewable by the user) may evaluate other abilities such as attention, recognition, memory, image processing or perception based on experience, conditioning, or pathology like a Rorschach test. As another example, mental imagery and rotation tests (e.g., asking the user to create an image of a 2D or 3D object mentally, to rotate the object mentally, and/or to make a comparison/contrast with the rotated object) may evaluate visualization and thinking skills. In addition, virtual spatial navigation may be used to identify memory disorders.

Referring to block 1720 in FIG. 11, in various embodiments configured to perform a neglect and/or construction-based test, the display system may be configured to sense user reaction to the stimulus (e.g., task to draw, read, visualize, etc.). In some embodiments, the display system may include a physical user interface (e.g., a writing or drawing tablet), a virtual user interface (e.g., a virtual tablet for writing or drawing, or a gesture based CAD/graphical user interface for using primitives, blocks, lines, or shapes to create/recreate virtual objects, maps, or worlds), an audio recognition system (e.g., a voice recorder to sense a user's verbal response), a movement recognition system (e.g., a motion detector to sense a user's actions), or other sensor system (e.g., to detect head pose, eye tracking, and/or other gestures) to allow a user to indicate his or her response to the stimulus, while allowing the display system to sense the user reaction. As another example, some embodiments may use one or more cameras (e.g., camera 24 or 28 in FIG. 10) to detect the user's response (e.g., the response on a piece of paper or the manipulation of blocks). One or more cameras may also detect attention and/or eye gaze for possible indications of difficulty and/or confusion and/or to help determine how the user is interpreting the stimulus. As yet another example, some embodiments may detect the time lapse from providing the stimulus (e.g., via a timing device) for possible indications of difficulty and/or confusion.

Referring to block 1730 in FIG. 11, in various embodiments configured to perform a neglect and/or construction-based test, the display system may be configured to determine a neurological condition associated with the user reaction. For example, the user reaction may demonstrate one or more disorder characteristics. In a drawing test or reading test, the user may neglect to draw one side of a figure or may neglect to read one side of the text. A user's eye gaze may also tend avoid one side of view. Other aspects of neglect may include sensory neglect (e.g., neglecting visual, somatosensory, or auditory stimuli on one side), motor neglect (e.g., neglecting one limb although the limb is normal), anosognosia (e.g., unawareness of dysfunction), and/or hemi-asomatognosia (e.g., denial of dysfunction). In some embodiments, visuospatial testing may be combined other sensory testing. For example, visuospatial testing may be combined with somatosensory testing. In some such tests, the user may be presented in addition to visual stimuli, somatosensory stimuli such as stimuli for pressure, temperature, transcutaneous electrical nerve stimulation (TENS), electrical muscle stimulation (EMS), etc. A movement recognition system may detect the physical stimuli response of the user.

In some instances, abnormal constructions (e.g., impaired visuospatial functions) may demonstrate right parietal lobe lesions. Some embodiments may determine lesions in the right side and other parts of the brain. For example, some embodiments may determine hemi-neglect in which one side is neglected to be indicative of dysfunction and/or lesion in the area of the brain controlling such functions. If the user neglects stimuli on their left side, the display system may determine that the user has a lesion in the right parietal lobe. In other instances and along with other inputs, the display system may determine right frontal lesions, right thalamic lesions, basal ganglia lesions, and/or right midbrain lesions. If the user neglects stimuli on their right side, the display system may determine the user has a left parietal lesion. In some instances indicating signs of neglect, the display system may determine the user had an injury such as a stroke.

Based at least in part on the user reaction, some embodiments may determine problems with visual perception such as micropsia or macropsia. In some such instances, the display system may determine that the user has an injury such as a migraine. Some embodiments may determine issues with visual information interpretation. In some instances, the display system may determine the user has a learning disorder (e.g., visual motor deficit), a cognitive disorder (e.g., visual processing disorder), a memory disorder (e.g., Lewy body dementia or vascular dementia), and/or a motor disorder (e.g., Parkinson's disease). Some embodiments may determine problems with spatial awareness. In some instances, the display system may determine the user has a learning disorder (e.g., a non-verbal learning disability), a motor disorder (e.g., dyspraxia), and/or an injury (e.g., stroke). Furthermore, some embodiments may determine signs of visuospatial dysgnosia (e.g., loss of sense of one's relationship with one's surroundings). In some such instances, the display system may determine the user has a learning disorder (e.g., non-verbal learning disability or visual motor visual motor deficit) and/or a memory disorder (e.g., dementia, Alzheimer's disease, or posterior cortical atrophy).

Referring now to FIG. 12, in some embodiments, the display system may perform the method 1800 to provide therapy to the user. In some such instances, the neglect and/or construction-based test may be provided to the user by the display system (e.g., as shown and described in relation to block 1710 in FIG. 11), or by an external source such as another individual (e.g., a physician, a therapist, a teacher, a family member, a stranger, etc.).

Referring to block 1810 in FIG. 12, when presented with the stimulus (e.g., task to draw, read, visualize, etc.), the display system may be configured to sense the stimulus directed to the user (e.g., using environmental sensor 34 in FIG. 10) as well as the user reaction (e.g., as shown and described in relation to block 1720 in FIG. 11). Referring to block 1820 in FIG. 12, various embodiments may be configured to determine a neurological condition of the user (e.g., as described with respect to block 1730 in FIG. 11) based at least in part on the sensed information. In some other embodiments, the neurological condition may be known to the display system and its existence may be determined by loading a profile for the user.

Further, referring to block 1830 in FIG. 12, in some embodiments, the display system may display a perception aid for the user. The display system may provide visual content (e.g., guided imagery) as a visual stimulus in neglected areas (e.g., to force attention and/or to focus on multiple stimuli to help improve neglect). For example, in some embodiments, the display system may be configured to display images of objects from the neglected side on the non-neglected side, so as to make objects from the neglected side visible to the user. As another example, as discussed herein, if the user is diagnosed to have issues with observation and memory skills (e.g., via ROOF testing) in block 1820 of FIG. 12, the display system may provide aids to help the user remember and/or tasks to help the user practice and improve observation and memory skills. As yet another example, if the user is diagnosed to have issues with thinking and visualization (e.g., via mental imagery and rotation tests) in block 1820 of FIG. 12, the display system may provide aids to help the user with these tasks. For example, the display system may display the object that the user is having difficulties visualizing. The display system may also provide additional rotation problems to help improve thinking and visualization strategies. The display system may also provide video games to help improve mental rotations. As a further example, if the user is diagnosed to have issues with spatial navigation, the display system may provide reminders and/or alerts of proximity to objects or to other individuals. The display system may also provide mazes to help improve memory and navigation skills.

Executive Cognitive Functions

In some embodiments, the display system may be configured to perform cognitive tests (e.g., sequencing tests) to provide access to a user's executive functions (e.g., various cognitive processes including problem solving, planning, organizing, short-term memory, selective attention, inhibitory control, etc.). Without being limited by theory, tasks involving these functions may be associated with areas of the frontal lobes. Abnormalities with these functions may indicate lesions to these areas.

Referring to block 1710 in FIG. 11, in such tests, the display system may be configured to provide a stimulus that instructs a user to perform one or more tasks involving the cognitive functions, e.g., to evaluate frontal lobe dysfunction. In some embodiments, the display system may administer a test through interactive instructions and content, such as visual images and/or audio (e.g., guided imagery). The tests may include card sorting tests, such as a Wisconsin Card Sort Test (e.g., asking the user to match virtual cards but not explaining how to match them), in which the user's capability to learn new concepts may be measured. The tests may include following commands, such as an Auditory Go-No-Go Test (e.g., asking the user to wiggle a finger in response to a sound, and to keep it still in response to two sounds), in which motor impersistence, behavior suppression, abulia (e.g., slow reaction time), changes in judgement, and/or changes in personality may be evaluated. As another example, the tests may include a Stroop Effect Test (e.g., asking the user to read the word written in a color indicated by its name), in which reaction time, attention, inhibition, and/or inhibition switching may be evaluated. Other example tests may include a Written Alternating Sequence Task Test (e.g., asking the user to write or draw the next sequence in a pattern) or a Manual Alternating Sequence Task Test (e.g., asking the user to repeat a manual sequence of tasks), in which perseveration (e.g., difficulty in changing actions) may be evaluated. As yet another example, the tests may include a Mismatch Negativity Test (e.g., measuring the event-related potential component of the user in response to an odd image or audio in a sequence). As a further example, the tests may include a Grasp Reflex Test (e.g., asking the user to rub hands with a therapist to see if he or she will grab the therapist's finger or pen) to evaluate existence of infant reflexes in adult users.

Referring to block 1720 in FIG. 11, in various embodiments configured to perform a cognitive test, the display system may be configured to sense user reaction to the stimulus (e.g., task). In some embodiments, the display system may include a physical user interface (e.g., buttons on a touch sensor on a surface of the display system or a writing or drawing tablet), a virtual user interface (e.g., a virtual touch screen), an audio recognition system (e.g., a voice recorder to sense a user's verbal response), or a movement recognition system (e.g., a motion detector to sense a user's actions), or other sensor system (e.g., to detect head pose, eye tracking, and/or other gestures) to allow a user to indicate his or her response to the stimulus, while allowing the display system to sense the user reaction. As another example, some embodiments may use one or more cameras (e.g., camera 24 or 28 in FIG. 10) to detect the user's response (e.g., the response on a piece of paper or the manipulation of objects). One or more cameras may also detect attention and/or eye gaze for possible indications of difficulty and/or confusion. As yet another example, some embodiments may detect the time lapse from providing the stimulus (e.g., via a timing device) for possible indications of difficulty and/or confusion.

Referring to block 1730 in FIG. 11, in various embodiments configured to perform a cognitive test, the display system may be configured to determine a neurological condition associated with the user reaction. Such tests may determine the user has frontal dysfunction and may help localize lesions in the frontal lobes. For example, in the Wisconsin Card Sort Test, the user reaction may demonstrate one or more dysfunction characteristics. Based at least in part on the user reaction, some embodiments may determine issues with executive functions. In some such instances, the display system may determine the user has a memory disorder (e.g., Alzheimer's disease), a nervous system disorder (e.g., Balo's disease), a motor disorder (e.g., Huntington's disease), a development disorder (e.g., fetal alcohol spectrum disorder or schizophrenia), and/or an injury (e.g., stroke or traumatic brain injury). In the Wisconsin Card Sort Test, the user reaction may demonstrate disorganization. In some instances, the display system may determine the user has a memory disorder (e.g., vascular dementia) and/or a developmental disorder (e.g., Attention Deficit Hyperactivity Disorder).

As another example, in the Auditory Go-No-Go Test, some user reactions may demonstrate processing difficulties. In some instances, the display system may determine the user has a nervous system disorder (e.g., Balo's disease) and/or an injury (e.g., hydrocephalus). Some embodiments may determine changes in behavior. In some such instances, the display system may determine the user has a motor disorder (e.g., Huntington's disease), a memory disorder (e.g., progressive supranuclear palsy or frontotemporal dementia), and/or an injury (e.g., hydrocephalus or brain tumor). Some embodiments may determine changes in personality. In some such instances, the display system may determine the user has a nervous system disorder (e.g., Schilder's disease), a motor disorder (e.g., Huntington's disease), a memory disorder (e.g., Creutzfeldt-Jakob disease or frontotemporal dementia), and/or an injury (e.g., hydrocephalus). Furthermore, some embodiments may determine extraordinary creativity, talent in art, talent in music, and/or talent in numerical abilities. In some such instances, the display system may determine the user has a developmental disorder (e.g., autism spectrum disorder) or a memory disorder (e.g., frontotemporal dementia).

As another example, in the Stroop Test, the user reaction may demonstrate cognitive impairment. In some embodiments, the display system may determine the user has a memory disorder (e.g., Lewy body dementia), a motor disorder (e.g., motor neuron disease or Parkinson's disease), and/or an injury (e.g., traumatic brain injury).

As yet another example, in the Written or Manual Sequencing Task Tests, the user reaction may demonstrate signs of perseveration. In some such instances, the display system may determine the user has a developmental disorder (e.g., autism spectrum disorder). Some embodiments may determine the development disorder using perception aids such as Cognitive Substitution/Enhancement as described herein.

Logic and/or Abstraction

In some embodiments, the display system may be configured to perform logic and/or abstraction-based tests to provide access to a user's thinking and reasoning skills. Referring to block 1710 in FIG. 11, in such tests, the display system may be configured to provide a stimulus that may include one or more problems involving logic and/or an analogy or may be configured to detect such a stimulus in the environment. For example, a display system may administer a problem through interactive instructions and content, such as visual images and/or audio (e.g., guided imagery). Example problems include simple, intermediate, or advanced problems involving a simple query, interpretation, comparisons, generalization, patterns, etc.

Referring to block 1720 in FIG. 11, in various embodiments configured to perform a logic and/or abstraction-based test, the display system may be configured to sense user reaction to the stimulus (e.g., a presented problem) similarly as described herein for tests relating to executive cognitive functions. In some embodiments, the display system may include a physical user interface, a virtual user interface, an audio recognition system, or a movement recognition system to allow a user to indicate his or her response to the stimulus, while allowing the display system to sense the user reaction. As another example, some embodiments may use one or more cameras (e.g., camera 24 or 28 in FIG. 10) to detect the user's response (e.g., the response on a piece of paper or the manipulation of objects). One or more cameras may also detect attention and/or eye gaze for possible indications of difficulty and/or confusion. As yet another example, some embodiments may detect the time lapse from providing the stimulus (e.g., via a timing device) for possible indications of difficulty and/or confusion.

Without being limited by theory, functions relating to logic and abstraction may be associated with areas of the brain involving higher-order association cortex. Abnormalities with these functions may indicate damage to these areas. Referring to block 1730 in FIG. 11, in various embodiments configured to perform a logic and/or abstraction-based test, the display system may be configured to determine a neurological condition associated with the user reaction. For example, based at least in part on the user reaction, some embodiments may determine signs of decline in thinking and reasoning skills including concentration, judgment, planning, and/or organization. In some such instances, the display system may determine the user has a motor disorder (e.g., Huntington's disease or Parkinson's disease), a cognitive disorder (e.g., mild cognitive impairment), a memory disorder (e.g., Creutzfeldt-Jakob disease, Lewy body dementia, frontotemporal dementia, progressive supranuclear palsy, or vascular dementia), a behavior disorder (e.g., depression), a development disorder (e.g., bipolar affective disorder), and/or injuries (e.g., brain tumor, hydrocephalus, or traumatic brain injuries). As another example, based at least in part on the user reaction, some embodiments may determine signs of multi-step instructions or categorizing difficulties. In some such instances, the display system may determine the user has a learning disorder (e.g., non-verbal learning disabilities) or a developmental disorder (e.g., autism spectrum disorder).

Referring now to FIG. 12, in some embodiments, the display system may perform the method 1800 to provide therapy to the user. In some such instances, the logic and/or abstraction-based test may be provided to the user by the display system (e.g., as shown and described in relation to block 1710 in FIG. 11), or by an external source such as another individual (e.g., a physician, a therapist, a teacher, a family member, a stranger, etc.).

Referring to block 1810 in FIG. 12, when presented with the stimulus (e.g., a problem), the display system may be configured to sense the stimulus directed to the user (e.g., using environmental sensor 34) as well as the user reaction (e.g., as shown and described in relation to block 1720 in FIG. 11). Referring to block 1820 in FIG. 12, various embodiments may be configured to determine a neurological condition of the user (e.g., as described with respect to block 1730 in FIG. 11) based at least in part on the sensed information and/or by accessing a profile of the user.

Further, referring to block 1830 in FIG. 12, in some embodiments, the display system may display a perception aid for the user. For example, the display system may provide visual content (e.g., guided imagery) as a visual and/or kinesthetic learning aid for the user (e.g., to help the user solve the problem). As another example, video games with feedback may increase decision-making skills, reducing cognitive biases (e.g., bias blind spot, confirmation bias, fundamental attribution error, anchoring projection, or representativeness). Video games may also improve adaptability, focus/attention, memory, reasoning speed/metal agility, problem solving, and/or flexibility. Furthermore, video games may help break down steps to help improve tracking multiple objects.

Perception Detection and other Visual Response Detection

It will be appreciated that the visual perception states of dominance and suppression may be evaluated using optokinetic nystagmus (OKN), visual evoked potential (VEP), magnetoencephalography (MEG), and/or blood-oxygen level dependent (BOLD) contrast imaging using functional magnetic resonance imaging (fMRI). The amplitude of dominance and suppression may be determined using, e.g., VEP, MEG, and/or BOLD, and the velocity of dominance and suppression may be determined using, e.g., OKN.

Advantageously, in some embodiments, the display system (e.g., display systems 80, 1000, and 2010 of FIGS. 9D, 6, and 10, respectively) may be configured to infer the user's visual perception using various features of the display system, including the unique delivery of light to the user's eyes, eye tracking, and other sensors, such as electrodes that measure electrical potentials of the user's body. The display system may also measure components of the efferent visual system, e.g. fixation, saccades, pursuits, accommodation, vergence, and the like, for additional variables to infer perception. Various examples of methods for inferring and evaluating the user's visual perception are discussed below.

Visual Evoked Potentials ("VEP")

In some embodiments, the display system may be configured to use VEP to determine optical nerve dysfunctions and to measure the integrity of the visual pathways via the optical nerves that run from the retina to the visual cortex. For example, the display system may take electrical potential measurements measured from the scalp overlying the visual cortex and determine anomalies in the visual pathways. Such measurements may be performed using the peripheral sensor 30a (FIG. 9D), which may be an electrode and may be positioned on the user's scalp. In some other embodiments, the electrical potentials are measured from different and/or additional locations on the user's body. The display system may measure electrical potentials before, during, and/or after visual stimulus has been presented to the user's eye.

The VEP analysis may include the steps illustrated in FIG. 11. At block 1710, the user may be presented with a stimulus, e.g., in the form of the image content displayed by the display system to the user. The display system may sense a user's reaction to the stimulus at block 1720 using one or more electrodes attached to the user to determine an electrical potential. It will be appreciated that the one or more electrodes may be the peripheral sensor electrode 30a illustrated in FIG. 9D. The display system may process the electrical potentials to determine the presence of a neurological condition associated with the user's reaction. Such a determination may be made by, e.g., identifying conditions associated with the reaction measured based on the particular combination of stimulus provided. The neurological condition determination may conclude that one or more possible conditions are present, may provide probabilities that the user has the one or more possible conditions, and/or may be used to determine a weight or a factor to be used in another determination.

It will be appreciated that the display system may be configured to calculate an average of sweep responses to reduce noise, filter the signal, analyze data in the frequency domain, and/or perform other signal processing techniques to obtain a stronger signal over the noise and/or over other signals. The display system may compare the measured signal with a predetermined signal of a normal user, predetermined signals of users with specific conditions, and/or other predetermined signals. The display system may determine the latency and amplitude of the measurements.

The display system may perform a variety of different VEP tests, some examples of which are mentioned below. Although the examples of VEP tests below are described separately, the display system may conduct multiple VEP tests simultaneously or in series. As disclosed herein, the various stimuli discussed below for block 1710 may be presented by the display system to the user at various locations in space (at various locations along x, y, and z axes), and the measurement of reactions at block 1720 may be performed by one or more electrodes attached to the user.

In some embodiments, visual stimuli presented to the user may have therapeutic effects. In one example, a perception aid delivered at block 1830 of the method of FIG. 12 may include providing light of certain frequencies (e.g., at the frequency of gamma waves or other frequencies) to affect neural patterns. For example, Alzheimer's disease may be associated with abnormal neural oscillations. In some embodiments, the perception aid can include delivering light at selected frequencies to the user to normalize the abnormal neural oscillations. In some embodiments, the light presented to the user may flicker at a particular frequency, e.g. 40 Hz, selected to attenuate beta-amyloid plaques in users, such as those suffering from Alzheimer's disease.

In some embodiments, flickering or strobing light may be presented to the user from a subset of waveguides of the display system, or a subset of the images presented by the display system. For example, flickering light may be presented to the user from one component color waveguide (e.g., a waveguide for providing red, green, or blue component color images) while other waveguides for providing other component colors may be utilized to provide normal (non-flickering) virtual content. In some embodiments, a background flicker may be presented to the user in one or more of the RGB component colors by providing a flickering light corresponding to a depth plane on which the user is not fixated. In such embodiments, normal non-flickering virtual content may be provided on the depth plane at which the user is fixating.

Light Source Goggle VEP

With reference to FIG. 10, the display system may include a light source 26 to provide stimulation to the user. It will be appreciated that a plurality of light sources 26 (e.g., LEDs) may be arrayed around the frame 64. In some embodiments, the display itself may simulate one or more discrete light sources, e.g., by displaying content that shows one or more discrete sources of light.

With reference to FIG. 11, in some embodiments, the plurality of discrete light sources 26, or a simulation of the same shown as an image, may generate stimulus 120 for the user. The real or simulated light sources may produce a large field of stimulus that minimizes the effect of gaze direction. It will be appreciated that the light sources may be disposed in the display system, may be peripherally attached to the display system, or may be separate but in electronic communication with the display system. The light sources may be arrayed in a pattern or a grid. The light sources may be configured to generate content having one or more of a variety of colors and one or more desired light intensities, patterns, brightness, two- or three-dimensional enhancement or de-enhancement, sharpened or blurred focus, higher or lower resolution, enhanced or de-enhanced contrast, motion, lack of motion, higher or lower refresh rate, magnification, shape, intensity, distortion or other qualities, all of which may change over time. The display system may be configured to generate images corresponding to the light sources in various depth planes, to provide proper accommodation and vergence to the user for viewing comfort.

With continued reference to FIG. 11, at block 1720, the user's reaction to stimulation using real or simulated light sources may be measured. For this purpose, the display system may include peripheral sensor electrodes such as the electrodes 30a of FIG. 9D. As discussed herein, the electrodes may be disposed on a part of the display frame 64, may be an attached or detached part of the display frame 64, and/or may be in communication with the display frame 64 using wired or wireless communication. The reactions may be stored and processed by a local processing and data module 70, or a remote processing module 72. In some embodiments, the stimulus may be applied and the subsequent measurement of the user reaction may be assessed to test the efficacy of the stimulus for achieving a particular reaction and/or may be implemented to provide a feedback loop to help induce a particular state in the user. Light source goggle VEP may be evaluated for variability between people (inter-individual variability) and within a given person (intra-individual variability), e.g., over time.

Monocular and Binocular VEP

In some embodiments, the display system may conduct monocular and/or binocular VEP testing. It will be appreciated that such testing may be used to measure functional integrity, cell viability, and interference in the visual pathway.

With reference to FIG. 11, a stimulus may be presented to the user at block 1710. For monocular VEP, the display system may project the stimulus onto one eye at a time. For binocular VEP, the stimulus may be projected simultaneously to both eyes. As an example, the stimulus may include images to the left and right eyes and may alternate the images at a high rate. Three examples of stimuli include dynamic random dot correlograms where dots alternate between correlated and anticorrelated, dynamic random dot stereograms where portions of dot patterns presented to each eye are shifted horizontally relative to each other at a fixed rate, and dichoptic checkerboard stimuli that alternate color at different frequencies for each eye. The display system may be configured to generate images corresponding to the light sources in various depth planes, to provide proper accommodation and vergence to the user for viewing comfort. Another example of a stimulus is the change of dark-colored squares to light-colored squares, and light-colored squares to dark-colored squares, with the size of the squares being, e.g., 15-40 arcmin of the eye, and the squares forming a checkerboard pattern presented to one eye at a time. In such embodiments, VEP may be generated by foveal and parafoveal elements. The light sources may be configured to generate content having one or more of a variety of colors and one or more desired light intensities, patterns, brightness, two- or three-dimensional enhancement or de-enhancement, sharpened or blurred focus, higher or lower resolution, enhanced or de-enhanced contrast, motion, lack of motion, higher or lower refresh rate, magnification, shape, intensity, distortion or other qualities, all of which may change over time. Monocular and Binocular VEP may be evaluated for variability between people (inter-individual variability) and within a given person (intra-individual variability), e.g., over time.

With continued reference to FIG. 11, the display system may sense the user reaction to the stimulus at block 1720. The display system may determine neurological conditions, or other abnormalities, associated with the user reaction 140. For example, if the reaction to the stimulus is atypical, the display system may determine that lesions of the optic nerve anterior to the optic chiasm may be present. Select portions of the visual field may be simulated and postchiasmal, prechiasmal, and/or chiasmal abnormalities may be correspondingly determined. Monocular and Binocular VEP testing may be evaluated to determine optic neuropathy, which refers to damage to the optic nerve, which can be a result of many causes, e.g. ocular disorders. Monocular and Binocular VEP testing may also be evaluated to diagnose photosensitive epilepsy and identify which stimuli, e.g. patterns, cause seizures.

Sweep VEP

In some embodiments, the display system may be configured to conduct a sweep VEP test, which enables the display system to evaluate visual acuity. Referring to FIG. 11, at block 1710, a stimulus may be presented to the user. The stimulus may take the form of patterns that are alternated at a high temporal frequency rate. Typically, the rate is between 5 to 15 Hz, but it is appreciated that this rate may be faster or slower. In some embodiments, the display system may reduce the size of the pattern and/or may present a variety of patterns within a certain period of time and in the x, y, and z planes with images displayed on depth planes having proper accommodation and vergence matching. For example, the size of the pattern may be reduced so that within a certain amount of time (e.g., 10 seconds), a large number of differently-sized patterns (e.g., 20 different pattern sizes) are presented in succession.

The display system may sense a user reaction to the stimulus at block 1720. For example, from its sweep of the spatial resolution domain, the display system may determine the smallest pattern producing a response. From this determination, the display system may estimate visual acuity. This estimated visual acuity may be used to determine a neurological condition associated with the user 140. In some other embodiments, the amplitudes of the readings may be checked and compared based on the size of the stimuli presented. In some other embodiments, the display system may sweep other characteristics of the stimuli, such as the luminance, frequency of change, sharpness of the image, and the like in the x, y, and z planes with images displayed on depth planes having proper accommodation and vergence matching. Multiple sweeps may be performed, and results may be averaged to reduce the noise floor and improve the signal-to-noise ratio to provide a cleaner signal. The light sources may be configured to generate content having one or more of a variety of colors and one or more desired light intensities, patterns, brightness, two- or three-dimensional enhancement or de-enhancement, sharpened or blurred focus, higher or lower resolution, enhanced or de-enhanced contrast, motion, lack of motion, higher or lower refresh rate, magnification, shape, intensity, distortion or other qualities, all of which may change over time. Sweep VEP may be evaluated for variability between people (inter-individual variability) and within a given person (intra-individual variability), e.g., over time.

It will be appreciated that the display system may perform a discrete Fourier transform on the recorded signals, or other type of signal processing transformation. The display system may provide real time measurement of the amplitude and phase of the response, thus allowing the display system to detect a response quickly. The display system may display a response amplitude versus a pattern size plot. The display system may conduct several sweeps. Multiple sweeps may be used to increase signal strength over the noise floor, may be used to confirm prior determinations, may be used as weights or factors for other calculations, and/or may be used to determine trends. As an example, sweep VEP testing may be particularly helpful for determining vision impairment in children and people with albinism by evaluating visual acuity. Sweep VEP testing may also be used to diagnose photosensitive epilepsy and identify which stimuli, e.g. frequency, causes seizures.

Chromatic VEP

In some embodiments, the display system may use color stimulus to test color vision. It is appreciated that a Chromatic VEP analysis may correspond to the process described in FIG. 11. At block 1710, the stimulus applied to the user may include image content having the colors red and green, blue and yellow, black and white, or other combination of colors. The stimulus may be altered between two colors or a different plurality of colors. A plurality of portions of the stimulus may change color simultaneously. The stimulus may be altered between different shades of similar colors. The stimulus may be two dimensional or may be projected in a three-dimensional color space. The stimulus may alter the color pattern in a single rate or a variety of different rates. The light sources may be configured to generate content having one or more of a variety of colors and one or more desired light intensities, patterns, brightness, two- or three-dimensional enhancement or de-enhancement, sharpened or blurred focus, higher or lower resolution, enhanced or de-enhanced contrast, motion, lack of motion, higher or lower refresh rate, magnification, shape, intensity, distortion or other qualities, all of which may change over time. The stimulus may change color in one visual area but not in another. Chromatic VEP may be evaluated for variability between people (inter-individual variability) and within a given person (intra-individual variability), e.g., over time.

The display system may sense the user's reaction to the applied stimulus at block 1720. For example, the display system may determine the user's color contrast sensitivity by measuring evoked potentials using a peripheral sensor or an electrode (e.g., electrical 30a, FIG. 9D). In some embodiments, at block 1730, the display system may generate chromatic VEP waveforms from the responses and perform signal processing to identify neurological conditions, or other abnormalities, such as loss in color vision capacity in both congenital and acquired color vision deficiency. For example, color vision deficits may be determined by differences in the waveform, due to, e.g., lower amplitudes and increased latencies. Stimulus directed to a particular type of chromatic deficiency may also be used, to allow for identification of that particular deficiency. Chromatic VEP may help to provide information on the integrity of a user's color visual pathway. As an example, Chromatic VEP may be helpful when evaluating young patients with demyelinating disease. Chromatic VEP may also be used to characterize development, maturation, and aging of the chromatic visual pathways. It is appreciated that Chromatic VEP may be used in other applications. Chromatic VEP may also be used to diagnose photosensitive epilepsy and identify which stimuli, e.g. colors, cause seizures.

Hemifield VEP

In some embodiments, the display system may use stimulus presented to one side of a visual field. It is appreciated that the Hemifield VEP process may correspond to the process described in FIG. 11. At block 1710, the stimulus applied to the user may be presented in a sector of a visual field at a particular location relative to a fixation point. The stimulus may be presented by alternating between the different designated fields. For example, stimulus may be presented to the left visual field first and then the right visual field. In some embodiments, other parts of the visual field may be used, such as any location in the x, y, and z planes with adjustment for proper accommodation and vergence using depth planes. The light sources may be configured to generate content having one or more of a variety of colors and one or more desired light intensities, patterns, brightness, two- or three-dimensional enhancement or de-enhancement, sharpened or blurred focus, higher or lower resolution, enhanced or de-enhanced contrast, motion, lack of motion, higher or lower refresh rate, magnification, shape, intensity, distortion or other qualities, all of which may change over time. For example, the top and bottom visual field may be used, or specific quadrants may be stimulated. Hemifield VEP may be evaluated for variability between people (inter-individual variability) and within a given person (intra-individual variability), e.g., over time.

The display system may sense the response to the stimulus at block 1720. For example, the display system may determine an amplitude difference between evoked potentials between the left and right hemifield stimulation. The display system may use the sensed response to identify a neurological condition, or other abnormality. For example, the hemi-field response may be compared with responses from normal subjects or compared to subjects that have known abnormalities that produce a particular response. The display may assess amplitude and latency to determine abnormalities. For example, hemifield VEPs may help to detect functional monocular hemianopia. In another example, the measurement of hemifield VEPs may provide an objective tool to distinguish functional hemianopia from hemifield loss caused by an organic lesion. In some embodiments, the sensitivity of half-field vision may be tested to identify lesions of the visual system at chiasmal, prechiasmal, or postchiasmal sites. In some circumstances, the cause of ambiguity in full-field testing may be clarified using hemifield VEP testing. Furthermore, for hemispatial neglect, where damage to a hemisphere of the brain results in a deficit to awareness of one side of space, the display system may use hemifield VEP information to determine if the brain is receiving a response signal, in which case the display system may determine a higher probability of a neuropsychological condition and not an inability for the brain to receive a signal.

Flash VEP

The display system may be configured to conduct a flash VEP analysis. In such an analysis, at block 1710, the display system may provide stimulus comprising bright flashes of light to the user. The flashes of light may be unpatterned in some embodiments. The applied stimulus may comprise several flashes over the course of a specific period of time. For example, six major peak flashes may be provided in the first 250 ms, alternating in negative and positive polarity. It is appreciated that a different number of flashes during different periods of times may be used. The flashes may be created by a light sources 26 (FIG. 10) and/or may be displayed as image content comprising flashes of light. The flashes may be presented in a predetermined number of cycles per second. The stimulus may be flashed in the whole visual field so that the direction of the gaze is unimportant. In some other embodiments, specified regions of the visual field may be targeted, and/or the stimulus may span a section of the visual field. The light sources may be configured to generate content having one or more of a variety of colors and one or more desired light intensities, patterns, brightness, two- or three-dimensional enhancement or de-enhancement, sharpened or blurred focus, higher or lower resolution, enhanced or de-enhanced contrast, motion, lack of motion, higher or lower refresh rate, magnification, shape, intensity, distortion or other qualities, all of which may change over time. Flash VEP may be evaluated for variability between people (inter-individual variability) and within a given person (intra-individual variability), e.g., over time.

The display system may measure the response to the stimulus at block 1720. It will be appreciated that flash VEP testing may identify responses to flash stimulation that do not require stimulus locked eye movement or muscle movement. Flash VEP may provide the ability to measure responses if the patient's acuity is 20/40 (6/120) or worse, or if the patient is uncooperative, unconscious, sedated, or has ocular opacities. Flash VEP may also provide the display system the ability to determine responses for infants who have trouble remaining fixed on a certain pattern. The display system may use the flash VEP measurements to detect neurological conditions 140, or other abnormalities, such as optical atrophy and other abnormalities of the central visual pathways. Flash VEP testing may also be used to diagnose photosensitive epilepsy and identify which stimuli, e.g. frequency, cause seizures.

Motion VEP

In some embodiments, the display system may be configured to conduct a Motion VEP analysis as part of the process described in FIG. 11. At block 1710, the visual content stimulus applied to the user may include features that move within the field of view. For example, the features may move from one area of the visual field to another in the x, y, and z planes with adjustment for proper accommodation and vergence using depth planes, may change in orientation, and/or may change in boundary sharpness. The features may change at one time, or multiple parts of the display content may change simultaneously. The light sources may be configured to generate content having one or more of a variety of colors and one or more desired light intensities, patterns, brightness, two- or three-dimensional enhancement or de-enhancement, sharpened or blurred focus, higher or lower resolution, enhanced or de-enhanced contrast, motion, lack of motion, higher or lower refresh rate, magnification, shape, intensity, distortion or other qualities, all of which may change over time.

The display system may measure the response to the stimulus at block 1720. The display system may assess the effects, as determined using one or more electrodes attached to the user, of varying the form, scale, location, or other change of the stimulus. The display system may determine the extrastriate motion-sensitive area localization of visual perception of the motion based upon the applied stimulus and the measured reaction. The latency between the time the stimulus was presented to the user and the time of a response peak measured by the one or more electrodes may also be determined.

At block 1730, the display system may process electrical potentials to determine a neurological abnormality associated with the user's reaction. It will be appreciated that the motion VEP may be evaluated for variability between people (inter-individual variability) and within a given person (intra-individual variability), e.g., over time. For example, motion VEP testing may be applied to evaluate disorders including multiple sclerosis, encephalopathies, dyslexia, and glaucoma.

Multifocal VEP

In some embodiments, the display system may be configured to conduct a Multifocal VEP analysis as part of the process described in FIG. 11. The display system may be configured to provide simultaneous stimulation at different locations in the user's visual field and may simultaneously measure reactions to the stimulation. At block 1710, the display system may display visual content in which different areas, or sectors, of the content may have different patterns, each of which may change according to an individual stimulus sequence. For example, the image content may contain 60 sectors, each with a checkerboard pattern. The displayed visual content may include reversing check patterns, for example, by reversing a check pattern that is in a shape of a dartboard. However, it is appreciated that other types of stimuli may be used in the x, y, and z planes with adjustment for proper accommodation and vergence using depth planes, such as flickering patterns. It will be appreciated that particular patterns displayed at particular locations in the user's visual field may stimulate a unique response or set of responses by the user. The light sources may be configured to generate content having one or more of a variety of colors and one or more desired light intensities, patterns, brightness, two- or three-dimensional enhancement or de-enhancement, sharpened or blurred focus, higher or lower resolution, enhanced or de-enhanced contrast, motion, lack of motion, higher or lower refresh rate, magnification, shape, intensity, distortion or other qualities, all of which may change over time.

At block 1720, one or more electrodes may measure the user's reaction to the applied stimulus. Using multifocal VEP, the display system may isolate dysfunctional areas within the user's visual processing pathway quickly by simultaneously presenting and measuring reactions to a large number of stimuli, instead of presenting and measuring a response for each stimulus serially. Multifocal VEP may be evaluated for variability between people (inter-individual variability) and within a given person (intra-individual variability), e.g., over time.

To assess defects in the visual field, the display system may take measurements of the responses to the stimulus measured at block 1720, and determine a neurological condition, or other abnormality, based on these readings at block 1730. The display system may be configured to process the electrical measurements to differentiate responses originating from different locations in the visual field. Different locations in the visual field may be correlated with different retinal locations. In some embodiments, the display system may take the multifocal VEP responses and compare them with normal responses or a different predetermined response. Multifocal VEP testing may allow a display system to detect small abnormalities in the optic nerve transmission and provide topographic correlation along the visual pathway. Multifocal VEP testing may also be used to diagnose photosensitive epilepsy and identify which stimuli, e.g. patterns, cause seizures.

Multi-Channel VEP

In some embodiments, the display system may use multiple channels of electrodes to measure multiple electrical potentials. Multiple electrodes (e.g., multiple peripheral sensor electrodes 30a, FIG. 9D) may be disposed in contact with the user. For example, an array or grid of electrodes may also be created and used. Sixteen electrodes may be distributed into a 4×4 multi-channel array for measurement. Multi-channel VEP may be evaluated for variability between people (inter-individual variability) and within a given person (intra-individual variability), e.g., over time. Multiple channels may be used to assess central visual pathways. Additional channels may provide the display system with the ability to better diagnose chiasmal, prechiasmal, and postchiasmal dysfunction. For example, two channels may be used to detect lateral asymmetries.

Multi-Frequency VEP

In some embodiments, the display system may conduct a Multi-Frequency VEP analysis as part of the process described in FIG. 11. At block 1710, the display system may provide the same stimulus at different frequencies and/or may display different stimuli at different frequencies to the user. For example, the display system may display two pattern stimuli at different temporal frequencies the user, for example at 10 Hz for stimulus for the right hemifield and 15 Hz for stimulus for the left hemifield. Multi-frequency VEP may be evaluated for variability between people (inter-individual variability) and within a given person (intra-individual variability), e.g., over time. The light sources may be configured to generate content having one or more of a variety of colors and one or more desired light intensities, patterns, brightness, two- or three-dimensional enhancement or de-enhancement, sharpened or blurred focus, higher or lower resolution, enhanced or de-enhanced contrast, motion, lack of motion, higher or lower refresh rate, magnification, shape, intensity, distortion or other qualities, all of which may change over time.

The display system may measure the responses of the user at block 1720 using one or more electrodes as described herein. At block 1730, the measured responses may be analyzed to identify neurological conditions or other abnormalities. For example, a discrete Fourier transform may be performed on the measured signals to provide real time, simultaneous measurement of the responses to both hemifield stimulations. Using the example above, the display system may identify amplitudes in the frequency spectrum that are in the 10 Hz and 15 Hz frequency band for the right and left hemifields. Advantageously, in some embodiments, the display system using multi-frequency VEP may provide the ability to detect a response very rapidly. In some embodiments, the multi-frequency VEP may be applied to examine the visual processing functioning of patients with chiasmatic, prechiasmatic, or post-chiasmatic disorders. Multi-frequency VEP testing may also be used to diagnose photosensitive epilepsy and identify which stimuli, e.g. frequency, cause seizures.

Stereo-elicited VEP

In some embodiments, the display system may be configured to conduct a Stereo-elicited VEP analysis as part of the process described in FIG. 11. As part of this analysis, at block 1710, the display system may display random dot stereograms as stimuli to evaluate a user's depth perception. It will be appreciated that different stereograms may be presented to the user to provide images corresponding to different depths. This change in stereograms may occur once or repetitively, quickly or slowly, for a single target or multiple targets, and/or simultaneously with other stimuli or on its own. In some embodiments, the stereoscopic stimuli may create and remove stimuli at different perceived depths. The content of the stereograms may have sharp edges or blurred edges. The light sources may be configured to generate content having one or more of a variety of colors and one or more desired light intensities, patterns, brightness, two- or three-dimensional enhancement or de-enhancement, sharpened or blurred focus, higher or lower resolution, enhanced or de-enhanced contrast, motion, lack of motion, higher or lower refresh rate, magnification, shape, intensity, distortion or other qualities, all of which may change over time. Stereo-elicited VEP may be evaluated for variability between people (inter-individual variability) and within a given person (intra-individual variability), e.g., over time.

The display system may measure the reaction of the user to the stereograms at block 1720. Typically, a change in stereoscopic disparity is associated with muscular eye movements due to vergence. These muscular changes may produce electrical potentials that may be measured by peripheral sensor electrodes (e.g., electrodes 30a, FIG. 9D). The display system may use the measured responses to determine abnormalities 140. For example, the display system may determine vergence abnormalities of the eye by measuring muscular changes based on varying the perceived depth of the stimuli. Stereo-elicited VEP testing may also determine vergence abnormalities by tracking the eye(s) of the user.

Steady State VEP

In some embodiments, the display system may be configured to conduct a Steady State VEP process as part of the process described in FIG. 11. In some embodiments, the display system may detect user responses to stimuli displayed to the user at certain frequencies. For example, at block 1710, the display system may display visual content to the user at a specific base frequency, e.g. from 3.5 Hz to 75 Hz. In some embodiments, the visual content may be a strobing light turning on and off at the base frequency. The light sources may be configured to generate content having one or more of a variety of colors and one or more desired light intensities, patterns, brightness, two- or three-dimensional enhancement or de-enhancement, sharpened or blurred focus, higher or lower resolution, enhanced or de-enhanced contrast, motion, lack of motion, higher or lower refresh rate, magnification, shape, intensity, distortion or other qualities, all of which may change over time. Steady State VEP may be evaluated for variability between people (inter-individual variability) and within a given person (intra-individual variability), e.g., over time.

The display system may measure user responses to the stimulus at block 1720. Without being limited by theory, it is believed that when a user views such a stimulus, the frequency of the signal in the stimulus may cause the user's brain to produce electrical signals both at the base frequency and multiples of the base frequency. For example, if a user views the flashing light stimulus at 20 Hz, the brain may produce electrical activity (in the form of steady state VEP's) at a frequency of 20 Hz, 40 Hz, 60 Hz, and so forth. It is believed that such a reaction by the brain may occur for stimuli presented at frequencies in the range of 3.5 Hz to 75 Hz. Localized and distributed sources of stimulation, in the form of image content displayed to the user, may generate these steady state VEPs. At block 1730, the display system may then identify abnormalities in the measured steady state VEP's. In some embodiments, the display system may analyze the measurements using a fast Fourier transform. In some embodiments, steady state VEP's provide the ability to assess the visual field and acuity of infants. Steady State VEP's may also provide a means to characterize preferred frequencies of the neocortical dynamic processes. Steady State VEP testing may also be used to diagnose photosensitive epilepsy and identify which stimuli, e.g. frequency, cause seizures.

Event Related Potentials ("ERP")

In some embodiments, the display system may be configured to use ERP to assess health and function of the brain and nervous system, including the optic nerve, retinal cells, muscles, and/or motor neurons. In various embodiments, ERP techniques may include electroretinography ("ERG"), electrocardiography ("EKG"), and/or electromyography ("EMG"), which advantageously are noninvasive means of evaluating brain and nervous system function. ERP may utilize electrodes (e.g., EEG) to obtain information regarding nervous system activity of the user, including the response of the user to stimuli.

For example, in some embodiments, the display system may take electrical potential measurements from the scalp overlying the visual cortex and determine anomalies in the visual or other pathways. Such measurements may be performed using the peripheral sensor 30*a* (FIG. 9D), which may be an electrode and may be positioned on the user's scalp or other locations on the user's head or body, such as on the cornea or skin near the eye, or on the skin near the user's heart. In some other embodiments, the electrical potentials are measured from different and/or additional locations on the user's body. The display system may measure electrical potentials before, during, and/or after a stimulus has been presented to a user (e.g., a visual stimulus presented to the user's eye, an audio stimulus presented to the user's ear, or the like).

In some embodiments, ERG may be implemented by measuring the electrical responses of retinal cells (e.g., bipolar cells, amacrine cells, ganglion cells, photoreceptors, etc.) to a visual stimulus, which may include a standardized set of stimuli. ERG may utilize sensors on the user's cornea and/or skin adjacent to or near the eye to detect electrical responses of the retinal cells. ERG techniques may include ratio ERG for detection and/or monitoring of glaucoma (including late stage glaucoma), flash ERG for detecting conditions related to specific types of retinal cells (e.g. rods, cones, amacrines, etc.), multi-focal ERG for measuring cell function across the retina to quantify retinal dysfunction, and/or pattern ERG for measurement of functionality of retinal cells, optic neuropathy, and/or dysfunction of ganglion cells.

In some embodiments, EKG may be implemented by measuring the electrical activity of cells in and around the heart, for example, in response to a stimulus. EKG may utilize sensors on the user's skin in the vicinity of the heart to detect electrical responses of cells in the heart. EKG may be used, for example, to monitor a cardiac response to a stimulus or aid provided to the user, for example, sound therapy, sounds intended to relax the user, visual and/or audio stimuli intended to lower heart rate or blood pressure, etc.

In some embodiments, EMG may be implemented by measuring the electrical activity of muscles and/or motor neurons controlling the muscles. EMG may utilize sensors on the user's skin in proximity to the muscles and/or motor neurons to be monitored. EMG may be used, for example, to detect a user's response to a stimulus (e.g., an instruction to move a body part, etc.) and/or monitor a user's ability to comply or partially comply with an instructed movement.

In some embodiments, the ERP analysis may include the steps illustrated in FIG. 12. At block 1710, the user may be presented with a stimulus, e.g., in the form of image content displayed by the display system to the user. The display system may sense a user's reaction to the stimulus at block 1720 using one or more electrodes attached to the user to determine an electrical potential. For example, the system at block 1720 may use ERG to detect a retinal response to a visual stimulus, may use EKG to detect a change in heart rate in response to an audio or visual stimulus, and/or may use EMG to detect a movement or lack of movement made by the user in response to the stimulus. It will be appreciated that the one or more electrodes may be the peripheral sensor electrode 30*a* illustrated in FIG. 9D. The display system may process the electrical potentials to determine the presence of a neurological condition associated with the user's reaction. Such a determination may be made by, e.g., identifying conditions associated with the reaction measured based on the particular combination of stimulus provided. The neurological condition determination may conclude that one or more possible conditions are present, may provide probabilities that the user has one or more possible conditions, and/or may be used to determine a weight or a factor to be used in another determination.

In some embodiments, the ERP analysis may include the steps illustrated in FIG. 13. In one example, a perception aid delivered at block 1830 of the method of FIG. 13 may include providing stimuli previously determined to be calming (e.g., calming sounds, calming visual content, or other calming stimulus) in response to a determination that the user is experiencing high blood pressure or an elevated heart rate.

It will be appreciated that the display system may be configured to calculate an average of sweep responses to reduce noise, filter the signal, analyze data in the frequency domain, and/or perform other signal processing techniques to obtain a stronger signal over the noise and/or over other signals. The display system may compare the measured signal with a predetermined signal of a normal user, predetermined signals of users with specific conditions, and/or other predetermined signals. The display system may determine the latency and amplitude of the measurements.

Biofeedback with Body Sensors

In some embodiments, the display system may be configured to provide biofeedback in conjunction with body sensors to retrain and/or alter neural tissues of the user's brain. The display system can be used with body electrodes, sensors, and/or stimulators to measure and/or stimulate muscle activity while providing feedback (e.g., visual cues). Such treatment can include neural interface technology, sensory motor training, cognitive rehabilitation, neuroprosthesis, electromyography, and the like. It may be used for both diagnostic and therapeutic (e.g., rehabilitation) applications.

As a particular example, biofeedback with body sensors can be used to treat a stroke patient. For example, a stroke patient, either alone or with help, can move his arm frequently (e.g., daily) to retrain a new part of the damaged brain. The display system can be configured to provide feedback on the range of motion to improve measurement and/or accelerate changes in the patient's neural plasticity. This can be an improvement over solely providing subjective feedback on whether the patient judges or is told a level of improvement.

Analyses Utilizing Eye Movement

It will be appreciated that the display system (e.g., display systems 80, 1000, and 2010 of FIGS. 9D, 6, and 10, respectively) may be configured to detect the oculomotor response (e.g., fixation, saccadic, pursuit, vestibular, optokinetic, accommodation, pupil dilation/constriction and/or vergence) of the visual system, including responses in the eye and the brain, to one or more visual stimuli. The detected oculomotor response may be used to reverse engineer and evaluate different processes occurring in the eye and/or the brain that are responsible for how visual information is understood and perceived. Various analyses or assessments utilizing oculomotor responses are described below.

Extraocular/Ocular Motility Assessment

In some embodiments, the display system may be configured to evaluate and/or detect abnormalities in a user's oculomotor nerve (also referred to as cranial nerve III), abducens nerve (also referred to as cranial nerve VI), and/or trochlear nerve (also referred to as cranial nerve VI) by detecting extraocular eye movements in response to one or more visual stimuli. For example, the display system may be configured to perform an extraocular/ocular motility assessment to evaluate weakness and/or abnormalities in portions of the brain that control the extraocular muscles controlling eye movement.

To perform an extraocular/ocular motility assessment, the display system may be configured to present a stimulus to the user as shown in block 1710 of the method 1700 depicted in FIG. 11. The stimulus may comprise an image of an object (e.g., a pen or a pencil) that is projected by the display system (e.g., from the waveguide stacks 2005, 2006 of the display system 2010) such that the image appears to be at distance at which the user's eye can accommodate and verge (e.g., about 16 inches) from the user's eye. The display system may be further configured to move the projected image of the object in one or more directions.

The display system may sense the user's reaction to the stimulus in block 1720 (FIG. 11). To sense the user's reaction to the stimulus, some embodiments of the display system may be configured to track the movement of one or both of the user's eye (e.g., using the cameras 24, 28 of the display system 2010, FIG. 10). In various embodiments, the user may be instructed to follow the projected image of the object without moving his/her head similar to a smooth pursuits test. In block 1730, a neurological condition associated with the tracked movement of one or both of the user's eyes may be determined. In various embodiments, the depth plane on which the image is placed may be varied, such that the image of the object appears to originate from different depth so that vergence and/or accommodation of the user's eyes can be tested. For example, a weakness or other anomalies in the portions of the brain that control the extraocular muscles may be determined from the tracked movement of one or both of the user's eyes. Such a determination may be made, for example, by comparing how closely the user's eyes track the projected image in an absolute sense, or in comparison to how closely other individuals track the projected image. In some embodiments, the determination of a weakness or other anomalies in the portions of the brain that control the extraocular muscles may be made by a health care professional who reviews the tracked movement of one or both of the user's eye and/or a diagnostic system in communication with the display system.

In some embodiments, the stimulus presented to user at block 1710 may be a stimulus that is present in the external environment and which has been categorized by the display system. For example, the display system's forward-facing camera may be configured to image the ambient environment and the display system may be configured to perform image analysis on the images to determine the presence of various features in the ambient environment. For example, the display system may be configured to perform face and/or eye recognition to determine the presence and location of faces and/or human eyes in the user's field of view. In yet other embodiments, the display system may be configured to display various types of content (e.g., images of people and/or abstract images) at block 1710.

At block 1720, the display system may be configured to track vergence and possibly accommodation. For example, the display system may be configured to perform fixation testing by tracking the line of sight or gaze direction of each of the user's eyes, and the display system may be configured to optionally also detect glint. The eyes may be tracked using one or more inward facing camera's directed to the eye. The location or object on which the user's eyes are fixating may be determined by determining the point at which the gaze direction of each eye converges. In addition, the display system may be configured to detect microsaccades or microfluctuations in vergence and accommodation as a user views his/her environment, such as when the user is fixating on an object.

It will be appreciated that across a population of users, particular norms may be expected for various parameters such as the duration of fixation on the object, and/or the amount of microsaccades or microfluctuations in vergence and/or accommodation. It will be appreciated that these norms may vary depending on the object and the norms may be stored locally on a local data module 70 of the display device or on a remote data repository 74 (FIG. 9D). For example, where the object is the human eye, a user with social fears or autism may avoid eye contact and/or may favor focusing on abstract images or objects (in a real or virtual scene in which both a human face and abstract images are present), instead of social images or people. Consequently, the display system may be configured to detect that the user spends less time fixated on another person's eyes (thereby avoiding eye contact), relative to norms for the general population. As a result, the display system may be configured to make the conclusion that the user may have social fears or autism.

Other abnormalities in a user's fixation pattern may also be noted and possible occurrences of various disorders may be determined by the display system. For example, abnormalities in fixation patterns may be indicative of mental disorders, Parkinson's disease, attention deficit hyperactivity disorder (ADHD), or fetal alcohol spectrum disorder. Disorders such as autism and ADHD do not currently have identifiable biomarkers, instead, a diagnosis of autism, ADHD and other developmental disorders may depend on the observation of subjects in their natural environments. The display system may function as a diagnostic tools to facilitate detection of these disorders by automatically tracking the user's fixation, accommodation, microsaccades, and/ or microfluctuations in response to various objects displayed to the user or present in the user's field of view in the ambient environment. Deviations from norms for fixation, accommodation, microsaccades, and/or microfluctuations, relative to particular types of objects, may be detected and may be determined by the display system to indicate a disorder, as noted above. For example, it has been found that certain eye movement patterns may be indicative of Parkinson's disease. In some embodiments, the display system may be configured to display perception aids as discussed below with respect to FIG. 12, in response to a determination of a neurological condition.

With continued reference to FIG. 11, in some embodiments, block 1720 may be performed before block 1710. For example, the display system may be configured to determine where the user's eyes are fixating, and then determine what feature (e.g., what object) the user is fixating on.

In some embodiments, to track eye movements and/or make ophthalmological diagnosis, the display system may be configured to perform Electrooculography (EOG/E.O.G.). It will be appreciated that EOG is a technique used to measure the corneo-retinal standing potential that exists between the front and the back of the human eye. A display system configured to perform EOG may include a pair of electrodes (e.g., peripheral sensor electrodes 30*a*, FIG. 9D) that are placed either above and below an eye or to the left and right of the eye. If the eye moves from the center position toward one of the two electrodes, the electrode towards which the eye moved senses one side of retina (also referred to as the positive side of the retina) and the other electrode senses another side of the retina (also referred to as the negative side of the retina). Consequently, a potential difference occurs between the electrodes. This voltage signal resulting from the potential difference can be referred to as the electrooculogram. Assuming that the resting potential is constant, the recorded voltage signal can provide a measure of the eye's position to, e.g., determine the fixation point of the eyes and/or to otherwise track eye movement.

Saccadic Movement Assessment

The display system may be configured to detect impairments in smooth saccadic movement in some embodiments. To test the smoothness of the user's saccadic movement, the display system may be configured to present a stimulus to the user in FIG. 11 at block 1710. The stimulus may appear to be located, on a given depth plane, at various locations along the horizontal and vertical axes, and on different depths. The stimulus may comprise a first image that is projected by the display system in FIG. 10 (e.g., out from the waveguide stacks 2005, 2006 of the display system 2010) at a first location for a first interval of time and a second image that is projected by the display system (e.g., out from the waveguide stacks 2005, 2006 of the display system 2010) at a second location for a second interval of time. The difference between the first and the second time intervals may be short (e.g., less than about 30 seconds, less than about 10 second, between about 2.5-5 seconds, between about 1-3 seconds, or less than 1 second) such that the user's gaze is rapidly switching between fixating on the first image and fixating on the second image. The first and the second locations may be widely spaced apart in the user's field of view. The user may be instructed to fixate his/her gaze on the first and the second images. The saccadic movement test may be used to test voluntary saccadic movement.

The display system can also be made to detect differences between voluntary saccadic movement that occurs in response to a visual stimulus, an instruction or a symbolic cue and reflexive, or involuntary saccadic movement that occurs in response to a peripheral stimulus. For example, the display system can be configured to sense a stimulus in the peripheral visual field of the user's eyes as shown in block 1810 of FIG. 12 and sense the involuntary saccadic movement that occurs in response to the stimulus in the peripheral visual field of the user's eyes using any of the sensors and/or cameras described herein (e.g., sensors and/or cameras 24, 28, 30, 32, 34). If abnormalities in the involuntary saccadic movement are detected, then the display system may be configured to determine an associated neurological condition. The display system may be configured to monitor saccadic movement periodically (e.g., daily, hourly, weekly, monthly, etc.). The display system can also be configured to monitor the saccade accuracy by aligning precision of gaze location with objects that the user interacts with on a daily, hourly or weekly basis. Similarly, the display system can be configured to monitor involuntary saccadic movement if a new stimulus appears in the user's field of view.

The display system can also be made to detect differences between voluntary saccadic movement that occurs in response to a visual stimulus, an instruction or a symbolic cue and reflexive or involuntary saccadic movement that occurs in response to a peripheral stimulus. For example, the display system can be configured to sense a stimulus in the peripheral visual field of the user's eyes as shown in block 1810 of FIG. 12 and sense the involuntary saccadic movement that occurs in response to the stimulus in the peripheral visual field of the user's eyes using any of the sensors and/or cameras described herein (e.g., sensors and/or cameras 24, 28, 30, 32, 34). If abnormalities in the involuntary saccadic movement are detected, then the display system may be configured to determine an associated neurological condition. The display system can be configured to monitor saccadic movement periodically (e.g., daily, hourly, weekly, monthly, etc.). The display system can also be configured to monitor the saccade accuracy by aligning precision of gaze location with objects that the user interacts with on a daily, hourly or weekly basis. Similarly, the display system can be configured to monitor involuntary saccadic movement if a new stimulus appears in the user's field of view.

The display system may sense the user's reaction to the stimulus as shown at block 1720 in FIG. 11. To sense the user's reaction to the stimulus, some embodiments of the display system may be configured to track the movement of one or both of the user's eye (e.g., using the cameras 24, of the display system 2010) as the user's gaze is switching between fixating on the first image and fixating on the second image. In some embodiments, the user may be instructed to switch between fixating on the first image and fixating on the second image without moving their head.

From the tracking information obtained by the display system as the user's gaze is switching between fixating on the first image and fixating on the second image, defects in smooth saccadic movement may be detected. At block 1730, the display system may be configured to determine that a neurological condition, such as, for example, cognitive disorders, motor disorders and/or memory disorders associated with defects in smooth saccadic movement may be present in the user. Examples of possible neurological conditions include cognitive impairment, dementia, or Alzheimer's disease. As another example, if prolonged saccades latency and/or slowing of saccades are detected by the display system, in FIG. 11 at block 1730, the display system may make a determination that the user may have a neurological condition such as Huntington's disease, Parkinson's disease, dementia, Alzheimer's disease, cortical basal degeneration, Lewy body dementia or progressive supranuclear palsy. It will be appreciated prolonged saccades latency and/or slowing of saccades may be determined by the display system by taking periodic saccadic movement assessments over time. As yet another example, if the display system detects a disturbance of saccadic eye movement or reduced saccadic accuracy over time, at block 1730, the display system may determine that a neurological condition such as Huntington's disease or Parkinson's disease may be present in the user. As another example, if an increased frequency of square wave jerks or decreased saccadic amplitude/velocity is detected from the periodic saccadic movement assessments over time, the display system may be configured to make a determination of a neurological condition such as cognitive impairment, dementia, multiple sclerosis (MS), Alzheimer's disease or progressive supranuclear palsy. In some embodiments, where catch-up saccades are detected, the display system may be configured to interpret catch-up saccades as an indication of vestibular loss.

Advantageously, as disclosed herein, the display system allows assessments to be conducted over long durations, e.g., periodically over weeks, months, years, including over a user's lifetime. Such periodic assessments can facilitate the diagnoses of conditions that progress over time, by providing data that tracks this progression. As a result, in some embodiments, the determination made at block 1730 may include an analysis of the progression of the measured user reaction at block 1720.

In various embodiments, the display system can be configured as an assistive device that tracks the movement of the pupils (e.g., defects in smooth saccadic movement, nystagmus, etc.) and displays visual information where the eyes are directed. The display system can be further configured to dither the projected image such that the projected image moves synchronously with the movement of the eyes. Some embodiments of the display system can be configured to individually track the movement of the each pupil and dither the image projected towards each eye at different rates to compensate for defects in saccadic movement or nystagmus in each eye.

Anti-Saccades Test

The display system may be configured to detect failure to inhibit reflexive saccadic movement. To test failure to inhibit reflexive saccadic movement, at block 1710 in FIG. 11, the display system may be configured to present an image of a motionless target (e.g., a small dot) that is projected by the display system (e.g., from the waveguide stacks 2005, 2006 of the display system 2010 in FIG. 10) at a first location. The user is instructed to fixate his/her gaze on the motionless target. The display system may be further configured to present another stimulus to the user. The stimulus may comprise a second image of a second target that is projected by the display system (e.g., from the waveguide stacks 2005, 2006 of the display system 2010), such that the second target appears to be at a second location within the user's field of vision. The second location may be at one side of the first location, e.g., to the left or right of the first location. The display system may instruct the user to pivot his/her gaze to a side opposite the side on which the second image is located. For example, if the stimulus is presented to the left of the motionless target, the display system may be configured to instruct the user to pivot his/her gaze to the right of the motionless target.

At block 1720 in FIG. 11, the display system may be configured to sense the user's reaction to the stimulus. To sense the user's reaction to the stimulus, some embodiments of the display system may be configured to track the movement of one or both of the user's eyes (e.g., using the cameras 24 of the display system 2010 in FIG. 10) as the user's gaze pivots to the side opposite to the side on which the second image is projected. From the tracking information obtained by the display system as the user pivots his/her gaze to the side opposite to the side on which the second image is projected, failure to inhibit a reflexive saccade may be detected. For example, the user's ability to inhibit the reflexive saccade to gaze at the second image may be evaluated from the tracking information obtained by the display system.

At block 1730, the display system may be configured to determine that a neurological condition, such as, for example, memory disorders, motor disorders and/or developmental disorders associated with failure to inhibit a reflexive saccade may be present in the user. For example, the display system may determine that a neurological condition (e.g., dementia, Huntington's disease, Parkinson's disease, Alzheimer's disease, cortical basal degeneration, Lewy body dementia, schizophrenia or frontotemporal dementia) is present in the user if failure to inhibit a reflexive saccade is detected from the tests performed by the display system.

Smooth Pursuit Test

The display system may be configured to detect impairments in the smooth pursuit of the user's gaze along the vertical and/or horizontal directions. To test the smooth pursuit of the user's gaze, the display system may be configured to present a stimulus to the user as shown at block 1710 of FIG. 11. The stimulus may comprise an image of an object that is projected by the display system (e.g., out from the waveguide stacks 2005, 2006 of the display system 2010) such that the image appears to be at a particular distance from the user's eye. The display system may be further configured to move the projected image of the object along the vertical (y) and/or horizontal (x) directions. The display system may also be configured to move the image of the object along the direction perpendicular to the horizontal (x) and vertical (y) directions such that the object appears to be at different depths.

The display system may sense the user's reaction to the stimulus at block 1720. To sense the user's reaction to the stimulus, some embodiments of the display system may be configured to track the movement of one or both of the user's eye (e.g., using the cameras 24, 28 of the display system 2010) as the user is instructed to follow the projected image as it is moved along the vertical and/or horizontal direction in a plane (e.g., a depth plane) parallel to the optical axis or moved in a direction parallel to the optical axis (e.g., moved across different depth planes). In various embodiments, the user may be instructed to follow the projected image without moving his/her head. From the tracking information obtained by the display system as the user follows the projected image along the vertical and/or horizontal direction, deficiencies in the full range of horizontal and/or vertical eye movements may be detected. The deficiencies in the full range of horizontal and/or vertical eye movements may indicate impairments in smooth pursuit.

At block 1730, a neurological condition, such as, for example, cognitive disorders, motor disorders, memory disorders and/or behavioral disorders associated with detected impairments in smooth pursuit may be determined by the display system to be present. For example, the display system may make a determination that one or more neurological conditions are present in user (e.g., cognitive impairment, Parkinson's disease, dementia, Alzheimer's disease, frontotemporal dementia, progressive supranuclear palsy, intoxication, addiction, traumatic brain injuries, multiple sclerosis, etc.). In some users, the display system may detect the absence of visual tracking at block 1720 and this may be interpreted to be indicative of cortical blindness at block 1730.

Vestibulo-Ocular Reflex Test

In some embodiments, the display system may be configured to a vestibulo-ocular reflex test to determine if brainstem eye movement pathways are intact. The vestibulo-ocular reflex test may be used for diagnostic purposes in, e.g., comatose or severely lethargic patients. In patients who are conscious or awake, the vestibulo-ocular reflex is generally masked by voluntary eye movements. In some embodiments of a vestibulo-ocular reflex test, the patient's eye may be held open and the head may be rotated from side to side or up and down (e.g., by a clinician) at block 1710.

The display system may sense the patient's reaction to the head movement at block 1720. To sense the patient's reaction to the stimulus, some embodiments of the display system may be configured to track the movement of one or both of the patient's eyes (e.g., using the cameras 24, 28 of the display system 2010 in FIG. 10) as the patient's head is moved. If the brainstem eye movement pathways are intact and the vestibulo-ocular reflex is functioning correctly in the patient, the patient's eyes should move in a direction opposite the direction in which the head is moved. For example, if the head is moved to the left, the eyes should move to the right. At block 1730 in FIG. 11, if the expected movement of the eyes is present, the display system may be configured to conclude that the brainstem eye movement pathways are intact and the vestibule-ocular reflex is functioning correctly.

In some embodiments of a vestibulo-ocular reflex test, the inner ear and nearby nerves of the patient may be stimulated by, e.g., caloric stimulation. The stimulation may comprise delivering cold water, warm water, cold air or warm air into the ear canal at different times and block 1710. When cold water enters the ear and the temperature of the inner ear changes it causes rapid side-to-side eye movements called nystagmus. In response to being stimulated by cold water or air, the eyes generally move away from the ear into which the cold water or air is delivered and then slowly move back to their resting position. When warm water or air is delivered into the ear, the eyes move toward the ear into which the warm water or air is delivered and then slowly moves back to their resting position.

The display system may sense the patient's reaction to the delivery of cold water/air or warm water/air at block 1720. To sense the patient's reaction to the stimulus, some embodiments of the display system may be configured to track the movement of one or both of the patient's eyes (e.g., using the cameras 24, 28 of the display system 2010 in FIG. 10) as the cold water/air or warm water/air is delivered into the ear canal of the patient. If the brainstem eye movement pathways are intact in the patient, the patient's eyes should move as noted above. At block 1730 in FIG. 11, it eyes do move as noted above, then the display system may be configured to conclude that the brainstem eye movement pathways are intact.

In some embodiments, at block 1730, if the user's eyes do not move as expected, the display system may conclude that an abnormal neurological condition (e.g., hemispatial neglect, stroke, Parkinson's disease, intoxication, brainstem dysfunction, a balance disorder, vertigo, etc.) is present in the user.

With reference to FIG. 12, the system may further provide a perception aid at block 1830 corresponding to the abnormal neurological condition. For example, for a user having a balance disorder, a vestibular disorder, a vestibulo-ocular disorder or the like, the perception aid may include placing virtual content in space such that the virtual content matches the user's incorrect vestibulo-ocular reflex. To treat the disorder, the content may optionally be reoriented over time such that the virtual content begins to match the movements of objects in the real world.

Head Tilt Test

Embodiments of the display system may be configured to track the movement of one or both of the patient's eyes (e.g., using the cameras 24, 28 of the display system 2010) and to use the eye tracking information in conjunction with the user's head pose and the objects in the surrounding environment to determine if the head is straight or tilted. For example, any of the sensors and/or cameras described herein (e.g., sensors and/or cameras 24, 28, 30, 32, 34) can determine if the head is horizontally aligned with the environment by observing the orientation of the eyes. For example, if the eyes are not on a plane parallel with the environment, ground, tables, floors, etc. then the head is tilted. The angle at which the head is tilted and the direction along which it is tilted can be determined from the angular difference between the optical axis of the eye and the plane parallel with the environment, ground, tables, floors, etc. Various embodiments of the display system can be configured to project a horizontal line across the user's view and make a determination that the head is tilted if the projected horizontal line is not parallel with the environment, e.g. horizon. At block 1710, the display system may be configured to detect objects in the surrounding environment (e.g., using external camera 34), to determine what the user is viewing. At block 1720, the user's reaction to the object in the surrounding environment may also be measured using the external cameras to determine the orientation of the user's head (e.g., relative to the horizon). Abnormal head tilt and/or turn may be exhibited when the user suffers from superior oblique palsy or other eye problems because the abnormal position of the head may provide better alignment of the eyes and/or sometimes aid in relief of diplopia. At block 1730, the display system may be configured to make a determination of a neurological condition (e.g., superior oblique palsy) if abnormalities in the position of the head is detected by the display system.

At block 1710, the display system may be configured to detect objects in the surrounding environment (e.g., using external camera 34 in FIG. 10), to determine what the user is viewing. At block 1720 in FIG. 11, the display system can be configured to determine the orientation of the eye-tracking axis which corresponds to the axis along which the user's pupils are directed using any of the sensors and/or cameras described herein (e.g., sensors and/or cameras 24, 28, 30, 32, 34) with respect to the object axis which corresponds to the axis perpendicular to the plane of the object. The display system can be configured to determine the head tilt based on the determined orientation. In various embodiments, the display system can comprise an accelerometer. In such embodiments, the determination of the eye-tracking axis can be correlated with the data obtained by the accelerometer. For example, the data from the accelerometer can indicate whether the head is aligned with the object axis and the sensors and/or cameras described herein (e.g., sensors and/or cameras 24, 28, 30, 32, 34) can determine if the eye are coplanar or non-coplanar. Abnormal head tilt and/or turn may be exhibited when the user suffers from superior oblique palsy or other eye problems because the abnormal position of the head may provide better alignment of the eyes and/or sometimes aid in relief of diplopia. At block 1730, the display system may be configured to make a determination of a neurological condition (e.g., superior oblique palsy) if abnormalities in the position of the head is detected by the display system.

Optokinetic Nystagmus Test

The display system may be configured to administer an optokinetic nystagmus test to detect nystagmus induced by objects moving across the user's field of view. At block 1710 (FIG. 11), the display system may be configured to present a stimulus comprising projecting an image having one or more features (e.g., from the waveguide stacks 2005, 2006 of the display system 2010 in FIG. 10) that are moved across the field of view of the user. For example, the image may include a series of contrasting stripes (e.g., black and white stripes). As another example, the image may include a series of different colored stripes. The user may be instructed to watch the stripes move across their field of view. In some embodiments, the display system may be configured to project multiple images and/or images of multiple objects. For example, the display system may be configured to project multiple spaced-apart and adjacent shapes.

At block 1720 in FIG. 11, the display system may sense the user's reaction to the stimulus. In some embodiments, the display system may be configured to track the movement of one or both of the user's eyes (e.g., using the cameras 24, 28 of the display system 2010 in FIG. 10) as the user watches the stripes move across their field of view. A normal response to the optokinetic nystagmus test is for the user's eyes to follow one or more stripes until it moves out of sight and the eyes snap back to fixate and follow on another set of stripes. The display system may also be configured to sense which color stripe or stripes the user is following using any of the sensors and/or cameras described herein (e.g., sensors and/or cameras 24, 28, 30, 32, 34) to infer which color is dominant for perceptual testing. For example, if the user only follows black stripes, then the display system may determine that the user has a stronger association and domination related to black stripes.

It will be appreciated that abnormalities in the response to the optokinetic nystagmus test may be indicative of various neurological conditions and the display system may be configured to make a determination that the user has one of these conditions at block 1730 in FIG. 11. For example, abnormalities in the response may be indicative of neglect, which refers to a condition in which patients exhibit lack of response or sluggish response to stimuli from a side of the brain that is opposite to the side that has sustained an injury. Abnormalities in the response to the optokinetic nystagmus test may also be indicative of: vestibular disorders, which relate to inner ear or balance disorders; stroke; and internuclear ophthalmoplegia, a disorder of conjugate lateral gaze. The affected eye of a user suffering from internuclear ophthalmoplegia shows impairment of adduction while the partner eye diverges from the affected eye during abduction. Due to disorder of conjugate lateral gaze, internuclear ophthalmoplegia may produce diplopia. During extreme abduction, compensatory nystagmus may be seen in the partner eye.

Other examples of possible conditions associated with abnormalities in the response to the optokinetic nystagmus test include memory disorders, motor disorders, behavioral disorders, hemispatial neglect, stroke, neuromyelitis optica, multiple sclerosis, Ataxia, intoxication, addiction, and alcoholism.

The display system can also be configured to detect nystagmus without performing an optokinetic nystagmus test. For example, as discussed above in the section labelled "Involuntary Eye Movement," nystagmus can be detected by the display system by sensing/observing how the user's eye(s) fixates, moves and/or tracks objects, any abnormal oscillations or repetitive uncontrolled movements (e.g., microsaccades) that are detected by the display system can be attributed to nystagmus. Nystagmus can cause the user to perceive that objects in the field of view are oscillating (also referred to as oscillopsia). Various embodiments of the display system may be configured to move the projected image synchronously with the involuntary eye movements to improve visual acuity and alleviate oscillopsia. Various embodiments of the display system may also be configured to monitor the involuntary movements throughout the day and identify triggers or causes that may cause an increase in nystagmus.

The display system may also be configured as a therapeutic device configured to train the user's eyes to slow down nystagmatic movement. For example, the display system may be configured to move images presented by the display device by an amount that is smaller than an amplitude of the nystagmatic eye movement in order to train the user's eyes to slow down eye movements.

Involuntary Eye Movement

Nystagmus is a condition associated with involuntary movement of the eyes and may be detected from the images of the user's eye/eyelids obtained by the display system at block 1720. At block 1730, the display system may be configured to make a determination of possible neurological conditions associated with nystagmus if such a condition is detected from the images of the user's eye/eyelids obtained by the display system. Examples of possible neurological conditions include drug overdose or alcohol intoxication or peripheral or central vestibular dysfunction.

It may be possible to detect movement of a user's eye from side-to-side and/or rolling up of the eye from images of the user's eye/eyelids obtained by the display system at block 1720. For example, the system may be configured to detect side-to-side movement and/or rolling up of the eye by sensing movement (e.g., lateral, vertical or rotational movement) of the iris. At block 1730, the display system may be configured to make a determination of possible neurological conditions associated with a movement of the eye from side-to-side and/or rolling up of the eye detected from the images of the user's eye/eyelids obtained by the display system. Examples of possible neurological conditions include epilepsy, Guillain-Barre syndrome, Huntington's disease, progressive supranuclear palsy, attention deficit hyperactive disorder (ADHD), oscillopsia, and/or stroke.

Convergence Test

The display system may be configured to detect impairments in convergence, which refers to the simultaneous inward movement of the user's eyes when viewing an object that is moved closer to the user's eyes. To test convergence, the display system may be configured to present a stimulus to the user at block 1710. The stimulus may comprise an image of an object that is projected by the display system (e.g., through a particular depth plane of the waveguide stacks 2005, 2006 of the display system 2010, FIG. 10) such that the image appears to be at a particular distance from the user's eye. The display system may be further configured to project the image on different depth planes such that it appears to move closer to the user's eyes. The display system may sense the user's reaction to the stimulus as shown at block 1720. To sense the user's reaction to the stimulus, some embodiments of the display system may be configured to track the movement of one or both of the user's eye (e.g., using the cameras 24, 28 of the display system 2010) as the user is instructed to follow the projected image as it appears closer to the user's eye. In various embodiments, the user may be instructed to follow the projected image without moving the head. From the tracking information obtained by the display system as the user follows the projected image as it is moved closer to the user's eye, convergence insufficiency may be detected. In some embodiments, the display system may be configured to determine the near point of convergence (NPC), which is the closest point from the eyes of the user at which the user may converge their eyes (by maintaining simultaneous inward movement of their eyes toward each other) while focusing on an object and before diplopia or double vision occurs.

At block 1730, the display system may determine that one or more neurological conditions, such as, for example, motor disorders and/or memory disorders associated with convergence insufficiency may be present in the user. Examples of possible neurological conditions include Parkinson's disease, cortical basal degeneration, amblyopia, and Lewy body dementia. In some embodiments, such changes in NPC may be sudden, e.g., NPC may be measured before a physical activity (e.g., engaging in a sport) and after sustaining one or more bodily impacts. Changes in NPC that exceed a predetermined threshold may be determined to be indicative of concussions or repetitive subconcussive impacts.

In some users, the display system may detect oculogyric crisis, which refers to extreme and sustained deviation (e.g., upward deviation) of the eyes as the eyes begin to converge which may lead to diplopia (double vision). At block 1730, the display system may make a determination that dystonia may be present if oculogyric crisis is detected from the tests performed by the display system.

In some users, the display system may detect saccadic movement, which refers to simultaneous movement of both eyes between two or more points of fixation in the same direction when the user is being tested for smooth pursuits. Such saccadic eye movements also referred to as catch-up saccades may be indicative of cognitive or memory disorders. For example, at block 1730, the display system may be configured to make a determination that cognitive impairment, dementia, or Alzheimer's disease may be present in the user if increased catch-up saccades are detected from the tests performed by the display system. As another example, at block 1730, the display system may be configured to make a determination that the user is suffering from vestibular loss if increased catch-up saccades are detected from the tests performed by the display system.

Pupillary Assessment

In some embodiments, the display system may be configured to perform a pupillary assessment to detect various abnormalities in a user's oculomotor nerve, pretectal area, the ipsilateral parasympathetics travelling in cranial nerve III, the pupillary constrictor muscle of the iris and/or other diseases. For example, the display system may be configured to perform a pupil light reflex test, in which the display system is configured to record the pupil size, shape of the user's eyes and/or surrounding eye tissue (e.g., using the cameras 24, 28 of the display system 2010, FIG. 10) before a visual stimulus is presented, present a visual stimulus to the user as shown in block 1710 of the method 1700 depicted in FIG. 11, and sense the user's reaction to the stimulus as shown in block 1720 of the method 1700 depicted in FIG. 11.

For the pupil light reflex test, the visual stimulus may be a bright light pattern (e.g., a circular, rectangular or a square patch of light) that is projected by the display system (e.g., from one or both of the waveguide stacks 2005, 2006 of the display system 2010, FIG. 10) into one or both pupils of the user's eyes. Some embodiments of the display system may be configured to perform chromatic pupillary assessments. In such embodiments, the visual stimulus may be light patterns of different colors. The display system may be configured to record the pupillary response to the bright light stimulus and/or light patterns of different colors, for example, by using the user response cameras 24, 28 of the display system 2010.

Pupillary Response to Bright Light Stimulus

The pupillary response to the bright light stimulus may include a change in the size or shape of the pupil that is illuminated by the bright light (also referred to as direct response), a change in the size or shape of the other pupil that is not illuminated by the bright light (also referred to as consensual response), rhythmic dilation and constriction of the pupil that may be observed under illumination but is independent of eye movements or changes in illumination (also referred to as hippus or pupillary athetosis) and/or the rate at which the illuminated pupil responds to the visual stimulus.

A neurological condition associated with the pupillary response to the bright light stimulus may be determined as shown in block 1730 of the method 1700 depicted in FIG. 11. For example, abnormalities in the rhythmic dilation and constriction of the pupil (e.g., increases in the amplitude or frequency of the rhythmic dilation and constriction of the pupil) may be indicative of an underlying abnormality in the cardiac function of the user, an abnormality in the part of the brain (e.g., frontal lobe) that controls the pupillary muscles due to injury or as a result of a drug or a chemical, abnormalities in other autonomic functions such as heart rate and/or abnormalities in liver or renal function of the user. For example, rhythmic dilation and constriction of the pupil may be correlated with the contraction and relaxation of the heart. Accordingly, the rhythmic dilation and constriction of the pupil may be used to monitor and/or detect abnormalities in the heart rate of the user. The period of the rhythmic dilation and constriction of the pupil (e.g., time interval between two consecutives dilations of the pupil) and/or amplitude (e.g., spacing between a dilation and a constriction) can be correlated to various autonomic system functions such as heart rate. Some embodiments of the system can be configured to monitor and/or detect abnormalities in blood pressure, blood circulation, and/or vasculature of the user. For example, the system can be configured to sense and/or measure minute corneal displacements that occur along a direction parallel to the optical axis of the user's eye as a result of pulsations caused by blood pressure behind the eye. The system can be configured to compare the measured minute corneal displacement values with one or more values of minute corneal displacements that indicate normal blood pressure or vascular function. Abnormalities in the blood pressure of the user and/or vascular function of the user can be detected if the measured minute corneal displacement values deviate from the one or more values of minute corneal displacements that indicate normal blood pressure or vascular function.

In another example, blood circulation may be detected by applying an Eulerian algorithm to video captured from a user's view (e.g., a doctor wearing the system and observing a patient, or a patient viewing a reflection of him/herself), so as to observe small movements in the user such as shallow breaths, pulse, etc. It will be appreciated that the observed pulse (e.g., the movement of blood vessels over time) may be analyzed to determine heart rate. In addition, by performing a color analysis of images of the patient or the user's reflection, the system may determine a location of blood flow based on areas and/or spikes of redness in various body parts, e.g., as observed by an outward facing camera of the system. For example, areas with increased redness may be interpreted to be areas with increased blood flow. This imaging-based analysis may be performed on any visible body part (e.g., face, wrist, chest, legs, etc.)

As another example, an impaired direct response of the illuminated pupil may be indicative of the presence of lesions of the ipsilateral optic nerve, the pretectal area or the pupillary constrictor muscle of the iris and/or abnormalities in the ipsilateral parasympathetics traveling in the cranial nerve III. As yet another example, an impaired consensual response in the other pupil that is not illuminated may be indicative of lesions of the contralateral optic nerve, the pretectal area or the pupillary constrictor muscle and/or abnormalities in the ipsilateral parasympathetics traveling in cranial nerve III. As another example, a determination that the user is suffering from some type of a nervous system disorder (e.g., epilepsy), a behavioral disorder (e.g., anxiety, intoxication, under the influence of a drug or alcohol) or a neurological disorder (e.g., a stroke, a brain aneurysm or a brain injury) may be made if the illuminated pupil remains dilated (also referred to as mydriasis). Pupils may also dilate as part of a sympathetic fight-or-flight response during fear, pain, emotional distress, etc. Accordingly, dilation of pupils in response to the bright light stimulus may indicate fear, pain or emotional distress. As yet another example, changes in the pupil reactivity to the visual stimulus may be indicative of Guillain-Barre Syndrome or Alzheimer's diseases. For example, sluggish pupillary response to bright light stimulus, and reduced amplitude or speed with which the pupil responds to the bright light stimulus (e.g., less responsive or less reactive pupil) may provide early indication of Alzheimer's disease.

Pupillary Response to Light Patterns of Different Colors

Embodiments of the display system configured to perform chromatic pupillary assessments may present visual stimulus including light or patterns of light of particular ranges of wavelengths or colors at block 1710 of FIG. 11. For example, the visual stimulus may include light having wavelengths in one or more spectral ranges (e.g., spectral ranges of the visible spectrum corresponding to different colors, such as red, blue, green, yellow and/or orange), with light of different wavelengths forming a pattern in some embodiments. The constriction of the pupil may vary depending on the wavelength of the light comprising the visual stimulus. For example, the pupil may constrict by different amounts when illuminated by light having different wavelengths. Neurological conditions associated with the pupillary response to the light patterns having different wavelengths may be determined at block 1730 based on deviations of the spectral sensitivity of a user's pupil from normal ranges. For example, abnormalities in the amount of constriction of the pupil when exposed to light having certain wavelengths may aid in determining abnormalities in circadian rhythms. Without being limited by theory, melanopsin (a photoreceptor present in the eye) is considered to be involved with regulating circadian rhythms. Melanopsin is sensitive to light in the blue spectral range (e.g., light having a wavelength between about 440 nm-490 nm) and may be activated by light in that spectral range. Melanopsin is also considered to affect pupil constriction and dilation. For example, after exposure to a pattern of light including blue light, melanopsin may cause sustained pupil constriction. By measuring the pupillary response to this light, abnormalities in melanopsin response may be detected, which may be indicative of abnormalities in circadian rhythms and/or sleep abnormalities. The display system may also be configured to monitor the effects of exposure to light having other wavelengths. For example, the effects of red light exposure on pre-existing melanopsin-driven post-illumination pupil response may also be observed by having the display system expose the pupil to red light after exposure to blue light.

Pupillary Response to other Visual Stimuli

In some embodiments, the display system may be configured to detect relative afferent pupillary defect (RAPD) which may be caused by lesions of the optic nerve, retinal disease or degeneration, nervous system disorders (e.g., multiple sclerosis or neuromyelitis optica) and/or optic neuropathies (e.g., optic neuritis or traumatic optic neuropathy). To detect RAPD, the display system may be configured to present a visual stimulus to the user as shown in block 1710 of the method 1700 depicted in FIG. 11 and to sense the user's reaction to the stimulus as shown in block 1720 of the method 1700 depicted in FIG. 11. The visual stimulus presented to the user to detect RAPD may be a swinging patch of light that is projected by the display system (e.g., from the waveguide stacks 2005, 2006 of the display system 2010) and moved back and forth between the eyes of the user. For example, the swinging patch of light may be moved back and forth between the eyes of the user at a time interval of less than ten seconds (e.g., two to three seconds). The display system may be configured to record the pupillary response of both eyes to the swinging patch of light (e.g., constriction or dilation), for example, by using the user response cameras 24, 28 of the display system 2010.

At block 1730, the display system may be configured to make a determination regarding whether or not the user is afflicted with RAPD. For an eye unaffected by RAPD, the normal pupil will constrict when the swinging patch of light illuminates the pupil and dilate when the swinging patch of light is moved away. However, in an eye affected by RAPD, the pupil will constrict less when the swinging patch of light is moved from the unaffected eye to the affected eye. In some users, the pupil of the eye affected by RAPD may appear to dilate when the swinging patch of light is moved from the unaffected eye to the affected eye.

In some embodiments, the display system may be configured to test the user's pupillary response to accommodation by presenting a visual stimulus to the user as shown in block 1710 of the method 1700 depicted in FIG. 11 and sensing the user's reaction to the stimulus as shown in block 1720 of the method 1700 depicted in FIG. 11. Without being limited by theory, the pupils of a normal eye are understood to constrict when focusing on an object that is moved from a distant vision zone to a near vision zone. Accordingly, the visual stimulus presented to the user to test their pupillary response to accommodation may include one or more images projected by the display system (e.g., from the waveguide stacks 2005, 2006 of the display system 2010) that appears to originate from a location in the distant vision zone (e.g., on a depth plane corresponding to a distance greater than about 3 feet from the user's eye) and moved to a location in the near vision zone (e.g., on a depth plane corresponding to a distance of about 30-40 cm from the user's eye). The pupillary response as the eye focuses on the object at different distances is sensed, for example by using the user response cameras 24, 28 of the display system 2010.

With reference to FIG. 11, at block 1730, a neurological condition associated with the abnormalities in pupillary response to accommodation may be determined. For example, a user pupil that does not constrict as the eye is presented with the object located in the near vision zone may be indicative of impaired accommodation. At block 1730, the display system may be configured to conclude that the user has impaired accommodation. As discussed herein, the display system may also be configured to recognize and/or notify the user and/or a third party (e.g., a clinician) that the impaired accommodation may be a result of lesions of the ipsilateral optic nerve, the ipsilateral parasympathetics traveling in cranial nerve III, or the pupillary constrictor muscle, or in bilateral lesions of the pathways from the optic tracts to the visual cortex.

When testing the pupillary response to accommodation, the display system may also be configured to detect visual fixation in which the ability of the user's eyes to maintain visual gaze on an object located at a particular location is evaluated. At block 1730, the display system may determine that the lack of visual fixation or inability to suppress reflexive saccades may be indicative of cognitive disorders (e.g., mild cognitive impairment), memory disorders (e.g., dementia, Alzheimer's disease, Lewy body dementia) and/or injuries (e.g., cortical blindness).

Embodiments of the display system described herein (e.g., systems depicted in and described with reference to FIGS. 9D and 10) may be used to perform a chromatic pupillometry test to evaluate the health of the retina. The chromatic pupillometry test may be performed by presenting a visual stimulus to the user as shown in block 1710 of the method 1700 depicted in FIG. 11 and sensing the user's reaction to the stimulus as shown in block 1720 of the method 1700 depicted in FIG. 11. The visual stimulus presented to the user during the chromatic pupillometry test may include red and blue images that are projected by the display system (e.g., from the waveguide stacks 2005, 2006 of the display system 2010) to one or more of the user's eyes at different intensities. The pupillary responses to the red and blue images at different intensities are sensed, such as, for example by using the user response cameras 24, 28 of the display system 2010 (FIG. 10). A neurological condition associated with the abnormalities in pupillary response to the red and blue images at different intensities may be determined at block 1730. Examples of possible conditions include retinitis pigmentosa, glaucoma and/or retinal degenerative disease in sensitivity to blue light is reduced. The chromatic pupillometry test discussed above can be used to test outer retinal functions, retinal functional statuses, melanospin function as well as rod and cone function.

Eye & Eyelid Assessment

In some embodiments, the display system may be configured to detect various conditions that cause abnormalities in the position of the eyelids and/or eyes of the user. For example, the display system may be configured to obtain still images or video images (e.g., via the user response cameras 24, 28 of the display system 2010) of the user's eyes/eyelids (e.g., when the eyes/eyelids are at rest, in a relaxed position). The obtained images of the user's eye/eyelids may be used to detect abnormalities in one or more surfaces of the eye/eyelid, abnormalities in eye and muscle movements, asymmetric eye gaze, etc. Neurological conditions associated with the abnormalities of one or both of the user's eyes or eyelids may be determined based on the detected abnormalities. Various abnormalities associated with the user's eyes/eyelids are discussed below.

Abnormalities in the Position of the Eye/Eyelid

Eyelid ptosis is a condition associated with drooping of the upper eyelid. At block 1720, the display system may be configured to image the user's eye/eyelids and may detect this condition based on that imaging. At block 1730, the display system may be configured to determine possible neurological conditions associated with the detected eyelid ptosis. Examples of possible neurological conditions include oculomotor nerve palsy including isolated and bilateral oculometer nerve palsies, nervous system disorders, such as, for example, epilepsy, and/or congenital spinal muscular atrophy with arthrogryposis.

One or both eyes of some users may exhibit outward and/or downward deviation. At block 1720, the display system may be configured to image the eye/eyelids to detect such deviation. Some users may exhibit dilation of the ipsilateral pupil in one or both eyes which may also be detected from the images of the user's eye/eyelids obtained by the display system. At block 1730, the display system may be configured to determine possible neurological conditions associated with the detected downward deviation or dilation of ipsilateral pupil. Examples of possible neurological conditions include oculomotor nerve palsy including isolated and bilateral oculometer nerve palsies.

One or both eyes of some users may be turned medially or laterally in the relaxed position when the eye is not gazing at any particular object. At block 1720, the display system may be configured to image the user's eye/eyelids. At block 1730, the display system may be configured to determine possible neurological conditions associated with the detected medial or lateral turning of the eye. Examples of possible neurological conditions include injury to cranial nerve VI (abducens nerve) or cranial nerve III (oculomotor nerve)).

In some users, one or both eyes may be observed to be at midline at rest but the user may not be capable of deviating the eye laterally. To detect this condition, the display system may be configured to obtain one or more images of the eye at rest (e.g., using the user response cameras 24, 28 of the display system 2010). The display system may be further configured to project (e.g., from the waveguide stacks 2005, 2006 of the display system 2010) an image that appears to be at a position that is lateral with respect to the eye and to obtain images of the user's eyes (e.g., using the user response cameras 24, 28 of the display system 2010) to sense the user's reaction to the projected image. If images of the user's eyes obtained when the visual stimulus is presented to the user indicate that the user is not capable of deviating the eye laterally, then, at block 1730, the display system may be configured to make a determination of the neurological condition associated with the detected inability to deviate the eye laterally. Examples of possible neurological conditions include injury to the cranial nerve VI (abducens nerve).

Double Vision

Double vision is a condition in which the user may see two images of the same object displaced horizontally (in which the two images are side-by-side), displaced vertically (in which one image is above the other image), or displayed obliquely (in which the two images are separated horizontally or vertically). Vertical diplopia may improve with contralateral head tilt and may worsen with ipsilateral head tilt. Accordingly, some users suffering from diplopia may tilt their head since the abnormal head position can allow better alignment of the eyes thus aiding in relief of diplopia. Head tilt and/or turn can be exhibited by users suffering from superior oblique palsy. In some embodiments, at block 1710, the user may be displayed an image of an object and, at block 1720, the user may be prompted to indicate whether two images are seen by the user. If two images are seen, the display system may be configured to ask the user whether the two images are horizontally, vertically, or obliquely displaced. In some embodiments, the display system may be configured to sense the images formed on the retina of the user's eyes using any of the sensors and/or cameras described herein (e.g., sensors and/or cameras 24, 28, 30, 32, 34) and determine the position on the retina where the images are formed. If the display system determines that the image is not formed on the fovea either partly or entirely, then the display system can determine how the images are perceived by the user based on their position on the retina. At block 1730, the display system may be configured to make a determination of the neurological condition (e.g., injury to the cranial nerve IV (trochlear nerve) and/or superior oblique palsy) associated with diplopia if such a condition is detected from the images of the user's eye/eyelids and/or the tilt of the head obtained by the display system.

Loss of Depth Perception

In some embodiments, at block 1710, the display system may be configured to project (e.g., from the waveguide stacks 2005, 2006 of the display system 2010) one or more images that appear to originate from different depths and, at block 1720, to sense the response of the user's eyes to the images. The response may be sensed by, e.g., using the user response cameras 24, 28 of the display system 2010, and/or by prompting the user to indicate whether a change is depth plane of the projected image is detected. Based on the detected response, a loss of depth perception and/or problems associated with visual scanning may be detected.

In some embodiments, the user may be asked to interact with the virtual content. Such interactions may be used to determine if a lesion is present in the dorsal or ventral stream, which provide different functionality and may impact the interactions differently. For example, if there is a change of depth plane and the user attempts to touch a virtual object, mistakes or inability to accomplish this task would indicate problems with the dorsal stream, which mediates grasping and reaching movements for visual processing. On the other hand, the ventral stream processes intrinsic features of an object and would not be expected to impact the grasping task.

At block 1730, the display system may be configured to make a determination of the possible neurological conditions causing the detected loss of depth perception and/or problems associated with visual scanning. Examples of possible neurological conditions include traumatic brain injury, injury to cranial nerves II, IV and/or V, posterior cortical atrophy, memory disorders, etc.

Proptosis

Proptosis is a condition associated with bulging of the eye and may be detected from the images of the user's eye/eyelids obtained by the display system at block 1720. At block 1730, the display system may be configured to make a determination of the possible neurological conditions causing the detected proptosis. Examples of possible neurological conditions include compressive optic neuropathy, high intraocular pressure, thyroid eye disease, or glaucoma. The display system may be configured to triangulate various factors to determine the source of protopsis. In addition the neurological conditions above, the display may be configured to image the eye to detect the presence of observable physiological conditions that may contribute to proptosis. For example, the display system may be configured to image the user's orbit and perform image analysis of those images to determine the presence of the abnormal proliferation of blood vessels and/or the formation of lymphatic vessels, both of which are believed to contribute proptosis.

Abnormalities of the Eye Muscle

Abnormalities associated with the eye muscles, such as, for example, involuntary contraction of the eye muscles, movement of the muscles around the eyes (e.g., muscles around the eyebrows), imbalance between the various eye muscles, ophthalmoplegia (which is associated with paralysis of the muscles within or surrounding the eye) etc. may be detected from the images of the user's eye/eyelids obtained by the display system at block 1720. These abnormalities may be detected based on, e.g., visible abnormalities in the contraction of the eye muscles. At block 1730, the display system may be configured to make a determination of the possible neurological conditions causing a detected abnormality in the eye muscles. Examples of possible neurological conditions include epilepsy, cerebral palsy, and progressive supranuclear palsy. The display system can also be configured to determine behavioral response to some stimulus. For example, if the display system senses that the user is squinting his/her eyes, then it may determine that the user is exposed to some harsh or unpleasant stimulus (e.g., bright light, pain, etc.). As another example, if the display system senses that the user's eyes are widened, then it could determine that the user is shocked. As yet another example, the display system can be configured to sense the movement of the eyebrows and determine a behavioral response to some stimulus.

Other Analyses

In accordance with some embodiments, the display system may be configured to detect various other abnormalities in the human visual system (HVS) that do not involve eye tracking. Some other applications of the display system described herein are discussed below. It will be appreciated that some evaluations of the human visual system are observational and do not require the application of a stimulus to the user.

Examination of the Fundus

Cranial Nerves (CN) are part of the peripheral nervous system (PNS) and emerge directly from the brain. There are twelve different CNs each serving a different function but all relaying information between the body, mainly regions of the neck and head, and the brain. As discussed above some abnormalities associated with position and/or movement of the user's eyes/eyelids may be indicative of defects or injuries to one or more cranial nerves. In some embodiments, the display system may be configured to detect damage to the optic nerve. The display system may be configured as an ophthalmoscope and used to examine various parts of the user's eye including but not limited to the fundus of the eye. The fundus comprises the retina, optic disc, macula, fovea and posterior pole of the eye, and other structures.

The display system may be configured to project a light beam (e.g., from the waveguide stacks 2005, 2006 of the display system 2010 in FIG. 10) through the pupil of the user's eye to illuminate the fundus. In some embodiments, the display system may be configured to obtain images of the fundus (e.g., via the cameras 24, 28 of the display system 2010) for the purpose of examination of the fundus.

The display system may be further configured to examine the fundus (e.g., the retina and/or the optic nerve) for damage or abnormalities based on these images. In some embodiments, the display system may monitor the fundus over time (e.g., by periodically imaging the fundus over days, weeks, months, years, etc.), which may establish long-term norms for the shape, size, etc., of a user's fundus. It will be appreciated that various conditions may be determined based on the examination of the fundus and a comparison of the fundus with long-term norms for the user and/or an average within a given population. For example, the display system may detect atrophic changes in the optic nerve that may be caused by multiple sclerosis. The display system may also be configured to detect abnormalities in the optic disc. For example, the examination of the fundus may determine that the optic disc is swollen, which may be indicative of an increase in intracranial pressure (ICP) or various optic neuropathies including but not limited to compressive optic neuropathy, ischemic optic neuropathy (arteritic/non-arteritic), optic neuritis or radiation optic neuropathy.

In other examples, examination of the fundus by the display system may detect the presence of blurred edges or boundaries along the optic disc; abnormalities in the size, shape and/or color of the optic disc; and abnormalities in the optic disc/cup ratio. Each of these abnormalities may be indicative of various neurological disorders. For example, an optic disc that is pale and/or featureless may be indicative of optic atrophy as a result of multiple sclerosis and/or various optic neuropathies including but not limited to compressive optic neuropathy, ischemic optic neuropathy (arteritic), or mitochondrial optic neuropathy. As another example, increased optic disc cupping (or increase in optic disc/cup ratio) may be a result of glaucoma and/or various optic neuropathies including but not limited to ischemic optic neuropathy (arteritic), or mitochondrial optic neuropathy. As yet another example, decreased optic disc cupping (or decrease in optic disc/cup ratio) may be caused by optic neuropathies including but not limited to ischemic optic neuropathy (non-arteritic). Examination of the fundus may also help in diagnosing other diseases such as Alzheimer's disease or intracranial hypertension. For example, if amyloid plaques are detected through an examination of the fundus, then the display system may that an indication of Alzheimer's disease is present. As another example, detection of peripapilarry wrinkles, peripapillary outer retinal folds, inner retinal folds, choroidal folds, etc. during an examination of the fundus may be an indication of intracranial hypertension.

Brightness Test

In some embodiments, the display system may be used to administer a brightness test in which objective measurements of functional visual acuity are obtained under different brightness and/or glare conditions. In various embodiments, the display system can be configured to administer a brightness acuity test to determine the functional visual acuity in various bright light conditions. For example, the display system can be configured to simulate three or more bright-light conditions: 1) high-direct overhead sunlight; 2) medium-partly cloudy day; and 3) low-bright overhead commercial lighting. The visual acuity measurements can be similar to those that would be measured in these three conditions using a standard eye chart. The result of such a test may be an assessment of functional visual acuity. Such tests can be used to test for sensitivity to bright light, photophobia, impaired scotopic vision, and the like. In some embodiments, the display system can be configured to determine refractive errors for individual colors (e.g., red, green, blue, yellow, etc.). In various embodiments, the display system can be configured to evaluate the user's contrast sensitivity by projecting an image of relatively high contrast and gradually reducing the contrast of the image. The display system can be further configured to combine the contrast sensitivity testing with glare testing. For example, the display system may be configured to simulate glare conditions by activating an inward-facing light source to direct bright light at the eyes so as to determine the effect of glare on the contrast sensitivity of the user.

As another example, the display system may be configured to administer the Aulhorn flicker test in which the display system is configured to project, to the user's eyes, an image of a circular patch of light divided into two hemispheres by a dark line. One of the hemispheres may be configured to flicker at a frequency between about 0 Hz to about 50 Hz such that the luminance of the flickering hemisphere is perceived as half the luminence of the non-flickering hemisphere. The user may be instructed to adjust the luminence of the non-flickering hemisphere to match the luminence of the flickering hemisphere for different flicker frequencies. Users with acute optic neuritis have reduced sensitivity to brightness of flickering light. Accordingly, the display system configured to administer the Aulhorn flicker test may be used to detect optic neuritis, or inflammation of the optic nerve. Users with acute inflammation of the optic nerve may perceive a change in hue as light intensity changes which is referred to as Brucke's shift or Brucke's effect. The user may be prompted to indicate whether he/she perceives a change in hue with changes in the luminance of the displayed image. Such a perception of a change in hue may be interpreted by the display system as a further indication that the optic nerve is inflamed. The results of the various brightness tests described herein can exhibit characteristic variations as optic neuritis progresses. Thus, various brightness tests described herein can be used to distinguish between five different stages of optic neuritis i.e., acute, chronic, recurrent, diminishing, and subsided optic neuritis. Accordingly, the display system can be additionally configured to detect the stage of optic neuritis, e.g., by automatically conducting the brightness tests periodically over the span of weeks, months, or years as the user wears the device over that time span.

Visual Fields Test

The display system may be used to administer a blink-to-threat test in which the display system projects an image of some object, such as, for example, a hand, fingers or some other object (e.g., from the waveguide stacks 2005, 2006 of the display system 2010) that is moved rapidly towards the patient's eye (e.g., through the different depth planes displayed by the waveguide stacks 2005, 2006 of the display system 2010) from different directions. The display system may be configured to detect a blink response to the moving hand and/or fingers (e.g., using the cameras 24, 28 of the display system 2010). A neurological condition associated with a lack of a blink response may be determined at block 1730. For example, a blink response may not be detected in comatose patients. In addition to testing for blink response, the visual fields test can be configured to detect, diagnose and/or compensate for visual field deficiencies. Visual fields testing may be used to detect visual deficiencies in the central and/or peripheral vision by analyzing a subject's ability to see stationary and/or moving objects and/or images at various locations of the subject's visual field. Generally, visual pathways from the temporal region of the right eye and the nasal region of the left eye lead to the left side of the brain and visual pathways from the nasal region of the right eye and the temporal region of the left eye lead to the right side of the brain. Accordingly, different portions of the user's left and right eyes can be directly correlated with different portions of the brain. As a result of direct correlations between different visual fields regions and different regions of the brain, different areas of the left and right eye can be mapped to different regions of the brain. Accordingly, defects in the visual field region determined by one or more visual fields test can be correlated with lesions or defects in various portions of the brain or defects in different portions of the visual pathway (e.g., optic nerve, optic chiasm, optic tracts, optic radiations, etc.). Additionally, defects in different visual fields regions of the user's left and right eyes obtained by an eye exam (e.g., any of the diagnostic tests described herein) can be correlated with one or more responses to a stimulus presented by the display system and/or with one or more visual/aural/physical/neurological symptoms experienced by the user and used to diagnose potential lesions or abnormalities of the brain.

For example, defects in one or more visual regions of the user's left and/or right eye can be correlated with at least one of: (i) abnormalities in pupillary response; (ii) droopy eyelids; (iii) double vision; (iv) blurry vision; (v) abnormalities in ocular pursuits; (vi) defects in binocular vision; (vii) inability to maintain contact; (viii) difficulties in shifting gaze; (ix) user provided symptoms such as, headaches, nausea, tinnitus, vertigo, etc. can be used to diagnose potential lesions or abnormalities of the brain. This application also contemplates that various embodiments of the display system can be configured to initiate an eye exam (e.g., a visual fields test or any of the other eye exams discussed herein) in response to a user's symptom. For example, the display system can be configured to initiate an eye exam and acquire information about the eye in response to a user's audible expression of a symptom (e.g., a user complaining aloud that he or she is suffering from a headache). Visual field testing may indicate the presence of various conditions, such as scotoma, trauma to the cornea, vitreous tears, traumatically induced cataracts, retinal hemorrhage, retinal detachment, macular degeneration, or intrabulbar hemorrhage (Torsion's syndrome).

Visual Extinction Test

Visual extinction is a neuropsychological disorder and does not arise from a lack of visual input. Visual extinction can be a form of hemineglect in which patients do not report seeing an object on one side of the eye when the object is presented on both sides of the eye, although they can see the object when it is presented to that one side only. Visual extinction is caused more often by contralateral parietal lesions and less often by frontal or thalamic lesions.

The display system may be used to administer a visual extinction test in which the display system presents a double simultaneous stimulus on either side of the user's eyes at the same time. For example, the display system may be configured to project an image, such as a hand and/or fingers on either side of the user's eyes. The user may be requested to identify the image, such as, for example, by indicating how many fingers are presented on either side of the eye. Visual extinction may be detected if the user does not report seeing the image on one side of the eye when the image is projected simultaneously on both sides but reports seeing the image on the one side when the image is projected only on that one side. The display system may be configured to make a determination of a neurological condition (e.g., stroke, injury to parietal lobe of the brain) if visual extinction is detected by the display system. The display system may be configured to administer the visual extinction test in conjunction with visual fields testing, for example, to differentiate between visual inputs and neurological conditions.

Laser Speckle Flowgraphy (LSFG)

Various embodiments of the display system disclosed herein can be configured as conduct Laser speckle flowgraphy (LSFG) and/or laser Doppler flowmetry to perform a quantitative estimation of blood flow in the optic nerve head, choroid, retina and iris in vivo. The display system config-ured as a LSFG can include a source of high-intensity, narrow light beams (e.g., laser light) to illuminate the structures in the eye (e.g., retina) and generate a speckle pattern. The speckle pattern can be detected using any of the sensors and/or cameras described herein (e.g., sensors and/or cameras 24, 28, 30, 32, 34) and analyzed to study blood flow in the retinal and/or choroidal layers of the eye. For example, normalized blur (NB) which is an approximate reciprocal of speckle contrast can be correlated with blood flow rates in the ocular tissue. The square blur ratio (SBR), which is proportional to the square of the NB can provide a quantitative estimation of blood velocity. Various embodiments of the display system configured as a laser speckle flowgraphy (LSFG) system can be used to illuminate and image other parts of the user's body. In such embodiments, the high intensity, narrow light beams may be directed to the other parts of the user's body and a sensor and/or camera may be configured to detect a speckle pattern caused by the light beams in the illuminated parts of the user's body.

Transcranial Doppler Device

Various embodiments of the display system disclosed herein may be configured as a Transcranial Doppler Device, which may be configured to map blood flow in the brain. The display system configured as a Transcranial Doppler Device may employ ultrasound to map blood flow in the brain (e.g., velocity of the blood flow through the blood vessels of the cranium). For example, an ultrasound wave may be delivered to the user's cranium using one or more probes 1081 (FIG. 10). The display system may be configured to receive and measure echoes of the ultrasound wave traversing and reflected through the cranium using the ultrasonic receiver 1079 or the ultrasound transceiver 1075. The display system 2010 may be configured to diagnose emboli, stenosis, bleeding, etc. based upon the reflected sound waves. Some embodiments of the display system may be configured as an advanced Transcranial Doppler Device, which may obtain one or more images of blood flow through the middle cerebral artery, one of the major arteries in the brain. In some embodiments, such images may be analyzed (e.g., by the display system) for abnormalities indicative of concussions in users. Various embodiments of the display system may be configured to create a three-dimensional (3D) real time map of the blood flow in the brain that can be viewed and/or analyzed by a clinician. Various embodiments of the display system configured as a transcranial Doppler device can be used to image other parts of the user's body. In such embodiments, the one or more probes 1081 to be positioned to direct ultrasound waves to other parts of the user's body and the ultrasonic receiver 1079 or the ultrasound transceiver 1075 may be configured to detect the ultrasound wave traversing and reflected by these other parts of the user's body.

Photoacoustic Imaging

Various embodiments of the display system disclosed herein may further be configured as a photoacoustic imaging device to image biological tissue structures (e.g., blood vessels) of the user or others. The display system configured for photoacoustic imaging may use one or more laser sources (e.g., non-ionizing laser sources) and one or more ultrasonic transducers. The laser sources may send pulsed emissions into a region of interest, which may result in ultrasonic emissions from the tissue in the region of interest. The ultrasonic emissions may be received by the one or more ultrasonic transducers, which may produce a signal that can be processed to image the tissue. It will be appreciated that particular ultrasonic emissions may be associated with different physiological properties, such as hemoglobin concentration or oxygen saturation. Consequently, an analysis of the ultrasonic emissions (e.g., magnitude and location) may be utilized to form 2D or 3D images of the area into which the laser energy is directed. In some embodiments, the laser energy may be replaced by radio frequency pulses in an otherwise similar process known as thermoacoustic imaging.

With reference to FIG. 10, a plurality of sensors 30 of display system 2010 may be photoacoustic imaging sensors configured to emit laser or radio frequency pulses of appropriate wavelengths into a biological tissue and to detect ultrasonic emissions to thereby image the area. It will be appreciated that a plurality of the sensors 30 may be attached to the head (e.g., scalp) of the user in some embodiments.

Functional near Infrared Spectroscopy (fNIRS) Device

Various embodiments of the display system disclosed herein may further be configured as a functional near infrared spectroscopy (fNIRS) device to map blood flow in the brain. The display system configured for fNIRS may use emitters of certain wavelengths of infrared light, and sensors to detect the infrared light reflected back from the body. The display system may then determine the absorption spectra of the body part into which the light was directed. Oxygenated and deoxygenated hemoglobin have different absorption spectra, thus allowing a measurement of cerebral oxygenated and deoxygenated hemoglobin, which may be correlated with neuronal activity (through the blood-oxygen-level dependent (BOLD) response). Advantageously, fNIRS measurements can be objective and non-invasive to the mental task being measured.

With reference to FIG. 10, a plurality of sensors 30 of display system 2010 may be fNIRS sensors configured to emit infrared light of appropriate wavelengths and to detect reflected infrared light to obtain infrared absorption spectra. It will be appreciated that a plurality of the sensors may be attached to the head (e.g., scalp) of the user in some embodiments. In various implementations, fNIRS may allow the system 2010 to detect, measure, or otherwise detect neuronal activity, which may be interpreted to be indicative of one or more mental status indicators of a user, such as mental workload, divided attention, situational awareness, neural activity, pain, and/or other mental responses to stimuli delivered or detected by the system 2010.

In some embodiments, depending on the characteristics of the infrared spectra detected, the display system may be configured to determine whether the user is suffering from or prone to suffer from Alzheimer's disease or other conditions. The characteristics of the infrared spectra can also aid the display system to determine the progression of disease in user's suffering from Alzheimer's.

It will be appreciated that various embodiments of the display system configured to perform fNIRS can be used to image other parts of the user's body. In such embodiments, the fNIR sensors may be located and configured so as to detect oxygenated and deoxygenated hemoglobin in these other parts of the body.

Fluorescent Ligand Scanning

Fluorescent Ligand Scanning (FLS) is a method in which fluorescent ligands introduced into the eye bind to amyloids in the eye (e.g., retina or supranucleus regions of the lens) and are optically excited to emit fluorescence which may be measured to detect the presence and/or concentration of beta-amyloids in the eye. Beta-amyloid levels in the retina may be significantly correlated with beta-amyloid levels in the brain. It will be appreciated that beta-amyloids are associated with Alzheimer's disease. Accordingly, FLS may be useful to differentiate between Alzheimer's and non-Alzheimer's patients as well as to aid doctors and healthcare providers to track the progress of the disease in patients and to aid doctors and pharmaceutical researchers to monitor the efficacy of Alzheimer's drugs. The display system (e.g., display systems 80, 1000, and 2010 of FIGS. 9D, 6, and 10, respectively) may be configured to administer the FLS. For example, a compound comprising beta amyloid-specific small molecules may be introduced (e.g., by spraying, squirting, etc.) into the user's eye, e.g., by the display system and/or a 3rd party. Without being limited by theory, the beta amyloid-specific small molecules are believed to be absorbed into the lens and to bind to the amyloid aggregates. The beta amyloid-specific small molecules may include fluorescent ligands which may be excited by radiation delivered by the display system. After excitation, the fluorescence emitted by the fluorescent ligands may be measured by the display system (e.g., by one or more inward facing cameras described herein) to detect the presence and concentration of amyloids. In various embodiments of the display system (e.g., display systems 80, 1000, and 2010 of FIGS. 9D, 6, and 10, respectively), the fiber scanner (e.g., the image injection devices in FIGS. 6-200, 202, 204, 206, 208), can be configured to image the fluorescence emitted by the fluorescent ligands. The display system may be further configured to determine the specific locations in the eye where the ligands are present, e.g., by imaging the eye. In some embodiments, depending on the characteristics of the fluorescence detected, the display system may be configured to determine whether the user is suffering from or prone to suffer from Alzheimer's disease. The characteristics of the fluorescence detected can also aid the display system to determine the progression of disease in user's suffering from Alzheimer's. Various embodiments of the display system configured to perform fluorescent ligand scanning can be used to image other parts of the user's body. In such embodiments, the fluorescent ligands may be introduced in other parts of the body and the display system may be configured to detect the fluorescence emitted by the fluorescent ligands in these other parts of the body.

Iris Camera

In some embodiments, the display system may be configured to function as an iris camera to detect Down's syndrome. For example, the display system may be configured to sense/observe the iris using any of the sensors and/or cameras described herein (e.g., sensors and/or cameras 24, 28, 30, 32, 34 of FIG. 10) and determine if any white spots exist on the iris (also referred to as Brushfield spots). In various embodiments of the display system (e.g., display systems 80, 1000, and 2010 of FIGS. 9D, 6, and 10, respectively), the fiber scanner (e.g., the image injection devices in FIGS. 6-200, 202, 204, 206, 208), can be configured to sense/observe the iris and determine if any white spots exist on the iris (also referred to as Brushfield spots). The display system may be configured to determine that the user is suffering from Down's syndrome if the presence of Brushfield spots is detected.

Optical Coherence Tomography (OCT)

Various embodiments of the display system may be configured to function as an optical coherence tomography (OCT) system. The display system may be configured to project a beam of light into the eyes of the user. A portion of the projected beam may be reflected, scattered, and/or diffracted by various anatomical features of the eyes of the user and received by any of the sensors and/or cameras described herein (e.g., sensors and/or cameras 24, 28, 30, 32, 34). The display system and/or an electronic hardware processor in communication with the display system may be configured to analyze light received from the eyes of the user to track changes in the thickness of selected tissue layers in the eye. Such changes may be determined to be indicative of the presence and/or progression of neurological diseases such as multiple sclerosis (MS). As another example, MS patients may also exhibit microcystic macular edema (MME), in which fluid collections (considered to be pseudocysts) are present in the inner nuclear layer. Through processing of the reflected light received by the various inward-facing sensors and/or cameras, the display system may be configured to detect the presence of the fluid collections in the inner nuclear layer and, thus, make a determination that MME is present in the user. This determination of MME may then be utilized to make a determination that the user may be suffering from multiple sclerosis.

The display system configured as an OCT may be configured to detect retinal vascular biomarkers, such as biomarkers that have been delivered to the user's eye. Signals from the detection and imaging of these biomarkers may be analyzed to determine the presence of retinal vascular changes/degeneration. In some embodiments, such changes are degeneration may be determined to be indicative of Alzheimer's Disease.

The display system configured as an OCT may also be used to detect optic neuropathies by scanning around the optic nerve head to analyze the peripapillary nerve fiber.

The display system may be configured to perform OCT Angiography (OCT-A) which may detect blood flow in the retina and choroid. OCT-A may be used to identify perfused retinal vessels, determine angio flow density, and visualize perfusion density and blood flow in the retina and choroidal layers, etc. The display system may be configured to determine ischemic damage based on the detected retinal perfusion.

Altering Neural Tissues of the Brain Including Altering Functions and Structures The brain's processing hierarchy (e.g., visual processing hierarchy) and feed-forward, feedback, and horizontal cortical-to-cortical connections and structures are mainly determined (e.g., "wired") during the critical period of the immature brain when the brain is most plastic. Although the brain is always plastic, it demonstrates a higher level of plasticity during the critical period. It will be appreciated that specific details of the brain's processing may be different for different people and may change. Advantageously, mechanisms described herein allow a determination of how the above-noted connections influence perception and/or cognition and also allow a customized understanding of a particular person's processing.

In addition to providing an understanding of how a particular brain is structured, mechanisms described herein may allow for altering neural tissues of the brain. Without being limited by theory, it is believed that the brain's processing pathways may be restructured, e.g., to influence the user's perception and processing of information. Because the brain is plastic, it is possible to reopen the critical period (e.g., a window of time when the brain has heightened plasticity during development). A number of drugs and cell therapies along with environmental factors have been proven to return plasticity to levels comparable to those found in childhood during the critical period. Some of these environmental factors include physical exercise, meditation, video-game training, and the like.

In some embodiments, the display systems described herein (for example, as shown and described with respect to FIG. 6, 9D and FIG. 10) may be configured to reopen the critical period and/or increase plasticity for a user. For example, the display system may be configured to adjust and/or tailor the user's environmental factors, including particular stimuli that the user is exposed to, to reopen the critical period and/or increase plasticity. The display system can utilize applications, such as video games, that utilize one or more of the techniques described herein that are designed to mimic the way a person learns or the way that effectively engages a person, e.g., positive and/or negative reinforcement, providing interesting content, etc. The display system may provide messages, such as subliminal messages, during sleep while the brain is processing information received during the day. In some embodiments, without being limited by theory, the display system may be configured to lead the user through various activities that are believed to place the user in a "flow" state in which the brain's critical period is reopened and plasticity is increased. Examples of such tasks include, e.g., physical exercise, meditation, and yoga. The display system can also provide experiences that mirror or mimic experiences that naturally occur during critical brain development periods. As an example, during childhood development, a child with amblyopia may have an eye patch placed on the stronger eye to retrain the brain and strengthen the weaker eye. Once neural plasticity reaches a level sufficient for the user's brain to readily accept change, the display systems described herein may be used to train the brain of the user and alter it to mitigate deficits and/or to improve functioning.

As an example, the display systems and methods described herein may be configured to alter how the user's visual processing hierarchy and connections influence the user's visual perception. The induced increase in neural plasticity may result in more effective brain training, which may cause a performance change in the user through perceptual learning and response modification of neuron assemblies in various visual processing stages. It will be appreciated that such an increase in neural plasticity may advantageously be applied to facilitate any of the learning activities (e.g., mental exercises) disclosed herein.

In some embodiments, using the display systems and methods described herein and through unique content delivery, the user's brain receives tailored stimuli with which the user may interact. The systems described herein may be configured to monitor in real time the user's interactions and responses (physical, emotional, and behavioral, as described herein) and to adjust the training accordingly. For example, the systems described herein may be configured to be adaptive. The system may be configured to increase the difficulty of brain training tasks when the user is doing well and vice versa (decrease the difficulty when the user is performing poorly and/or unable to complete training activities). The system may also be configured to utilize positive and negative reinforcement (positive reinforcement may be more beneficial) to increase user engagement. This may be used to make the training more game-like and enjoyable, thereby increasing the likelihood that the user will continue with a training program. This may also be used in a purposefully artificial manner to provide positive feedback, for example, where user performance is decreasing to boost self-esteem such as for terminal patients and the like.

The stimuli and/or brain training programs (e.g., video games) may be configured to utilize immersive techniques to simulate an environmental scene that the brain perceives as "real" through the use of a biomimetic light delivery system and multiple depth planes rendering content in 3D, as described herein. For example, and without being limited by theory, by providing multiple depth planes, the therapies described herein may be more effective as the brain is more likely to perceive the stimuli provided from the multiple depth planes as real-life, enhancing therapeutic results. The display system may manipulate the simulated environment in real time based at least in part on how the user is doing through a biofeedback system, in which sensors monitor the external environment, the content being provided to the user, and the user's physiological and/or psychological (e.g., behavioral, emotional) reactions to modify the stimulus provided to the user. Such biofeedback may be used in perception modification and a number of other applications described herein.

In accordance with certain embodiments described herein, the display system may be configured to provide tailored stimuli or perception aids to aid in training and/or altering neural tissues of the brain of the user to mitigate deficits and/or to improve functioning. In some embodiments, the method 1800 illustrated in FIG. 12 may be applied to provide a perception aid in response to environmental stimuli. Advantageously, due to the wearability of the display system, the system may be configured to provide a perception aid, including a brain training program, in any arbitrary environment. Without being limited to theory, the efficacy of retraining and/or altering neural tissues of the brain is enhanced by long and repeated exposure to the stimuli and/or therapies described herein. Thus, due at least in part to the wearability of the display system, it is likely that a user will wear the display system for longer periods of time and more frequently, thereby increasing the effects and efficacy of the treatments and therapies described herein. Similarly, the user can use the display system in a variety of environments, increasing compliance of the user. For example, the program may be conducted while the user is outside in the world, or may be conducted in a controlled setting (e.g., in the user's home or a clinician's office). Preferably, before conducting the method 1800, the display system has stored within it, or has access to, a profile cataloging stimuli that may trigger, or not trigger, a particular reaction in the user due to the presence of a neurological condition in the user. The system may also be configured in advance to use the presence of the stimuli to trigger a perception aid, which may be a program designed to modify the user's reaction to the stimulus. Consequently, in some embodiments, at block 1810, the display system may be configured to sense the stimulus or stimuli that the user is exposed to. At block 1820, the display system may be configured to determine that a particular stimulus is associated with a neurological condition that causes a reaction (or the lack of a reaction) that the user may desire be altered. At block 1830, the display system may be configured to provide a perception aid, which may be configured to alter the user's reaction to, perceptions of, or cognitive processing of, the stimulus. The system can be configured to alert the user when perception aids are provided. The system can also be configured to suggest a particular perception aid that can alter the user's reaction to, or perceptions of, the stimulus and provide the perception aid in response to an input from the user.

As an example, at block 1810, the display system may sense that the user is exposed to an environmental stimulus which causes significant emotions, such as, anxiety or fear in the user. For example, the stimulus may be an object or an insect for which the user has a phobia and/or a traumatic association. At block 1820, the display system may be configured to determine that the user has the corresponding phobia and/or traumatic association. At block 1830, the display system may commence a program to modulate or mitigate the users and first reaction to the stimulus. For example, the display system may conduct guided imagery to calm the user.

In some embodiments, for any of the systems and methods disclosed herein, predictive algorithms and/or artificial intelligence methods may be used to provide perception aids before they are required. For example, the display system may detect environments and/or stimuli frequently or repetitively requiring a particular perception aid and, based on the frequency and/or number of repetitions, may be configured to provide the perception aid before it is required. For example, a user with a memory deficiency may frequently ask for particular information. Based on the context of these questions, the display system may be configured to automatically display the relevant information whenever the user is in a particular context.

It will be appreciated, that in some embodiments, certain ones of the blocks 1810, 1820, 1830 may be omitted. For example, the display system may conduct block 1830 without conducting blocks 1810, 1820. This may occur, e.g., in instances where the user simply desires to undergo a therapy program for modifying a reaction, without requiring a stimulus to trigger the program. Rather, the display system may be configured to receive subjective and/or objective input from the user to engage in block 1830 while bypassing 520, 530. For example, by monitoring physical and behavioral signs (e.g., pupil dilation in the case of fear or nervousness), block 1830 may be triggered. Similarly, the user may actively conduct block 1830. In some instances, for example, the user may wish to preemptively conduct block 1830 before entering an environment in which stimuli that elicit strong reactions are likely to be present.

Examples of various types of therapy that may be applied to the user are discussed below.

Perception Modification

In some embodiments, the display system may be configured to modify a user's perception at block 1830 through perceptual learning techniques. The therapy may include ocular and aural stimuli tailored to teach a user improved skills of perception or to modify the user's typical perception. For example, the display system may be configured to provide guided imagery therapy, obscuration, aural stimulation, or the like to modify the user's perception.

The display system may be configured to provide therapeutic benefits through perception modification. For example, the display system may provide exposure therapy. Exposure therapy can be used to treat anxiety disorders, for example. Exposure therapy includes exposing the user to a feared object or context without any danger in order to overcome their anxiety. As another example, the display system may provide eye movement desensitization and reprocessing (EMDR) therapy. EMDR may be used to reduce long-lasting effects of distressing memories by developing more adaptive coping mechanisms. In some embodiments, the therapy includes requesting that the user recall distressing images while receiving one of several types of bilateral sensory input from the display system, which may cause side-to-side eye movements. These therapies provided by the display system may be effective in treating behavioral disorders such as post-traumatic stress disorder.

The display system may be configured to provide perceptual learning to the user, where perceptual learning refers to the ability to learn improved skills of perception. Improvements may include simple sensory discriminations (e.g., distinguishing two musical tones from one another) to complex categorizations of spatial and temporal patterns relevant to real-world expertise (e.g., reading, seeing relations among chess pieces, knowing whether or not an X-ray image shows a tumor, etc.). Sensory modalities may include visual, auditory, tactile, olfactory, and/or taste. Perceptual learning may be an important foundation of complex cognitive processes (e.g., language) and may interact with other kinds of learning to produce perceptual expertise.

The display system may be configured to provide perceptual learning functionality to aid the user in acquiring a particular skill or skills. In some embodiments, the display system may be configured to provide video games configured to enhance perceptual and cognitive abilities. For example, the video games can be configured to have multiple different interaction elements to target specific abilities (e.g., hand-eye coordination). The video games can be configured to adjust a difficulty level based on how the user is performing (e.g., assessed through user feedback). The video games can also have positive and negative reinforcement in response to the user's actions. By utilizing these techniques in the context of a game with interesting content, the user's engagement and attention level increase. Using such video games, a user may experience an improvement in a variety of skills including improved hand-eye coordination, increased processing in the periphery, enhanced mental rotation skills, greater divided attention abilities, faster reaction times, a functional increase in the size of the effective visual field (within which viewers may identify objects), problem solving, creativity, etc. The display system can also use video games to teach or enhance problem solving skills and/or creativity by providing unexpected interactions. For example, a person that has a proclivity for repetitive actions may be exposed to unexpected interactions such as exits from situations that are to the left when one usually turns right, kissing frogs to get princes or princesses, rewarding coloring outside the lines, increasing a speed of flying when one is still and meditates or concentrates, or the like. In some embodiments, the display system may be configured to provide auditory discrimination applications to address speech and language difficulties such as enhanced and extended speech signals.

The display system may be configured for automated tracking of patient progress and data collection that may be examined by a clinician. As another example, through addition of psychophysiological measurement or motion tracking, the display system may be configured to provide exposure therapy (e.g., virtual reality graded exposure therapy or VRGET) that may be used to examine participant affective response throughout the exposure process. This may be particularly efficacious as fear reduction may be central to successful treatment. As yet another example, the display system that provides exposure therapy may be configured to track motor responses and to determine whether those responses are consistent with successful treatment (e.g., guarding or bracing behavior). Accordingly, exposure therapy may be configured to reduce fear and disability in the context of chronic musculoskeletal pain.

Perception Testing and Modification

In some embodiments, the display system may be configured to perform perception testing, as described in greater detail herein. The display system may be configured to provide a stimulus and measure a user response, as described in greater detail herein and as illustrated in FIG. 11. An example of perception testing includes binocular rivalry. The perception testing techniques disclosed herein, including backmasking for exposure therapy, may also be used as methods or retraining the brain (altering neural tissues) and/or modifying associations.

Sensory Substitution/Enhancement

In some embodiments, the display system may be configured to substitute or enhance sensory stimuli. Such a substitution or enhancement may be utilized to address deficiencies in one of the user's senses by shifting the detection of stimuli by that sense to another one of the user's senses. For example, deficiencies in the ability to detect heat or hearing may be addresses by converting heat or sounds to visual outputs by the display system. For example, a hot stove may be the stimulus is detected at block 1810, the inability to detect heat may be the neurological condition associated with the stimulus at block 1820, and the displaying of a changing color corresponding to a temperature of the stove may be the perception aid provided at block 1830. Thus, the display system may be configured to convert heat detected from the stove to color and the display system allows the user's sense of sight to compensate for his/her inability to detect heat.

As another example, where the user is completely or partially deaf, a loud sound may be the stimulus that is detected at block 1810, the inability to hear may be the neurological condition associated with the stimulus at block 1820, and the displaying of a changing color corresponding to the loud sound may be the perception aid provided at block 1830. Thus, the display system may be configured to convert sound detected in the environment to color or visual imagery and the display system may be configured to allow the user's sense of sight to compensate for his/her inability to hear. In some embodiments, color or patterns may be displayed to convey mood, to be a proxy for music (e.g., blue color for blues music), to be a proxy for other sounds (e.g., EKG traces for heartbeats), or to be a substitute for background noise. Colors and/or patterns can be displayed on a depth plane that is not used for text or other objects of interest. In some other embodiments, the display system may be programmed with speech recognition functionality and the perception aid displayed by the system may be the output of speech recognition by the display system. The system may be further configured to recognize various aspects of speech, such as, for example tone of speech, pitch of speech, speed of speech, volume of speech to help the user recognize accents and sentence structure and identify the underlying emotion therefrom. Thus, the display system may be configured to display the words spoken by a third party in some embodiments. Similarly, the display system may be configured to speak words corresponding to where an eye is gazing, which may be useful for a user that is blind or that has other vision impairments. The display system may be configured to provide different alerts to a user regarding objects and/or people in the surrounding environment. For example, the display system may be configured to alert a person regarding an obstacle in his/her path or regarding oncoming traffic. As another example, the display system may be configured to inform a user that his/her friend is in the vicinity. In this way, the display system may be configured to help the user navigate their environment (e.g., let them know that there is chair 3 feet ahead of where they are gazing) or otherwise gain information about features and their placement in their immediate surroundings without use of sight. Preferably, the words may be displayed on the same depth plane as the person speaking the words, thereby allowing the user to see the words without needing to change the focus of their eyes. It will be appreciated that this ability to place text on a desired depth plane may allow for a more natural and comfortable interaction between the user and the third party speaker, since the user does not need to shift their focus away from the speaker (since text may be displayed over or superimposed on the third party, at the same depth plane as the third party). In some embodiments, the display system may be configured to recognize speech in a language foreign to the user, and to display text in a language that the user understands.

In some embodiments, the substitution or enhancement of sensory stimuli may be used in behavioral conditioning, as described herein, and to provide therapy for different conditions, such as seizures. The therapy may include ocular and/or aural stimuli tailored to replace or enhance environmental stimuli. The display system may be configured to utilize methods similar to those described herein related to classical conditioning and operant conditioning with respect to positive and negative reinforcement.

The display system may be configured to include one or more sensors and to provide sensory stimulation. For example, a user may view an object (either in the real world or in a simulated environment) and that object may be presented to the user with accompanying colors, sounds, and/or other stimuli (e.g., temperature changes).

In some embodiments, the association and stimulation of senses may be useful in aborting seizures, for example, using flashes, clicks, white noise by audio and/or video or the like. This may be useful as well in protection from seizures, for example, by deconvoluting audiovisual cues present at previous seizures and/or blocking or canceling out dangerous signals. This may be useful as well to compensate for hearing impairment, macular degeneration, and/or other age-related maladies.

The display system may be configured to include one or more sensors and to provide spatial augmentation. Systems and methods similar to those described herein with respect to perceptual learning and perception modification may be used in conjunction with spatial augmentation. In some embodiments, objects may be selectively obscured or blurred to enhance focus on targeted objects. For example, the display system may be configured to blur or obscure objects in the distance to help the user focus on closer objects.

Synesthesia

The display system may be configured to use techniques that involve synesthesia to modify a user's perception. As used herein, synesthesia generally refers to a situation where stimulating a primary sensory or cognitive pathway causes a sensory or cognitive pathway to be simulated as well. Common examples of synesthesia include letters and/or numbers being associated with colors, pitch of sound being associated with colors (e.g., a song in the key of G may appear blue while a song in the key of C may appear red), spatial sequence synesthesia where numerical sequences are positioned in space (e.g., larger numbers may appear farther apart), times or dates appearing organized in 3D space, and the like. Synesthesia may aid in memorization, perfect pitch, math, and the like.

The display system may be configured to provide perception aids in block 1830 of FIG. 12 that mimic synesthesia to aid in training the brain. The display system may include sensory inputs and outputs and may be configured to present realistic sounds and visuals in 3D space, while also capturing audiovisual information of the user's environment using microphones, cameras and/or depth sensors. The display system, for example, may be configured to link visuals to sound, either pre-recorded or captured using a microphone, by providing the appropriate sound and/or visual in conjunction with another sound and/or visual. Similarly, the display system may link certain sounds to particular visual information in the user's environment. In some embodiments, the display system includes tactile feedback (e.g., using a haptic controller, glove, or other touch based device) and/or smell.

To provide perceptual learning that leverages synesthesia, the display system may be configured to, e.g., link pitch to color. For example, the display system may include an application designed to help the user learn to play the piano or other instrument where keys are highlighted with particular colors. When the user is recalling how to play something, the user may recall not only the sounds but the color also. Similarly, the display system may include an application designed to help the user detect pitch. The display system may be configured to detect pitch and key and to display visualizations that link the musical key to color. For example, songs in E flat Major may appear in sea green. In some embodiments, the sea green color may be overlaid the user's view of the environment. This may be used for "ear training" that may be a part of musical education.

In some embodiments, the display system may be configured to provide sensory or perceptual deprivation to the user. The display system may use audio and/or visual functionality to reduce or eliminate the user's perception of stimuli in the surrounding environment. For example, the perception aids in block 1830 of FIG. 12 may include visual content in the form of a uniform dark field, produced by projection of light, or by providing and activating an opaque element such as a liquid crystal film or other selectively opaque layer in the display system, such that the user does not perceive any identifiable visual stimulus. Similarly, the system may be configured to present audio content such as noise cancelling soundwaves (such that the user does not perceive any identifiable audio stimulus). The display system may provide audio and/or visual sensory deprivation content for various time periods as desired, such as a period of seconds, minutes, or hours. In some embodiments, similar therapeutic implementations may be achieved based on the ganzfeld effect, wherein perceptual deprivation may be achieved by presenting the user with a uniform, non-structured stimulation. For example, the display system may provide visual content including a uniform color across the entire field of view, and/or audio content such as white noise. Ganzfeld effect content may similarly be presented for a short period, or for an extended period of minutes or hours. Sensory or perceptual deprivation techniques as described herein may be administered for therapeutic implementations, such as for reduction of anxiety, stress, or other emotional response, or to induce hallucinations or altered states of consciousness.

In some embodiments, to provide perceptual learning that leverages synesthesia, the display system may be configured to link words to color, size, and/or spatial positioning. This may be useful in language learning because the user may learn to associate particular words with color and spatial position to improve recall. For example, the Japanese word for elephant may appear large and bluish grey. This can increase the effectiveness of teaching techniques due at least in part to the incorporation of more than one sense (e.g., vision, hearing, etc.) with an association (e.g., object, word, etc.) thereby increasing the strength of the association.

Multisensory Integration

In some embodiments, the display system may be configured to utilize multiple sensory modalities and/or to integrate displayed content with stimuli detected by non-visual senses. It will be appreciated that cross-modal interactions may be significant in sensory perception, for example, as perception through a first sense may be modified by other simultaneously received stimuli from other senses. In one example, visual dominance may bias information detected by the other senses. In some embodiments, providing a coherent multi-sensory representation of virtual content may heighten the realism of displayed content. In some other embodiments, stimuli for various senses may be presented with various amounts of mismatch as a perception aid (e.g., spatial and/or temporal mismatch). For example, the timing of stimuli presented to a user may be mismatched (to provide a temporal mismatch) and/or the perceived auditory location of auditory stimuli may be mismatched from the perceived visual location of the visual stimuli (to provide a spatial mismatch).

It will be appreciated that neurological conditions may alter ordinary multisensory integration. For example, amblyopia may cause audiovisual cues to be spatially and/or temporally mismatched, causing a ventriloquist effect. The ability of the display system to provide stimuli with precisely defined spatial and/or temporal mismatches may be used to treat multisensory integration abnormalities. For example, the display system may provide spatially and/or temporally mismatched stimuli with progressively less mismatch over time.

In some embodiments, the display system may be configured to deliver multiple sensory cues matched or mismatched temporally and/or spatially. With reference to FIG. 12, temporal and/or spatial manipulation of multisensory integration may be used as a perception aid at block 1830. In one example, for a user exhibiting signs of amblyopia, audio and visual stimuli or cues can be delivered to the user at different times or locations in space. In some embodiments, the audio and visual cues may be delivered with a mismatch determined so as to compensate for the user's mismatch so as to mitigate the ventriloquist effect to aid the user's processing of the audio and visual stimuli. In a therapeutic application, the audio and visual stimuli may be initially delivered with a mismatch, and incrementally delivered with decreasing mismatch until they are delivered with no mismatch.

In some other embodiments, the display system may be configured to implement binaural beats, for example by providing sound to the user in the form of sine waves with a different frequency in each ear. For example, a combination of frequencies both lower than 1500 Hz, with a difference of approximately 40 Hz or less between the two frequencies may result in an auditory illusion in the user of a third tone, or binaural beat. The binaural beat may correspond to the frequency difference between the frequencies provided to the ears of the user.

In further example implementations, the display system may be configured to deliver multiple sensory cues with modal, spatial, and/or temporal mismatching. In one example, the system may use the McGurk effect in a diagnostic test. Referring to FIG. 11, stimuli may be presented at block 1710 by providing mismatched audio and visual stimuli to the user, for example, video content of a mouth or face speaking one or more phonemes, and audio content including different phonemes from those shown in the video content. At block 1720, a user reaction can be sensed. For example, the user may be directed to repeat the phoneme perceived from the audio and visual content. Depending on how susceptible the user is to the McGurk effect, the perceived phoneme may be a third phoneme different from the phonemes represented in the visual and audio content. At block 1730, one or more neurological conditions associated with the reaction may be determined. For example, if the user exhibits a relatively small McGurk effect, such as by repeating one of the two presented phonemes rather than a third phoneme, disorders such as autism spectrum disorders, Alzheimer's disease, dyslexia, or other conditions may be indicated. In some embodiments, blocks 1710 and 1720 may be repeated any number of times to determine a result based on how frequently the user repeats one of the two presented phonemes or speaks a third phoneme.

In another example, the system may use ventriloquism to determine the relative weighting of audio stimuli and visual stimuli in spatial localization. In ventriloquism, the perception of the location of audio stimuli is shifted toward a visual cue. With continued reference to FIG. 11, stimuli at block 1710 may include a virtual object accompanied by one or more sounds, some of which are selected to appear to emanate from a location coinciding with the virtual object and some at locations away from the virtual object. At block 1720, a user response to the stimulus may be received. For example, the user may be asked to indicate where the virtual object appears to be located and/or the location of the sounds. Depending on the extent of the ventriloquism effect in the user, sounds located away from the position of the virtual object may nevertheless appear to coincide with the location of the virtual object. At block 1730, the extent of the ventriloquism effect in the user may be determined, and/or one or more neurological conditions associated with an increased or decreased ventriloquism effect may be indicated based on the user's response. For example, individuals with amblyopia appear to exhibit the ventriloquism effect more than typical, leading to decreased ability to detect mismatches in the location of a virtual object with the perceived location of the sound.

In another example, the system may use the double-flash illusion in a diagnostic test. With continued reference to FIG. 11, stimuli at block 1710 may include one or more flashes of light accompanied by one or more sounds, for example, beeps or other audible tones. At block 1720, a user response to the stimulus may be received. For example, the user may be asked to indicate how many flashes were perceived. Depending on the user's level of audio and visual integration, the number of sounds may influence the accuracy of the user's perception of the number of flashes. At block 1730, a level of audio and visual integration may be determined, and/or one or more neurological conditions associated with a heightened or decreased level of audio and visual integration, may be indicated based on the user's response. In some embodiments, blocks 1710 and 1720 may be repeated any number of times to determine a result based on how frequently the user accurately or inaccurately identifies the number of flashes that were presented.

In another example, the system may use the rubber hand illusion and/or body transfer illusion for therapeutic functionality. With reference to FIG. 12, the system may determine at block 1820 that a stimulus is associated with a neurological condition such as phantom limb pain or other condition that can be mitigated based on the rubber hand and/or body transfer illusion. In the example of phantom limb pain, a user may feel sensations such as pain that seem to come from a limb that the user no longer has, e.g., due to amputation. At block 1830, the system can display a perceptual aid, for example, visual content depicting the phantom limb. Because phantom limb pain involves a mismatch between the user's visual sensation and tactile sensation, providing visual content matching the tactile sensation may mitigate the effect of the phantom limb pain.

In some embodiments, various treatments for the example conditions noted above may be provided. For example, stimuli applied to the user may be altered and adjusting in real time based on feedback from the user. In the example of ventriloquism, the ability to separately determine the location of an object and the location of a sound may be further developed by making the determination harder by bringing the sound to locations closer to, but not specifically coinciding with the virtual object. The determination may vary and may be made harder based on the user's correct or incorrect perception of the locations of images and sounds, e.g. harder when the user is doing well in separately locating the visual and audio stimuli and easier when they are incorrectly perceiving the respective locations of the visual and audio stimuli.

Mirror Therapy

In some embodiments, the display system may be configured to perform mirror therapy which is effective, for example, for phantom limb pain and stroke rehabilitation. The therapy may include guided imagery configured to aid a user in improving or regaining the ability to move portions of the body that have been lost or amputated. Rather than using a physical mirror, the display system may be configured to display a virtual mirror image of the user to the user, the image having lateral symmetry. The mirror image may be provided by allowing half of a mirror image through the display system and projecting a reversed version of that image for the other half. The mirror image may be provided by augmenting the same movement (and image) of the good limb but flipped or reversed (as in a reflection) and superimposed over the missing limb. This can provide the illusion that the missing limb is present and functioning properly. When the user makes mirror symmetric movements, the display system provides an image of the user with two good limbs moving. This may provide the sensation of movement of a missing limb to the user which may help to alleviate phantom limb pain. Because the user sees an image of the good and missing limbs moving, this artificial visual feedback causes the user to feel as though they are moving the amputated limb. This may assist in helping a user to unclench muscles associated with an amputated limb from potentially painful positions.

Mental State and Cognitive Alteration
Cognitive Substitution/Enhancement

In some embodiments, the display system may be configured to stimulate cognition. Cognition stimulation may be provided through the use of ocular and aural stimuli tailored to stimulate memory, perception and/or learning. The display system may provide cognitive substitution and cognitive enhancement using techniques similar to those described herein with reference to perceptual learning and perception modification.

In some embodiments, the display system may monitor the speech of the user through one or more microphones and provide suggestions for sentence completion and word completion. The display system may be configured to provide context words for objects (e.g., "you strike a match"). The display system may be configured to label objects, people, and places. In some embodiments, the display system may be configured to provide repetitive and consistent routines that may be useful in treating memory disorders such as dementia and Alzheimer's disease.

The display system may be configured to include one or more sensors and to provide cognitive augmentation. For example, as noted above regarding users that are deaf, the display system may provide text to speech. The provision of text to speech may be used to augment the user's view of the world even if the user is not deaf. The system may be configured to recognize various aspects of speech, such as, for example tone of speech, pitch of speech, speed of speech, and volume of speech to help the user recognize accents and sentence structure and identify the underlying emotion therefrom. For example, the system may be configured to alert the user if a person talking to a user is angry or hurt, based upon an analysis of their speech and the above-noted aspects of that speech. The system may be configured to record conversations and allow the user to retrieve and review conversations at a later date or time. The system may be configured to provide the user with a summary (e.g., a text-based summary) of various conversations that are taking place in environments where the user's ability to follow conversations maybe limited. The system may be configured to observe body language and other social cues of various people in the environment and provide feedback to the user on the display system's interpretation of the body language. In some embodiments, the system may be configured to provide instructions and information in situations where such instructions and information would be beneficial, e.g., in an emergency. For example, in case of a fire emergency, the system could determine that the noise is a fire alarm and provide directions regarding evacuation procedures.

In some embodiments, the display system may be configured to provide cognitive tasks to the user to train the user's brain. The tasks may include ocular and aural stimuli that require interaction from the user. Cognitive tasks are described in greater detail herein and may include, for example and without limitation, perception action, motivation, decision and reward, learning and memory (e.g., 3D games to boost memory and concentration, which may be useful in treating memory disorders such as dementia and Alzheimer's), space, time and numbers, sensory processing (e.g., including visualization strategies, story mapping, social story, etc. which may be useful in treating cognitive disorders such as language processing disorder), and multimodal perception.

Guided Imagery and Cognitive Behavioral Therapy

In some embodiments, the display system may be configured to perform guided imagery therapy and/or cognitive behavioral therapy, e.g., as a part of block 1830. The therapy may include ocular and/or aural stimuli tailored to result in behavioral and/or lifestyle modification.

Referring to block 1830 of FIG. 12, the display system may be configured to provide perception aids that may take various forms, including guided imagery, guided music, guided music and imagery, role playing scenarios, futuristic scenarios based on continuation of a habit (e.g., presenting the consequences of continued smoking for various times into the future), etc. to alter unhelpful thinking habits and to bring about improvements in emotional health. This type of therapy may lead to changes in activation patterns in parts of the frontal cortex and the temporal cortex, parts of the brain associated with the way a person thinks of themselves and with storing and processing memories. By using therapy to affect these portions of the brain, the way the user interprets the world and the user's place in it may be altered to improve the emotional health of the user. This therapy may be used in conjunction with other beneficial activities such as, for example, self-monitoring (e.g., daily logs) and weekly activities schedules (e.g., directed positive experiences).

Guided imagery may be used to improve a user's emotional health by providing images that provoke a response in the user. For example, imagery that is related to a tragic event (e.g., rather than images of the event itself) in a user's life may cause the user to experience emotions associated with the tragic event. When the user experiences this effect, the user may be able to overcome the grief associated with the event and/or become desensitized to the event. Such a systematic use of directed, guided imagery may provoke an emotional response in the user and may then be used to generate healthier, helpful behavior.

Music, other sounds (e.g., beach waves, droplets, crickets, children playing, etc.), and/or pink noise (e.g., sounds configured to filter out offending signals, decrease sensory input, and promote concentration such as for people with attention deficit disorder (ADD) or autism) may assist in the therapy process as well. It has been observed that music and other sounds may elicit emotional responses from the hearer (the display system user) and may even aid the hearer in accessing emotions below consciousness. By providing this access to the hearer, the hearer may be able to engage in self-exploration that may result in experiencing emotions and moods not felt previously. Music may be used in conjunction with guided imagery to provide additional tools to the user to access emotions that may be repressed or that the user may be unaware. Music may be configured to aid in accessing the imaginative process in the user, enhancing the effect of imagery presented to the user. The combination of the music and the imagery may, for example and without limitation, evoke an emotional response, activate the senses, impact physiology on the body, and stimulate symbolic representation or imagery. By helping the user to navigate internal emotions, outward therapeutic changes may be realized.

Such therapy may be used to reduce fatigue and may aid in the treatment of such diseases as multiple sclerosis. The therapy may be used in conjunction with applied behavioral analysis and may aid in the treatment of developmental disorders such as autism spectrum disorder. The therapy may be used to develop social skills in the user and may aid in the treatment of developmental disorders such as autism spectrum disorder and/or Down syndrome. The therapy may be used to help the user to develop self-help skills and may aid in the treatment of developmental disorders such as autism spectrum disorder and/or Down syndrome.

Such therapy may be effective to change a user's pattern of thinking or behavior (e.g., cognitive processes) to consequently change the way the user feels. This therapy may be effective for treating a variety of problems or emotional issues including, for example and without limitation, anger management, anxiety and panic attacks, child and adolescent problems, chronic fatigue syndrome, chronic pain, depression, drug or alcohol problems, eating problems, general health problems, habits such as facial tics, mood swings, obsessive-compulsive disorder, phobias, post-traumatic stress disorder, sexual and relationship problems, and sleep problems. This therapy may also help the user to learn coping skills, to change behaviors and beliefs, to create healthy relationships, and to help address life problems.

Positive/Negative Reinforcement

In some embodiments, the display system may be configured to train or alter neural tissue of a user's brain through positive and/or negative reinforcement. The therapy may include ocular and aural stimuli to respectively provide positive and/or negative feedback in association with desirable and/or undesirable behavior. The display system may be configured to include one or more sensors, such as, for example and without limitation, EEG sensors, temperature sensors, breathing rate sensors, heart rate sensor, eye tracking, eye sensor, eyelid sensor, and the like. The one or more sensors may be configured to detect a user's physical state using one or more parameters. In some embodiments, environmental sensors such as external cameras 34 (FIG. 10) may be utilized to monitor the external environment, while the sensors for monitoring the user such as downward facing cameras 28 may be utilized to determine the outward behavior of the user. At block 1810 (FIG. 12), this user behavior, possibly in conjunction with other parameters such as heart rate, eye tracking, etc., may be understood to be the user stimuli sensed by the display system. At block 1820, the display system may be configured to determine the neurological condition associated with the stimulus. For example, the display system may determine that the stimuli are indicative of a pattern of behavior that the user has previously flagged as being undesirable. For example, the stimuli may be indicative of behaviors associated with anger disorders. As a result, at block 1830, the display system may be configured to provide an output to the user that discourages undesirable behavior (or that reinforces and encourages desirable behavior, in some other instances).

It will be appreciated, that positive and negative reinforcement therapy may be used to condition the user to behave in a targeted or desirable manner. Such therapy may be particularly effective in behavioral management and to address behavioral disorders such as anger disorders. Without wishing to be bound to a particular theory, it is believed that a person's behavior is a consequence of the person's history which includes reinforcement and punishment. Behavior is also affected by the person's current motivational state and other controlling stimuli. Conditioning may be used to address behavior, then, by introducing stimuli, reinforcement, and/or punishment in a tailored manner to develop targeted or desirable behavior.

The display system may be configured to provide perception aids that are configured to condition the user through classical conditioning (or Pavlovian conditioning or respondent conditioning) techniques. For example, in some embodiments, the user may have no reaction to particular stimulus, although the user may desire a reaction be present. In such instances, the perception aids may be configured to train the user to generate an innate response to the previously neutral stimulus (e.g., a stimulus that previously elicited a neutral response). This may occur through repeated pairings of the neutral stimulus with the potent stimulus. After the course of time, the user will generate the innate response to the potent stimulus when presented with the previously neutral stimulus due to a conditioned response to the previously neutral stimulus. For example, the neutral stimulus may be an object in the ambient environment and upon detecting that object, the display system may be configured to display a perception aid that evokes a strong reaction from the viewer. The display system may be configured to provide the perception aid each time that the object is observed an ambient environment, thereby linking the strong reaction with the object.

The display system may be configured to provide perception aids for conditioning the user through operant conditioning (or instrumental conditioning) techniques. For example, the perception aids may be configured to modify the strength of a behavior of the user by providing consequences (e.g., reward or punishment) and the behavior itself may be controlled by antecedents (e.g., discriminative stimuli) that come to signal those consequences. The discriminative stimuli that are present when a behavior is rewarded or punished come to control that behavior. Accordingly, the display system may be configured to provide perception aids that act as discriminative stimuli for the user. The display system may also be configured to provide rewards and punishments as appropriate in conjunction with the discriminative stimuli.

The display system may be configured to associate visual stimuli and/or audio stimuli with positive or negative values. Such visual stimuli may acquire positive or negative value through their association with rewards and punishments. Without desiring to be limited to any particular theory, it is believed that a person's brain encodes the positive and negative values of visual stimuli in distinct populations of neurons. Accordingly, the positive or negative value provided by the user's brain may influence behavioral, emotional, and physiological responses to visual stimuli. For example, a child with autism may be positively rewarded when making eye contact to influence the child to make more eye contact.

It will be appreciated that the positive and negative reinforcement may take various forms. In some embodiments, the positive and negative reinforcement may be provided as visual and/or audible content. For example, positive reinforcement may take the form of pleasing audible tones, colors, and/or imagery that are outputted by the display system. For example, the display system may be configured to bathe the user's view of the environment with a pleasing color to reinforce a desirable behavior. On the other hand, negative reinforcement may take the form of unpleasant sounds, colors, and/or imagery. For example, the display system may be configured to behave the user's view of the environment in an unpleasant color to discourage undesirable behavior.

Pain Management and Distraction Therapy

In some embodiments, the display system may be configured to help a user manage pain through a variety of techniques that include ocular and aural stimuli. The display system may be configured to present perception aids to the user to help the user to deal with pain through a number of techniques including, for example and without limitation, guided imagery (as described herein), distraction through image placement and movement, hypnotherapy, relaxation techniques (e.g., deep breathing, music, guided music, etc.), deep brain stimulation, guided music, and the like.

The display system may be configured to detect user stimuli in block 1810 of FIG. 12 to determine the presence of pain. In certain embodiments, the display system may be configured to detect dilation of the pupils, wide opening of the eyelids, changes in blood pressure and/or heart rate, increased respiration rate and/or depth, piloerection, changes in skin and body temperature, increased muscle tone, sweating, goosebumps, slowing of gut activity, clotting factors and sugar concentration in the blood, increased tension and blood flow in large muscles, increased defecation and urination, and the like. In some embodiments, the display system includes one or more sensors configured to measure one or more of the above physiological signs to determine the presence of pain in the user. In some embodiments, the display system may be configured to receive a direct user input (e.g., via a physical button on the display system, or on a virtual menu for the display system) that allows a user to provide information to the display system, such as the existence and/or amount of pain (e.g., a pain score).

The display system may be configured to provide perception aids that are configured to address cognitive issues associated with pain to reduce the feeling of pain. For example, the display system may aid the user in employing strategies such as patient distraction, breathing exercises, reinforcement of positive behavior, the use of age-appropriate imagery, and/or behavioral rehearsal. The display system may provide distractions such as soothing music and/or interesting videos.

Mood Altering

In some embodiments, the display system may be configured to provide perception aids to a user to alter their mood through a variety of techniques that include ocular and aural stimuli. For example, the display system may be configured to provide guided imagery (as described elsewhere herein), binaural beats, and/or electro-acupuncture (e.g. by providing a power source for the electro-acupuncture). The display system may be configured to include one or more sensors, such as, for example and without limitation, EEG sensors, temperature sensors, breathing rate sensors, heart rate sensor, eye tracking, eye sensor, eyelid sensor, and the like. The one or more sensors may be configured to detect a user's mood based on one or more measured parameters. The measured parameters may be the user stimuli described herein with respect to block 1810 in FIG. 12 and the display system may use the user stimuli to determine the neurological condition of the user (e.g., the user's mood) as described herein with respect to block 1820. This feedback may be used by the system in block 1830 to determine an appropriate perception aid for the user to alter the user's mood. It will be appreciated, that the perception aid may be any of those described. The system may be used to induce particular states or to alter moods including, for example and without limitation, relaxation, depression, meditation, hypnosis, etc. The display system may be configured to update a database of mood altering stimuli based on the user's response to various mood altering stimuli. The system may be further configured to detect particular stimuli that may cause mood altering behavior and take steps to mitigate the mood altering behavior when sensing that the particular stimuli are being presented. For example, the display system may be configured to block out visual stimuli that the user has previously determined is undesirable. The system may also be configured to analyze particular mood-altering stimuli and the mood-altering behavior for root cause analysis. For example, historical analysis of the user's reaction to particular stimulus and the resulting mood may be performed, and the degree of correlation between the stimulus and the mood may be determined, to determine when the link between the stimulus and the mood was first observed. Other stimuli experienced at the time of this first observation of the link may be evaluated (e.g., by a clinician or the display system) to determine whether other stimuli may be involved with establishing the link between the stimulus and the mood.

Neural Stimulation

Transcranial Electric Stimulation or (TES)

In some embodiments, the display system may be configured to provide non-invasive brain stimulation to retrain and/or alter neural tissues of the user's brain. The non-invasive brain stimulation can be provided using electrical impulses applied to the head of the user, e.g., through electrodes attached to the user and connected to the display system. For example, the electrode 30 of the display system 2010 (FIG. 10) may be used to provide the electrical impulses. The electrical impulses can affect the brain by altering the baseline activity level of targeted neurons and/or by modifying functioning at the synapses. In some embodiments, providing electrical impulses to affect the level of activity of neurons can provide benefits during the treatment. In certain embodiments, modifying functioning at the synapses may provide longer-lasting effects. By combining both, the user may experience immediate and long-lasting benefits. The electrical impulses can be configured to be anodal to increase neuronal activity, or cathodal to decrease neuronal activity. By providing the appropriate or targeted electrical signals to the head of the user during treatment and/or cognitive therapies, the user may experience enhanced results relative to treatment without the targeted electrical signals.

In some embodiments, the display system may be configured to provide Transcranial Direct Current Stimulations or (tDCS), Transcranial Random Noise Generation or (tRNG), and/or Transcranial Alternating Current Stimulations or (tACS), which may improve learning. For example, the display system may be configured to provide electrical signals to different parts of the brain (e.g., through electrodes attached to the user) of the user while the user is being taught a particular skill. The electrical signals that are provided to the user may replicate the brain activity (e.g., the electrical signals) detected in the brains of experts or teachers while performing or teaching that particular skill, to thereby facilitate learning of that skill.

In another example, TES may be used to excite and activate specific sections of the brain to stimulate particular emotions for thoughts or aid in developing motor functions or visual abilities. For example, the motor cortex may be selectively excited for stroke rehab or injury-related therapy, the visual cortex may be selectively excited for therapy of visual impairment, the hippocampus may be selectively excited for treatment of conditions related to memory and emotion (including depression), etc. In yet another embodiment, the electrodes of the system 2010 may be used to record activity of the brain. In some embodiments, some electrodes attached to the user may be used to record neural activity while other of the electrodes are used to provide transcranial electric stimulation.

Transcranial Magnetic Stimulation or (TMS)

In some embodiments, the display system may be configured to provide non-invasive magnetic brain stimulation (e.g., as a perception aid) to retrain and/or alter neural tissues of the user's brain. The non-invasive brain stimulation can be provided using magnetic fields applied to the head of the user, e.g., through one or more magnetic field generators attached to the user and connected to the display system. For example, the magnetic field generator 30 of the display system 2010 (FIG. 10) may be used to provide a pulsed magnetic field to the head. In some embodiments, the magnetic fields may affect the brain by stimulating nerve cells in portions of the brain associated with depression so as to mitigate symptoms of depression, which depression has been identified as a condition afflicting the user.

Near Field IR

Light has been shown to have photobiomodulation capability that may stimulate cellular function and provide therapeutic benefits. For example, without being limited by theory, it is believed that photons of light in the wavelength range of 600-1200 nm may be absorbed by cytochrome c oxidase in the mitochondrial respiratory chain and may be responsible for photobiomodulation. The energy provided by these photons are believed to modulate reactive oxygen species, activate mitochondrial DNA replication, increase early-response genes, increase growth factor expression, induce cell proliferation, and alter nitric oxide levels.

It has also been found that near-infrared light may pass efficiently through bone, which may allow near-infrared light projected by the display system to be directed into the brain, thereby allowing for treatment of e.g., traumatic brain injury (TBI). Accordingly, in some embodiments, the display device may be configured as a near-infrared therapeutic device that provides treatment for brain damage due to traumatic brain injury or repetitive concussion. In such embodiments, the display device may be configured to deliver light in the red to near-infrared spectral range (e.g., in the wavelength range between about 600 nm-1200 nm) to the cranial region of the user. Light in the red to near-infrared spectral range may be delivered to the cranial region of the user using visible and/or infrared light sources (e.g., light source 26 mounted on the frame 64 or other optical sources) that are integrated with the display system. In some embodiments, light in the red to near-infrared spectral range may be projected through the waveguide stacks 2005, 2006 and delivered to the living tissue through the skull bones of the user. Advantageously, without being limited by theory, the light propagating to the brain may activate and/or accelerate metabolic pathways in the cells in the brain, as described above, thereby facilitating repair and healing of the brain.

Optogenetics, Light Delivery System

In some embodiments, the display system may be configured as an optogenetics system that employs optical signals to activate and/or inhibit activity in living tissue (e.g., a single neuron or a group of neurons in the brain). As known in the art, the living tissue may be genetically modified to synthesize functional gene products, such as for example, light-sensitive ion channels (e.g., pore-forming membrane proteins whose functions may include establishing a resting membrane potential, shaping action potentials and other electrical signals by gating the flow of ions across the cell membrane, controlling the flow of ions across secretory and epithelial cells, and regulating cell volume) and/or enzymes. In some embodiments, the light-sensitivity of these gene products allows cellular and tissue function to be regulated by the application of light to these gene products. For example, light-sensitive channels in the living tissue may be activated (e.g., opened) or inhibited (e.g., closed) by optical signals directed towards the living tissue. Where the living tissue is brain matter, the function of the user's brain may be regulated by the application of optical stimulation (light) to parts of the brain that are sensitive to the light. For example, optogenetic activation of olfactory sensory neurons may be used to provide mediated olfactory guided behaviors (e.g. to inhibit aggressive behavior based upon perceptions of smell). As another example, a user's reaction to various chemicals (e.g., addictive substances) may be regulated through the activation of light-sensitive neurons (e.g., in the areas of the brain impacted by the chemicals). In addition, the ability to selectively activate parts of the brain may be utilized to map circuits. In some embodiments, the light-sensitive cells are in the eye of the user, and may be regulated by the application of light from the display system to modify the user's visual perception. Various embodiments of the display system configured as an optogenetics system can be used to pace and/or resynchronize cardiac cycles and/or to control or suppress seizures and/or neural firing patterns. For example, the shape of the lens and/or iris may be altered based on a vergence cue indicative of where a user is looking, to correct for myopia, hyperopia, presbyopia, or other visual conditions. In another example, light-based activation of other muscles in and around the eye may be used to treat strabismus, amblyopia, or other conditions. In addition, light activation may be used with visual/audio outputs from the display system to help stimulate thoughts, emotions, etc.

In another example implementation, optogenetic control of retinal cells may be used to provide a perceptual aid for a user with retinal damage. Retinal cells of a user may be stimulated based on virtual content and/or based on light from the real world. In some embodiments, the red, green, and blue cones of the retina may be made to be individually activated and inhibited using light of different, associated wavelengths. Thus, the cones may be activated individually based on the wavelength of light directed by the display system to the retina of the user. In some embodiments, selective activation and inhibition of retinal cells may be used to aid the user in adjusting to changing light conditions (e.g., activate more rods and inhibit more cones, or vice versa, as ambient light levels chamber). For example, a user with macular degeneration may not transition well as light levels change, such that the system may be configured to automatically activate more and more rods and inhibit more and more cones as light levels decrease (or vice versa if the light levels increase). In some embodiments, only cells that are needed are activated. For example, if a user has difficulties focusing, only the fovea would be activated and retinal cells in the periphery would be inhibited to decrease distractions. In some embodiments, activation of the retinal cells may depend on the time of day; for example, blue cones would be inhibited so they don't mess with our circadian rhythms. In some other embodiments, retinal cells in blind spots may be activated. Also, over a given time period, it will be appreciated that the applied light stimulation may be cycled in different frequencies, precise locations of the applied light, wavelengths, intensities, etc.

Embodiments of the display system configured as an optogenetics system may be configured to deliver optical signals to a living tissue (e.g., neurons of the brain) using light sources (e.g., the light source 26 mounted on the frame 64 or other optical sources) integrated in the display system. In some embodiments, the light sources may be configured to emit non-visible (e.g., UV or infrared) and/or visible light. In some embodiments, light may be projected through the waveguide stacks 2005, 2006 and delivered to the living tissue to activate/inhibit activity in living tissue. In some embodiments, the light emitter of the display system may be configured to direct light to a light probe that is then positioned to specifically direct light to the desired body tissue. In some embodiments, the optical signals may be delivered in short bursts, e.g., on a time scale of about 1-100 milliseconds to probe cells in living tissue in the brain of the user. For example, some embodiments of the display system configured as an optogenetic system may deliver a pulsed optical signal having a frequency about 1-50 Hz. The pulses in the pulsed optical signal may have a duty cycle between about 10%-50%.

Sonogenetics

It will be appreciated that some body tissue in a user (e.g., some neurons in the brain) may be sensitive to vibrations (e.g., acoustic or ultrasonic waves) and/or may be modified to be sensitive to ultrasonic sound waves, as known in the art. In some embodiments, the display system may be configured as a sonogenetic system that may employ ultrasound signals to non-invasively activate/inhibit activity in living tissue (e.g., a single neuron or a group of neurons in the brain). For example, low-pressure ultrasound may be directed to the user by the display system to non-invasively activate specific ultrasonically-sensitive neurons. Embodiments of the display system configured as a sonogenetic system may be configured to deliver ultrasound signals to a living tissue (e.g., neurons of the brain) using, for example, the one or more 1081 and the ultrasonic transmitter 1077, receiver 1079 and transceivers 1075 integrated with the display system 2010. In some embodiments, ultrasound signals may stimulate expression of ion-channels of genetically modified cells similar to optogenetics. Similar to optogenetics, sonogenetics may also be used to map neural circuits in the brain (e.g., neural circuits in the amygdala) and/or to stimulate different parts of the brain.

It will be appreciated that, in some embodiments, ultrasound may penetrate the skull and permit the selective stimulation of various parts of the brain. For example, individual neurons or areas of neurons may be stimulated selectively (e.g., the motor cortex for post-injury treatment or stroke rehab, visual cortex for treatment of visual impairment, or the hippocampus for treatment of memory and/or emotion-related conditions). The applied ultrasound waves may vary in different frequency, precise location, wavelength, and/or intensity over time to depending upon the desired effect of the stimulation.

In some other embodiments, low-intensity ultrasound may be applied to a patient (e.g., user) for various therapies. For example, such low-intensity ultrasound may be applied to stimulate the thalamus of a coma patient, for example, to aid in waking the patient. In another example, focused ultrasound may be implemented for ablation of tissues, for example, through constructive and destructive interference so as to focus the ultrasound stimulation at a desired target without damaging surrounding tissues. The focused ultrasound waves may raise the temperature of a targeted region sufficiently to cause thermal ablation to kill cells in the targeted region. For example, ultrasound ablation may be implemented to treat tumors and/or to sever damaged connections (e.g., in users experiencing seizures, etc.).

In some embodiments, the ultrasound stimulation may be combined with other sensory stimuli to form multi-sensory stimulation. For example, ultrasound stimulation for eliciting particular thoughts or emotions (e.g. by stimulating particular parts of the brain associated with those thoughts or emotions) may be augmented with visual and/or audio stimuli (e.g., in the form of virtual content and/or sounds) which further aid in eliciting those particular thoughts or emotions.

Neurological Interface

It will be appreciated that the described systems may be used as a biomimetic neurological interface. These systems may be used to provide a tailored stimulus that isolates a targeted area of the brain and measures the brain's response to it. If the response is abnormal, the systems may be configured to determine that there may be a deficit in the associated area. The systems may also use this same sequence to determine how the brain processes and perceives the provided stimulus. The systems may be configured to change the user's environment to increase plasticity and to alter how the stimulus is processed and perceived. This could improve functioning or accommodate for deficits.

It will be appreciated that various embodiments of the display systems described herein can be configured to suggest or provide possible treatment options or provide information about various drugs that may be useful in alleviating symptoms associated with one or more ocular and/or neurological defects detected. For example, various embodiments of the display systems described herein can be configured to suggest to the user to consult with their physician about one or more drugs or medicines if a possible ophthalmic and/or neurological condition is detected after performing one or more of the eye exams described above. As another example, various embodiments of the display systems described herein can be configured to display information about vacation destinations, spas, massage centers, etc. in response to detecting a possible ophthalmic and/or neurological condition after performing one or more of the eye or brain exams described above. Embodiments of the display system can be configured to provide coupons or deals associated with the vacation destinations, spas, massage centers, etc. displayed. As yet another example, various embodiments of the display systems described herein can be configured to schedule an appointment with a health care provider who may be able to provide treatment for a possible ophthalmic and/or neurological condition detected upon performing one or more of the eye exams described above. Embodiments of the display system can be configured to provide further reminders about the upcoming appointments and/or directions to the health care provider's location.

It will also be appreciated that each of the processes, methods, and algorithms described herein and/or depicted in the figures may be embodied in, and fully or partially automated by, code modules executed by one or more physical computing systems, hardware computer processors, application-specific circuitry, and/or electronic hardware configured to execute specific and particular computer instructions. For example, computing systems may include computers (e.g., servers) programmed with specific computer instructions or special purpose computers, special purpose circuitry, and so forth. A code module may be compiled and linked into an executable program, installed in a dynamic link library, or may be written in an interpreted programming language. In some embodiments, particular operations and methods may be performed by circuitry that is specific to a given function.

Further, certain embodiments of the functionality of the present disclosure are sufficiently mathematically, computationally, or technically complex that application-specific hardware or one or more physical computing devices (utilizing appropriate specialized executable instructions) may be necessary to perform the functionality, for example, due to the volume or complexity of the calculations involved or to provide results substantially in real-time. For example, a video may include many frames, with each frame having millions of pixels, and specifically programmed computer hardware is necessary to process the video data to provide a desired image processing task or application in a commercially reasonable amount of time.

Code modules or any type of data may be stored on any type of non-transitory computer-readable medium, such as physical computer storage including hard drives, solid state memory, random access memory (RAM), read only memory (ROM), optical disc, volatile or non-volatile storage, combinations of the same and/or the like. In some embodiments, the non-transitory computer-readable medium may be part of one or more of the local processing and data module (140), the remote processing module (150), and remote data repository (160). The methods and modules (or data) may also be transmitted as generated data signals (e.g., as part of a carrier wave or other analog or digital propagated signal) on a variety of computer-readable transmission mediums, including wireless-based and wired/cable-based mediums, and may take a variety of forms (e.g., as part of a single or multiplexed analog signal, or as multiple discrete digital packets or frames). The results of the disclosed processes or process steps may be stored, persistently or otherwise, in any type of non-transitory, tangible computer storage or may be communicated via a computer-readable transmission medium.

Any processes, blocks, states, steps, or functionalities in flow diagrams described herein and/or depicted in the attached figures should be understood as potentially representing code modules, segments, or portions of code which include one or more executable instructions for implementing specific functions (e.g., logical or arithmetical) or steps in the process. The various processes, blocks, states, steps, or functionalities may be combined, rearranged, added to, deleted from, modified, or otherwise changed from the illustrative examples provided herein. In some embodiments, additional or different computing systems or code modules may perform some or all of the functionalities described herein. The methods and processes described herein are also not limited to any particular sequence, and the blocks, steps, or states relating thereto may be performed in other sequences that are appropriate, for example, in serial, in parallel, or in some other manner. Tasks or events may be added to or removed from the disclosed example embodiments. Moreover, the separation of various system components in the embodiments described herein is for illustrative purposes and should not be understood as requiring such separation in all embodiments. It should be understood that the described program components, methods, and systems may generally be integrated together in a single computer product or packaged into multiple computer products.

Computer Vision and Sensor Based Detection of Stimulus

As discussed above, the display system may be configured to sense a stimulus present in the environment surrounding the user. The stimulus may be detected using a variety of techniques, including various environmental sensors, as discussed herein. For example, the stimulus present in the environment may be detected using computer vision techniques. In some embodiments, the display system's forward-facing camera may be configured to image the ambient environment and the display system may be configured to perform image analysis on the images to determine the presence of various features in the ambient environment. The display system may analyze the images acquired by the outward-facing imaging system to perform scene reconstruction, event detection, video tracking, object recognition, object pose estimation, learning, indexing, motion estimation, or image restoration, etc. As another example, the display system may be configured to perform face and/or eye recognition to determine the presence and location of faces and/or human eyes in the user's field of view. One or more computer vision algorithms may be used to perform these tasks. None limiting examples of computer vision algorithms include: Scale-invariant feature transform (SIFT), speeded up robust features (SURF), oriented FAST and rotated BRIEF (ORB), binary robust invariant scalable keypoints (BRISK), fast retina keypoint (FREAK), Viola-Jones algorithm, Eigenfaces approach, Lucas-Kanade algorithm, Horn-Schunk algorithm, Mean-shift algorithm, visual simultaneous location and mapping (vSLAM) techniques, a sequential Bayesian estimator (e.g., Kalman filter, extended Kalman filter, etc.), bundle adjustment, Adaptive thresholding (and other thresholding techniques), Iterative Closest Point (ICP), Semi Global Matching (SGM), Semi Global Block Matching (SGBM), Feature Point Histograms, various machine learning algorithms (such as e.g., support vector machine, k-nearest neighbors algorithm, Naive Bayes, neural network (including convolutional or deep neural networks), or other supervised/unsupervised models, etc.), and so forth.

One or more of these computer vision techniques may also be used together with data acquired from other environmental sensors (such as, e.g., microphone) to detect and determine various properties of the stimulus.

The stimulus may be detected based on one or more criteria, or factors. These criteria may be defined by a health care professional. When the display system detects the presence or absence of the criteria in the ambient environment using a computer vision algorithm or using data received from one or more sensor assemblies (which may or may not be part of the display system), the display system may then signal the presence of the stimulus and record/monitor the user's reaction to the stimulus.

Additionally or alternatively, the display system may learn to identify the presence of the stimulus in the environment based on the user's behaviors (or behaviors of a group of users). For example, the display system may learn to identify the presence of stimulus in the environment by associating certain actions or behaviors of the user or a group of users to certain objects that are present in the ambient environment and use this association to predict whether the stimulus is present.

Machine Learning of Stimulus

A variety of machine learning algorithms may be used to learn to identify the presence of stimuli. Once trained, the machine learning algorithm may be stored by the display system. Some examples of machine learning algorithms may include supervised or non-supervised machine learning algorithms, including regression algorithms (such as, for example, Ordinary Least Squares Regression), instance-based algorithms (such as, for example, Learning Vector Quantization), decision tree algorithms (such as, for example, classification and regression trees), Bayesian algorithms (such as, for example, Naive Bayes), clustering algorithms (such as, for example, k-means clustering), association rule learning algorithms (such as, for example, a-priori algorithms), artificial neural network algorithms (such as, for example, Perceptron), deep learning algorithms (such as, for example, Deep Boltzmann Machine, or deep neural network), dimensionality reduction algorithms (such as, for example, Principal Component Analysis), ensemble algorithms (such as, for example, Stacked Generalization), and/or other machine learning algorithms. In some embodiments, individual models may be customized for individual data sets. For example, the wearable device may generate or store a base model. The base model may be used as a starting point to generate additional models specific to a data type (e.g., a particular user), a data set (e.g., a set of additional images obtained), conditional situations, or other variations. In some embodiments, the display system may be configured to utilize a plurality of techniques to generate models for analysis of the aggregated data. Other techniques may include using pre-defined thresholds or data values.

The criteria for detecting a stimulus may include one or more threshold conditions. If the analysis of the data acquired by the environmental sensor indicates that a threshold condition is passed, the display system may detect the presence of the stimulus in the ambient environment. The threshold condition may involve a quantitative and/or qualitative measure. For example, the threshold condition may include a score or a percentage associated with the likelihood of the stimulus being present in the environment. The display system may compare the score calculated from the environmental sensor's data with the threshold score. If the score is higher than the threshold level, the display system may detect the presence of the stimulus. In some other embodiments, the display system may signal the presence of the stimulus in the environment if the score is lower than the threshold.

The threshold condition may be determined based on objects (or people) in the user's physical environment, the user's emotional state and/or the user's interactions with the ambient environment. As described with reference to FIGS. 9D and 10, the display system may acquire information from the ambient environment from the outward-facing camera, the inward facing camera and/or the one or more sensors associated with the display system. As yet other examples, the threshold condition may be determined based on the presence or absence of certain objects in the user's environment.

The threshold condition may also be determined based on the virtual objects being displayed to the user. As one example, the threshold condition may be based on the presence of certain numbers of virtual objects. As another example, the threshold condition may be based on the user's interaction with the virtual object.

In some embodiments, the threshold conditions, the machine learning algorithms, or the computer vision algorithms may be specialized for a specific context. For example, in a diagnostic context, the computer vision algorithm may be specialized to detect certain responses to the stimulus. As another example, the display system may execute facial recognition algorithms and/or event tracing algorithms to sense the user's reaction to a stimulus.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than restrictive sense. For example, for any of the embodiments herein in which light is presented to a user, the light may be provided to the user in one or more colors and one or more intensities, and content provided to the user may have various desired patterns, various levels of brightness, two- or three-dimensional enhancement or de-enhancement, sharpened or blurred focus, higher or lower resolution, enhanced or de-enhanced contrast, motion, lack of motion, higher or lower refresh rate, magnification, shape, intensity, distortion or other qualities, all of which may change over time.

Indeed, it will be appreciated that the systems and methods of the disclosure each have several innovative aspects, no single one of which is solely responsible or required for the desirable attributes disclosed herein. The various features and processes described above may be used independently of one another, or may be combined in various ways. All possible combinations and subcombinations are intended to fall within the scope of this disclosure.

Certain features that are described in this specification in the context of separate embodiments also may be implemented in combination in a single embodiment. Conversely, various features that are described in the context of a single embodiment also may be implemented in multiple embodiments separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination. No single feature or group of features is necessary or indispensable to each and every embodiment.

It will be appreciated that conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise. Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one more example processes in the form of a flowchart. However, other operations that are not depicted may be incorporated in the example methods and processes that are schematically illustrated. For example, one or more additional operations may be performed before, after, simultaneously, or between any of the illustrated operations. Additionally, the operations may be rearranged or reordered in other embodiments. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products. Additionally, other embodiments are within the scope of the following claims. In some cases, the actions recited in the claims may be performed in a different order and still achieve desirable results.

Accordingly, the claims are not intended to be limited to the embodiments shown herein, but are to be accorded the widest scope consistent with this disclosure, the principles and the novel features disclosed herein.

We claim:

1. An augmented reality display system comprising:
    a head-mountable display configured to:
        transmit light from an ambient environment to allow a view of the ambient environment; and
        output light with different amounts of wavefront divergence to display virtual content on a plurality of depth planes;
    one or more outwardly-directed sensors;
    one or more processors; and
    one or more computer storage media storing instructions that, when executed by the one or more processors, cause the one or more processors to perform operations comprising:
        performing a neurological analysis by:
            determining a reaction to a stimulus by receiving data from the one or more outwardly-directed sensors; and
            identifying a neurological condition associated with the reaction.

2. The augmented reality display system of claim 1, wherein the operations further comprise:
    determining a presence of an environmental trigger; and
    causing the display system to display a perception aid in response to the presence of the environmental trigger.

3. The augmented reality display system of claim 2, wherein the perception aid is selected based on the identified neurological condition.

4. The augmented reality display system of claim 2, wherein the perception aid is selected based on a user profile.

5. The augmented reality display system of claim 1, wherein the outwardly-directed sensors are configured to detect one or more of objects, stimuli, people, animals, and locations.

6. The augmented reality display system of claim 1, wherein the outwardly-directed sensors comprise a camera.

7. The augmented reality display system of claim 1, wherein the outwardly-directed sensors comprise one or more of an altimeter, a barometer, a chemical sensor, a humidity sensor, a temperature sensor, an external microphone, and a thermal imaging sensor.

8. The augmented reality display system of claim 1, wherein identifying the neurological condition comprises generating a list of potential neurological conditions.

9. The augmented reality display system of claim 1, wherein the operations further comprise:
    automatically repeating the neurological analysis a plurality of times over a plurality of months,
    wherein repeating the neurological analysis comprises updating the identified neurological condition.

10. The augmented reality display system of claim 1, wherein the operations further comprise transmitting the identified neurological condition to a plurality of other display systems.

11. The augmented reality display system of claim 10, wherein the operations comprise identifying the neurological condition based upon a norm determined from a population of users of the other display systems.

12. The augmented reality display system of claim 1, wherein the display is configured to output virtual content with an accommodation-vergence mismatch of less than 0.25 diopters for each of the depth planes.

13. A method performed by a display system comprising one or more processors, one or more outwardly-directed sensors, and a head-mounted display, the method comprising:
    performing a neurological analysis by:
        determining a user reaction to a stimulus by collecting data from the one or more outwardly-directed sensors; and
        identifying a neurological condition associated with the reaction.

14. The method of claim 13, further comprising:
    determining a presence of an environmental trigger; and
    displaying a perception aid in response to the presence of the environmental trigger.

15. The method of claim 14, further comprising selecting the perception aid based on one or more of the identified neurological condition, the reaction, or a user profile.

16. The method of claim 13, further comprising automatically repeating the neurological analysis a plurality of times over a plurality of months and updating the identified neurological condition.

17. The method of claim 13, wherein the stimulus comprises visual content, further comprising providing the stimulus via the head-mounted display.

18. The method of claim 13, further comprising detecting one or more of objects, stimuli, people, animals, and locations with the outwardly-directed sensors.

19. The method of claim 13, wherein the outwardly-directed sensors comprise a camera.

20. The method of claim 13, wherein the outwardly-directed sensors comprise one or more of an altimeter, a barometer, a chemical sensor, a humidity sensor, a temperature sensor, an external microphone, and a thermal imaging sensor.

* * * * *